(12) United States Patent
McKinnell et al.

(10) Patent No.: US 11,697,648 B2
(45) Date of Patent: Jul. 11, 2023

(54) FUSED PYRIMIDINE PYRIDINONE COMPOUNDS AS JAK INHIBITORS

(71) Applicant: THERAVANCE BIOPHARMA R&D IP, LLC, South San Francisco, CA (US)

(72) Inventors: Robert Murray McKinnell, Millbrae, CA (US); Erik Fenster, San Bruno, CA (US); Tom M. Lam, San Francisco, CA (US); Diana Jin Wang, Madison, WI (US); Anthony Francesco Palermo, Toronto (CA); Luke Boralsky, San Francisco, CA (US); Breena Fraga, San Francisco, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 238 days.

(21) Appl. No.: 17/103,717

(22) Filed: Nov. 24, 2020

(65) Prior Publication Data
US 2021/0188844 A1   Jun. 24, 2021

Related U.S. Application Data

(60) Provisional application No. 62/940,370, filed on Nov. 26, 2019.

(51) Int. Cl.
C07D 471/04 (2006.01)
A61K 45/06 (2006.01)

(52) U.S. Cl.
CPC ............ *C07D 471/04* (2013.01); *A61K 45/06* (2013.01)

(58) Field of Classification Search
CPC .............................. C07D 471/04; A61K 45/06
USPC .................................................. 514/210.18
See application file for complete search history.

(56) References Cited

U.S. PATENT DOCUMENTS

| | | | |
|---|---|---|---|
| 8,680,099 B2 | 3/2014 | Campbell et al. | |
| 9,346,801 B2 | 5/2016 | Tasker et al. | |
| 9,630,963 B2 | 4/2017 | Brameld et al. | |
| 9,862,688 B2 | 1/2018 | Gray et al. | |
| 10,017,477 B2 | 7/2018 | Gray et al. | |
| 2003/0149001 A1 | 8/2003 | Barvian et al. | |
| 2008/0255162 A1* | 10/2008 | Bruendl ................... | A61P 3/00 514/264.11 |
| 2017/0025648 A1 | 1/2017 | Yu et al. | |

FOREIGN PATENT DOCUMENTS

| CN | 103012399 A | 4/2013 |
|---|---|---|
| CN | 104418860 A | 3/2015 |
| CN | 105622638 A | 6/2016 |
| CN | 106699785 A | 5/2017 |
| EP | 1470124 B1 | 12/2005 |
| EP | 1749004 B1 | 9/2007 |
| EP | 2142543 B1 | 5/2013 |
| JP | 2009007342 A | 1/2009 |
| WO | 9634867 A1 | 11/1996 |
| WO | 9833798 A2 | 8/1998 |
| WO | 0155148 A1 | 8/2001 |
| WO | 0170741 A1 | 9/2001 |
| WO | 02059083 A2 | 8/2002 |
| WO | 02085853 A2 | 10/2002 |
| WO | 05105801 A1 | 11/2005 |
| WO | 07044698 A1 | 4/2007 |
| WO | 07117995 A2 | 10/2007 |
| WO | 08118454 A2 | 10/2008 |
| WO | 08127678 A1 | 10/2008 |
| WO | 09132980 A1 | 11/2009 |
| WO | 10071846 A2 | 6/2010 |
| WO | 11044535 A2 | 4/2011 |
| WO | 11130232 A1 | 10/2011 |
| WO | 11134831 A1 | 11/2011 |
| WO | 11140338 A1 | 11/2011 |
| WO | 11156640 A2 | 12/2011 |
| WO | 11156780 A2 | 12/2011 |
| WO | 12018540 A1 | 2/2012 |
| WO | 12061537 A2 | 5/2012 |

(Continued)

OTHER PUBLICATIONS

Abcouwer, "Angiogenic factors and cytokines in diabetic retinopathy", J Clin Cell Immunol, Supplement 1: 1-12 (2013).

Bao et al., "The involvement of the JAK-STAT signaling pathway in . . . skin disease atopic dermatitis", JAK-STAT, 2(3): e24137-1-e24137-8 (2013).

Brameld et al., "Discovery of the irreversible covalent FGFR inhibitor 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one (PRN1371) for the treatment of solid tumors", Journal of Medicinal Chemistry (2017).

(Continued)

*Primary Examiner* — Niloofar Rahmani
(74) *Attorney, Agent, or Firm* — Sheppard Mullin Richter & Hampton LLP

(57) ABSTRACT

The disclosure provides compounds of formula (I):

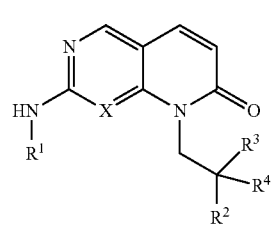

(I)

or a pharmaceutically-acceptable salt thereof, wherein the variables are defined in the specification, that are inhibitors of JAK kinases, particularly JAK3. The disclosure also provides pharmaceutical compositions comprising such compounds, and methods of using such compounds to treat gastrointestinal inflammatory diseases.

22 Claims, No Drawings

(56) References Cited

FOREIGN PATENT DOCUMENTS

| WO | 13041605 A1 | 3/2013 |
|---|---|---|
| WO | 13149194 A1 | 10/2013 |
| WO | 14079232 A1 | 5/2014 |
| WO | 14109858 A1 | 7/2014 |
| WO | 14134308 A1 | 9/2014 |
| WO | 14144737 A1 | 9/2014 |
| WO | 14182829 A1 | 11/2014 |
| WO | 15084936 A1 | 6/2015 |
| WO | 15120049 A1 | 8/2015 |
| WO | 15164604 A1 | 10/2015 |
| WO | 15164614 A1 | 10/2015 |
| WO | 16061751 A1 | 4/2016 |
| WO | 2016115412 A1 | 7/2016 |
| WO | 16133935 A1 | 8/2016 |
| WO | 16179605 A1 | 11/2016 |
| WO | 16191172 A1 | 12/2016 |
| WO | 17054484 A1 | 4/2017 |
| WO | 17101763 A1 | 6/2017 |
| WO | 17143014 A1 | 8/2017 |
| WO | 17148440 A1 | 9/2017 |
| WO | 18004306 A1 | 1/2018 |
| WO | 18050052 A1 | 3/2018 |
| WO | 19132560 A1 | 7/2019 |
| WO | 19132561 A1 | 7/2019 |
| WO | 19132562 A1 | 7/2019 |
| WO | 2019224096 A1 | 11/2019 |
| WO | 20006210 A1 | 1/2020 |

OTHER PUBLICATIONS

Coghill et al., "Effector CD4+ T cells, the cytokines they generate, and GVHD: something old and something new", Blood, 117(12): 3268-3276 (Mar. 24, 2011).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Forster et al., "Selective JAK3 inhibitors with a covalent reversible binding mode targeting a new induced fit binding pocket", Cell Chemical Biology, 23:1335-1340 (2016).
Goedken et al., "Tricyclic covalent inhibitors selectively target JAK3 through an active site thiol", Journal of Biological Chemistry, 290(8):4573-4589 (2015).
Horai et al, "Cytokines in autoimmune uveitis", Journal of Interferon & Cytokine Research, 31(10): 733-744 (2011).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Liu et al., "Developing irreversible inhibitors of the protein kinase cysteinome", Chemistry & Biology, 20:146-159 (2013).
Lynch et al., "Strategic use of conformational bias and structure based design to identify potent JAK3 inhibitors with improved selectivity against the JAK family and the kinome", Bioorganic & Medicinal Chemistry Letters, 23:2793-2800 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Reimund et al., "Mucosal inflammatory cytokine production by intestinal biopsies in patients with ulcerative colitis and Crohn's disease", Journal of Clinical Immunology, 16(3): 144-150 (1996).
Ritzen et al., "Fragment-based discovery of 6-arylindazole JAK inhibitors", ACS Medicinal Chemistry Letters, 7:641-646 (2016).
Scott, "Tofacitinib: a review of its use in adult patients with rheumatoid arthritis", Drugs, 73:857-874 (2013).
Shchuko et al., "Intraocular cytokines in retinal vein occlusion and its relation to the efficiency of anti-vascular endothelial growth factor therapy", Indian Journal of Ophthalmology, 63: 905-911 (2015).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Soth et al., "3-Amido pyrrolopyrazine JAK kinase inhibitors: development of a JAK3 vs JAK1 selective inhibitor and evaluation in cellular and in vivo models", Journal of Medicinal Chemistry, 56:345-356 (2013).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tan et al., "Development of selective covalent Janus Kinase 3 inhibitors", Journal of Medicinal Chemistry, 58:6589-6606 (2015).
Tanaka et al., "New insight into mechanisms of pruritus from molecular studies on familial primary localized cutaneous amyloidosis", British Journal of Dermatology, 161: 1217-1224 (2009).
Thorarensen et al., "Design of a Janus Kinase 3 (JAK3) specific inhibitor 1-((2S,5R)-5-((7H-Pyrrolo[2,3-d]pyrimidin-4-yl)amino)-2-methylpiperidin-1-yl)prop-2-en-1-one(PF-06651600) allowing for the interrogation of JAK3 signaling in humans", Journal of Medicinal Chemistry, 60:1971-1993 (2017).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yu et al., "A structure-guided optimization of pyridol[2,3-d]pyrimidin-7-ones as selective inhibitors of EGFR L858R/T790M mutant with improved pharmacokinetic properties", European Journal of Medicinal Chemistry, 126: 1107-1117 (2017).
International Search Report for PCT/US2020/070816.
D'Amico et al., "Janus kinase inhibitors for the treatment of inflammatory bowel diseases: developments from phase I and phase II clinical trials", Expert Opinion on Investigational Drugs,27(7): 595-599 (2018).
Sun et al., "Discovery and rational design of Pteridin-7(8H)-one-based inhibitors targeting FMS-like tyrosine kinase 3 (FLT3) and its mutants", Journal of Medicinal Chemistry, 59:6187-6200 (2016).

(56) References Cited

OTHER PUBLICATIONS

Telliez et al., "Discovery of a JAK3-selective inhibitor: functional differentiation of JAK3-selective inhibition over pan-JAK or JAK1-selective inhibition", ACS Chemical Biology, 11:3442-3451 (2016).
Yano et al., "Ipilimumab augments antitumor activity of bispecific antibody-armed T cells", Journal of Translational Medicine, 12: 191 (2014).
Zhou et al., "Cytokines and Behcet's Disease", Autoimmunity Reviews, 11: 699-704 (2012).
O'Shea John J. et al., "Janus kinase inhibitors in autoimmune diseases", Annals of the Rheumatic Diseases, vol. 72, ii111-ii115, 10 pages (Apr. 2013).
Clark, James D., et al., "Discovery and development of Janus kinase (JAK) inhibitors for inflammatory diseases", Journal of Medicinal Chemistry, vol. 57, No. 12, pp. 5023-5038 (Jun. 26, 2014).
Sedano, Rocino et al., "Janus Kinase Inhibitors for the Management of Patients With Inflammatory Bowel Disease", Gastroenterology & Hepatology, vol. 18, No. 1, pp. 14-27 (Jan. 2022).

\* cited by examiner

FUSED PYRIMIDINE PYRIDINONE COMPOUNDS AS JAK INHIBITORS

CROSS-REFERENCE TO RELATED APPLICATIONS

This application claims the benefit of U.S. Provisional Application No. 62/940,370, filed on Nov. 26, 2019, the disclosure of which is incorporated herein by reference in its entirety.

BACKGROUND OF THE INVENTION

Field of the Invention

The invention is directed to fused pyrimidine pyridinone compounds useful as JAK kinase inhibitors and more particularly as JAK3 inhibitors that are selective for JAK3 over other members of the JAK kinase family such as JAK1, JAK2 and TYK2. The invention is also directed to pharmaceutical compositions comprising such compounds, and methods of using such compounds to treat inflammatory diseases.

State of the Art

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain. The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer. (e.g. Danese et al. *N Engl J Med*, 2011, 365, 1713-1725). Although there exists a variety of therapeutic options to promote and maintain remission of ulcerative colitis (UC) in patients, none is ideal. There remains an unmet medical need for an effective therapy to promote and maintain remission of moderate to severe UC without the safety concerns resulting from chronic, systemic immunosuppression.

Although the precise pathogenesis of UC is unclear, it is apparent that proinflammatory cytokines play a pivotal role in the immunological response (Strober et al., *Gastroenterol*, 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction. Additionally, tofacitinib, a JAK inhibitor, was recently approved for the treatment of moderate to severe ulcerative colitis in the United States. Tofacitinib however is not JAK3 selective and is distributed systemically and associated with severe side effects such as serious infections, malignancy, thrombosis and a higher risk of blood clots.

Crohn's disease is an inflammatory bowel disease (IBD) that may affect any part of the gastrointestinal tract. The main symptoms include abdominal pain, diarrhea, which may be bloody if inflammation is severe, fever, and weight loss. Crohn's disease affects about 3.2 per 1,000 people in Europe and North America. There are no medications or surgical procedures that can cure Crohn's disease. Treatment options are intended to help with symptoms, maintain remission, and prevent relapse. A need remains for effective treatment of Crohn's disease.

Celiac disease is an autoimmune disorder that primarily affects the small intestine. Classic symptoms include gastrointestinal problems such as chronic diarrhea, abdominal distention, malabsorption, and loss of appetite. Celiac disease affects about 3.3 million people in the United States. The only known effective treatment is a strict lifelong gluten-free diet. However, 30% of diagnosed patients poorly control the disease despite dietary efforts. Incidence of celiac disease is rising with about 1% of the worldwide population affected. There remains an unmet medical need for effective medicines to treat celiac disease. JAK3-dependent cytokines play a central role in the pathogenesis of celiac disease (Jabri et al., *J. Immunol.*, 2017, 198, 3005-14).

Inhibition of the JAK3 enzyme blocks the signaling of many key pro-inflammatory cytokines. Thus, JAK3 inhibitors are likely to be useful in the treatment of ulcerative colitis and other gastrointestinal inflammatory diseases such as Crohn's disease, celiac disease, and immune checkpoint inhibitor induced colitis. JAK3 inhibitors are also likely to be useful for the treatment of inflammatory skin diseases such as atopic dermatitis and inflammatory respiratory disorders such as allergic rhinitis, asthma, and chronic obstructive pulmonary disease (COPD). In addition, JAK3 inhibitors may also be useful in the treatment of many ocular diseases for which inflammation plays a prominent role such as uveitis, diabetic retinopathy, diabetic macular edema, dry eye disease, age-related macular degeneration, retinal vein occlusion (RVO) and atopic keratoconjunctivitis.

Selectivity for JAK3 over JAK1 is anticipated to be beneficial as there is evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 also allows sparing of erythropoietin (EPO) and thrombopoietin (TPO) signaling. Therefore, it would be desirable to provide new compounds which are selective JAK3 inhibitors over other members of the JAK kinase family such as JAK1, JAK2 and TYK2.

Finally, due to the modulating effect of the JAK/STAT pathway on the immune system, systemic exposure to JAK inhibitors may have an adverse systemic immunosuppressive effect. It would be desirable, therefore, to provide new JAK3 inhibitors which have their effect at the site of action without significant systemic effects. In particular, for the treatment of gastrointestinal inflammatory diseases, such as ulcerative colitis, it would be desirable to provide new JAK3 inhibitors which can be administered orally and achieve therapeutically relevant exposure in the gastrointestinal tract with minimal systemic exposure. For skin diseases, it would be desirable to provide new JAK3 inhibitors that could be administered topically to the skin with minimal systemic exposure.

Therefore, it would be desirable to provide new compounds which are selective JAK3 inhibitors over other members of the JAK kinase family such as JAK1, JAK2 and TYK2, and have minimal systemic exposure.

SUMMARY OF THE INVENTION

In one aspect, the invention provides novel compounds having activity as JAK kinase inhibitors and more particularly as JAK3 inhibitors.

Accordingly, the invention provides a compound of formula (I):

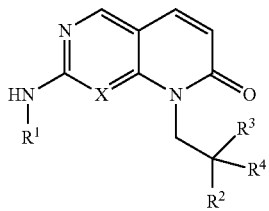

or a pharmaceutically acceptable salt thereof, wherein
X is CH or N;
R$^1$ is selected from the group consisting of:

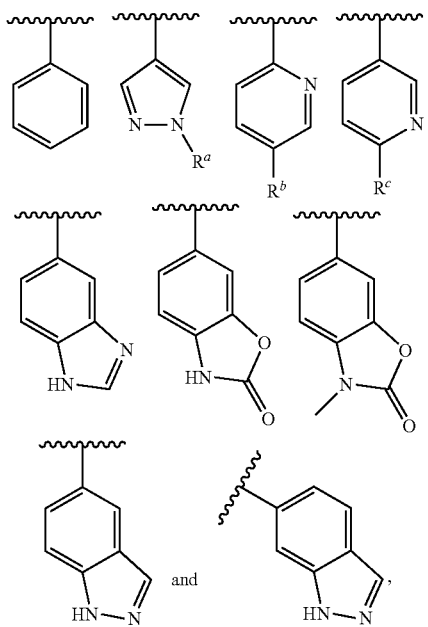

wherein

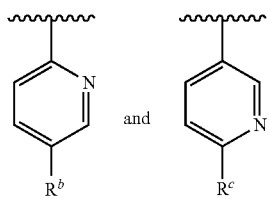

are optionally substituted with 1 or 2 F,
wherein

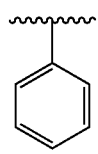

is optionally substituted with 1 to 3 substituents independently selected from:
(i) C$_{1-6}$ alkoxy optionally substituted with OH,
(ii) C$_{1-6}$ alkyl, halogen, CN, OH, NR$^p$R$^q$, —NHCO$_2$C$_{1-6}$ alkyl, —NHSO$_2$C$_{1-6}$ alkyl, 5 membered ring heteroaryl, partially unsaturated heterocyclic,
wherein the C$_{1-6}$ alkyl is optionally substituted with NR$^p$R$^q$,
wherein R$^p$ and R$^q$ are each independently selected from the group consisting of H, C$_{1-6}$ alkyl, C$_{2-6}$ alkyl-OH, C$_{1-6}$ alkyl-C$_{1-6}$ alkoxy, and —C$_{1-6}$ alkyl-aryl,
(iii) a 6 membered ring heterocyclic group optionally substituted with 1 to 3 substituents independently selected from:
(a) F, C$_{1-6}$ alkyl, C$_{1-6}$ alkyl-CF$_3$, CF$_3$, CHF$_2$, CH$_2$F, 3 to 8 membered ring cycloalkyl, —C$_{1-6}$ alkyl-C$_{1-6}$ alkoxy, —C$_{1-6}$ alkyl-C$_{3-8}$ cycloalkyl, SO$_2$ linked to a 4 to 8 membered ring heterocyclic group, C$_{1-6}$ alkyl substituted with a 4 to 8 membered ring heterocyclic group, —COCF$_3$, —C(O)S—C$_{1-6}$ alkyl, SO$_2$—NHMe, SO$_2$NMe$_2$, SO$_2$NR$^x$R$^y$, CONR$^x$R$^y$, CSNR$^x$R$^y$,
(b) SO$_2$C$_{1-6}$ alkyl optionally substituted with C$_{1-6}$ alkoxy or CN,
(c) CO$_2$C$_{1-6}$ alkyl optionally substituted with C$_{1-6}$ alkoxy,
(d) COC$_{1-6}$ alkyl optionally substituted with OH, C$_{1-6}$ alkoxy, —SO$_2$C$_{1-6}$ alkyl, —SOC$_{1-6}$ alkyl, —S—C$_{1-6}$ alkyl, CN or —S—C$_{1-6}$ alkyl, and wherein a carbon of the 6 membered ring heterocyclic group may optionally form a carbonyl,
(iv) —CH$_2$—R$^5$, —CHMe-R$^5$
wherein R$^5$ is a 6 membered ring heterocyclic group optionally substituted with 1 to 3 substituents independently selected from:
(a) F, C$_{1-6}$ alkyl, —C$_{1-6}$ alkyl-CF$_3$, CF$_3$, CHF$_2$, CH$_2$F, 3 to 8 membered ring cycloalkyl, —C$_{1-6}$ alkyl-C$_{1-6}$ alkoxy, —C$_{1-6}$ alkyl-C$_{3-8}$ cycloalkyl, SO$_2$ linked to a 4 to 8 membered ring heterocyclic group, C$_{1-6}$ alkyl substituted with a 4 to 8 membered ring heterocyclic, —COCF$_3$, —C(O)S—C$_{1-6}$ alkyl, SO$_2$NR$^x$R$^y$, CONR$^x$R$^y$, CO$_2$C$_{1-6}$ alkyl,
(b) —SO$_2$C$_{1-6}$ alkyl optionally substituted with C$_{1-6}$ alkoxy or CN,
(c) COC$_{1-6}$ alkyl optionally substituted with C$_{1-6}$ alkoxy or —S—C$_{1-6}$ alkyl, and
(v) —CO—R$^6$
wherein R$^6$ is a 6 membered ring heterocyclic group optionally substituted with 1 to 3 substituents independently selected from:
(a) F, C$_{1-6}$ alkyl, —C$_{1-6}$ alkyl-CF$_3$, CF$_3$, CHF$_2$, CH$_2$F, 3 to 8 membered ring cycloalkyl, —C$_{1-6}$ alkyl-C$_{1-6}$ alkoxy, —C$_{1-6}$ alkyl-C$_{3-8}$ cycloalkyl, SO$_2$ linked to a 4 to 8 membered ring heterocyclic group, C$_{1-6}$ alkyl substituted with a 4 to 8 membered ring heterocyclic, —COCF$_3$, —C(O)S—C$_{1-6}$ alkyl, SO$_2$NR$^x$R$^y$, CONR$^x$R$^y$,
(b) —SO$_2$C$_{1-6}$ alkyl optionally substituted with C$_{1-6}$ alkoxy or CN,
R$^a$ is selected from the group consisting of C$_{1-6}$ alkyl, a 4 to 8 membered ring heterocyclic group, a 3 to 8 membered ring cycloalkyl group, and an aryl group,
wherein the 4 to 8 membered ring heterocyclic group and the 3 to 8 membered ring cycloalkyl group are optionally substituted with 1 to 3 substituents independently selected from C$_{1-6}$ alkyl, —CO—C$_{1-6}$ alkyl, —CO—C$_{1-6}$ alkyl-S—C$_{1-6}$ alkyl, and —CO—C$_{1-6}$ alkyl-O—C$_{1-6}$ alkyl,
wherein the C$_{1-6}$ alkyl is optionally substituted with OH, NR$^x$R$^y$, 1 to 3 F, an aryl group, a 4 to 8 membered ring heterocyclic group, a 3 to 8 membered ring cycloalkyl group, or C$_{1-6}$ alkoxy optionally substituted with 1 to 3 F, R$^x$ and R$^y$ are each independently selected from H, and C$_{1-6}$ alkyl, or R$^x$ and R$^y$ are joined to form a 4 to 7 membered ring heterocyclic ring;

R$^b$ is a 4 to 8 membered ring heterocyclic group optionally substituted with 1 to 3 substituents independently selected from C$_{1-6}$ alkyl, and CO—C$_{1-6}$ alkyl;

R$^c$ is a 4 to 8 membered ring heterocyclic group optionally substituted with 1 to 3 substituents independently selected from C$_{1-6}$ alkyl, and CO—C$_{1-6}$ alkyl;

R$^2$ is selected from the group consisting of:

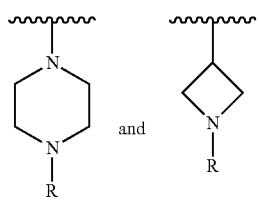

and which are optionally substituted with 1 to 3 R$^k$, each R$^k$ is independently C$_{1-4}$ alkyl, wherein the C$_{1-4}$ alkyl is optionally substituted with NR$^u$R$^v$, OH, O—C$_{1-4}$ alkyl, CN, or 1 to 3 F, wherein two R$^k$ substituents on the same carbon may optionally form a spiro C$_{3-5}$ cycloalkyl;

R$^u$ and R$^v$ are each independently selected from H and C$_{1-4}$ alkyl;

R is selected from the group consisting of:

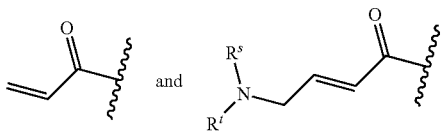

wherein R$^s$ and R$^t$ are each independently selected from the group consisting of H, C$_{3-5}$ cycloalkyl and C$_{1-6}$ alkyl, wherein the C$_{1-6}$ alkyl group may be optionally substituted with 1 to 3 substituents independently selected from the group consisting of C$_{1-3}$ alkoxy and —S—C$_{1-3}$ alkyl, or R$^s$ and R$^t$ form a 4 to 6 membered monocyclic heterocyclic group optionally substituted with 1 to 3 substituents independently selected from the group consisting of C$_{1-6}$ alkyl, C$_{1-3}$ alkoxy, —S—C$_{1-3}$ alkyl and —C$_{1-3}$ alkyl-C$_{1-3}$ alkoxy; and R$^3$ and R$^4$ are each independently selected from C$_{1-4}$ alkyl and H.

The invention also provides a pharmaceutical composition comprising a compound of the disclosure, or a pharmaceutically acceptable salt thereof, and a pharmaceutically-acceptable carrier.

The invention also provides a method of treating a gastrointestinal inflammatory disease in a mammal, the method comprising administering to the mammal a compound of the disclosure, or a pharmaceutically acceptable salt thereof, or a pharmaceutical composition of the disclosure.

The invention also provides a compound of the disclosure, or a pharmaceutically acceptable salt thereof, as described herein for use in medical therapy, as well as the use of a compound of the disclosure, or a pharmaceutically acceptable salt thereof, in the manufacture of a formulation or medicament for treating a gastrointestinal inflammatory disease.

DETAILED DESCRIPTION OF THE INVENTION

Among other aspects, the invention provides JAK kinase inhibitors of formula (I) which are selective for JAK3 over other members of the JAK kinase family such as JAK1, JAK2 and TYK2, and pharmaceutically-acceptable salts thereof.

In one aspect, the invention provides compounds having activity as JAK kinase inhibitors, particularly as JAK3 kinase inhibitors.

Accordingly, the invention provides a compound of formula (I):

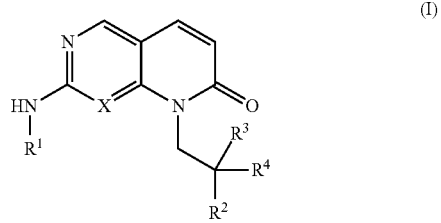

(I)

or a pharmaceutically acceptable salt thereof, wherein
X is CH or N;
R$^1$ is selected from the group consisting of:

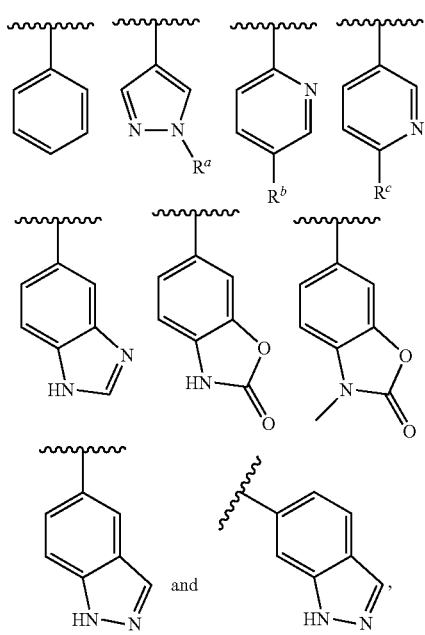

wherein

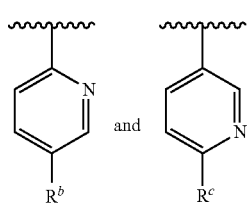

are optionally substituted with 1 or 2 F,
wherein

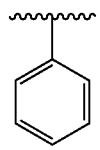

is optionally substituted with 1 to 3 substituents independently selected from:
(i) $C_{1-6}$ alkoxy optionally substituted with OH,
(ii) $C_{1-6}$ alkyl, halogen, CN, OH, $NR^pR^q$, —$NHCO_2C_{1-6}$ alkyl, —$NHSO_2C_{1-6}$ alkyl, 5 membered ring heteroaryl, partially unsaturated heterocyclic,
wherein the $C_{1-6}$ alkyl is optionally substituted with $NR^pR^q$,
wherein $R^p$ and $R^q$ are each independently selected from the group consisting of H, $C_{1-6}$ alkyl, $C_{2-6}$ alkyl-OH, $C_{1-6}$ alkyl-$C_{1-6}$ alkoxy, and —$C_{1-6}$ alkyl-aryl,
(iii) a 6 membered ring heterocyclic group optionally substituted with 1 to 3 substituents independently selected from:
(a) F, $C_{1-6}$ alkyl, $C_{1-6}$ alkyl-$CF_3$, $CF_3$, $CHF_2$, $CH_2F$, 3 to 8 membered ring cycloalkyl, —$C_{1-6}$ alkyl-$C_{1-6}$ alkoxy, —$C_{1-6}$ alkyl-$C_{3-8}$ cycloalkyl, $SO_2$ linked to a 4 to 8 membered ring heterocyclic group, $C_{1-6}$ alkyl substituted with a 4 to 8 membered ring heterocyclic group, —$COCF_3$, —C(O)S—$C_{1-6}$ alkyl, $SO_2$—NHMe, $SO_2NMe_2$, $SO_2NR^xR^y$, $CONR^xR^y$, $CSNR^xR^y$,
(b) $SO_2C_{1-6}$ alkyl optionally substituted with $C_{1-6}$ alkoxy or CN,
(c) $CO_2C_{1-6}$ alkyl optionally substituted with $C_{1-6}$ alkoxy,
(d) $COC_{1-6}$ alkyl optionally substituted with OH, $C_{1-6}$ alkoxy, —$SO_2C_{1-6}$ alkyl, —$SOC_{1-6}$ alkyl, —S—$C_{1-6}$ alkyl, CN or —S—$C_{1-6}$ alkyl, and wherein a carbon of the 6 membered ring heterocyclic group may optionally form a carbonyl,
(iv) —$CH_2$—$R^5$, —$CHMe$-$R^5$
wherein $R^5$ is a 6 membered ring heterocyclic group optionally substituted with 1 to 3 substituents independently selected from:
(a) F, $C_{1-6}$ alkyl, —$C_{1-6}$ alkyl-$CF_3$, $CF_3$, $CHF_2$, $CH_2F$, 3 to 8 membered ring cycloalkyl, —$C_{1-6}$ alkyl-$C_{1-6}$ alkoxy, —$C_{1-6}$ alkyl-$C_{3-8}$ cycloalkyl, $SO_2$ linked to a 4 to 8 membered ring heterocyclic group, $C_{1-6}$ alkyl substituted with a 4 to 8 membered ring heterocyclic, —$COCF_3$, —C(O)S—$C_{1-6}$ alkyl, $SO_2NR^xR^y$, $CONR^xR^y$, $CO_2C_{1-6}$ alkyl,
(b) —$SO_2C_{1-6}$ alkyl optionally substituted with $C_{1-6}$ alkoxy or CN,
(c) $COC_{1-6}$ alkyl optionally substituted with $C_{1-6}$ alkoxy or —S—$C_{1-6}$ alkyl, and
(v) —CO—$R^6$
wherein $R^6$ is a 6 membered ring heterocyclic group optionally substituted with 1 to 3 substituents independently selected from:
(a) F, $C_{1-6}$ alkyl, —$C_{1-6}$ alkyl-$CF_3$, $CF_3$, $CHF_2$, $CH_2F$, 3 to 8 membered ring cycloalkyl, —$C_{1-6}$ alkyl-$C_{1-6}$ alkoxy, —$C_{1-6}$ alkyl-$C_{3-8}$ cycloalkyl, $SO_2$ linked to a 4 to 8 membered ring heterocyclic group, $C_{1-6}$ alkyl substituted with a 4 to 8 membered ring heterocyclic, —$COCF_3$, —C(O)S—$C_{1-6}$ alkyl, $SO_2NR^xR^y$, $CONR^xR^y$, (b) —$SO_2C_{1-6}$ alkyl optionally substituted with $C_{1-6}$ alkoxy or CN,
$R^a$ is selected from the group consisting of $C_{1-6}$ alkyl, a 4 to 8 membered ring heterocyclic group, a 3 to 8 membered ring cycloalkyl group, and an aryl group,
wherein the 4 to 8 membered ring heterocyclic group and the 3 to 8 membered ring cycloalkyl group are optionally substituted with 1 to 3 substituents independently selected from $C_{1-6}$ alkyl, —CO—$C_{1-6}$ alkyl, —CO—$C_{1-6}$ alkyl-S—$C_{1-6}$ alkyl, and —CO—$C_{1-6}$ alkyl-O—$C_{1-6}$ alkyl,
wherein the $C_{1-6}$ alkyl is optionally substituted with OH, $NR^xR^y$, 1 to 3 F, an aryl group, a 4 to 8 membered ring heterocyclic group, a 3 to 8 membered ring cycloalkyl group, or $C_{1-6}$ alkoxy optionally substituted with 1 to 3 F,
$R^x$ and $R^y$ are each independently selected from H, and $C_{1-6}$ alkyl, or $R^x$ and $R^y$ are joined to form a 4 to 7 membered ring heterocyclic ring;
$R^b$ is a 4 to 8 membered ring heterocyclic group optionally substituted with 1 to 3 substituents independently selected from $C_{1-6}$ alkyl, and CO—$C_{1-6}$ alkyl;
$R^1$ is a 4 to 8 membered ring heterocyclic group optionally substituted with 1 to 3 substituents independently selected from $C_{1-6}$ alkyl, and CO—$C_{1-6}$ alkyl;
$R^2$ is selected from the group consisting of:

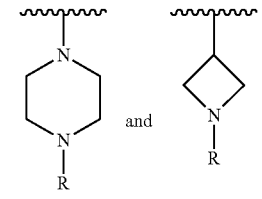

which are optionally substituted with 1 to 3 $R^k$,
each $R^k$ is independently $C_{1-4}$ alkyl, wherein the $C_{1-4}$ alkyl is optionally substituted with $NR^uR^v$, OH, O—$C_{1-4}$ alkyl, CN, or 1 to 3 F, wherein two $R^k$ substituents on the same carbon may optionally form a spiro $C_{3-5}$ cycloalkyl;
$R^u$ and $R^v$ are each independently selected from H and $C_{1-4}$ alkyl;
R is selected from the group consisting of:

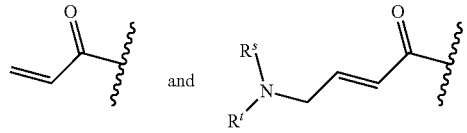

wherein $R^s$ and $R^t$ are each independently selected from the group consisting of H, $C_{3-5}$ cycloalkyl and $C_{1-6}$ alkyl, wherein the $C_{1-6}$ alkyl group may be optionally substituted with 1 to 3 substituents independently selected from the group consisting of $C_{1-3}$ alkoxy and —S—$C_{1-3}$ alkyl,
or $R^s$ and $R^t$ form a 4 to 6 membered monocyclic heterocyclic group optionally substituted with 1 to 3 substituents independently selected from the group consisting of $C_{1-6}$ alkyl, $C_{1-3}$ alkoxy, —S—$C_{1-3}$ alkyl and —$C_{1-3}$ alkyl-$C_{1-3}$ alkoxy; and
$R^3$ and $R^4$ are each independently selected from $C_{1-4}$ alkyl and H.
In some embodiments, X is N. In some embodiments, X is CH.
In some embodiments, $R^3$ and $R^4$ are each independently selected from $C_{1-2}$ alkyl and H. In some embodiments, $R^3$ and R⁴ are each independently selected from methyl and H. In some embodiments, R³ and R⁴ are both H.

In some embodiments, R is selected from the group consisting of:

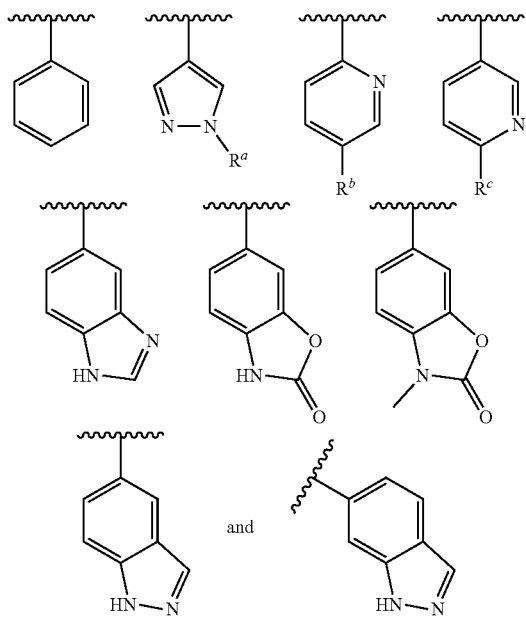

wherein

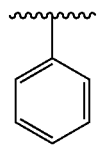

is optionally substituted with 1 to 2 substituents independently selected from:

(i) $C_{1-2}$ alkoxy optionally substituted with OH,
(ii) $C_{1-2}$ alkyl, F, Cl, CN, OH, $NR^pR^q$, —NHSO₂Me, triazolyl, pyrazolyl, imidazolyl, tetrahydropyridinyl,
  wherein the $C_{1-2}$ alkyl is optionally substituted with $NR^pR^q$
  wherein $R^p$ and $R^q$ are each independently selected from $C_{1-2}$ alkyl, (CH₂)₂—OH, and —CH₂-phenyl,
(iii) piperazinyl, morpholinyl, thiomorpholinyl, morpholinonyl, piperidinyl optionally substituted with one methyl or 2 F,
  wherein the piperazinyl is optionally substituted with 1 to 3 substituents independently selected from F, Me, Et, iPr, t-Bu, sec-Bu, CF₃, CH₂—CF₃, cyclopropyl, —$C_{2-3}$ alkyl-$C_{1-2}$ alkoxy, —C₂alkyl-cyclohexyl, —C₂alkyl-piperidinyl, COCF₃, $COC_{1-4}$alkyl, COCH₂OMe, COCH₂SMe, CO(CH₂)₂SMe, COCH₂SO₂Me, CO(CH₂)₂SOMe, CO(CH₂)₂SO₂Me, COCH₂SOEt, COCH₂CN, —$CO_2C_{1-3}$ alkyl, CO₂—(CH₂)₂—OMe, C(O)StBu, SO₂Me, —SO₂-oxetanyl, SO₂—(CH₂)₂—OMe, SO₂—CH₂—CN, SO₂—NHMe, SO₂NMe₂, CO₂Me, CO—NHMe, CONMe₂, C(S)NMe₂, COCH₂OMe, COCH₂SMe, CO(CH₂)₂SMe, $COC_{2-3}$alkyl substituted with OH;
(iv) —CH₂-piperazinyl, —CH₂-morpholinyl, —CH₂-thiomorpholinyl, and —CHMe-piperazinyl, wherein the piperazinyl is optionally substituted with 1 substituent selected from the group consisting of Me, SO₂Me, SO₂—CH₂CN, SO₂—(CH₂)₂—OMe, —SO₂-oxetanyl, CO₂Me, COMe, CO—CH₂—OMe, CO—CH₂—SMe, and CONMe₂, and
(v) —CO-morpholinyl, —CO-piperidinyl;

$R^a$ is selected from the group consisting of $C_{1-4}$ alkyl, piperidinyl, tetrahydropyranyl, and phenyl, wherein the piperidinyl and tetrahydropyranyl are optionally substituted with Me or CO—CH₂—SMe, wherein the $C_{1-4}$ alkyl is optionally substituted with OH, OMe, OEt, OiPr, —OCHF₂, $NR^xR^y$, 1 to 2 F, phenyl, or morpholinyl,
  $R^x$ and $R^y$ are each independently selected from $C_{1-2}$ alkyl, or $R^x$ and $R^y$ are joined to form a morpholinyl ring;

$R^b$ is selected from the group consisting of morpholinyl and piperazinyl wherein the piperazinyl is substituted by a methyl group; and $R^c$ is selected from the group consisting of thiomorpholinyl and piperazinyl wherein the piperazinyl is substituted with 1 or 2 methyl groups or a COMe group.

In some embodiments, R¹ is selected from the group consisting of:

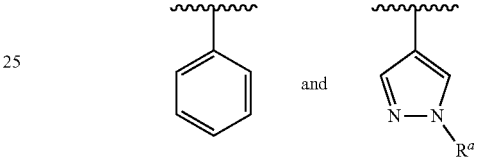

wherein $R^a$ is $C_{1-4}$ alkyl,
wherein

is substituted with piperazinyl, wherein the piperazinyl is substituted with a substituent selected from the group consisting of $C_{1-4}$ alkyl, —CO—$C_{1-4}$ alkyl, —COCH₂SMe, —CO(CH₂)₂SMe, and —CONMe₂.

In some embodiments, R¹ is selected from the group consisting of:

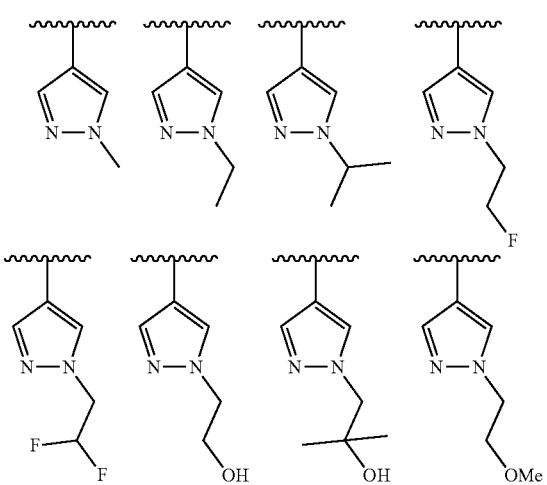

-continued
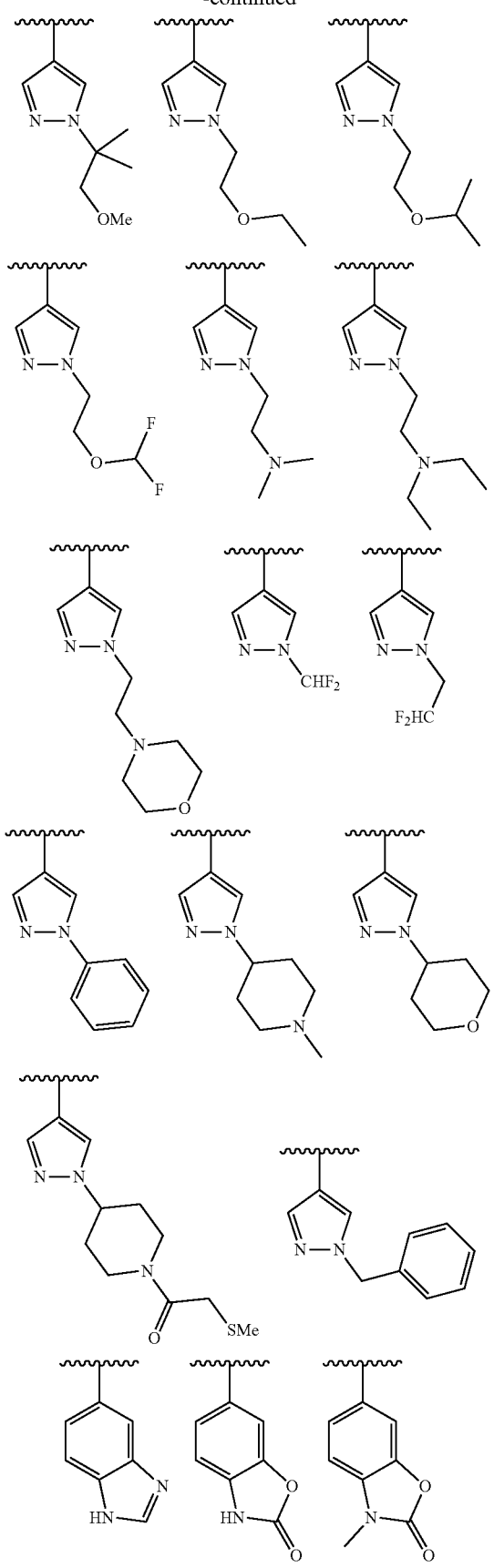
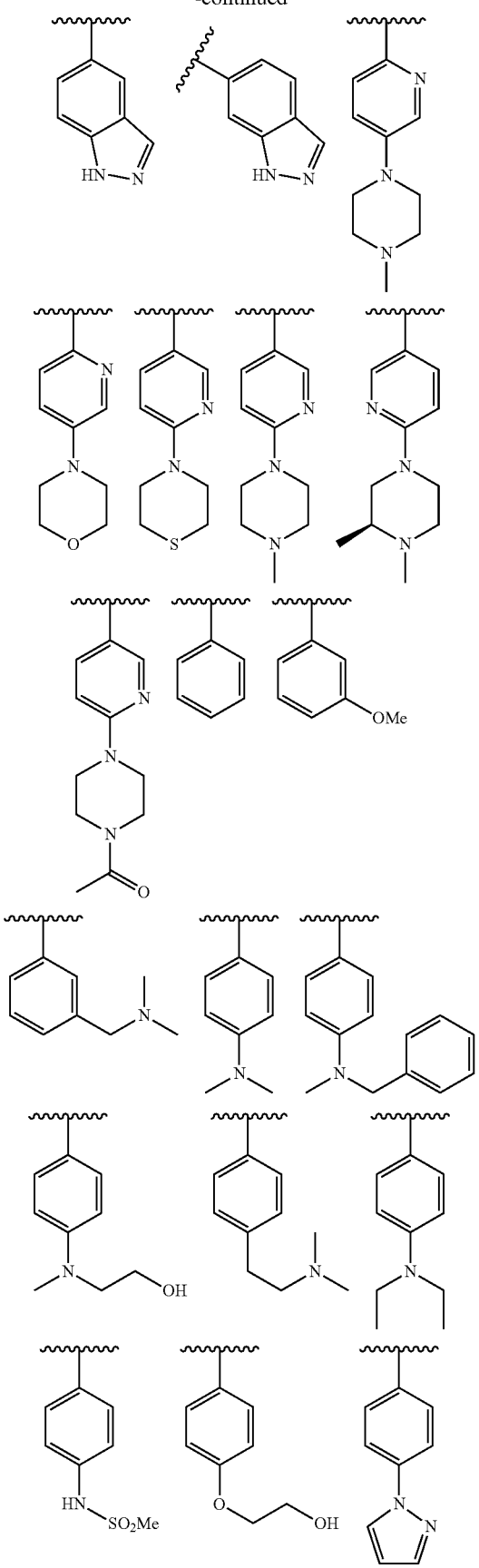

-continued
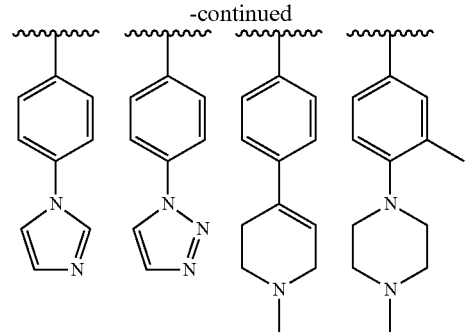
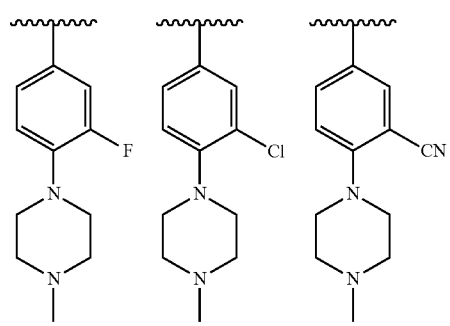
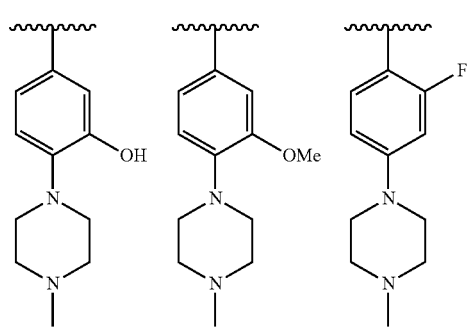
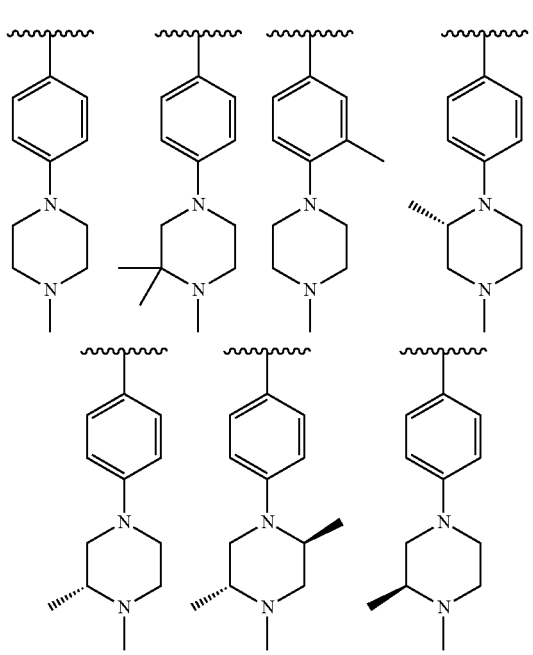
-continued
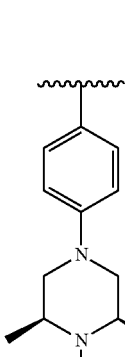
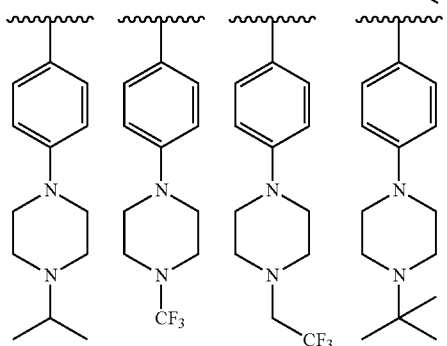
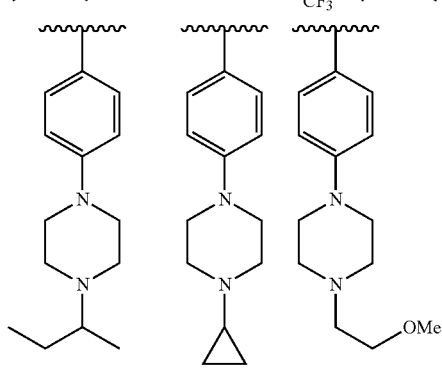
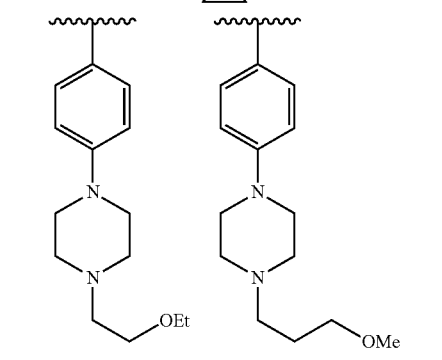
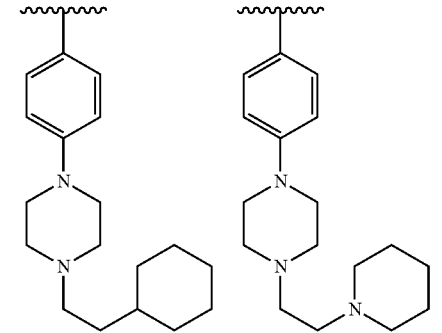

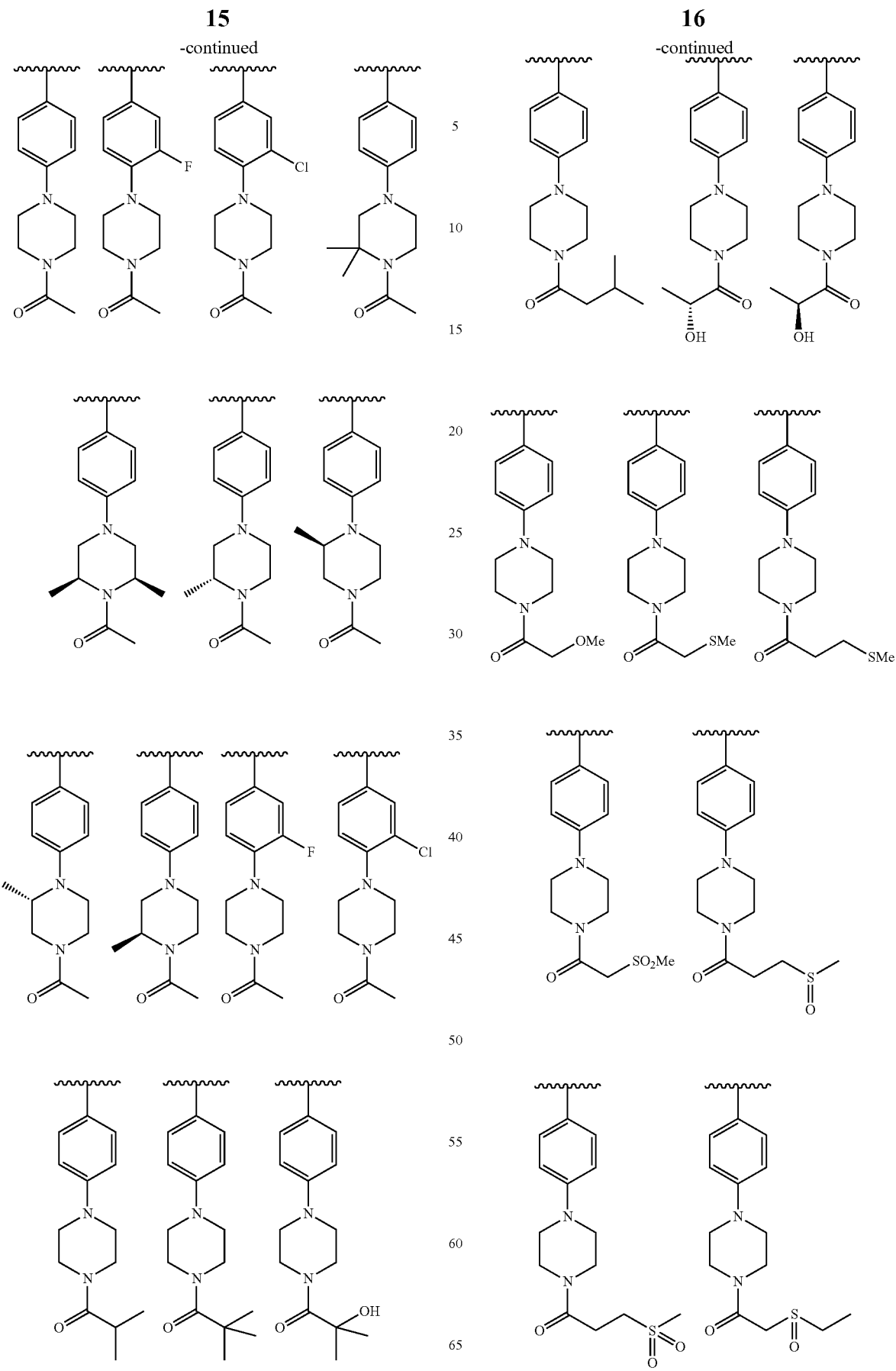

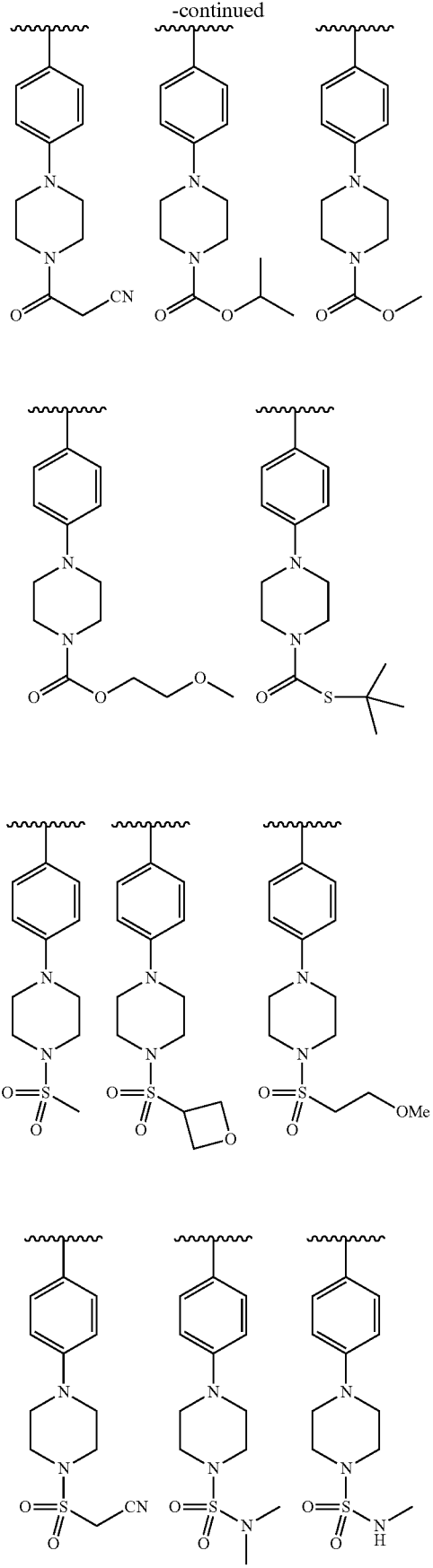
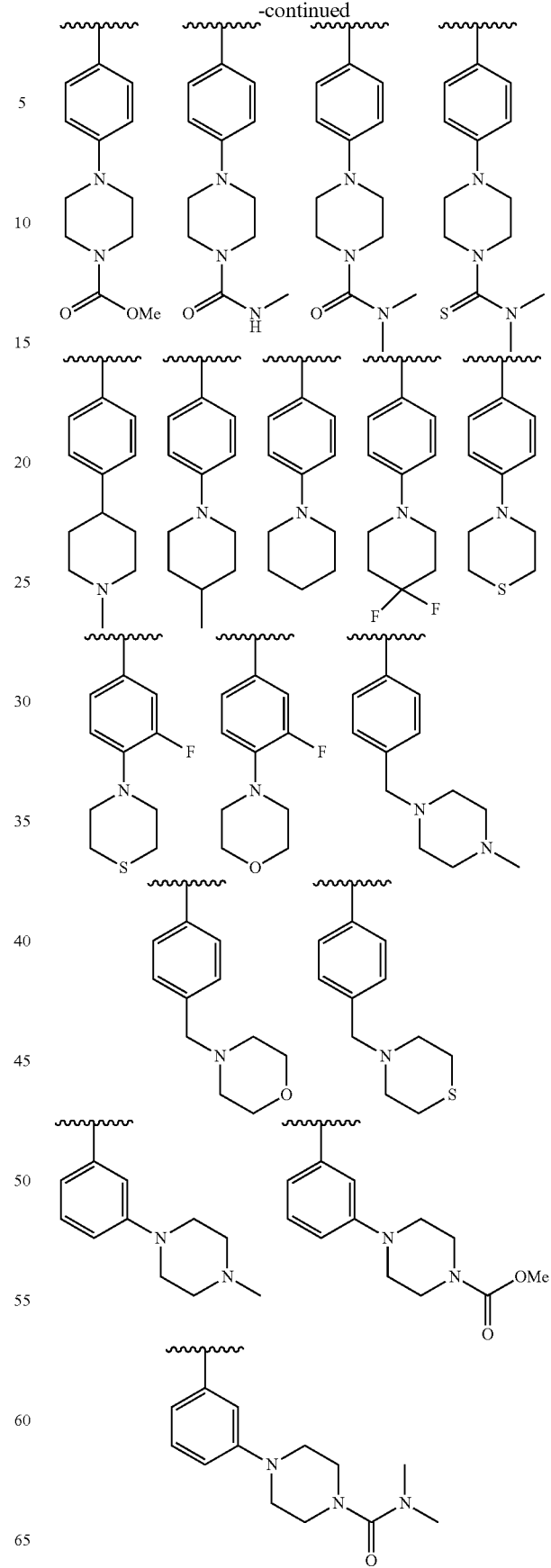

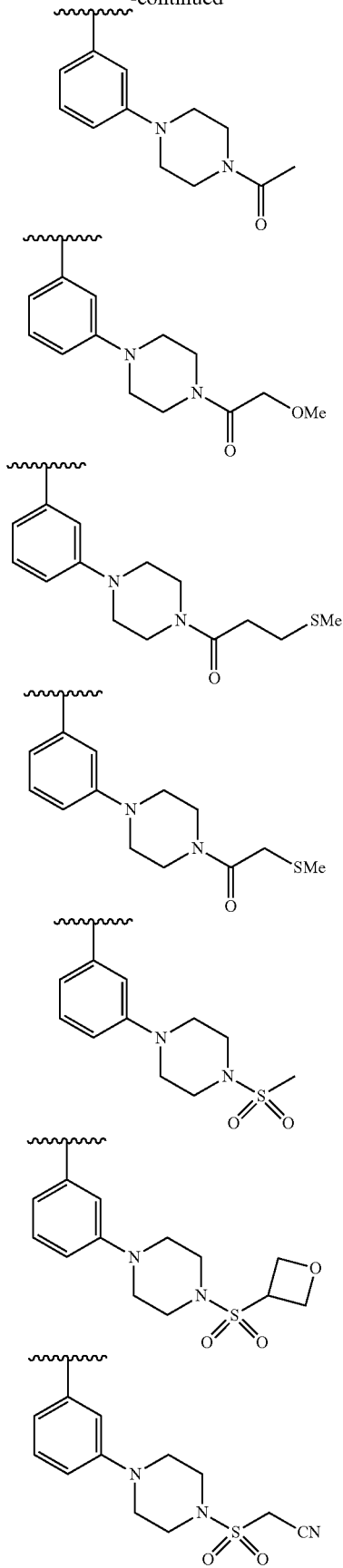
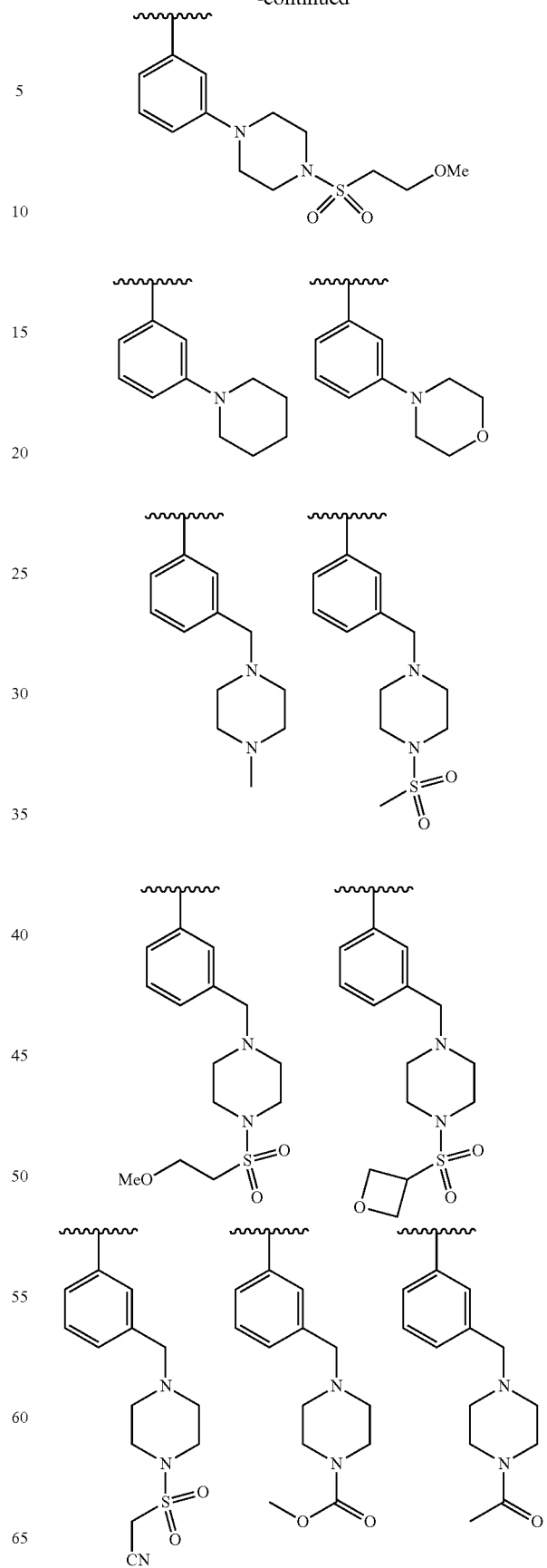

-continued

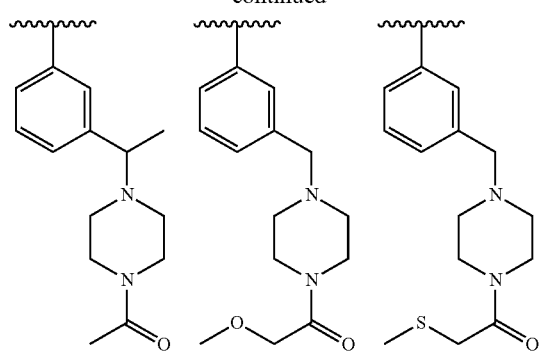

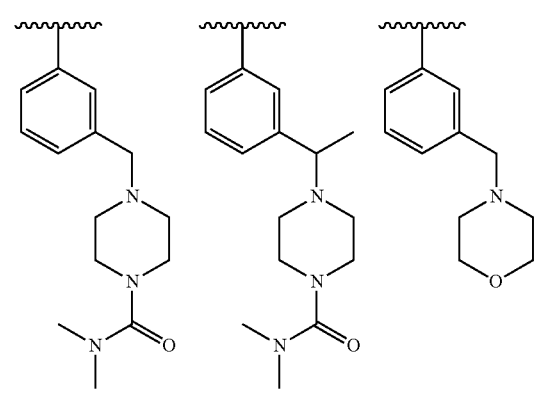

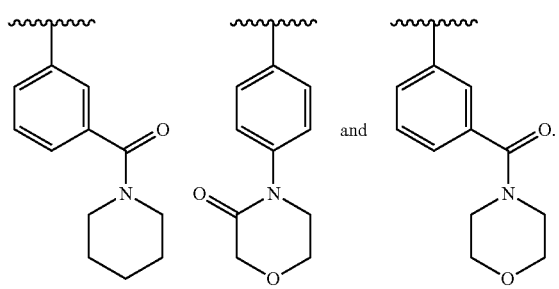

In some embodiments, R is selected from the group consisting of:

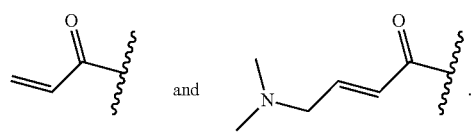
and

In some embodiments, R is

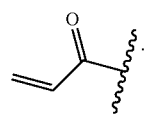

In some embodiments, R is

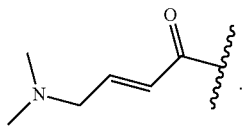 [SMILES: *C(=O)/C=C/CN(C)C]

In some embodiments, $R^2$ is selected from the group consisting of:

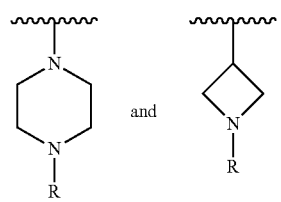
and which are optionally substituted with 1 to 2 $R^k$,
each $R^k$ is independently selected from the group consisting of $C_{1-3}$ alkyl, $CH_2OH$, $CH_2CN$, and $CH_2NMe_2$,
wherein two $R^k$ substituents on the same carbon may optionally form a cyclopropyl.

In some embodiments, $R^2$ is selected from the group consisting of:

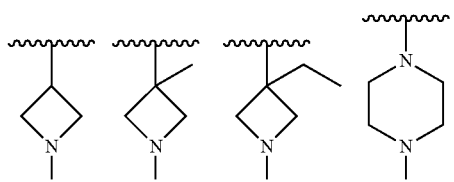

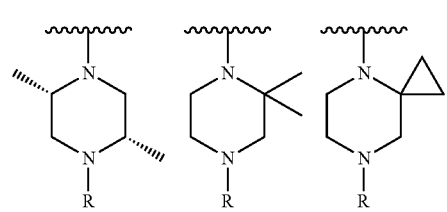

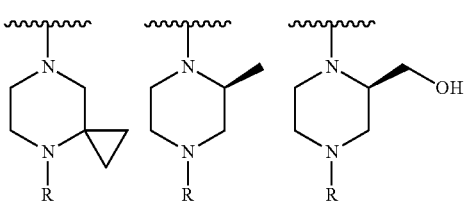

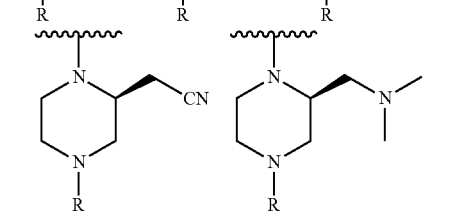

-continued

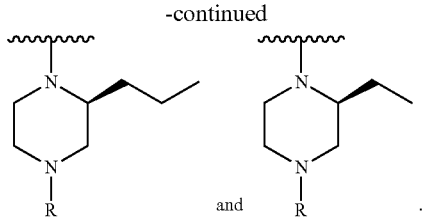

In some embodiments, R² is selected from the group consisting of:

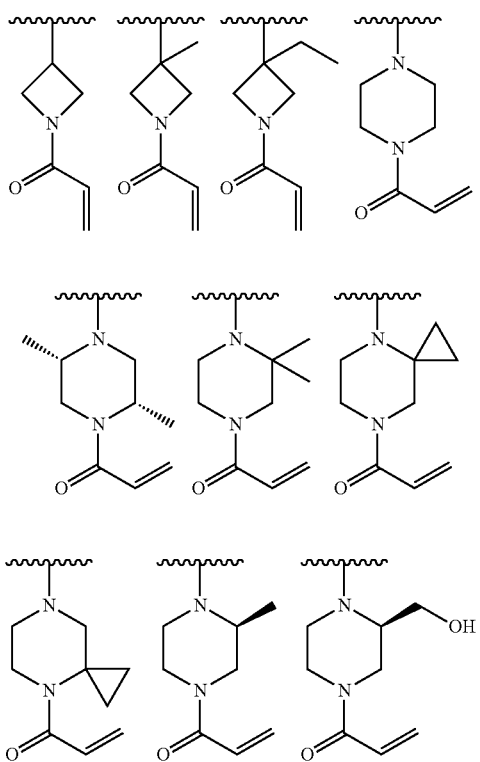

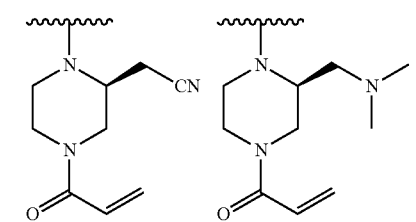

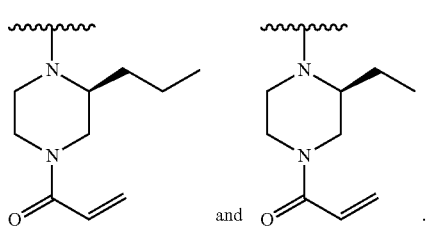

In some embodiments, R² is selected from the group consisting of:

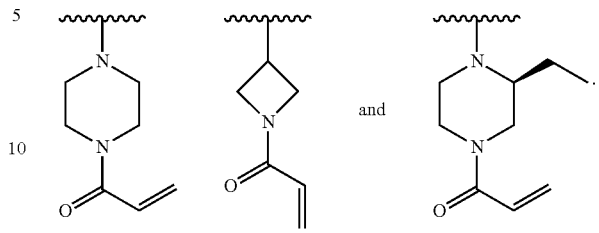

In some embodiments, X is N;
R¹ is selected from the group consisting of:

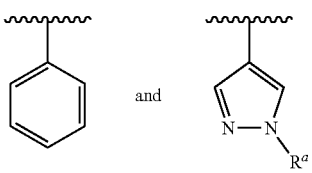

wherein $R^a$ is $C_{1-4}$ alkyl,
wherein

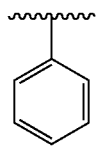 [SMILES: *c1ccccc1]

is substituted with piperazinyl, wherein the piperazinyl is substituted with a substituent selected from the group consisting of $C_{1-4}$ alkyl, —CO—$C_{1-4}$ alkyl, —COCH₂SMe, —CO(CH₂)₂SMe, and —CONMe₂;
R² is selected from the group consisting of:

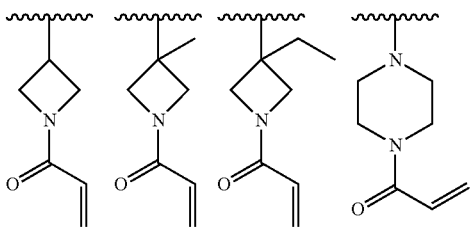

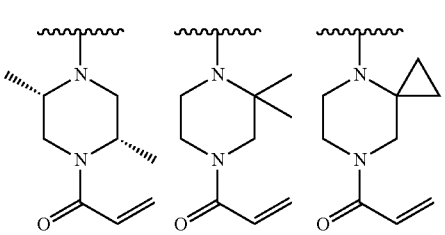

-continued
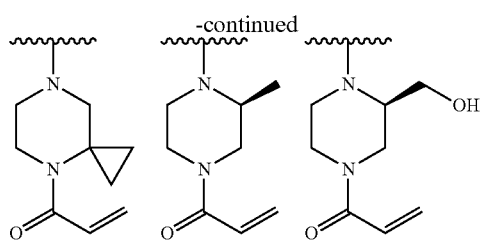
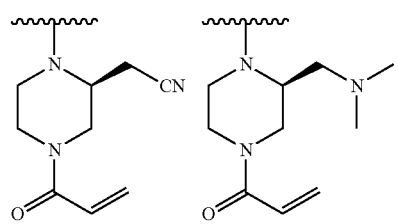
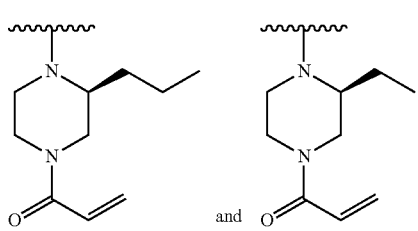
and R³ and R⁴ are both H.
In some embodiments, the compound is selected from the group consisting of
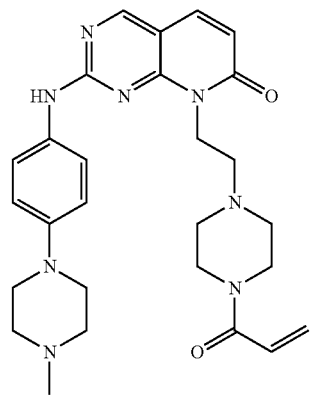
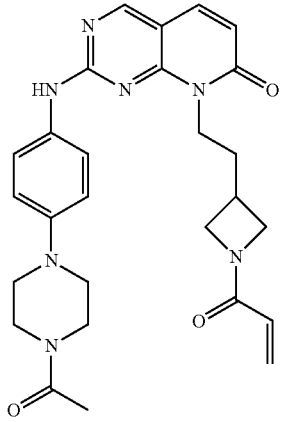
-continued
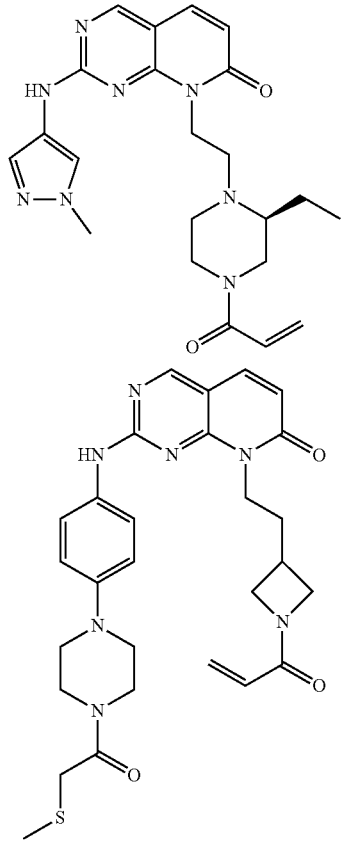
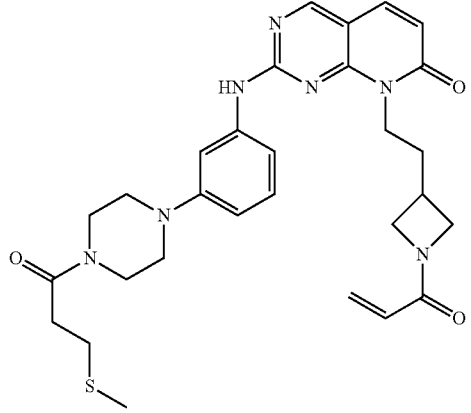
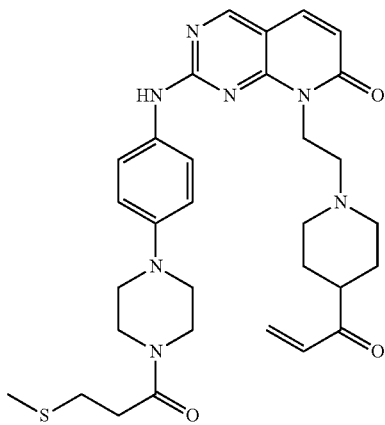 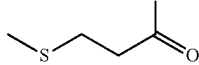

-continued

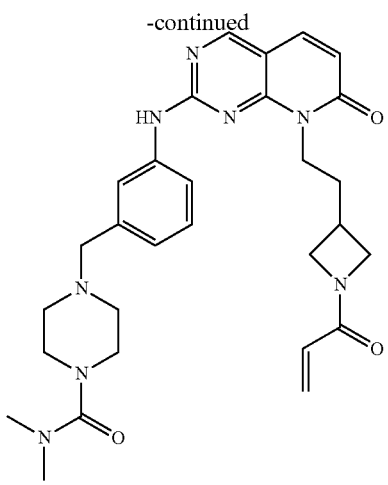

or a pharmaceutically acceptable salt thereof.

The invention also provides a pharmaceutical composition comprising a compound of the disclosure, or a pharmaceutically acceptable salt thereof, and a pharmaceutically-acceptable carrier. In some embodiments, the pharmaceutical composition further comprises one or more other therapeutic agents. In some embodiments, the one or more other therapeutic agent is useful for treating a gastrointestinal inflammatory disease, an inflammatory disease of the skin, an inflammatory disease of the lungs or an inflammatory disease of the eye. In some embodiments, the one or more other therapeutic agent is useful for treating a gastrointestinal inflammatory disease. In some embodiments the gastrointestinal inflammatory disease is ulcerative colitis. In some embodiments the gastrointestinal inflammatory disease is Crohn's disease. In some embodiments the gastrointestinal inflammatory disease is celiac disease.

Furthermore, some compounds may sometimes exist in tautomeric forms. It will be understood that although structures are shown, or named, in a particular form, the invention also includes the tautomer thereof. Also, some compounds may sometimes exist in atropoisomeric forms. It will be understood that although structures are shown in a particular form, the invention also includes the corresponding atropoisomeric forms thereof.

The compounds of the invention may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

This invention also includes isotopically-labeled compounds of the disclosure, for example isotopically-labeled compounds of formula (I), i.e., compounds of the disclosure and compounds of formula (I) where one or more atom has been replaced or enriched with an atom having the same atomic number but an atomic mass different from the atomic mass that predominates in nature. Examples of isotopes that may be incorporated into a compounds of the disclosure and a compound of formula (I) include, but are not limited to, $^2$H, $^3$H, $^{11}$C, $^{13}$C, $^{14}$C, $^{13}$N, $^{15}$N, $^{15}$O, $^{17}$O, $^{18}$O, $^{35}$S, and $^{18}$F. Of particular interest are compounds of the disclosure and compounds of formula (I) enriched in tritium or carbon-14, which compounds can be used, for example, in tissue distribution studies. Also of particular interest are compounds of the disclosure and compounds of formula (I) enriched in deuterium especially at a site of metabolism, which compounds are expected to have greater metabolic stability. Additionally, of particular interest are compounds of the disclosure and compounds of formula (I) enriched in a positron emitting isotope, such as $^{11}$C, $^{18}$F, $^{15}$O and $^{13}$N, which compounds can be used, for example, in Positron Emission Tomography (PET) studies.

Definitions

When describing this invention including its various aspects and embodiments, the following terms have the following meanings, unless otherwise indicated.

The term "about" means 5 percent of the specified value unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "aryl" means an aromatic hydrocarbon group having a single ring (i.e., phenyl) or fused rings (i.e., naphthalene). Unless otherwise defined, such aryl groups typically contain from 6 to 10 carbon ring atoms. Representative aryl groups include, by way of example, phenyl (i.e., a benzene ring), naphthyl (i.e., a naphthalene ring), and the like. As used herein, the term aryl includes monovalent, divalent or multivalent aryl groups.

The term "haloalkyl" refers to an alkyl group, as defined above, that is substituted by one or more halogen, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like.

When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heteroaryl" means an aromatic group having a single ring or two fused rings and containing in a ring at least one heteroatom (typically 1 to 3 heteroatoms) selected from nitrogen, oxygen or sulfur (i.e., a heteroaromatic group). Unless otherwise defined, such heteroaryl groups typically contain from 1 to 9 carbon atoms and from 5 to 10 total ring atoms. Representative heteroaryl groups include, by way of example, mono-, di- or multivalent species of benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the point or points of attachment are at any available carbon or nitrogen ring atom. As used herein, the term heteroaryl includes monovalent, divalent or multivalent heteroaryl groups.

The term "heterocycle", "heterocyclic", or "heterocyclic ring" means a saturated or partially unsaturated cyclic non-aromatic group, having from 4 to 10 total ring atoms, wherein the ring contains from 3 to 9 carbon ring atoms and from 1 to 4 ring heteroatoms selected from nitrogen, oxygen, and sulfur. Heterocyclic groups may be monocyclic or multicyclic (i.e., fused, spiro or bridged). When the heterocyclic group is multicyclic, at least one but not necessarily all of the cyclic groups contains a heteroatom. Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbomanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) ameliorating the disease, disorder, or medical condition, i.e., eliminating or causing regression of the disease, disorder, or medical condition in a patient, including counteracting the effects of other therapeutic agents;

(b) suppressing the disease, disorder, or medical condition, i.e., slowing or arresting the development of the disease, disorder, or medical condition in a patient; or (c) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), triisopropylsiliyl (TIPS), tert-butyldimethylsilyl (TBS or TBDMS), [2-(trimethylsilyl)-ethoxy]methyl (SEM); and the like. Numerous protecting groups, and their introduction and removal, are described in T. W. Greene and P. G. M. Wuts, *Protecting Groups in Organic Synthesis*, Third Edition, Wiley, New York General Synthetic Procedures Compounds of this disclosure, and intermediates thereof, can be prepared according to the following general methods and procedures using commercially-available or routinely-prepared starting materials and reagents. The substituents and variables (e.g., $R^1$, $R^2$, $R^3$, $R^4$, R etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compounds of the disclosure may be prepared by a variety of process routes in which reactants are combined in different orders to provide different intermediates en route to producing final products.

Scheme 1

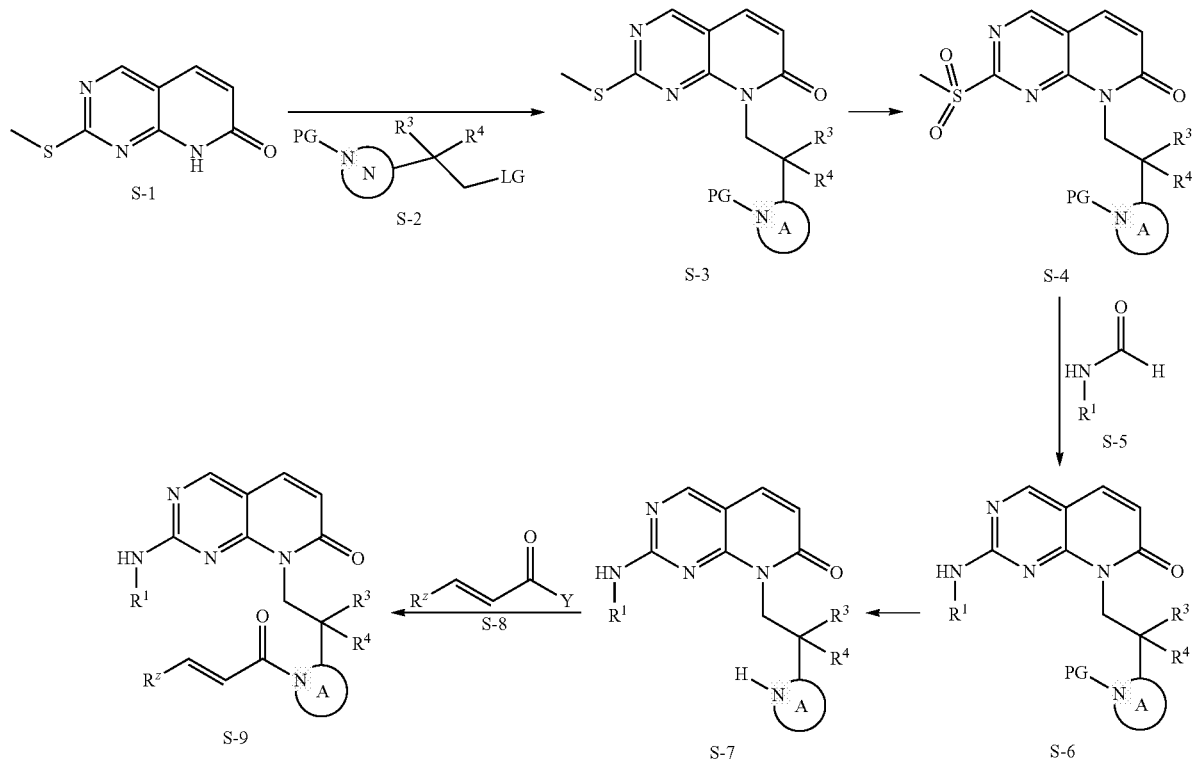

Compound S-1 is reacted with compound S-2, where A is an azetidine or a piperazine, each optionally substituted with 1 to 3 $R^k$ groups, PG is an amino protecting group, and LG is a leaving group such as mesylate, to give S-3. The reaction is conducted in presence of a base such as potassium carbonate. The reaction can be conducted in the presence of NaI in DMSO. Compound S-3 is then oxidized to give compound S-4. Such oxidation can be conducted in presence of N-chlorosuccinimide (NCS). The reaction with NCS may be conducted in acetic acid in the presence of a base such as triethylamine.

Alternatively, the oxidation may be conducted in the presence of mCPBA. S-4 is then reacted with compound S-5 to give intermediate S-6. The reaction can be conducted in the presence of lithium bis(trimethylsilyl)amide.
Alternatively, S-4 may be reacted with a precursor of S-5 which may contain one or more protecting groups, such as CBz.

The protecting group PG in S-6 may then be removed to give S-7. For example, when PG is Boc, the deprotection can be conducted in the presence of a strong acid such as HCl or TFA. Finally, S-7 may be reacted with S-8, where $R^z$ is H or —$CH_2$—$NR^sR^t$, and Y is OH or a leaving group such as Cl, to give S-9. When Y is OH, the reaction can be conducted in presence of a coupling agent such as HATU. When Y is Cl, the reaction can be conducted in presence of a base such as diisopropylethylamine.

Pharmaceutical Compositions

The compounds of the disclosure and pharmaceutically-acceptable salts thereof are typically used in the form of a pharmaceutical composition or formulation. Such pharmaceutical compositions may be administered to a patient by any acceptable route of administration including, but not limited to, oral, topical (including transdermal), rectal, ocular, nasal, inhaled, and parenteral modes of administration.

Accordingly, in one of its composition aspects, the invention is directed to a pharmaceutical composition comprising a pharmaceutically-acceptable carrier or excipient and a compound of formula (I), or a pharmaceutically-acceptable salt thereof. Optionally, such pharmaceutical compositions may contain other therapeutic and/or formulating agents if desired. When discussing compositions and uses thereof, "compound(s) of the disclosure" may also be referred to herein as "active agent(s)". As used herein, the term "compound(s) of the disclosure" is intended to include all active compounds specifically exemplified as well as all compounds encompassed by formula (I), and pharmaceutically-acceptable salts thereof.

The pharmaceutical compositions of the disclosure typically contain a therapeutically effective amount of a compound of the disclosure. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the disclosure are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the disclosure are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the disclosure will typically comprise the active agent and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the disclosure may also be formulated to provide slow or controlled release of the active agent using, by way of example, hydroxypropyl methylcellulose in varying proportions; or other polymer matrices, liposomes and/or microspheres. In addition, the pharmaceutical compositions of the disclosure may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this disclosure, or a pharmaceutically acceptable salt thereof, can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the disclosure and a powder suitable for use in a powder inhaler. Suitable powder bases include, by way of example, lactose or starch.

The compounds of the disclosure, or a pharmaceutically acceptable salt thereof, may also be formulated for topical administration to the skin as an ointment or cream. Ointment formulations are semisolid preparations having a base of an oily or greasy material that is typically clear. Suitable oily materials for use in ointment formulations include petrolatum (petroleum jelly), beeswax, cocoa butter, shea butter, and cetyl alcohol. Ointments may optionally additionally include emollients and penetration enhancers, if desired.

Cream formulations may be prepared as emulsions comprising an oil phase and aqueous phase, typically including purified water. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

The following non-limiting examples illustrate representative pharmaceutical compositions of the present invention.

Tablet Oral Solid Dosage Form

A compound of the disclosure or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of the disclosure or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising a compound of the disclosure (0.1%), water (98.9%) and ascorbic acid (1.0%) is formed by adding a compound of the disclosure to a mixture of water and ascorbic acid.

Enteric Coated Oral Dosage Form

A compound of the disclosure is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

A compound of the disclosure is combined with petrolatum, $C_8$-$C_{10}$ triglyceride, octylhydroxystearate, and N-methylpyrrolidone in a ratio to provide a composition containing 0.05% to 5% active agent by weight.

Ointment Formulation for Topical Administration

A compound of the disclosure is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

A compound of the disclosure is combined with mineral oil, paraffin, propylene carbonate, white petrolatum and white wax to provide a composition containing 0.05% to 5% active agent by weight.

Cream Formulation for Topical Administration

Mineral oil is combined with a compound of the disclosure, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising a compound of the disclosure, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising a compound of the disclosure, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Utility

Inhibition of JAK3 blocks the signaling of many key pro-inflammatory cytokines. Thus the compounds of the disclosure are expected to be useful in the treatment of inflammatory diseases.

The compounds of the disclosure have been designed to be selective for JAK3 over JAK1, JAK2 and TYK2. Selectivity for JAK3 over JAK1 is anticipated to be beneficial as there is some evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 allows sparing of erythropoietin (EPO) and thrombopoietin (TPO) signaling.

Without being limited by this theory, the compounds of the disclosure possess an electrophilic portion which may form a covalent bond with the cysteine (Cys909) present in JAK3, a residue replaced by a serine in the other three JAK isoforms (Goedken et al., *J Biol Chem.*, 2015, 290, 8, 4573-89). Such covalent binding to JAK3 could be beneficial by providing an extended target engagement which may translate in better efficacy.

Additionally, certain compounds of the disclosure have minimal systemic exposure, thereby avoiding potential adverse systemic immunosuppressive effects.

Gastrointestinal Inflammatory Disease

In addition to providing potent inhibition of JAK3, some compounds of the disclosure have been designed to be poorly absorbed to minimize systemic exposure. These compounds are designed to have their effect at the site of action, for example, in the colon. Certain compounds exhibit low permeabilities with $K_p$ values less than about $5 \times 10^{-6}$ cm/sec which is considered favorable to minimize systemic exposure and target the colon. Certain compounds have a $K_p$ value less than about $10 \times 10^{-6}$ cm/sec which may also be sufficient to minimize systemic exposure and target the colon. As described in the experimental section in assay 5, compounds 1, 3, 4, 13, 26, 38, 79, 102, 110, 155, and 171 exhibited a colon to plasma ratio in excess of 1000. Compounds 2, 5, 6, 7, 8, 15, 24, 27, 52, 74, 89, 92, 112, 133, 134, 150, 173, and 175 exhibited a colon to plasma ratio in excess of 100. Compounds 31, 44, 12, 107, and 159 exhibited a colon to plasma ratio in excess of 50. Compounds 76, 88, 156, and 174 exhibited a colon to plasma ratio in excess of 14. It is expected that a high colon to plasma ratio will provide robust, luminally-driven anti-inflammatory activity without associated, systemically-driven, adverse effects. The compounds of the disclosure are expected to be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., *Mol Immunology*, 2013, 55, 355-364), lymphocytic colitis (Kumawat et al., 2013), eosinophilic esophagitis (Weinbrand-Goichberg et al., *Immunol Res*, 2013, 56, 249-260), graft versus host disease-related colitis (Coghill et al., *Blood*, 2001, 117, 3268-3276), infectious colitis (Stallmach et al., *Int J Colorectal Dis*, 2004, 19, 308-315), Behcet's disease (Zhou et al., *Autoimmun Rev*, 2012, 11, 699-704), celiac disease (de Nitto et al., *World J Gastroenterol*, 2009, 15, 4609-4614, Jabri et al., *J Immunol.*, 2017, 198, 3005-14), immune checkpoint inhibitor induced colitis (e.g., CTLA-4 inhibitor-induced colitis; (Yano et al., *J Translation Med*, 2014, 12, 191), PD-1- or PD-L1-inhibitor-induced colitis), and ileitis (Yamamoto et al., *Dig Liver Dis*, 2008, 40, 253-259) are characterized by elevation of certain pro-inflammatory cytokine levels. As many pro-inflammatory cytokines signal via JAK activation, compounds described in this application are expected to be able to alleviate the inflammation and provide symptom relief.

In particular, the compounds of the disclosure are expected to be useful for the induction and maintenance of remission of ulcerative colitis, and for the treatment of Crohn's disease, immune checkpoint inhibitor induced colitis, celiac disease, and the gastrointestinal adverse effects in graft versus host disease.

In one aspect, therefore, the invention provides a method of treating a gastrointestinal inflammatory disease in a mammal (e.g., a human), the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof. In some embodiments, the gastrointestinal inflammatory disease is ulcerative colitis. In some embodiments, the gastrointestinal inflammatory disease is celiac disease. In some embodiments, the gastrointestinal inflammatory disease is Crohn's disease. In some embodiments, the gastrointestinal inflammatory disease is immune checkpoint inhibitor induced colitis. In some embodiments, the gastrointestinal inflammatory disease is gastrointestinal adverse effects in graft versus host disease.

The invention further provides a method of treating ulcerative colitis, celiac disease, or Crohn's disease in a mammal, the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof.

When used to treat ulcerative colitis, celiac disease, or Crohn's disease, the compounds of the disclosure, or a pharmaceutically acceptable salt thereof will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis, celiac disease, Crohn's disease and other gastrointestinal inflammatory disorders are expected to range from about 1 to about 400 mg/day of active agent, including from about 5 to about 300 mg/day and from about 20 to about 70 mg per day of active agent for an average 70 kg human. In some embodiments, the compounds of the disclosure, or a pharmaceutically acceptable salt thereof, are administered at 1, 2, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950 or, 1000 mg per day.

Combination Therapy

Compounds of the disclosure, or pharmaceutically acceptable salts thereof may also be used in combination with one or more agents which act by the same mechanism or by different mechanisms to effect treatment of gastrointestinal inflammatory disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin $α_4β_7$ antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the present JAK inhibitor compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $α_4β_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.)

Other compounds that may be used in combination with the present JAK inhibitor compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, Trichuris suis ova, K(D)PT, midismase, DNVX-078, vatelizumab, alequel, low molecular weight heparin, metenkefalin, tridecactide, HMPL-004, SB-012, olsalazine, balsalazide, propionyl-L-camitine, *Clostridium butyricum*, beclomethasone and acemannan.

In another aspect, therefore, the invention provides a therapeutic combination for use in the treatment of gastrointestinal inflammatory disorders, the combination comprising a compound of the disclosure, or a pharmaceutically acceptable salt thereof, and one or more other therapeutic agents useful for treating gastrointestinal inflammatory disorders, such as the ones illustrated above. For example, the invention provides a combination comprising a compound of the disclosure, or a pharmaceutically acceptable salt thereof, and one or more agents selected from aminosalicylates, steroids, systemic immunosuppressants, anti-TNFα antibodies, anti-VLA-4 antibodies, anti-integrin $α_4β_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the disclosure or a pharmaceutically acceptable salt thereof.

Also provided, therefore, is a pharmaceutical composition comprising a compound of the disclosure, or a pharmaceutically acceptable salt thereof, and one or more other therapeutic agents useful for treating gastrointestinal inflammatory disorders.

Further, in a method aspect, the invention provides a method of treating gastrointestinal inflammatory disorders, the method comprising administering to the mammal a compound of the disclosure, or a pharmaceutically acceptable salt thereof, and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Inflammatory Skin Disease

Atopic dermatitis and other inflammatory skin diseases have been associated with elevation of proinflammatory cytokines that rely on the JAK-STAT pathway. Therefore, the compounds of the disclosure, or a pharmaceutically acceptable salt thereof, or a crystalline form thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle.* 2014; 13, 3331-3335) and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30– cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of the disclosure, or a pharmaceutically acceptable salt thereof, have the potential to alleviate associated dermal inflammation or pruritus driven by these cytokines. In particular, compounds of the disclosure, or a pharmaceutically acceptable salt thereof, are expected to be useful for the treatment of atopic dermatitis and other inflammatory skin diseases.

In one aspect, therefore, the invention provides a method of treating an inflammatory skin disease in a mammal (e.g., a human), the method comprising applying a pharmaceutical composition comprising a compound of the disclosure, or a pharmaceutically acceptable salt thereof, and a pharmaceutical carrier to the skin of the mammal. In one aspect, the inflammatory skin disease is atopic dermatitis.

Compounds of the disclosure, or a pharmaceutically acceptable salt thereof, may also be used in combination with one or more compound useful to treat inflammatory skin diseases. In some embodiments, the one or more compound is a steroid, Histamine H1 receptor antagonist, calcineurin inhibitor, IL-13 antagonist, PDE 4 inhibitor, G-protein coupled receptor-44 antagonist, IL-4 antagonist, 5-HT 1a receptor antagonist, 5-HT 2b receptor antagonist, Alpha 2 adrenoceptor agonist, cannabinoid CB1 receptor antagonist, CCR3 chemokine, antagonist, collagenase inhibitor, cytosolic phospholipase A2 inhibitor, eotaxin ligand inhibitor, GATA 3 transcription factor inhibitor, Histamine H4 receptor antagonist, IL-10 antagonist, IL-12 antagonist, IL-17 antagonist, IL-2 antagonist, IL-23 antagonist, IL-4 receptor modulator, IL-5 antagonist, immunoglobulin E antagonist, immunoglobulin E modulator, interferon gamma receptor antagonist, Interleukin 33 ligand inhibitor, Interleukin-31 receptor antagonist, Leukotriene antagonist, Liver X receptor agonist, Liver X receptor beta agonist, nuclear factor kappa B inhibitor, OX-40 receptor antagonist, PGD2 antagonist, phospholipase A2 inhibitor, SH2 domain inositol phosphatase 1 stimulator, thymic stromal lymphoprotein ligand inhibitor, TLR modulator, TNF alpha ligand modulator, or vanilloid VR1 antagonist. In some embodiments, the one or more compound is a gram positive antibiotic, such as mupirocin or fusidic acid. In some embodiments, the one or more compound is tranilast, tacrolimus, epinastine, SB-011, AM-1030, ZPL-521, MM-36, FB-825, PG-102, viromed, GBR-830, AVX-001, AMG-0101, E-6005, DMT-210, AX-1602, bertilimumab, rosiptor acetate, Q-301, ANB-020, VTP-38543, ZPL-389, lebrikizumab, tezepelumab, fexofenadine, pimecrolimus, bepotastine, crisaborole, tralokinumab, fevipiprant, doxycycline, desloratadine, ALX-101, nemolizumab, asivatrep, ciclosporin, mepolizumab, dupilumab, secukinumab, timapiprant, or ustekinumab.

In one aspect, therefore, the invention provides a method of treating an inflammatory skin disease in a mammal, the method comprising applying a compound of the disclosure, or a pharmaceutically acceptable salt thereof, and a gram positive antibiotic to the skin of the mammal. In another aspect, the invention provides a pharmaceutical composition comprising a compound of the disclosure, or a pharmaceutically acceptable salt thereof, a gram positive antibiotic, and a pharmaceutically-acceptable carrier.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have also been implicated in asthma inflammation and in other inflammatory respiratory diseases. As described above, the compounds of the disclosure have been shown to be potent inhibitors of JAK3 and have also demonstrated potent inhibition of IL-2 pro-inflammatory cytokines in cellular assays.

The anti-inflammatory activity of JAK inhibitors has been robustly demonstrated in preclinical models of asthma (Malaviya et al., *Int Immunopharmacol,* 2010, 10, 829-836; Matsunaga et al., *Biochem and Biophys Res Commun,* 2011, 404, 261-267; Kudlacz et al., *Eur J Pharmacol,* 2008, 582, 154-161.) Accordingly, the compounds of the disclosure, or a pharmaceutically acceptable salt thereof, are expected to be useful for the treatment of inflammatory respiratory disorders such as asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. The compounds of the disclosure, or a pharmaceutically acceptable salt thereof, therefore, may be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, and sarcoidosis.

In one aspect, therefore, the disclosure provides a method of treating a respiratory disease in a mammal (e.g., a human), the method comprising administering to the mammal a compound of the disclosure, or a pharmaceutically-acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, allergic rhinitis or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, or immune-checkpoint-inhibitor induced pneumonitis.

The disclosure further provides a method of treating a respiratory disease, the method comprising administering to the mammal a pharmaceutical composition comprising a compound of the disclosure, or a pharmaceutically-acceptable salt thereof, and a pharmaceutically-acceptable carrier.

Compounds of the disclosure, or pharmaceutically acceptable salts thereof, may also be used in combination with one or more compound useful to respiratory diseases.

Ocular Diseases

Many ocular diseases have been shown to be associated with elevations of proinflammatory cytokines that rely on the JAK-STAT pathway.

The compounds of the disclosure, or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, retinal vein occlusion (RVO) and atopic keratoconjunctivitis.

In particular, uveitis (Horai and Caspi, *J Interferon Cytokine Res,* 2011, 31, 733-744), diabetic retinopathy (Abcouwer, *J Clin Cell Immunol,* 2013, Suppl 1, 1-12), diabetic macular edema (Sohn et al., *American Journal of Opthamology,* 2011, 152, 686-694), dry eye disease (Stevenson et al, *Arch Ophthalmol,* 2012, 130, 90-100), retinal vein occlusion (Shchuko et al, *Indian Journal of Ophthalmology,* 2015, 63(12), 905-911) and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compounds of the disclosure, or a pharmaceutically acceptable salt thereof, may be able to alleviate the associated ocular inflammation and reverse disease progression or provide symptom relief.

In one aspect, therefore, the disclosure provides a method of treating an ocular disease in a mammal, the method comprising administering a pharmaceutical composition comprising a compound of the disclosure, or a pharmaceutically-acceptable salt thereof, and a pharmaceutical carrier to the eye of the mammal. In one aspect, the ocular disease is uveitis, diabetic retinopathy, diabetic macular edema, dry eye disease, age-related macular degeneration, retinal vein occlusion or atopic keratoconjunctivitis. In one aspect, the method comprises administering the compound of the disclosure, or a pharmaceutically acceptable salt thereof, by intravitreal injection.

Compounds of the disclosure, or a pharmaceutically acceptable salt thereof, may also be used in combination with one or more compound useful to ocular diseases.

Other Diseases

The compounds of the disclosure, or a pharmaceutically acceptable salt thereof, may also be useful to treat other diseases such as other inflammatory diseases, autoimmune diseases or cancers.

The compounds of the disclosure, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

The compounds of the disclosure, or a pharmaceutically acceptable salt thereof, may also be useful to prevent the disease, disorder, or medical condition listed above from occurring, i.e., preventing the reoccurrence of the disease or medical condition or prophylactic treatment of a patient that is pre-disposed to the disease or medical condition.

Compounds of the disclosure have been demonstrated to be potent inhibitors of the JAK3 enzyme and to be selective for JAK3 over JAK1, JAK2 and TYK2 in enzyme binding assays and to have potent functional activity for JAK3 in a cellular assay as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
Calcd=calculated
Boc=tert-Butyloxycarbonyl
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
mCPBA=3-Chloroperoxybenzoic acid
MeOH=methanol
min=minute(s)
RT or rt=room temperature
SiG=Silica gel
TEA=triethylamine
THF=tetrahydrofuran
THP=tetrahydropyran
TFA=trifluoroacetic acid Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Unless otherwise indicated the following conditions were used for preparative HPLC purifications.
Column: C18, 5 µm 21.2×150 mm or C18, 5 µm 21×250 mm or
C14, 5 µm 21×150 mm
Column temperature: Room Temperature
Flow rate: 20.0 mL/mm
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.
Analytic HPLC Conditions
Method A
Column: LUNA C18 (2), 150×4.60 mm, 3 µm
Column temperature: 37° C.
Flow rate: 1.0 mL/min
Injection volume: 5 µL
Sample preparation: Dissolve in 1:1 ACN:water
Mobile Phases: A=Water:ACN:TFA (98:2:0.05)
B=Water:ACN:TFA (2:98:0.05)
Detector wavelength: 250 nm
Gradient: 32 min total (time (min)/% B): 0/2, 10/20, 24/90, 29/90, 30/2, 32/2
Method B
Column: LUNA C18 (2), 150×4.60 mm, 3 µm
Column temperature: 37° C.
Flow rate: 1.0 mL/min
Injection volume: 10 µL
Sample preparation: Dissolve in 1:1 ACN:water
Mobile Phases: A=Water:ACN:TFA (98:2:0.05)
B=Water:ACN:TFA (10:90:0.05)
Detector wavelength: 254 nm
Gradient: 35 min total (time (min)/% B): 0/2, 20/25, 23/90, 26/90, 27/2, 35/2

Preparation 1: ethyl(E)-3-(4-amino-2-(methylthio)pyrimidin-5-yl)acrylate

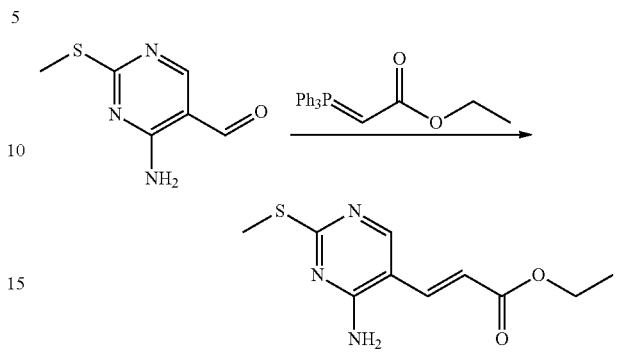

Methyl (triphenylphosphoranylidene)acetate (155 g, 443.26 mmol) was added to a solution of 4-amino-2-(methylthio)pyrimidine-5-carbaldehyde (50 g, 295.50 mmol) in THF (350 mL) at rt and the reaction mixture was refluxed at 75° C. for 3 h and then stirred at rt for 16 h. The reaction mixture was concentrated in vacuo to yield a crude mixture. The crude mixture was purified via flash column chromatography using a gradient of 25-30% ethyl acetate:hexanes to yield ethyl (E)-3-(4-amino-2-(methylthio)pyrimidin-5-yl) acrylate (60 g, 251 mmol, 86% yield). (m/z): [M+H]$^+$ calculated for $C_{10}H_4N_3O_2S$ 240.08 found 240.15.

Preparation 2: 2-(methylthio)pyrido[2,3-d]pyrimidin-7(8H)-one

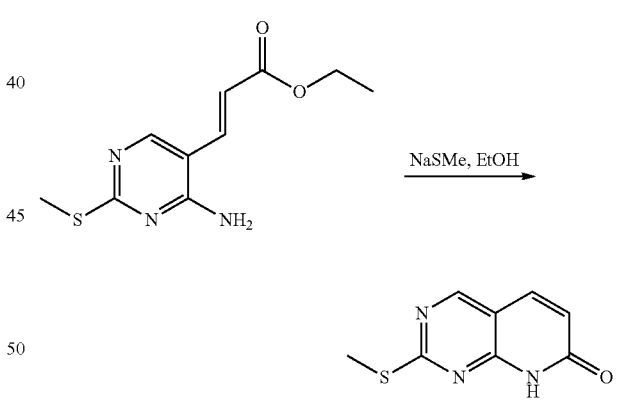

Sodium thiomethoxide (3.0 g, 41.79 mmol) was added to a solution of (E)-3-(4-amino-2-(methylthio)pyrimidin-5-yl) acrylate (10.0 g, 41.79 mmol) in ethanol (70.0 mL) and the reaction mixture was stirred at 80° C. for 2 h. The reaction mixture was concentrated in vacuo to yield a dry residue, and then diluted with water. A 1 N aqueous solution of hydrochloric acid was added until the pH of the solution reached pH 5, upon which a white precipitate appeared. The precipitate was filtered, the solid was washed with water and then diethyl ether, and then dried in vacuo to yield 2-(methylthio)pyrido[2,3-d]pyrimidin-7(8H)-one (6.55 g, 33.90 mmol, 81% yield) as a white solid. (m/z): [M+H]$^+$ calculated for $C_8H_8N_3OS$ 194.04 found 194.13.

Preparation 3: tert-butyl 4-(2-hydroxyethyl)piperazine-1-carboxylate

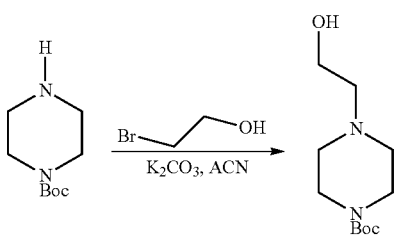

Potassium carbonate (37.1 g, 268.8 mmol) was added to solution of tert-butyl piperazine-1-carboxylate (25 g, 134.4 mmol) in acetonitrile (150 mL) at 0° C. and the reaction mixture was stirred at 0° C. for 20 min. 2-Bromoethan-1-ol (12.40 mL, 174.7 mmol) was added dropwise and the reaction mass was stirred at 70° C. for 16 h. The reaction mixture was diluted with ice-cold water and extracted with EtOAc (thrice). The organic layers were combined and washed with water, brine and dried over anhydrous sodium sulfate and concentrated in vacuo to yield a crude mixture. The crude mixture was purified via flash column chromatography using a gradient of 5-7% methanol in methylene chloride to yield tert-butyl 4-(2-hydroxyethyl)piperazine-1-carboxylate (23 g, 99.9 mmol, 74% yield) as a pale green liquid.

Preparation 4: tert-butyl 4-(2-((methylsulfonyl)oxy)ethyl)piperazine-1-carboxylate

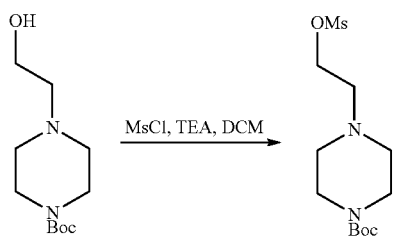 [SMILES: CC(C)(C)OC(=O)N1CCN(CCO)CC1 ; CC(C)(C)OC(=O)N1CCN(CCOS(C)(=O)=O)CC1]

Triethylamine (22 mL, 156.4 mmol) was added to a solution of tert-butyl 4-(2-hydroxyethyl)piperazine-1-carboxylate (12.0 g, 52.12 mmol) in methylene chloride (100 mL) at 0° C. and the reaction mixture was stirred at 0° C. for 20 min. Methanesulfonyl chloride (4.8 mL, 62.60 mmol) was added dropwise and the reaction mixture was stirred at rt for 3 h. The reaction mixture was diluted with water, the organic layer was separated, dried over anhydrous sodium sulfate and concentrated in vacuo to yield tert-butyl 4-(2-((methylsulfonyl)oxy)ethyl)piperazine-1-carboxylate (15 g, 48.70 mmol, 93% yield).

Preparation 5: tert-butyl 4-(2-(2-(methylthio)-7-oxopyrido[2,3-d]pyrimidin-8(7H)-yl)ethyl)piperazine-1-carboxylate

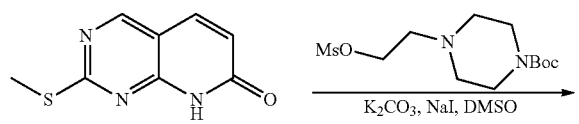

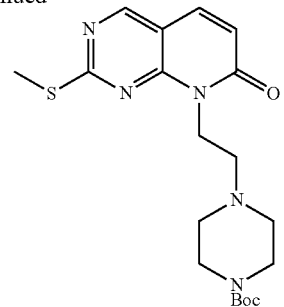

Potassium carbonate (12.8 g, 93.2 mmol) was added to a solution of 2-(methylthio)pyrido[2,3-d]pyrimidin-7(8H)-one (6.0 g, 31.1 mmol) in DMSO (80 mL), followed by sodium iodide (4.6 g, 31.1 mmol) and the reaction was stirred for 10 min. A solution of tert-butyl 4-(2-((methylsulfonyl)oxy)ethyl)piperazine-1-carboxylate (11.4 g, 37.3 mmol) in DMSO was then added dropwise and the reaction mixture was stirred at 90° C. for 16 h. Cold water was added and the mixture was extracted with methylene chloride (thrice). The organic layers were combined, washed with water and a saturated aqueous solution of sodium chloride, dried over anhydrous sodium sulfate and concentrated in vacuo to yield a crude mixture. The mixture was purified via flash column chromatography using a gradient of 20-25% acetone in hexane to yield tert-butyl 4-(2-(2-(methylthio)-7-oxopyrido[2,3-d]pyrimidin-8(7H)-yl)ethyl)piperazine-1-carboxylate (3.10 g, 7.64 mmol, 25% yield) as a pale yellow solid. (m/z): $[M+H]^+$ calcd for $C_{19}H_{28}N_5O_3S$ 406.19 found 406.26.

Preparation 6: tert-butyl 4-(2-(2-(methylsulfonyl)-7-oxopyrido[2,3-d]pyrimidin-8(7H)-yl)ethyl)piperazine-1-carboxylate

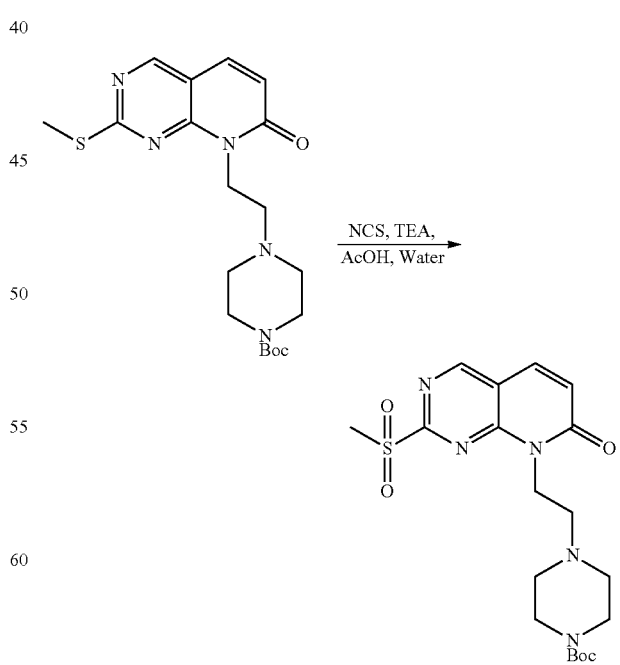

N-Chlorosuccinimide (5.93 g, 44.4 mmol) was added to a solution of 4-(2-(2-(methylthio)-7-oxopyrido[2,3-d]pyrimidin-8(7H)-yl)ethyl)piperazine-1-carboxylate (6.0 g, 14.8 mmol) in acetic acid (100 mL), followed by triethylamine (6.23 mL, 44.4 mol) and water (2 mL) and the reaction mixture was stirred for 2 h. The reaction mixture was concentrated in vacuo and the resulting crude semi-solid was dissolved in 10% methanol in methylene chloride. The solution was washed with a saturated aqueous solution of sodium bicarbonate, dried over anhydrous sodium sulfate and concentrated in vacuo to yield a crude mixture. The mixture was purified via flash column chromatography using 40% acetone in hexane to yield tert-butyl 4-(2-(2-(methylsulfonyl)-7-oxopyrido[2,3-d]pyrimidin-8(7H)-yl)ethyl)piperazine-1-carboxylate (3.7 g, 8.46 mmol, 68% yield) as a white solid. (m/z): [M+H]$^+$ calcd for $C_{19}H_{28}N_5O_5S$ 438.18 found 438.27.

Preparation 7: benzyl 4-(4-nitrophenyl)piperazine-1-carboxylate

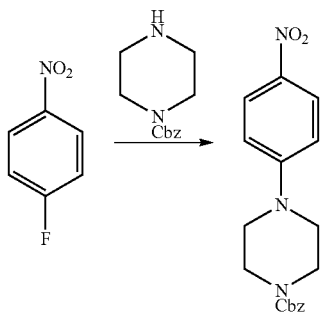

N,N-Diisopropylethylamine (39.2 mL, 213 mmol) was added to a solution of 1-fluoro-4-nitrobenzene (10.0 g, 70.9 mmol) in dimethylacetamide (50 mL), followed by benzyl piperazine-1-carboxylate (15.6 g, 70.9 mmol) and the reaction mixture was stirred at 80° C. for 16 h. Water was added and the mixture was extracted with ethyl acetate. The organic extract was washed with water and a saturated aqueous solution of sodium chloride, dried over anhydrous sodium sulfate and concentrated in vacuo to yield a crude mixture. The crude mixture was triturated with ethyl ether to yield benzyl 4-(4-nitrophenyl)piperazine-1-carboxylate (13.0 g, 38.1 mmol, 54% yield). (m/z): [M+H]$^+$ calcd for $C_{18}H_{20}N_3O_4$ 342.15 found 342.07.

Preparation 8: benzyl 4-(4-formamidophenyl)piperazine-1-carboxylate

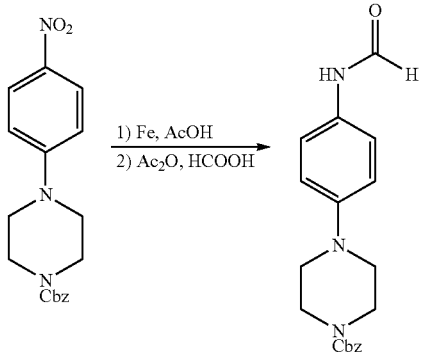 [SMILES: O=C(OCc1ccccc1)N1CCN(c2ccc([N+](=O)[O-])cc2)CC1 ; O=CNc1ccc(N2CCN(C(=O)OCc3ccccc3)CC2)cc1]

Iron powder (9.85 g, 176 mmol) was added portion-wise to a stirred solution of benzyl 4-(4-nitrophenyl)piperazine-1-carboxylate (12.0 g, 35.2 mmol) in acetic acid (120 mL) at 85° C. and the reaction mixture was stirred at 85° C. for 2 h. The reaction mixture was cooled to rt, filtered through Celite, and the Celite bed was washed with methanol. The filtrates were combined and concentrated in vacuo to yield the intermediate benzyl 4-(4-aminophenyl)piperazine-1-carboxylate.

The intermediate benzyl 4-(4-aminophenyl)piperazine-1-carboxylate was dissolved in THF (200 mL) and a few drops of dimethylacetamide, upon which a formylating mixture (6.6 mL of a previously prepared mixture of acetic anhydride (15.3 mL, 161 mmol) and formic acid (8.87 mL, 192 mmol), stirred at 85° C. for 1 h) was added dropwise at 0° C. and the reaction mixture was stirred at rt for 2 h. Ethyl acetate was added and the mixture was washed with water, a saturated aqueous solution of sodium bicarbonate and a saturated aqueous solution of sodium chloride, dried over anhydrous sodium sulfate and concentrated in vacuo to yield a crude mixture. The crude mixture was triturated with ethyl ether and then pentane to yield benzyl 4-(4-formamidophenyl)piperazine-1-carboxylate (12.0 g, 35.2 mmol, 100% yield). (m/z): [M+H]$^+$ calcd for $C_{19}H_{22}N_3O_3$ 340.17 found 340.20.

Preparation 9: benzyl 4-(4-((8-(2-(4-(tert-butoxycarbonyl)piperazin-1-yl)ethyl)-7-oxo-7,8-dihydropyrido[2,3-d]pyrimidin-2-yl)amino)phenyl)piperazine-1-carboxylate

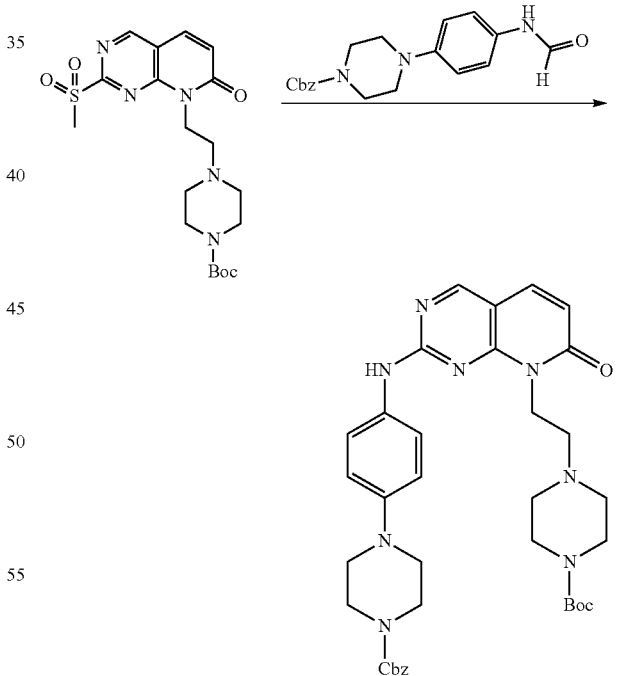

A 1 M solution of lithium bis(trimethylsilyl)amide in THF (7.41 mL, 7.41 mmol) was added to a solution of benzyl 4-(4-formamidophenyl)piperazine-1-carboxylate (2.09 g, 6.17 mmol) in dimethylacetamide (5 mL) at 0° C. and the reaction mixture was stirred at 0° C. for 40 min, upon which a solution of tert-butyl 4-(2-(2-(methylsulfonyl)-7-oxopyrido[2,3-d]pyrimidin-8(7H)-yl)ethyl)piperazine-1- carboxylate (2.7 g, 6.17 mmol) in dimethylacetamide (10 mL) was added at 0° C. and the reaction mixture was stirred at rt for 2 h. Methanol (10 mL) was added and the reaction mixture was stirred at rt for 30 min. Water was added and the mixture was extracted with methylene chloride (3 times). The methylene chloride extracts were combined, washed with water and a saturated aqueous solution of sodium chloride, dried over anhydrous sodium sulfate and concentrated in vacuo to yield a crude mixture. The mixture was purified via flash column chromatography using a gradient of 20-25% acetone in hexane to yield benzyl 4-(4-((8-(2-(4-(tert-butoxycarbonyl)piperazin-1-yl)ethyl)-7-oxo-7,8-dihydropyrido[2,3-d]pyrimidin-2-yl)amino)phenyl)piperazine-1-carboxylate (2.10 g, 3.14 mmol, 51% yield) as a white solid. (m/z): [M+H]$^+$ calcd for $C_{36}H_{45}N_8O_5$ 669.35 found 669.36.

Preparation 10: tert-butyl 4-(2-(7-oxo-2-((4-(piperazin-1-yl)phenyl)amino)pyrido[2,3-d]pyrimidin-8(7H)-yl)ethyl)piperazine-1-carboxylate

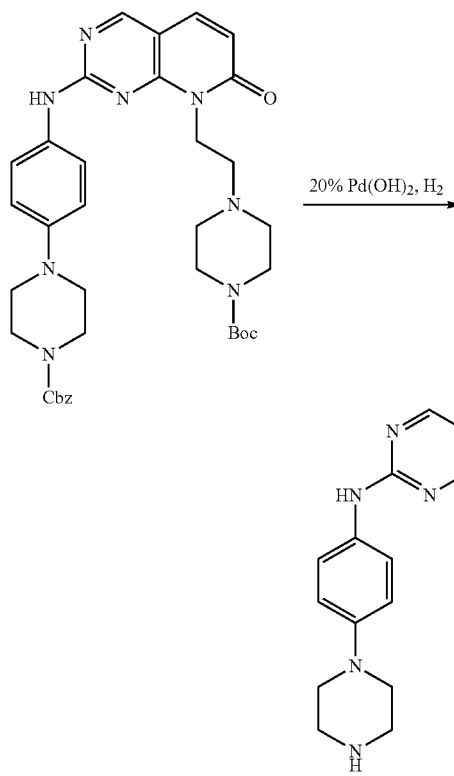

20% Palladium hydroxide on carbon (600 mg, 0.855 mmol) was added to a solution of benzyl 4-(4-((8-(2-(4-(tert-butoxycarbonyl)piperazin-1-yl)ethyl)-7-oxo-7,8-dihydropyrido[2,3-d]pyrimidin-2-yl)amino)phenyl)piperazine-1-carboxylate (1.40 g, 2.09 mmol) in isopropanol (15 mL) and THF (15 mL) and the reaction mixture was stirred under an atmosphere of hydrogen for 6 h. The reaction mixture was filtered through Celite and the Celite bed was washed with 5% methanol in methylene chloride. The resulting filtrates were combined and concentrated in vacuo to yield a crude residue. The crude residue was triturated with diethyl ether to yield tert-butyl 4-(2-(7-oxo-2-((4-(piperazin-1-yl)phenyl)amino)pyrido[2,3-d]pyrimidin-8(7H)-yl)ethyl)piperazine-1-carboxylate (1.00 g, 1.87 mmol, 90% yield). (m/z): [M+H]$^+$ calcd for $C_{28}H_{39}N_8O_3$ 535.31 found 535.51.

Preparation 11: tert-butyl 4-(2-(2-((4-(4-methylpiperazin-1-yl)phenyl)amino)-7-oxopyrido[2,3-d]pyrimidin-8(7H)-yl)ethyl)piperazine-1-carboxylate

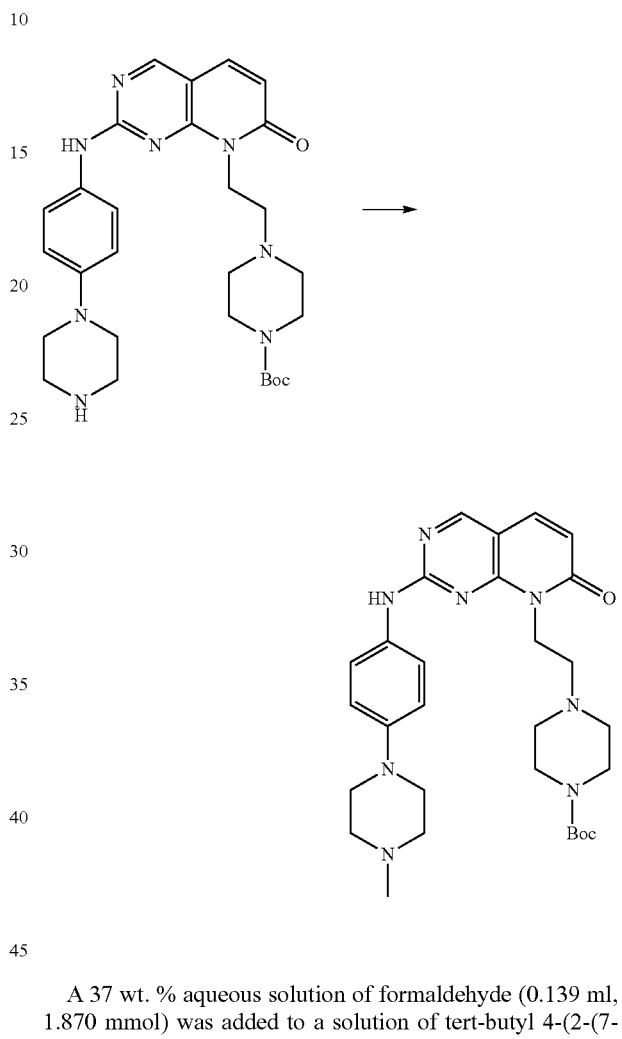

A 37 wt. % aqueous solution of formaldehyde (0.139 ml, 1.870 mmol) was added to a solution of tert-butyl 4-(2-(7-oxo-2-((4-(piperazin-1-yl)phenyl)amino)pyrido[2,3-d]pyrimidin-8(7H)-yl)ethyl)piperazine-1-carboxylate (500 mg, 0.935 mmol) in methanol (5.0 ml), followed by sodium cyanoborohydride (176 mg, 2.81 mmol) and the reaction mixture was stirred at rt for 1 hour. The reaction was quenched with the addition of water (1 mL) and the mixture was concentrated in vacuo to yield a yellow solid. Water (5 mL) was added to the crude solid and the resulting mixture was extracted with methylene chloride (3×5 mL). The methylene chloride extracts were combined, washed with a saturated aqueous solution of sodium chloride, dried over sodium sulfate and concentrated in vacuo to yield a yellow liquid. The crude liquid was purified via column chromatography using 20% methanol in methylene chloride to yield tert-butyl 4-(2-(2-((4-(4-methylpiperazin-1-yl)phenyl)amino)-7-oxopyrido[2,3-d]pyrimidin-8(7H)-yl)ethyl)piperazine-1-carboxylate (455 mg, 0.829 mmol, 89% yield) as a yellow solid. (m/z): [M+H]$^+$ calcd for $C_{29}H_{41}N_8O_3$ 549.33 found 549.20.

Preparation 12: 2-((4-(4-methylpiperazin-1-yl)phenyl)amino)-8-(2-(piperazin-1-yl)ethyl)pyrido[2,3-d]pyrimidin-7(8H)-one

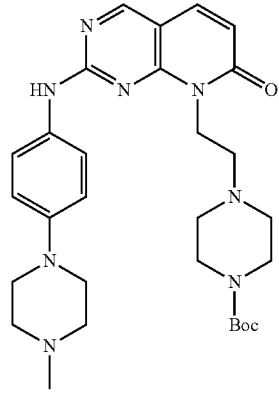

TFA ⟶

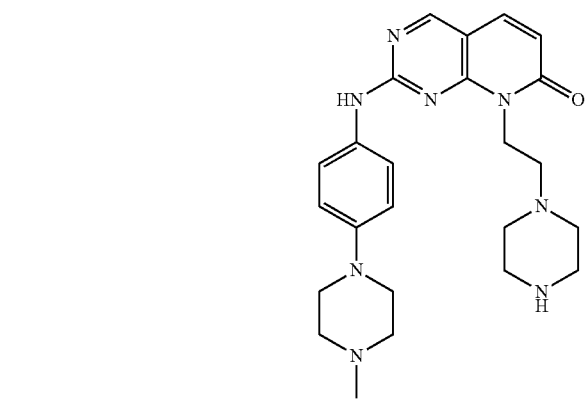

Trifluoroacetic acid (2 ml) was added to a solution of tert-butyl 4-(2-(2-((4-(4-methylpiperazin-1-yl)phenyl)amino)-7-oxopyrido[2,3-d]pyrimidin-8(7H)-yl)ethyl)piperazine-1-carboxylate (455 mg, 0.829 mmol) in methylene chloride (2.0 ml), and the reaction mixture was stirred at rt for 1 hour. The reaction mixture was concentrated in vacuo to yield 2-((4-(4-methylpiperazin-1-yl)phenyl)amino)-8-(2-(piperazin-1-yl)ethyl)pyrido[2,3-d]pyrimidin-7(8H)-one TFA salt (466 mg, 0.829 mmol, 100% yield) as a clear yellow liquid. (m/z): [M+H]$^+$ calcd for $C_{24}H_{33}N_8O$ 449.28 found 449.2.

Example 1: 8-(2-(4-acryloylpiperazin-1-yl)ethyl)-2-((4-(4-methylpiperazin-1-yl)phenyl)amino)pyrido[2,3-d]pyrimidin-7(8H)-one

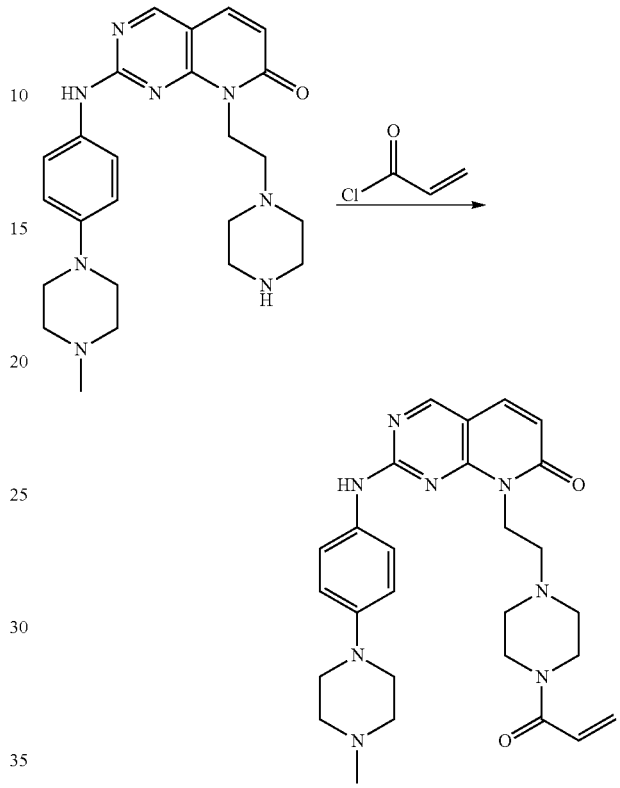

N,N-Diisopropylethylamine (0.723 ml, 4.15 mmol) was added to a solution of 2-((4-(4-methylpiperazin-1-yl)phenyl)amino)-8-(2-(piperazin-1-yl)ethyl)pyrido[2,3-d]pyrimidin-7(8H)-one TFA salt (466 mg, 0.829 mmol) in DMF (4 ml) at 0° C., followed by acryloyl chloride (0.074 ml, 0.912 mmol) and the reaction mixture was stirred at rt for 15 minutes. The reaction mixture was concentrated in vacuo to yield a clear yellow liquid. The crude liquid was purified via preparatory scale C18 column chromatography using a gradient of 10-60% acetonitrile in water with 0.05% trifluoroacetic acid to yield 8-(2-(4-acryloylpiperazin-1-yl)ethyl)-2-((4-(4-methylpiperazin-1-yl)phenyl)amino)pyrido[2,3-d]pyrimidin-7(8H)-one TFA salt (186.3 mg, 0.371 mmol, 44.7% yield) as a yellow solid. (m/z): [M+H]$^+$ calcd for $C_{27}H_{35}N_8O_2$ 503.29 found 503.2.

Preparation 13: tert-butyl 3-(2-((methylsulfonyl)oxy)ethyl)azetidine-1-carboxylate

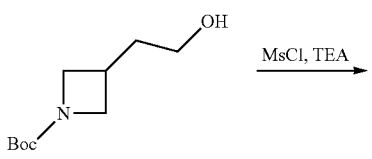

MsCl, TEA ⟶

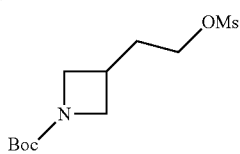

Triethylamine (10.47, 74.52 mmol) was added to a solution of tert-butyl 3-(2-hydroxyethyl)azetidine-1-carboxylate (5.00 g, 24.8 mmol) in methylene chloride (50 mL) at 0° C. followed by methanesulfonyl chloride (2.30 mL, 29.8 mmol) and the reaction mixture was stirred at rt for 2 h. Water was added and the mixture was extracted with methylene chloride (3 times). The methylene chloride extracts were combined, washed with water and a saturated aqueous solution of sodium chloride, dried over sodium sulfate and concentrated in vacuo to yield tert-butyl 3-(2-((methylsulfonyl)oxy)ethyl)azetidine-1-carboxylate (6.95 g, 24.8 mmol, 100% yield).

Preparation 14: tert-butyl 3-(2-(2-(methylthio)-7-oxopyrido[2,3-d]pyrimidin-8(7H)-yl)ethyl)azetidine-1-carboxylate

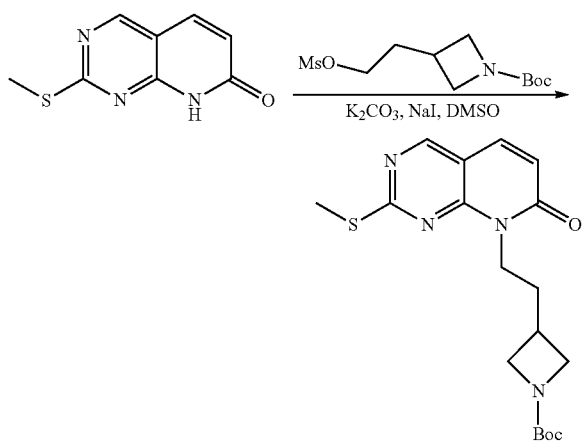

Potassium carbonate (5.70 g, 41.4 mmol) was added to a solution of 2-(methylthio)pyrido[2,3-d]pyrimidin-7(8H)-one (4.00 g, 20.7 mmol) in DMSO (50 mL), followed by sodium iodide (3.10 g, 20.7 mmol) and the reaction mixture was stirred for 10 min. A solution of tert-butyl 3-(2-((methylsulfonyl)oxy)ethyl)azetidine-1-carboxylate (6.95 g, 24.8 mmol) in DMSO was then added dropwise and the reaction mixture was stirred at 90° C. for 16 h. Cold water was added and the mixture was extracted with methylene chloride (3 times). The organic layers were combined, washed with water and a saturated aqueous solution of sodium chloride, dried over anhydrous sodium sulfate and concentrated in vacuo to yield a crude mixture. The mixture was purified via flash column chromatography using a gradient of 40-45% acetone in hexane to yield tert-butyl 3-(2-(2-(methylthio)-7-oxopyrido[2,3-d]pyrimidin-8(7H)-yl)ethyl)azetidine-1-carboxylate (5.10 g, 13.5 mmol, 65% yield) as a pale yellow solid. (m/z): [M+H]+ calcd for $C_{18}H_{25}N_4O_3S$ 377.16 found 377.25.

Preparation 15: tert-butyl 3-(2-(2-(methylthio)-7-oxopyrido[2,3-d]pyrimidin-8(7H)-yl)ethyl)azetidine-1-carboxylate

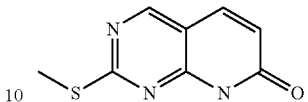

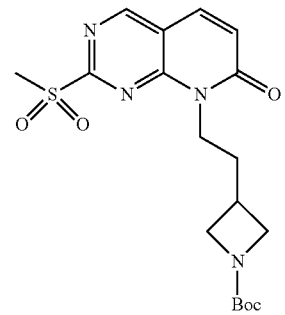

m-CPBA (11.4 g, 66.5 mmol) was added to a solution of tert-butyl 3-(2-(2-(methylthio)-7-oxopyrido[2,3-d]pyrimidin-8(7H)-yl)ethyl)azetidine-1-carboxylate (5.00 g, 13.3 mmol) in methylene chloride (200 mL) at 0° C. and the reaction mixture was stirred at rt for 2 h. Water was added and the mixture was basified using a saturated aqueous solution of sodium bicarbonate to pH~10, and then extracted with methylene chloride (3 times). The methylene chloride extracts were combined, washed with water, dried over anhydrous sodium sulfate and concentrated in vacuo to yield a crude mixture. The mixture was triturated with 1:5 acetonitrile/diethyl ether to yield tert-butyl 3-(2-(2-(methylthio)-7-oxopyrido[2,3-d]pyrimidin-8(7H)-yl)ethyl)azetidine-1-carboxylate (3.00 g, 7.34 mmol, 55% yield). (m/z): [M+H]+ calcd for $C_{18}H_{25}N_4O_5S$ 409.15 found 409.25.

Preparation 16: 1-(4-(4-nitrophenyl)piperazin-1-yl)ethan-1-one

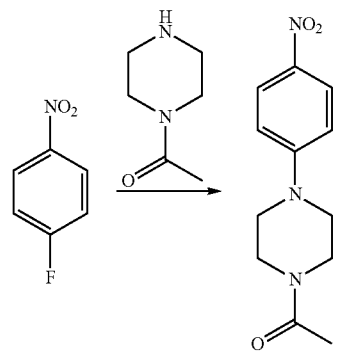

Potassium carbonate (9.78 g, 70.9 mmol) was added to a solution of 1-(piperazin-1-yl)ethan-1-one (4.50 g, 35.5 mmol) in dimethylformamide (50 mL), followed by 1-fluoro-4-nitrobenzene (5.00 g, 35.5 mmol) and the reaction mixture was stirred at 80° C. for 16 h. Water was added and the mixture was extracted with ethyl acetate. The organic extract was washed with water and a saturated aqueous solution of sodium chloride, dried over anhydrous sodium sulfate and concentrated in vacuo to yield 1-(4-(4-nitrophenyl)piperazin-1-yl)ethan-1-one (7.00 g, 28.1 mmol, 79% yield). (m/z): $[M+H]^+$ calcd for $C_{12}H_{16}N_3O_3$ 250.12 found 250.27.

Preparation 17: 1-(4-(4-aminophenyl)piperazin-1-yl)ethan-1-one

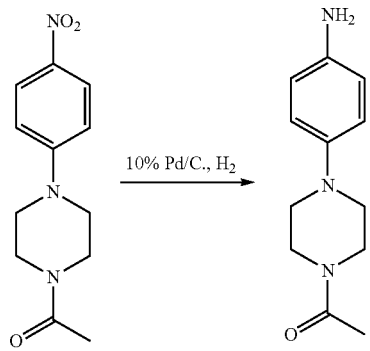 [SMILES: CC(=O)N1CCN(c2ccc([N+](=O)[O-])cc2)CC1 ; CC(=O)N1CCN(c2ccc(N)cc2)CC1]

10% palladium on carbon (5.0 g, 4.7 mmol) was added to a solution of 1-(4-(4-nitrophenyl)piperazin-1-yl)ethan-1-one (5.00 g, 20.1 mmol) in 3:1 isopropanol/THF (200 mL) and the reaction mixture was stirred under an atmosphere of hydrogen for 16 h. The reaction mixture was filtered through Celite and the Celite bed was washed with methanol. The resulting filtrates were combined and concentrated in vacuo to yield 1-(4-(4-aminophenyl)piperazin-1-yl)ethan-1-one (4.10 g, 18.7 mmol, 95% yield). (m/z): $[M+H]^+$ calcd for $C_{12}H_{18}N_3O$ 220.15 found 220.27.

Preparation 18: N-(4-(4-acetylpiperazin-1-yl)phenyl)formamide

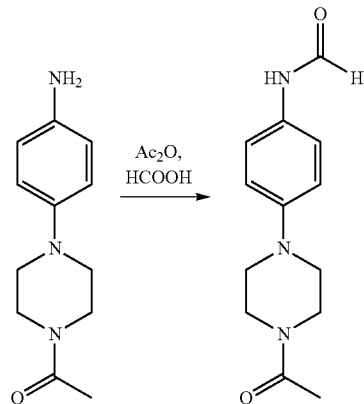 [SMILES: CC(=O)N1CCN(c2ccc(N)cc2)CC1 ; CC(=O)N1CCN(c2ccc(NC=O)cc2)CC1]

A formylating mixture (previously prepared from acetic anhydride (0.86 mL, 9.10 mmol) and formic acid (0.41 mL, 11.0 mmol), stirred at 70° C. for 1 h) was added dropwise to a solution of 1-(4-(4-aminophenyl)piperazin-1-yl)ethan-1-one (400 mg, 1.82 mmol) in THF (10 mL) at 0° C. and the reaction mixture was stirred at rt for 2 h. Ethyl acetate was added and the mixture was washed with water and a saturated aqueous solution of sodium chloride, dried over anhydrous sodium sulfate and concentrated in vacuo to yield N-(4-(4-acetylpiperazin-1-yl)phenyl)formamide (380 mg, 1.54 mmol, 84% yield) as a brown liquid. (m/z): $[M+H]^+$ calcd for $C_{13}H_{18}N_3O_2$ 248.14 found 248.22.

Preparation 19: tert-butyl 3-(2-(2-((4-(4-acetylpiperazin-1-yl)phenyl)amino)-7-oxopyrido[2,3-d]pyrimidin-8(7H)-yl)ethyl)azetidine-1-carboxylate

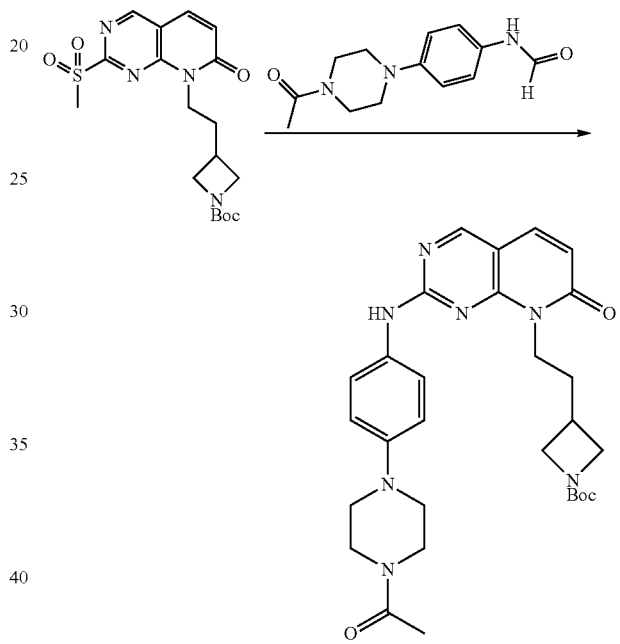

A 1 M solution of lithium bis(trimethylsilyl)amide in THF (1.17 mL, 1.17 mmol) was added to a solution of N-(4-(4-acetylpiperazin-1-yl)phenyl)formamide (290 mg, 1.17 mmol) in dimethylacetamide (8 mL) at 0° C. and the reaction mixture was stirred at 0° C. for 15 min, upon which a solution of tert-butyl 3-(2-(2-(methylsulfonyl)-7-oxopyrido[2,3-d]pyrimidin-8(7H)-yl)ethyl)azetidine-1-carboxylate (400 mg, 0.98 mmol) in dimethylacetamide (2 mL) was added at 0° C. and the reaction mixture was stirred at rt for 2 h. Methanol (10 mL) was added and the reaction mixture was stirred at rt for 15 min. Water was added and the mixture was extracted with 5% methanol in methylene chloride. The organic extracts were combined, washed with a saturated aqueous solution of sodium chloride, dried over anhydrous sodium sulfate and concentrated in vacuo to yield a crude residue. The residue was triturated with diethyl ether to yield tert-butyl 3-(2-(2-((4-(4-acetylpiperazin-1-yl)phenyl)amino)-7-oxopyrido[2,3-d]pyrimidin-8(7H)-yl)ethyl)azetidine-1-carboxylate (450 mg, 0.822 mmol, 84% yield) as a white yellow solid. (m/z): $[M+H]^+$ calcd for $C_{29}H_{38}N_7O_4$ 548.30 found 548.29.

Preparation 20: 2-((4-(4-acetylpiperazin-1-yl)phenyl)amino)-8-(2-(azetidin-3-yl)ethyl)pyrido[2,3-d]pyrimidin-7(8H)-one

Example 2: 2-((4-(4-acetylpiperazin-1-yl)phenyl)amino)-8-(2-(1-acryloylazetidin-3-yl)ethyl)pyrido[2,3-d]pyrimidin-7(8H)-one

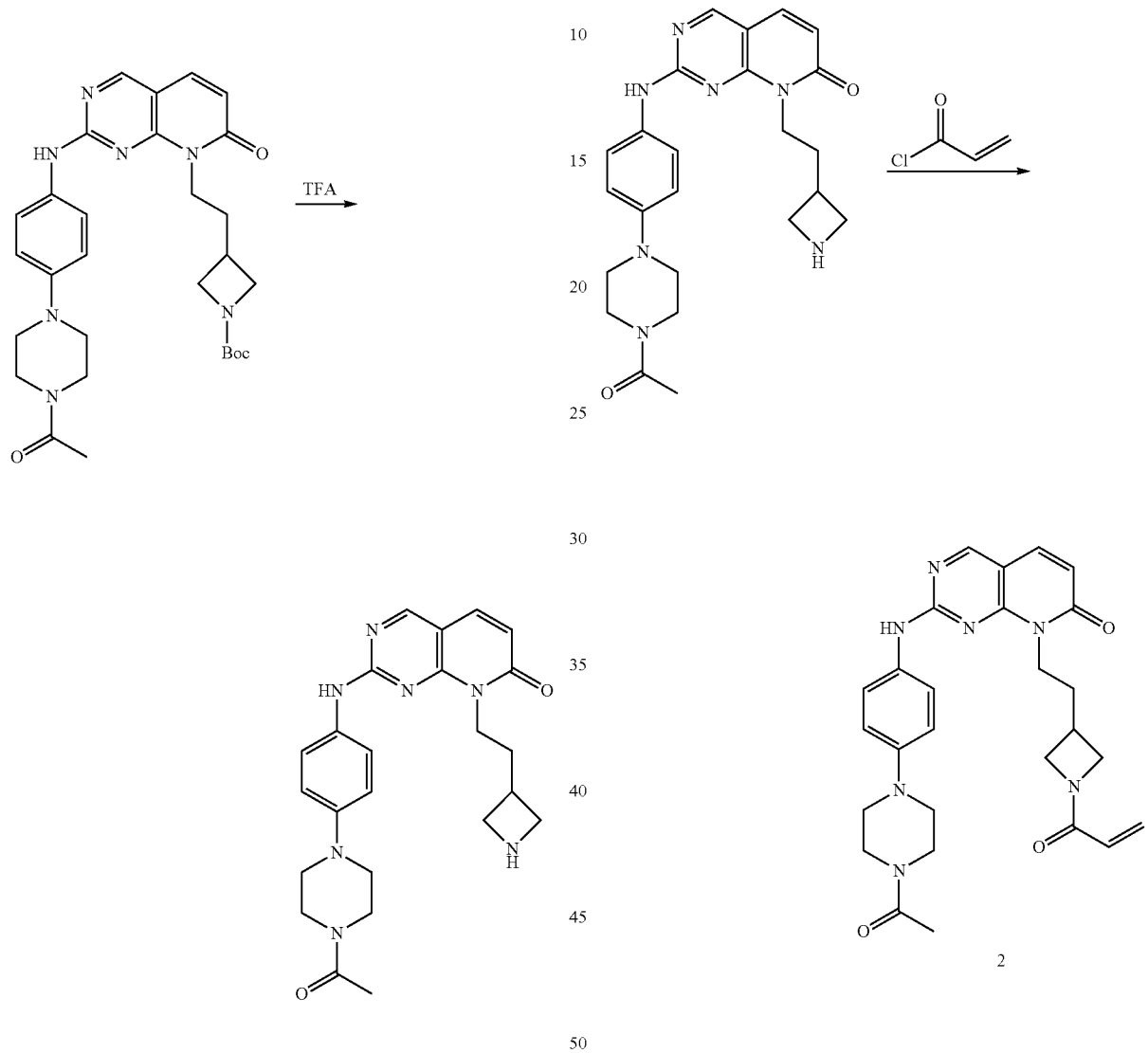

Trifluoroacetic acid (2 mL) was added to a solution of tert-butyl 3-(2-(2-((4-(4-acetylpiperazin-1-yl)phenyl)amino)-7-oxopyrido[2,3-d]pyrimidin-8(7H)-yl)ethyl)azetidine-1-carboxylate (510 mg, 0.931 mmol) in methylene chloride (2 mL) and the reaction mixture was stirred at rt for 1 hour. The reaction mixture was concentrated in vacuo to yield 2-((4-(4-acetylpiperazin-1-yl)phenyl)amino)-8-(2-(azetidin-3-yl)ethyl)pyrido[2,3-d]pyrimidin-7(8H)-one TFA salt (522 mg, 0.931 mmol, 100% yield) as a clear yellow liquid. (m/z): [M+H]+ calcd for $C_{24}H_{30}N_7O_2$ 448.25 found 448.2.

N,N-Diisopropylethylamine (0.813 mL, 4.66 mmol) was added to a solution of 2-((4-(4-methylpiperazin-1-yl)phenyl)amino)-8-(2-(piperazin-1-yl)ethyl)pyrido[2,3-d]pyrimidin-7(8H)-one TFA salt (522 mg, 0.931 mmol) in DMF (4 mL) at 0° C., followed by acryloyl chloride (0.083 mL, 1.03 mmol) and the reaction mixture was stirred at rt for 15 minutes. The reaction mixture was concentrated in vacuo to yield a clear yellow liquid. The crude liquid was purified via preparatory scale C18 column chromatography using a gradient of 10-60% acetonitrile in water with 0.05% trifluoroacetic acid to yield 2-((4-(4-acetylpiperazin-1-yl)phenyl)amino)-8-(2-(1-acryloylazetidin-3-yl)ethyl)pyrido[2,3-d]pyrimidin-7(8H)-one TFA salt (305 mg, 0.495 mmol, 53% yield) as a yellow solid. (m/z): [M+H]+ calcd for $C_{27}H_{32}N_7O_3$ 502.26 found 502.2.

Preparation 21: tert-butyl 3-(2-(7-oxo-2-((4-(piperazin-1-yl)phenyl)amino)pyrido[2,3-d]pyrimidin-8(7H)-yl)ethyl)azetidine-1-carboxylate

Preparation 22: tert-butyl 3-(2-(2-((4-(4-(3-(methylthio)propanoyl)piperazin-1-yl)phenyl)amino)-7-oxopyrido[2,3-d]pyrimidin-8(7H)-yl)ethyl)azetidine-1-carboxylate

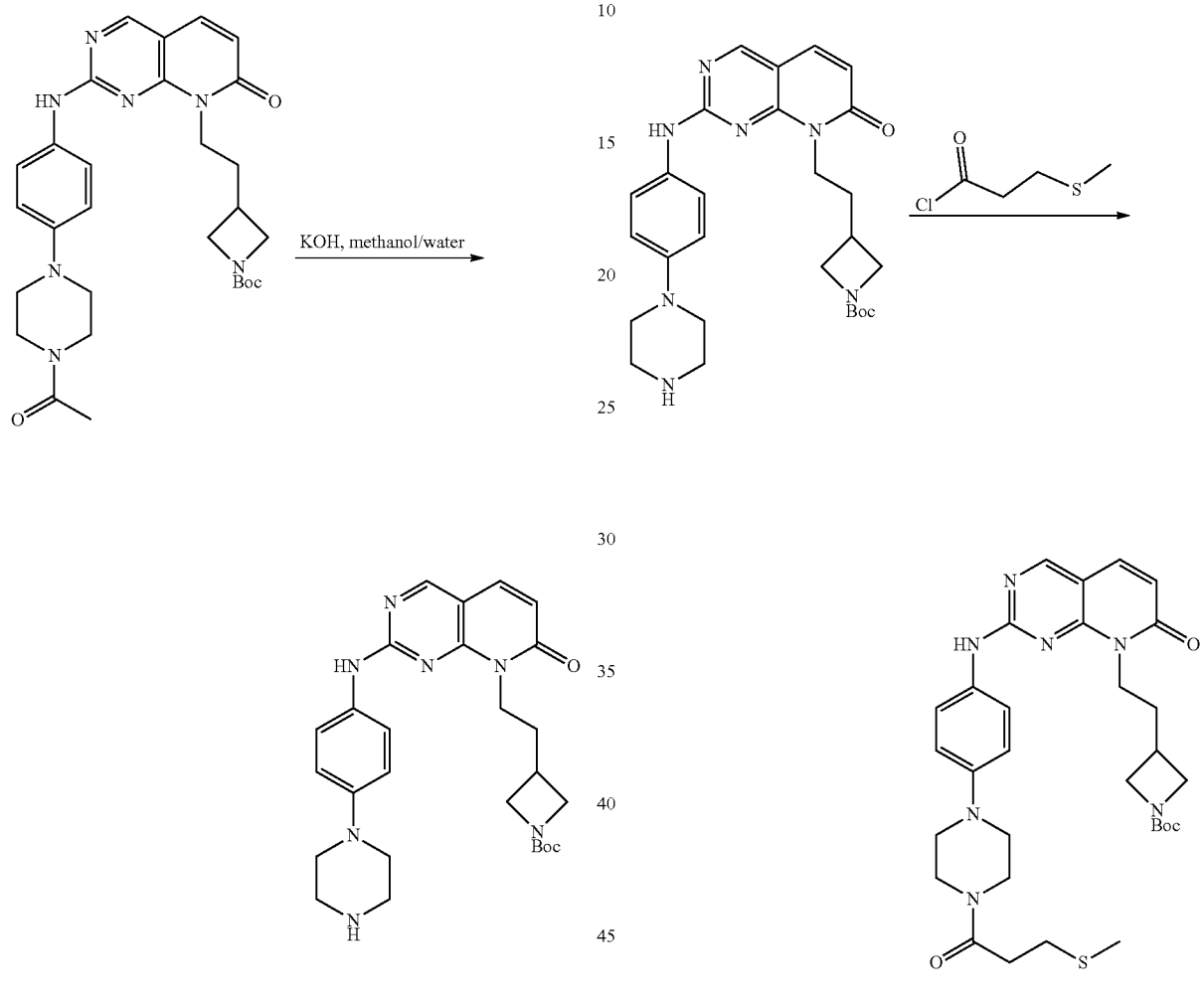

A solution of potassium hydroxide (350 mg, 5.93 mmol) in water (3.0 mL) was added to a solution of tert-butyl 3-(2-(2-((4-(4-acetylpiperazin-1-yl)phenyl)amino)-7-oxopyrido[2,3-d]pyrimidin-8(7H)-yl)ethyl)azetidine-1-carboxylate (650 mg, 1.19 mmol) in methanol (20 mL) and the reaction mixture was stirred at 80° C. for 30 h. The reaction mixture was concentrated in vacuo and then dissolved in a 10% solution of methanol in methylene chloride. The solution was washed with water and a saturated aqueous solution of sodium chloride, dried over anhydrous sodium sulfate and concentrated in vacuo to yield a crude mixture. The mixture was purified via flash column chromatography using a gradient of 34% methanol in methylene chloride to yield tert-butyl 3-(2-(7-oxo-2-((4-(piperazin-1-yl)phenyl)amino)pyrido[2,3-d]pyrimidin-8(7H)-yl)ethyl)azetidine-1-carboxylate (430 mg, 0.850 mmol, 71% yield) as a yellow solid (m/z): [M+H]$^+$ calcd for $C_{27}H_{36}N_7O_3$ 506.29 found 506.37.

3-Methylthiopropionyl chloride (41.1 μL, 0.356 mmol) was added to a solution of tert-butyl 3-(2-(7-oxo-2-((4-(piperazin-1-yl)phenyl)amino)pyrido[2,3-d]pyrimidin-8(7H)-yl)ethyl)azetidine-1-carboxylate (430 mg, 0.850 mmol) in methylene chloride at 0° C., followed by diisopropylethyl amine (155 μL, 0.890 mmol) and the reaction mixture was stirred at rt for 1.5 h. Water was added and the reaction mixture was concentrated in vacuo to yield a crude mixture. The mixture was purified via flash column chromatography using a gradient of 0-10% methanol in methylene chloride to yield tert-butyl 3-(2-(2-((4-(4-(3-(methylthio)propanoyl)piperazin-1-yl)phenyl)amino)-7-oxopyrido [2,3-d]pyrimidin-8(7H)-yl)ethyl)azetidine-1-carboxylate (78.5 mg, 0.129 mmol, 73% yield) as a yellow solid (m/z): [M+H]$^+$ calcd for $C_{31}H_{42}N_7O_4S$ 608.30 found 608.6.

Preparation 23: 8-(2-(azetidin-3-yl)ethyl)-2-((4-(4-(3-(methylthio)propanoyl)piperazin-1-yl)phenyl)amino)pyrido[2,3-d]pyrimidin-7(8H)-one

Example 3: 8-(2-(1-acryloylazetidin-3-yl)ethyl)-2-((4-(4-(3-(methylthio)propanoyl)piperazin-1-yl)phenyl)amino)pyrido[2,3-d]pyrimidin-7(8H)-one

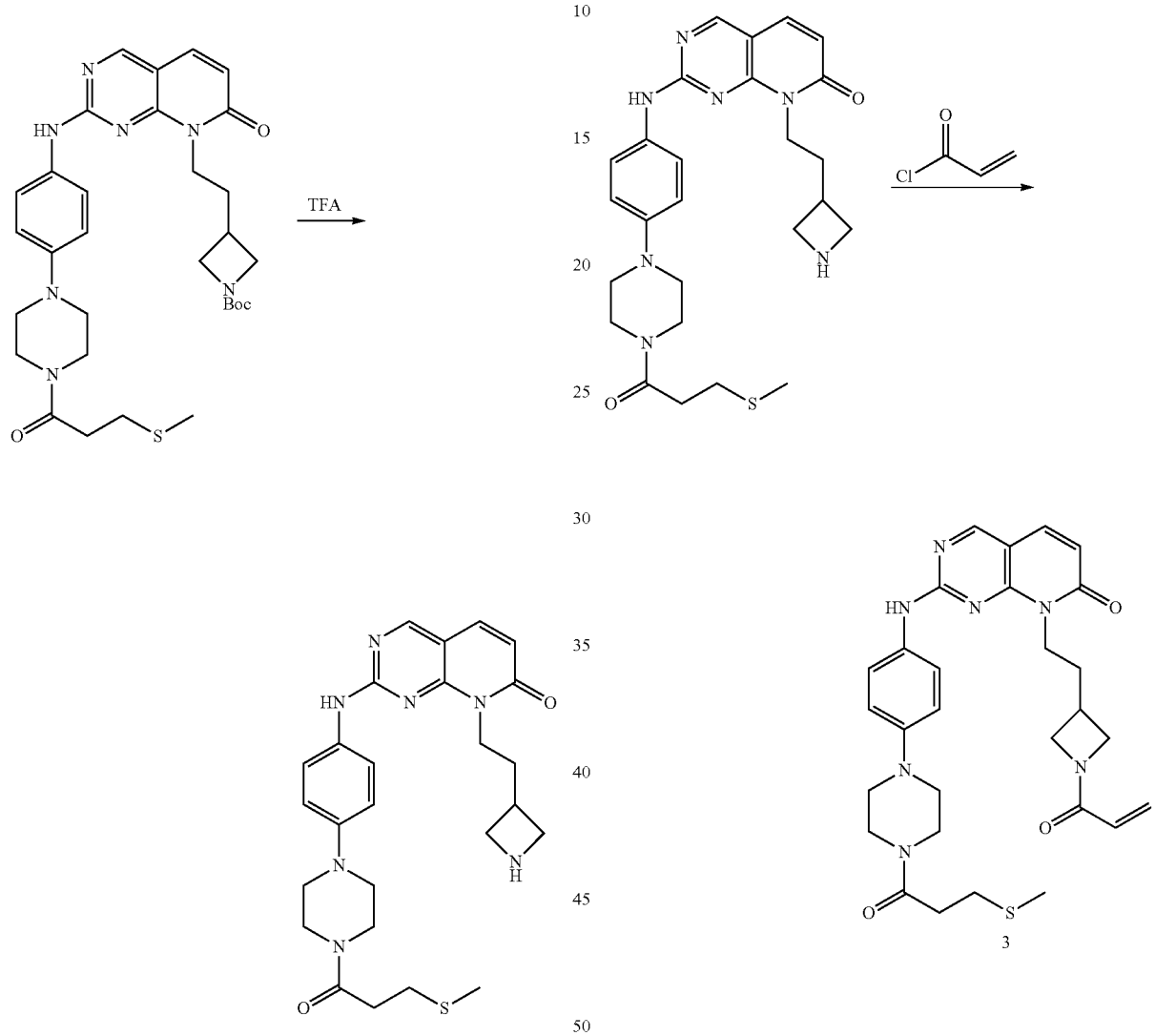

Trifluoroacetic acid (0.431 mL) was added to a solution of tert-butyl 3-(2-(2-((4-(4-(3-(methylthio)propanoyl)piperazin-1-yl)phenyl)amino)-7-oxopyrido[2,3-d]pyrimidin-8(7H)-yl)ethyl)azetidine-1-carboxylate (78.5 mg, 0.129 mmol) in methylene chloride (0.861 ml) and the reaction mixture was stirred at rt for 1.5 h. The reaction mixture was concentrated in vacuo to yield 8-(2-(azetidin-3-yl)ethyl)-2-((4-(4-(3-(methylthio)propanoyl)piperazin-1-yl)phenyl)amino)pyrido[2,3-d]pyrimidin-7(8H)-one TFA salt (80.2 mg, 0.129 mmol, 100% yield). (m/z): [M+H]$^+$ calcd for $C_{26}H_{34}N_7O_2S$ 508.25 found 508.4.

N,N-Diisopropylethylamine (0.173 mL, 0.991 mmol) was added to a solution of 8-(2-(azetidin-3-yl)ethyl)-2-((4-(4-(3-(methylthio)propanoyl)piperazin-1-yl)phenyl)amino)pyrido[2,3-d]pyrimidin-7(8H)-one TFA salt (80.2 mg, 0.129 mmol) in methylene chloride (0.25 mL), followed by acryloyl chloride (12.6 µl, 0.155 mmol) and the reaction mixture was stirred at rt for 30 minutes. The reaction mixture was concentrated in vacuo to yield a clear yellow liquid. The crude liquid was purified via preparatory scale C18 column chromatography using a gradient of 0-40% acetonitrile in water with 0.05% trifluoroacetic acid to yield 8-(2-(1-acryloylazetidin-3-yl)ethyl)-2-((4-(4-(3-(methylthio)propanoyl)piperazin-1-yl)phenyl)amino)pyrido[2,3-d]pyrimidin-7(8H)-one TFA salt (44.1 mg, 0.065 mmol, 50% yield). (m/z): [M+H]$^+$ calcd for $C_{29}H_{36}N_7O_3S$ 562.26 found 562.1.

Preparation 24: tert-butyl 3-(2-(2-((4-(4-(3-(methylthio)propanoyl)piperazin-1-yl)phenyl)amino)-7-oxopyrido[2,3-d]pyrimidin-8(7H)-yl)ethyl)azetidine-1-carboxylate

Preparation 25: 2-((4-(4-(3-(methylthio)propanoyl)piperazin-1-yl)phenyl)amino)-8-(2-(piperazin-1-yl)ethyl)pyrido[2,3-d]pyrimidin-7(8H)-one

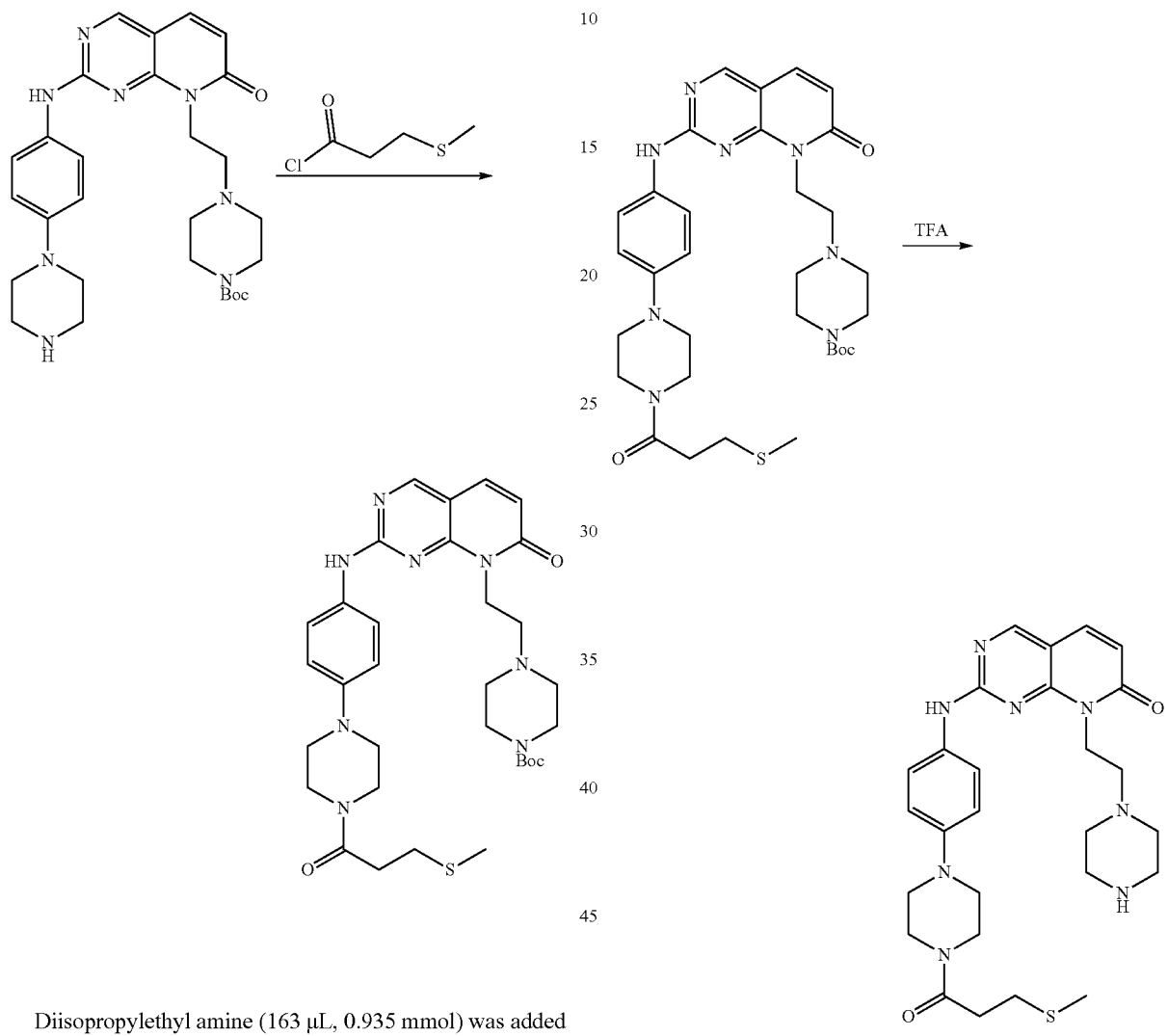

Diisopropylethyl amine (163 μL, 0.935 mmol) was added to a solution of tert-butyl 4-(2-(7-oxo-2-((4-(piperazin-1-yl)phenyl)amino)pyrido[2,3-d]pyrimidin-8(7H)-yl)ethyl)piperazine-1-carboxylate (100 mg, 0.187 mmol) in methylene chloride at 0° C., followed by 3-methylthiopropionyl chloride (32 μl, 0.281 mmol) and the reaction mixture was stirred at rt for 3 h. Water (2 mL) was added to the reaction mixture, the layers were separated and the aqueous layer was extracted with methylene chloride (2×5 mL). The methylene chloride layers were combined, washed with a saturated aqueous solution of sodium chloride (5 mL) and concentrated to yield a yellow liquid. The crude liquid was purified via flash column chromatography using 5% methanol in methylene chloride to yield tert-butyl 4-(2-(2-((4-(4-(3-(methylthio)propanoyl)piperazin-1-yl)phenyl)amino)-7-oxopyrido[2,3-d]pyrimidin-8(7H)-yl)ethyl)piperazine-1-carboxylate (80.1 mg, 0.126 mmol, 67% yield) as a yellow solid (m/z): [M+H]$^+$ calcd for $C_{32}H_{45}N_8O_4S$ 637.33 found 637.3.

Trifluoroacetic acid (1.00 mL) was added to a solution of tert-butyl 4-(2-(2-((4-(4-(3-(methylthio)propanoyl)piperazin-1-yl)phenyl)amino)-7-oxopyrido[2,3-d]pyrimidin-8(7H)-yl)ethyl)piperazine-1-carboxylate (80.1 mg, 0.126 mmol) in methylene chloride (0.50 ml) and the reaction mixture was stirred at rt for 30 min. The reaction mixture was concentrated in vacuo to yield 2-((4-(4-(3-(methylthio)propanoyl)piperazin-1-yl)phenyl)amino)-8-(2-(piperazin-1-yl)ethyl)pyrido[2,3-d]pyrimidin-7(8H)-one TFA salt (82.0 mg, 0.126 mmol, 100% yield). (m/z): [M+H]$^+$ calcd for $C_{27}H_{37}N_8O_2S$ 537.28 found 537.2.

Example 4: 8-(2-(4-acryloylpiperazin-1-yl)ethyl)-2-((4-(4-(3-(methylthio)propanoyl)piperazin-1-yl)phenyl)amino)pyrido[2,3-d]pyrimidin-7(8H)-one

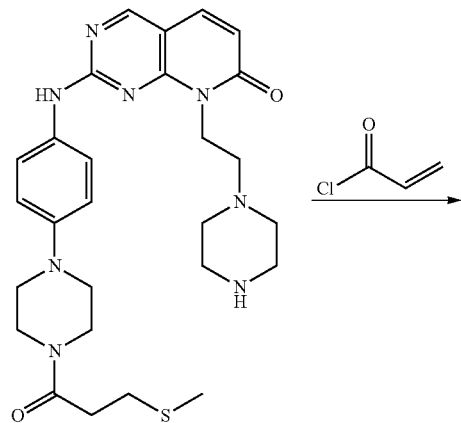

N,N-Diisopropylethylamine (0.066 mL, 0.377 mmol) was added to a solution of 2-((4-(4-(3-(methylthio)propanoyl)piperazin-1-yl)phenyl)amino)-8-(2-(piperazin-1-yl)ethyl)pyrido[2,3-d]pyrimidin-7(8H)-one TFA salt (82.0 mg, 0.126 mmol) in DMF (1 mL) at 0° C., followed by acryloyl chloride (0.011 ml, 0.138 mmol) and the reaction mixture was stirred at rt for 15 minutes. The reaction mixture was concentrated in vacuo to yield a yellow liquid. The crude liquid was purified via preparatory scale C18 column chromatography using a gradient of 10-80% acetonitrile in water with 0.05% trifluoroacetic acid to yield 8-(2-(4-acryloylpiperazin-1-yl)ethyl)-2-((4-(4-(3-(methylthio)propanoyl)piperazin-1-yl)phenyl)amino)pyrido[2,3-d]pyrimidin-7(8H)-one, TFA salt (31.6 mg, 0.043 mmol, 33.9% yield) as a yellow solid. (m/z): $[M+H]^+$ calcd for $C_{30}H_{39}N_8O_3S$ 591.29 found 591.2.

Preparation 26: 3-(((tert-butyldimethylsilyl)oxy)methyl)aniline

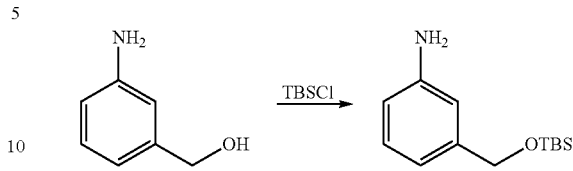

Imidazole (16.58 g, 243.9 mmol) was added to a solution of (3-aminophenyl)methanol (6.00 g, 48.8 mmol) in methylene chloride (60 mL) at 0° C., and the reaction mixture was stirred at 0° C. for 10 min. Tert-Butyldimethylsilyl chloride (10.97 g, 73.17 mmol) was added and the reaction mixture was stirred at 0° C. for 2 h. Ethyl acetate was added and the reaction mixture was washed with water and then a saturated aqueous solution of sodium chloride, dried over sodium sulfate and concentrated in vacuo to yield a crude mixture. The crude mixture was purified via flash column chromatography using a gradient of 20-25% ethyl acetate in hexane to yield 3-(((tert-butyldimethylsilyl)oxy)methyl)aniline (9.05 g, 38.1 mmol, 78% yield). (m/z): $[M+H]^+$ calcd for $C_{13}H_{24}NOSi$ 238.16 found 238.28.

Preparation 27: N-(3-(((tert-butyldimethylsilyl)oxy)methyl)phenyl)formamide

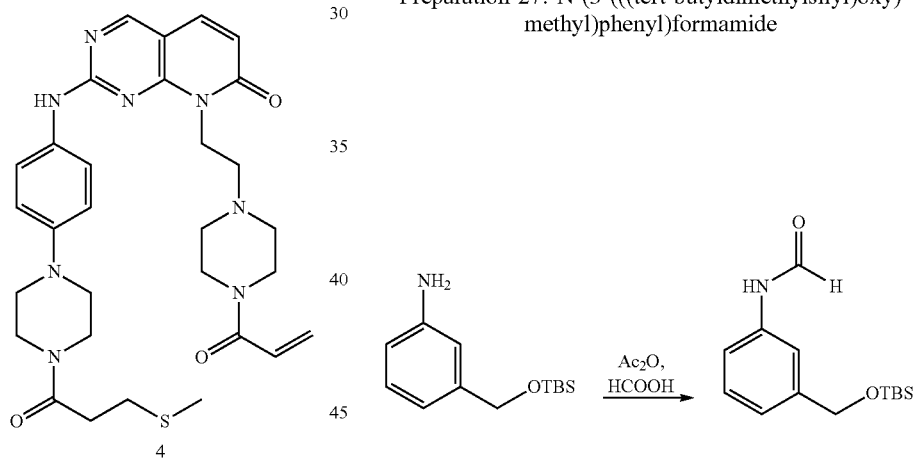

A formylating mixture (previously prepared from acetic anhydride (17.93 mL, 189.8 mmol) and formic acid (14.31 mL, 379.7 mmol), stirred at 70° C. for 2 h) was added dropwise to a solution of 3-(((tert-butyldimethylsilyl)oxy)methyl)aniline (9.00 g, 37.97 mmol) in methylene chloride (90 mL) at 0° C. and the reaction mixture was stirred at rt for 1 h. Water was added and the mixture was extracted with methylene chloride. The methylene chloride extracts were combined, washed with a saturated aqueous solution of sodium chloride, dried over anhydrous sodium sulfate and concentrated in vacuo to yield a crude mixture. The crude mixture was purified via flash column chromatography using 15% ethyl acetate in hexane to yield N-(3-(((tert-butyldimethylsilyl)oxy)methyl)phenyl)formamide (9.0 g, 33.9 mmol, 89% yield). (m/z): $[M+H]^+$ calcd for $C_{14}H_{24}NO_2Si$ 266.16 found 266.33.

Preparation 28: tert-butyl 3-(2-(2-((3-(hydroxymethyl)phenyl)amino)-7-oxopyrido[2,3-d]pyrimidin-8(7H)-yl)ethyl)azetidine-1-carboxylate

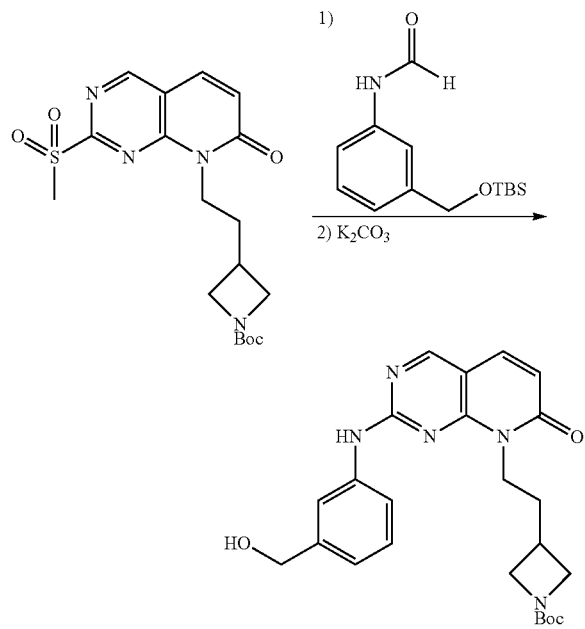

A 1 M solution of lithium bis(trimethylsilyl)amide in THF (14.7 mL, 14.7 mmol) was added to a solution of N-(3-(((tert-butyldimethylsilyl)oxy)methyl)phenyl)formamide (2.6 g, 9.80 mmol) in dimethylacetamide (50 mL) at 0° C. and the reaction mixture was stirred at 0° C. for 30 min, upon which a solution of tert-butyl 3-(2-(2-(methylthio)-7-oxopyrido[2,3-d]pyrimidin-8(7H)-yl)ethyl)azetidine-1-carboxylate (5.0 g, 12.25 mmol) in dimethylacetamide (25 mL) was added at 0° C. and the reaction mixture was stirred at rt for 1 h. Methanol (25 mL) was added and the reaction mixture was stirred at rt for 30 min. The reaction mixture was concentrated in vacuo and the resulting crude residue was dissolved in ethyl acetate, washed with water and a saturated aqueous solution of sodium chloride, dried over anhydrous sodium sulfate and concentrated in vacuo to yield a crude residue. The crude residue was purified via flash column chromatography using 20% acetone in hexane to yield a mixture of the expected product along with the formylated product.

This mixture was dissolved in methanol (50 mL), potassium carbonate (3.5 g, 8.43 mmol) was added and the reaction mixture was stirred at 80° C. for 16 h. The reaction mixture was concentrated in vacuo, water was added to the residue and the mixture was extracted with methanol/methylene chloride. The organic layers were combined, washed with water and a saturated aqueous solution of sodium chloride, dried over anhydrous sodium sulfate and concentrated in vacuo to yield a crude residue. The crude residue was purified via flash column chromatography using a gradient of 4-7% methanol in methylene chloride to yield tert-butyl 3-(2-(2-((3-(hydroxymethyl)phenyl)amino)-7-oxopyrido[2,3-d]pyrimidin-8(7H)-yl)ethyl)azetidine-1-carboxylate (3.6 g, 7.97 mmol, 65% yield). (m/z): $[M+H]^+$ calcd for $C_{24}H_{30}N_5O_4$ 452.23 found 452.49.

Preparation 29: tert-butyl 3-(2-(2-((3-(((methylsulfonyl)oxy)methyl)phenyl)amino)-7-oxopyrido[2,3-d]pyrimidin-8(7H)-yl)ethyl)azetidine-1-carboxylate

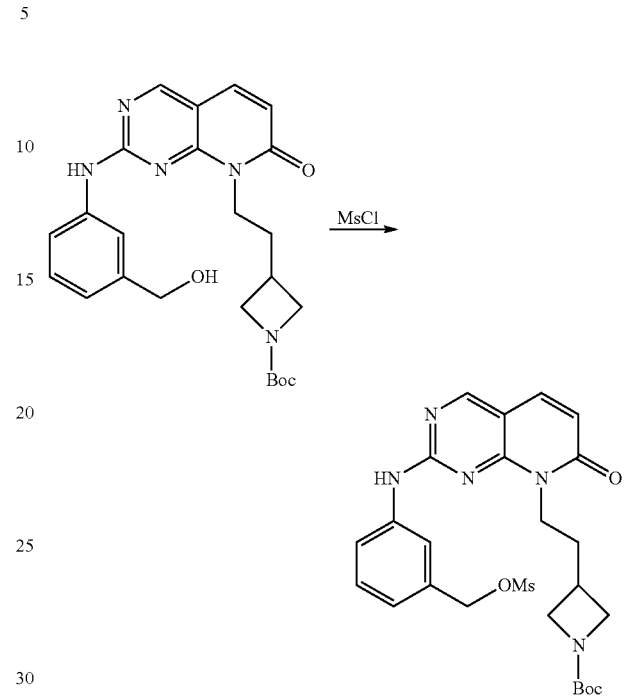

Triethylamine (3.3 mL, 23.3 mmol) was added to a solution of tert-butyl 3-(2-(2-((3-(hydroxymethyl)phenyl)amino)-7-oxopyrido[2,3-d]pyrimidin-8(7H)-yl)ethyl)azetidine-1-carboxylate (3.5 g, 7.75 mmol) in methylene chloride (10 mL) at 0° C., followed by methansulfonyl chloride (0.7 mL, 9.3 mmol) and the reaction mixture was stirred at rt for 1 h. Methylene chloride was added and the reaction mixture was washed with water and a saturated aqueous solution of sodium chloride, dried over anhydrous sodium sulfate and concentrated in vacuo to yield tert-butyl 3-(2-(2-((3-(((methylsulfonyl)oxy)methyl)phenyl)amino)-7-oxopyrido[2,3-d]pyrimidin-8(7H)-yl)ethyl)azetidine-1-carboxylate (3.62 g, 7.75 mmol, 100% yield). (m/z): $[M-H]^-$ calcd for $C_{25}H_{31}N_5O_4$ 528.19 found 528.36.

Preparation 30: tert-butyl 3-(2-(2-((3-(chloromethyl)phenyl)amino)-7-oxopyrido[2,3-d]pyrimidin-8(7H)-yl)ethyl)azetidine-1-carboxylate

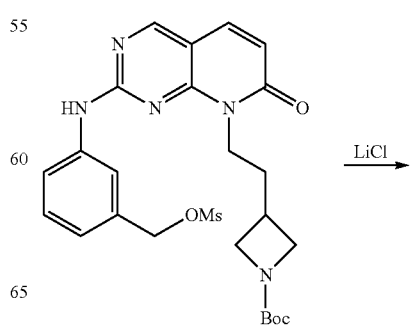

-continued

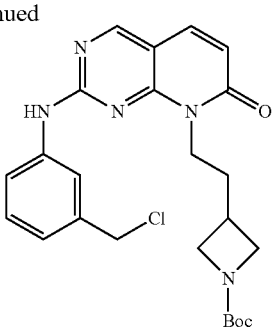

Lithium chloride (0.6 g, 13.6 mmol) was added to a solution of tert-butyl 3-(2-(2-((3-(((methylsulfonyl)oxy)methyl)phenyl)amino)-7-oxopyrido[2,3-d]pyrimidin-8(7H)-yl)ethyl)azetidine-1-carboxylate (3.6 g, 7.75 mmol) in DMF (50 mL) and the reaction mixture was stirred at rt for 1 h. Water was added, the reaction mixture was filtered and the resulting filtrate was triturated using hexane, diethyl ether and acetonitrile-diethyl ether to yield tert-butyl 3-(2-(2-((3-(chloromethyl)phenyl)amino)-7-oxopyrido[2,3-d]pyrimidin-8(7H)-yl)ethyl)azetidine-1-carboxylate (2.52 g, 5.36 mmol, 69% yield). (m/z): [M+H]$^+$ calcd for $C_{24}H_{29}ClN_5O_3$ 470.20 found 470.35.

Preparation 31: tert-butyl 3-(2-(7-oxo-2-((3-(piperazin-1-ylmethyl)phenyl)amino)pyrido[2,3-d]pyrimidin-8(7H)-yl)ethyl)azetidine-1-carboxylate

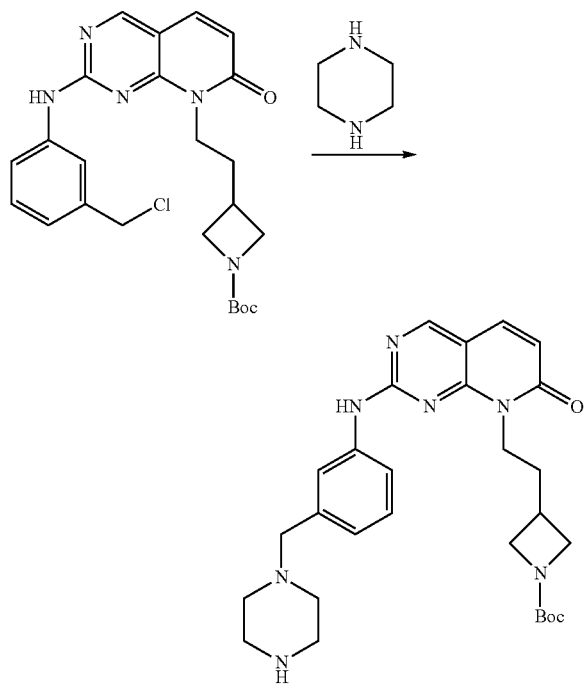

N,N-Diisopropylamine (0.284 mL, 1.628 mmol) was added to a solution of tert-butyl 3-(2-(2-((3-(chloromethyl)phenyl)amino)-7-oxopyrido[2,3-d]pyrimidin-8(7H)-yl)ethyl)azetidine-1-carboxylate (510 mg, 1.09 mmol), potassium iodide (36.0 mg, 0.217 mmol) and piperazine (374 mg, 4.34 mmol) in DMF (12.8 mL) and the reaction mixture was stirred at rt overnight. The reaction mixture was diluted with water (50 mL) and the mixture was extracted with ethyl acetate (3×15 mL). The organic extracts were dried over anhydrous sodium sulfate and concentrated in vacuo to yield a crude residue. The crude residue was purified via flash column chromatography using a gradient of 0-40% methanol in methylene chloride to yield tert-butyl 3-(2-(7-oxo-2-((3-(piperazin-1-ylmethyl)phenyl)amino)pyrido[2,3-d]pyrimidin-8(7H)-yl)ethyl)azetidine-1-carboxylate (377 mg, 0.725 mmol, 67% yield) as a yellow liquid.

Preparation 32: tert-butyl 3-(2-(2-((3-((4-(dimethylcarbamoyl)piperazin-1-yl)methyl)phenyl)amino)-7-oxopyrido[2,3-d]pyrimidin-8(7H)-yl)ethyl)azetidine-1-carboxylate

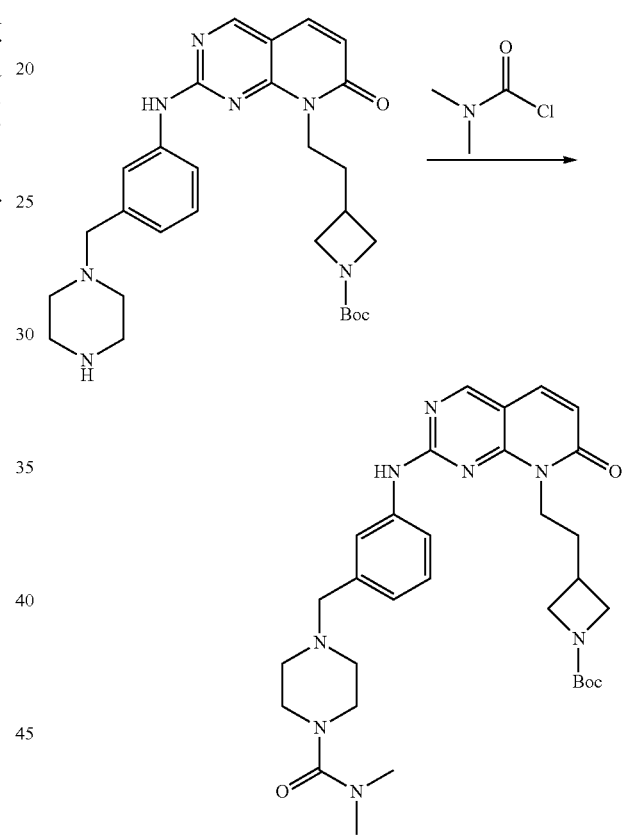

N,N-Diisopropylamine (50.4 μL, 0.289 mmol) was added to a solution of tert-butyl 3-(2-(7-oxo-2-((3-(piperazin-1-ylmethyl)phenyl)amino)pyrido[2,3-d]pyrimidin-8(7H)-yl)ethyl)azetidine-1-carboxylate (30.0 mg, 0.058 mmol) in DMF (0.29 mL) followed by N,N-dimethylaminocarbamoyl chloride (5.31 μL, 0.058 mmol) and the reaction mixture was stirred at rt for 5 min. Water (1.5 mL) was added and the mixture was extracted with ethyl acetate (2 mL). The organic extract was dried over anhydrous sodium sulfate and concentrated in vacuo to yield a crude residue. The crude residue was purified via flash column chromatography using a gradient of 0-40% methanol in methylene chloride to yield tert-butyl 3-(2-(2-((3-((4-(dimethylcarbamoyl)piperazin-1-yl)methyl)phenyl)amino)-7-oxopyrido[2,3-d]pyrimidin-8(7H)-yl)ethyl)azetidine-1-carboxylate (27.3 mg, 0.046 mmol, 80% yield) as a yellow liquid. (m/z): [M+H]$^+$ calcd for $C_{31}H_{43}N_8O_4$ 591.34 found 591.2.

73

Preparation 33: 4-(3-((8-(2-(azetidin-3-yl)ethyl)-7-oxo-7,8-dihydropyrido[2,3-d]pyrimidin-2-yl)amino)benzyl)-N,N-dimethylpiperazine-1-carboxamide

74

Example 5: 4-(3-((8-(2-(1-acryloylazetidin-3-yl)ethyl)-7-oxo-7,8-dihydropyrido[2,3-d]pyrimidin-2-yl)amino)benzyl)-N,N-dimethylpiperazine-1-carboxamide

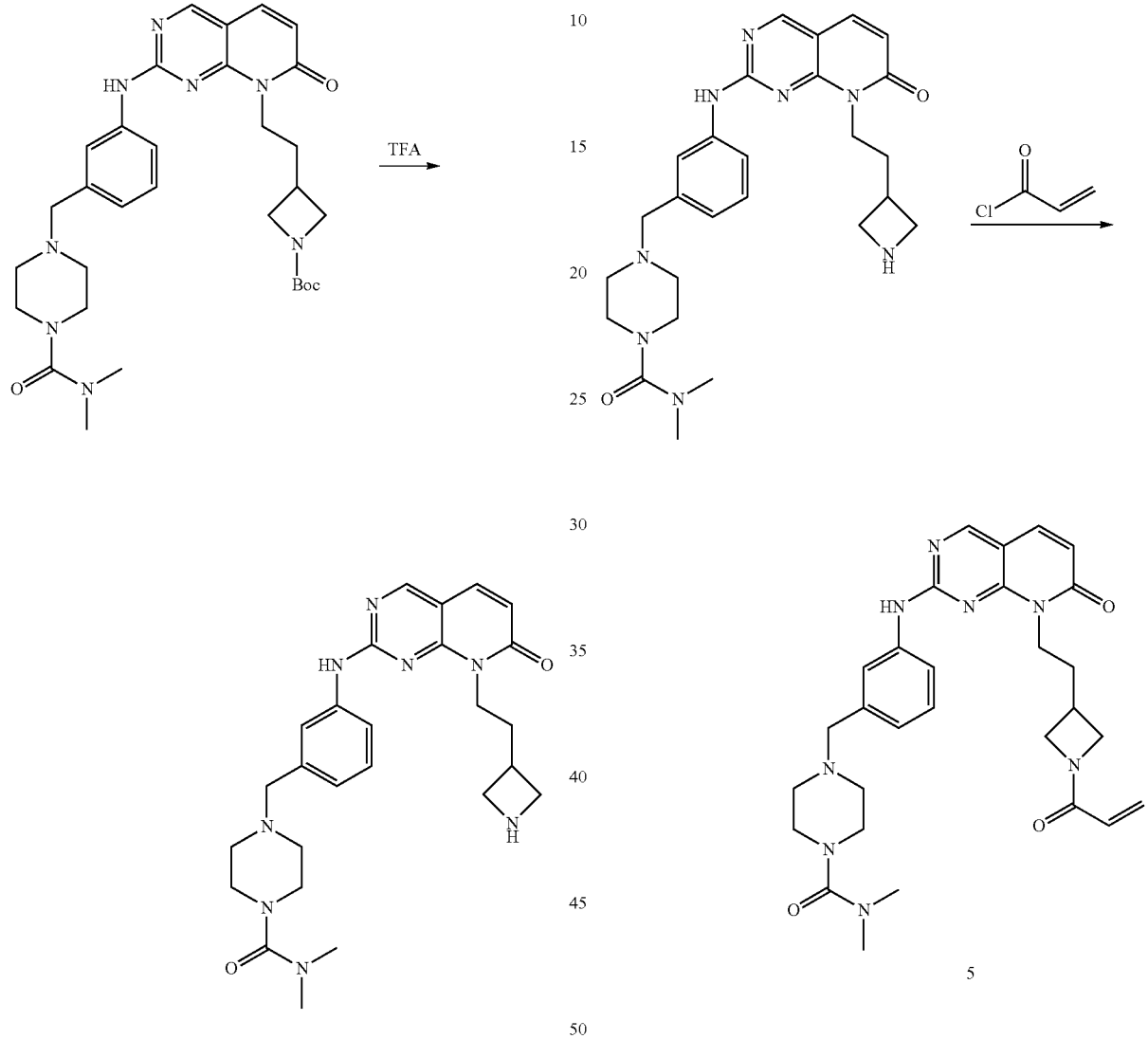

Trifluoroacetic acid (0.50 mL) was added to a solution of tert-butyl 3-(2-(2-((3-((4-(dimethylcarbamoyl)piperazin-1-yl)methyl)phenyl)amino)-7-oxopyrido[2,3-d]pyrimidin-8(7H)-yl)ethyl)azetidine-1-carboxylate (27.3 mg, 0.046 mmol) in methylene chloride (0.50 ml) and the reaction mixture was stirred at rt for 20 min. The reaction mixture was concentrated in vacuo to yield 4-(3-((8-(2-(azetidin-3-yl)ethyl)-7-oxo-7,8-dihydropyrido[2,3-d]pyrimidin-2-yl)amino)benzyl)-N,N-dimethylpiperazine-1-carboxamide TFA salt (27.6 mg, 0.046 mmol, 100% yield). (m/z): [M+H]$^+$ calcd for $C_{26}H_{35}N_8O_2$ 491.29 found 491.2.

N,N-Diisopropylethylamine (0.048 mL, 0.275 mmol) was added to a solution of 4-(3-((8-(2-(azetidin-3-yl)ethyl)-7-oxo-7,8-dihydropyrido[2,3-d]pyrimidin-2-yl)amino)benzyl)-N,N-dimethylpiperazine-1-carboxamide TFA salt (27.6 mg, 0.046 mmol) in DMF (0.23 mL) at rt, followed by acryloyl chloride (3.5 µl, 0.044 mmol) and the reaction mixture was stirred at rt for 5 minutes. The reaction mixture was concentrated in vacuo to yield a crude mixture. The crude mixture was purified via preparatory scale C18 column chromatography using a gradient of 5-65% acetonitrile in water with 0.05% trifluoroacetic acid to yield 4-(3-((8-(2-(1-acryloylazetidin-3-yl)ethyl)-7-oxo-7,8-dihydropyrido[2,3-d]pyrimidin-2-yl)amino)benzyl)-N,N-dimethylpiperazine-1-carboxamide, TFA salt (15.4 mg, 0.043 mmol, 51% yield) as a yellow solid. (m/z): [M+H]$^+$ calcd for $C_{29}H_{37}N_8O_3$ 545.30 found 545.2.

Preparation 34: tert-butyl 3-(2-(2-((3-((4-(methyl-sulfonyl)piperazin-1-yl)methyl)phenyl)amino)-7-oxopyrido[2,3-d]pyrimidin-8(7H)-yl)ethyl)azetidine-1-carboxylate

Preparation 35: 8-(2-(azetidin-3-yl)ethyl)-2-((3-((4-(methylsulfonyl)piperazin-1-yl)methyl)phenyl)amino)pyrido[2,3-d]pyrimidin-7(8H)-one

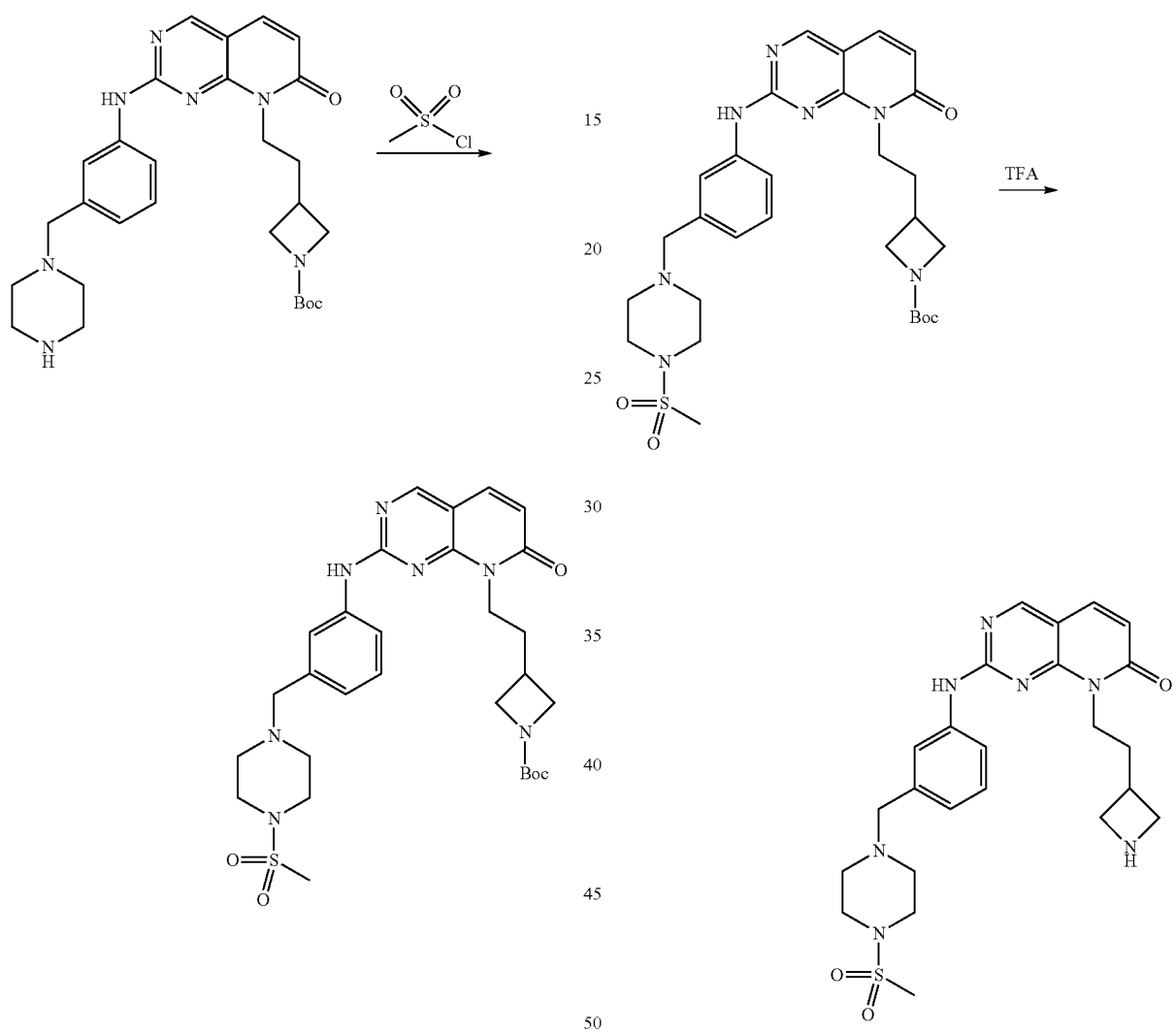

N,N-Diisopropylamine (50.4 μL, 0.289 mmol) was added to a solution of tert-butyl 3-(2-(7-oxo-2-((3-(piperazin-1-ylmethyl)phenyl)amino)pyrido[2,3-d]pyrimidin-8(7H)-yl)ethyl)azetidine-1-carboxylate (30.0 mg, 0.058 mmol) in DMF (0.29 mL) followed by methanesulfonyl chloride (4.47 μL, 0.058 mmol) and the reaction mixture was stirred at rt for 5 min. Water (2 mL) was added and the mixture was extracted with ethyl acetate (3×2 mL). The organic extracts were combined, dried over anhydrous sodium sulfate and concentrated in vacuo to yield a crude residue. The crude residue was purified via flash column chromatography using a gradient of 0-40% methanol in methylene chloride to yield tert-butyl 3-(2-(2-((3-((4-(methylsulfonyl)piperazin-1-yl)methyl)phenyl)amino)-7-oxopyrido[2,3-d]pyrimidin-8 (7H)-yl)ethyl)azetidine-1-carboxylate (27.6 mg, 0.046 mmol, 80% yield) as a yellow liquid. (m/z): [M+H]$^+$ calcd for $C_{29}H_{40}N_7O_5S$ 598.28 found 598.2.

Trifluoroacetic acid (0.50 mL) was added to a solution of tert-butyl 3-(2-(2-((3-((4-(methylsulfonyl)piperazin-1-yl)methyl)phenyl)amino)-7-oxopyrido[2,3-d]pyrimidin-8 (7H)-yl)ethyl)azetidine-1-carboxylate (27.6 mg, 0.046 mmol) in methylene chloride (0.50 ml) and the reaction mixture was stirred at rt for 15 min. The reaction mixture was concentrated in vacuo to yield 8-(2-(azetidin-3-yl)ethyl)-2-((3-((4-(methylsulfonyl)piperazin-1-yl)methyl)phenyl)amino)pyrido[2,3-d]pyrimidin-7(8H)-one TFA salt (28.5 mg, 0.046 mmol, 100% yield). (m/z): [M+H]$^+$ calcd for $C_{24}H_{32}N_7O_3S$ 498.23 found 498.2.

Example 6: 8-(2-(1-acryloylazetidin-3-yl)ethyl)-2-((3-((4-(methylsulfonyl)piperazin-1-yl)methyl)phenyl)amino)pyrido[2,3-d]pyrimidin-7(8H)-one

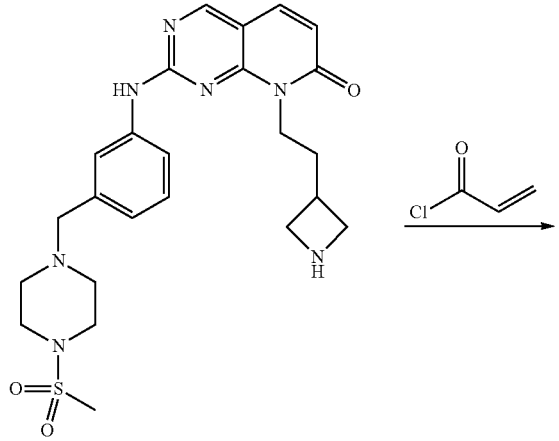

6

N,N-Diisopropylethylamine (0.082 mL, 0.471 mmol) was added to a solution of 8-(2-(azetidin-3-yl)ethyl)-2-((3-((4-(methylsulfonyl)piperazin-1-yl)methyl)phenyl)amino)pyrido[2,3-d]pyrimidin-7(8H)-one TFA salt (28.5 mg, 0.046 mmol) in DMF (0.5 mL) at rt, followed by acryloyl chloride (3.6 μl, 0.045 mmol) and the reaction mixture was stirred at rt for 5 minutes. The reaction mixture was concentrated in vacuo to yield a crude mixture. The crude mixture was purified via preparatory scale C18 column chromatography using a gradient of 10-85% acetonitrile in water with 0.05% trifluoroacetic acid to yield 8-(2-(1-acryloylazetidin-3-yl)ethyl)-2-((3-((4-(methylsulfonyl)piperazin-1-yl)methyl)phenyl)amino)pyrido[2,3-d]pyrimidin-7(8H)-one, TFA salt (14.9 mg, 0.022 mmol, 49% yield) as a yellow solid. (m/z): [M+H]$^+$ calcd for $C_{27}H_{34}N_7O_4S$ 552.24 found 552.0.

Preparation 36: N-(3-bromophenyl)formamide

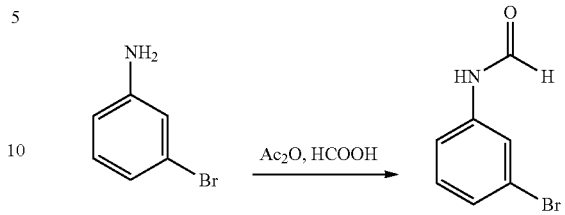

A formylating mixture (previously prepared from acetic anhydride (5.58 mL, 58.5 mmol) and formic acid (2.65 mL, 70.2 mmol), stirred at 70° C. for 1 h) was added dropwise to a solution of 3-Bromoaniline (2.00 g, 11.69 mmol) in THF (50 mL) at 0° C. and the reaction mixture was stirred at rt for 2 h. Ethyl acetate was added and the mixture was washed with water and a saturated aqueous solution of sodium chloride, dried over anhydrous sodium sulfate and concentrated in vacuo to yield N-(3-bromophenyl)formamide (1.9 g, 9.50 mmol, 81% yield) as a brown liquid. (m/z): [M+H]$^+$ calcd for $C_7H_7BrNO$ 201.78 found 201.97.

Preparation 37: tert-butyl 3-(2-(2-((3-bromophenyl)amino)-7-oxopyrido[2,3-d]pyrimidin-8(7H)-yl)ethyl)azetidine-1-carboxylate

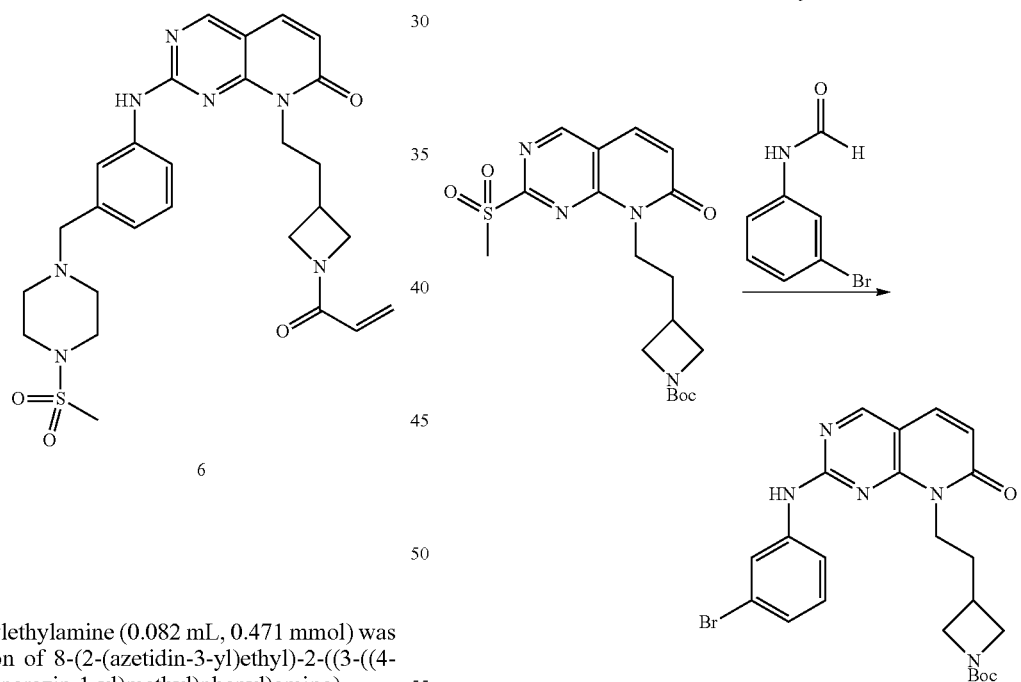

A 1 M solution of lithium bis(trimethylsilyl)amide in THF (8.82 mL, 8.82 mmol) was added to a solution of N-(3-bromophenyl)formamide (1.75 g, 8.82 mmol) in toluene (30 mL) at 0° C. and the reaction mixture was stirred at 0° C. for 15 min, upon which a solution of tert-butyl 3-(2-(2-(methylthio)-7-oxopyrido[2,3-d]pyrimidin-8(7H)-yl)ethyl)azetidine-1-carboxylate (3.0 g, 7.35 mmol) in THF (20 mL) was added at 0° C. and the reaction mixture was stirred at rt for 1 h. Methanol (5 mL) was added and the reaction mixture was stirred at rt for 30 min. The reaction mixture was concentrated in vacuo and the resulting crude residue was dissolved in ethyl acetate, washed with water and a saturated aqueous solution of sodium chloride, dried over anhydrous sodium sulfate and concentrated in vacuo to yield a crude residue. The crude residue was purified via flash column chromatography using a gradient of 90-100% ethyl acetate in hexane to yield tert-butyl 3-(2-(2-((3-bromophenyl)amino)-7-oxopyrido[2,3-d]pyrimidin-8(7H)-yl)ethyl)azetidine-1-carboxylate (1.99 g, 3.99 mmol, 54% yield). (m/z): [M+H]$^+$ calcd for $C_{23}H_{27}BrN_5O_3$ 502.18 found 502.14.

Preparation 38: tert-butyl 3-(2-(7-oxo-2-((3-(piperazin-1-yl)phenyl)amino)pyrido[2,3-d]pyrimidin-8(7H)-yl)ethyl)azetidine-1-carboxylate

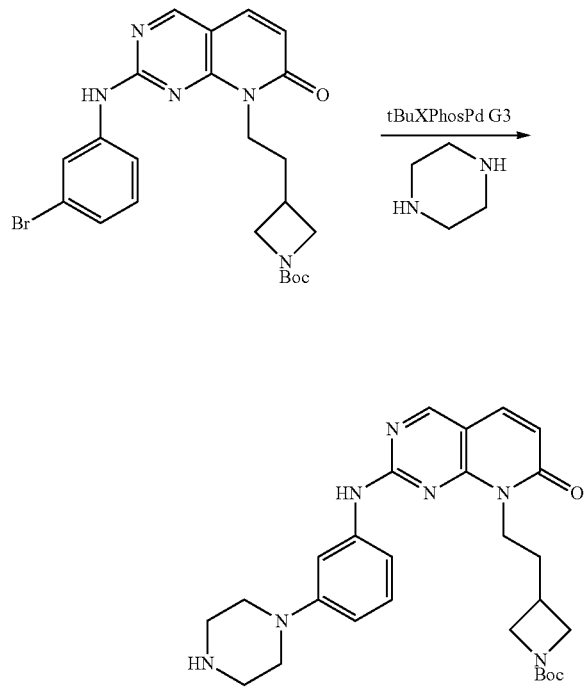

A suspension of tert-butyl 3-(2-(2-((3-bromophenyl)amino)-7-oxopyrido[2,3-d]pyrimidin-8(7H)-yl)ethyl)azetidine-1-carboxylate (830 mg, 1.66 mmol), piperazine (1.43 g, 16.6 mmol), sodium tert-butoxide (399 mg, 4.15 mmol) and tBuXPhos Pd G3 (130 mg, 0.164 mmol) in dioxane (10.5 mL) was heated under microwave irradiation at 120° C. for 8 h. The reaction mixture was concentrated in vacuo, water was added to the resulting crude residue, and the mixture was extracted with ethyl acetate (3×40 mL). The ethyl acetate extracts were combined, washed with water and a saturated aqueous solution of sodium chloride, dried over anhydrous sodium sulfate and concentrated in vacuo to yield a crude residue. The crude residue was purified via flash column chromatography using a gradient of 0-40% methanol in methylene chloride to yield tert-butyl 3-(2-(7-oxo-2-((3-(piperazin-1-yl)phenyl)amino)pyrido[2,3-d]pyrimidin-8(7H)-yl)ethyl)azetidine-1-carboxylate (436 mg, 0.863 mmol, 52% yield) as a yellow solid.

Preparation 39: tert-butyl 3-(2-(2-((3-(4-(3-(methylthio)propanoyl)piperazin-1-yl)phenyl)amino)-7-oxopyrido[2,3-d]pyrimidin-8(7H)-yl)ethyl)azetidine-1-carboxylate

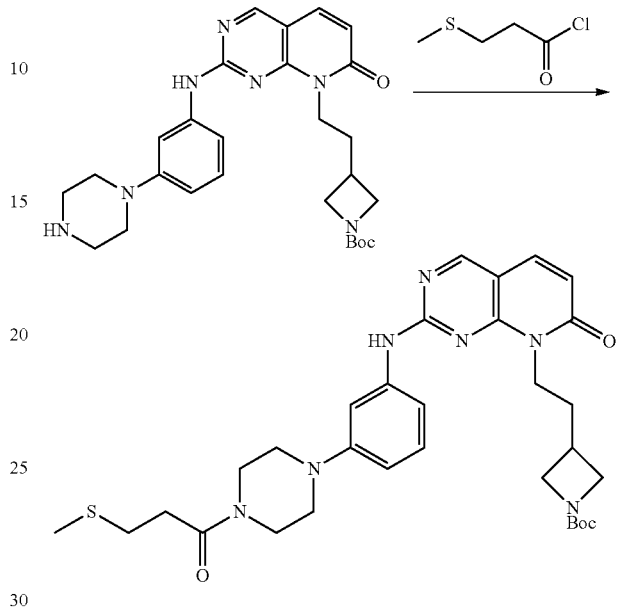

N,N-Diisopropylethylamine (0.180 mL, 1.03 mmol) was added to a solution of tert-butyl 3-(2-(7-oxo-2-((3-(piperazin-1-yl)phenyl)amino)pyrido[2,3-d]pyrimidin-8(7H)-yl)ethyl)azetidine-1-carboxylate in DMF (1 mL), followed by 3-methylthiopropionyl chloride (26.1 µl, 0.226 mmol) and the reaction mixture was stirred at rt for 10 minutes. Water (5 mL) was added and the reaction mixture was extracted with ethyl acetate (3×2 mL). The ethyl acetate extracts were combined, dried over anhydrous sodium sulfate and concentrated in vacuo to yield a crude residue. The crude residue was purified via flash column chromatography using a gradient of 0-100% ethyl acetate in hexane to yield tert-butyl 3-(2-(2-((3-(4-(3-(methylthio)propanoyl)piperazin-1-yl)phenyl)amino)-7-oxopyrido[2,3-d]pyrimidin-8(7H)-yl)ethyl)azetidine-1-carboxylate (113 mg, 0.185 mmol, 90% yield) as a yellow liquid. (m/z): [M+H]$^+$ calcd for $C_{31}H_{42}N_7O_4S$ 608.30 found 608.2.

Preparation 40: 8-(2-(azetidin-3-yl)ethyl)-2-((3-(4-(3-(methylthio)propanoyl)piperazin-1-yl)phenyl)amino)pyrido[2,3-d]pyrimidin-7(8H)-one

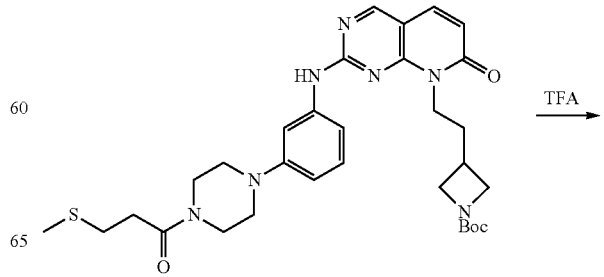

-continued

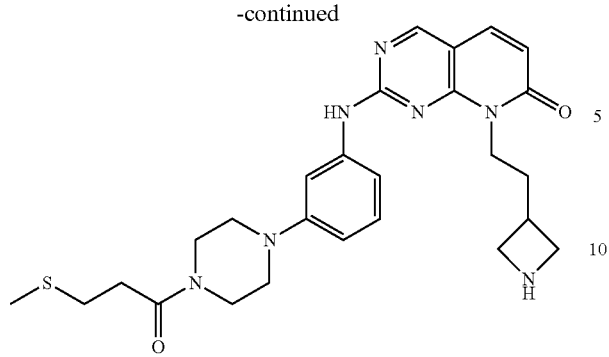

Trifluoroacetic acid (1.0 mL) was added to a solution of tert-butyl 3-(2-(2-((3-(4-(3-(methylthio)propanoyl)piperazin-1-yl)phenyl)amino)-7-oxopyrido[2,3-d]pyrimidin-8(7H)-yl)ethyl)azetidine-1-carboxylate (113 mg, 0.185 mmol) in methylene chloride (1.0 ml) and the reaction mixture was stirred at rt for 1 h. The reaction mixture was concentrated in vacuo to yield 8-(2-(azetidin-3-yl)ethyl)-2-((3-(4-(3-(methylthio)propanoyl)piperazin-1-yl)phenyl)amino)pyrido[2,3-d]pyrimidin-7(8H)-one TFA salt (116 mg, 0.186 mmol, 100% yield). (m/z): [M+H]$^+$ calcd for $C_{26}H_{34}N_7O_2S$ 508.25 found 508.2.

Example 7: 8-(2-(1-acryloylazetidin-3-yl)ethyl)-2-((3-(4-(3-(methylthio)propanoyl)piperazin-1-yl)phenyl)amino)pyrido[2,3-d]pyrimidin-7(8H)-one

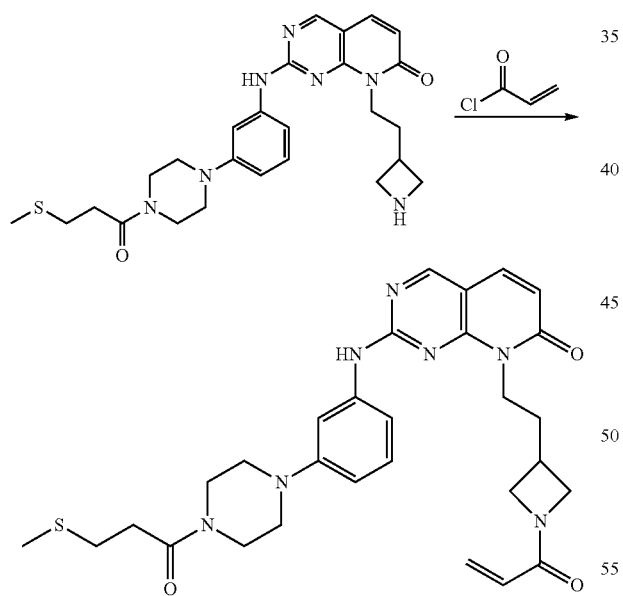

7

N,N-Diisopropylethylamine (0.196 mL, 0.112 mmol) was added to a solution of 8-(2-(azetidin-3-yl)ethyl)-2-((3-(4-(3-(methylthio)propanoyl)piperazin-1-yl)phenyl)amino)pyrido[2,3-d]pyrimidin-7(8H)-one TFA salt (116 mg, 0.186 mmol) in DMF (1 mL) at rt, followed by acryloyl chloride (13.6 μl, 0.168 mmol) and the reaction mixture was stirred at rt for 10 minutes. The reaction mixture was concentrated in vacuo to yield a crude mixture. The crude mixture was purified via preparatory scale C18 column chromatography using a gradient of 10-80% acetonitrile in water with 0.05% trifluoroacetic acid to yield 8-(2-(1-acryloylazetidin-3-yl)ethyl)-2-((3-(4-(3-(methylthio)propanoyl)piperazin-1-yl)phenyl)amino)pyrido[2,3-d]pyrimidin-7(8H)-one, TFA salt (39.0 mg, 0.0577 mmol, 52% yield) as a yellow solid. (m/z): [M+H]$^+$ calcd for $C_{29}H_{36}N_7O_3S$ 562.26 found 562.2.

Example 8: 8-(2-(1-acryloylazetidin-3-yl)ethyl)-2-(((6-(4-methylpiperazin-1-yl)pyridin-3-yl)amino)pyrido[2,3-d]pyrimidin-7(8H)-one

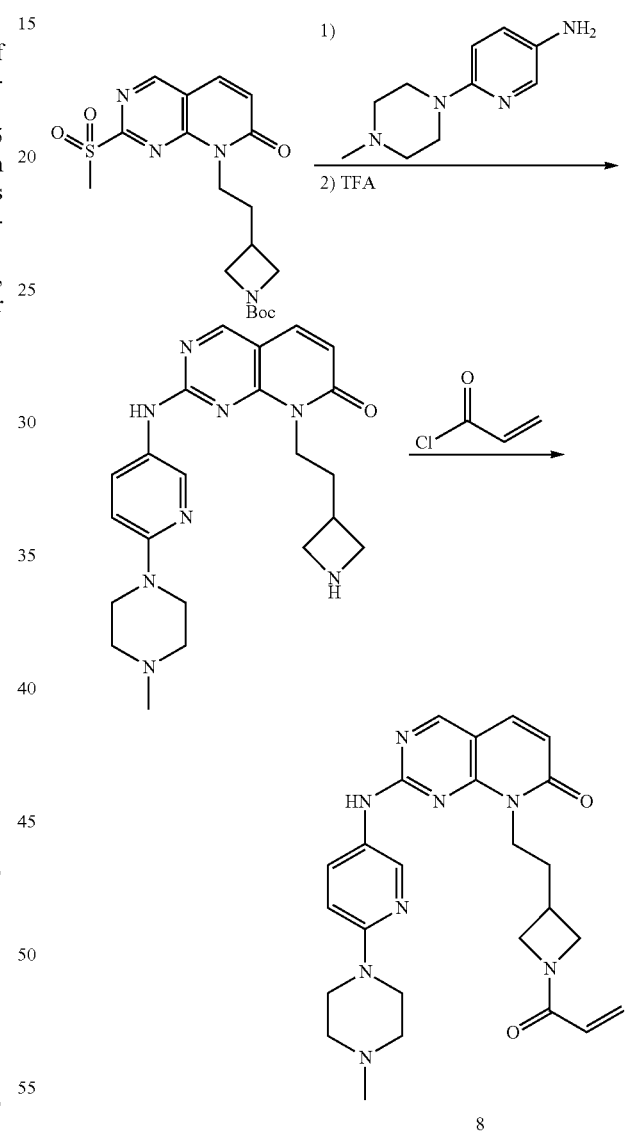

8

Trifluoroacetic acid (0.226 mL) was added to a solution of tert-butyl 3-(2-(2-(methylsulfonyl)-7-oxopyrido[2,3-d]pyrimidin-8(7H)-yl)ethyl)azetidine-1-carboxylate (200 mg, 0.490 mmol) and 6-(4-methylpiperazino)-3-pyridinamine (188 mg, 0.979 mmol) in dioxane (3.52 mL) and the reaction mixture was stirred at 100° C. for 3 h. The mixture was filtered and the filtered material was washed with methylene chloride. The filtrates were combined and concentrated to yield the crude tert-butyl 3-(2-(2-(((6-(4-methylpiperazin-1- yl)pyridin-3-yl)amino)-7-oxopyrido[2,3-d]pyrimidin-8 (7H)-yl)ethyl)azetidine-1-carboxylate, TFA salt intermediate.

Trifluoroacetic acid (1.22 mL) was added to a solution of the crude tert-butyl 3-(2-(2-((6-(4-methylpiperazin-1-yl) pyridin-3-yl)amino)-7-oxopyrido[2,3-d]pyrimidin-8(7H)-yl)ethyl)azetidine-1-carboxylate, TFA salt intermediate in methylene chloride (1.22 ml) and the reaction mixture was stirred at rt for 30 min. The reaction mixture was concentrated in vacuo to yield the crude 8-(2-(azetidin-3-yl)ethyl)-2-((6-(4-methylpiperazin-1-yl)pyridin-3-yl)amino)pyrido[2,3-d]pyrimidin-7(8H)-one, TFAsalt intermediate.

N,N-Diisopropylethylamine (0.856 ml, 4.90 mmol) was added to a solution of the crude 8-(2-(azetidin-3-yl)ethyl)-2-((6-(4-methylpiperazin-1-yl)pyridin-3-yl)amino)pyrido[2,3-d]pyrimidin-7(8H)-one, TFA salt intermediate in DMF (2.45 mL) at rt, followed by acryloyl chloride (27.9 µl, 0.343 mmol) and the reaction mixture was stirred at rt for 20 minutes. The reaction mixture was concentrated in vacuo to yield a crude mixture. The crude mixture was purified via preparatory scale C18 column chromatography using a gradient of 10-80% acetonitrile in water with 0.05% trifluoroacetic acid to yield 8-(2-(1-acryloylazetidin-3-yl)ethyl)-2-((6-(4-methylpiperazin-1-yl)pyridin-3-yl)amino)pyrido[2,3-d]pyrimidin-7(8H)-one, TFA salt (9.9 mg, 0.0168 mmol, 3% yield) as a yellow solid. (m/z): [M+H]$^+$ calcd for $C_{25}H_{31}N_8O_2$ 475.26 found 475.2.

Preparation 41:
2-(4-methylpiperazin-1-yl)-5-nitrobenzonitrile

Potassium carbonate (2.5 g, 18.06 mmol) and 1-methylpiperazine (662 mg, 6.62 mmol) were added to a solution of 2-fluoro-5-nitrobenzonitrile (1.0 g, 6.02 mmol) in DMF (12 mL) and the reaction mixture was stirred at rt for 30 min. Water was added and the reaction mixture was extracted with methylene chloride. The methylene chloride extracts were combined, washed with water and then a saturated aqueous solution of sodium chloride, dried over sodium sulfate and concentrated in vacuo to yield a crude mixture. The crude mixture was purified via flash column chromatography on neutral alumina using a methylene chloride to yield 2-(4-methylpiperazin-1-yl)-5-nitrobenzonitrile (810 mg, 3.29 mmol, 55% yield). (m/z): [M+H]$^+$ calcd for $C_{12}H_{15}N_4O_2$ 247.12 found 247.08.

Preparation 42:
5-amino-2-(4-methylpiperazin-1-yl)benzonitrile

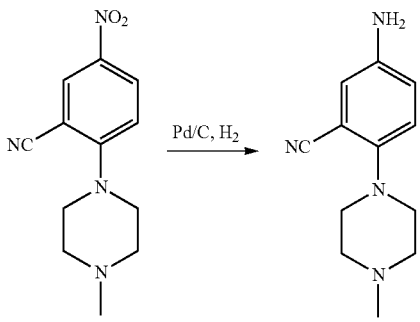 [SMILES: CN1CCN(c2ccc([N+](=O)[O-])cc2C#N)CC1 ; CN1CCN(c2ccc(N)cc2C#N)CC1]

10% Palladium on charcoal (800 mg, 0.752 mmol) was added to a solution of 2-(4-methylpiperazin-1-yl)-5-nitrobenzonitrile (800 mg, 3.25 mmol) in 1:5 THF/isopropanol (30 mL) and the reaction mixture was stirred under an atmosphere of hydrogen for 16 h. The reaction mixture was filtered through Celite, the filtered material was washed with methanol and the combined filtrate was concentrated in vacuo to yield 5-amino-2-(4-methylpiperazin-1-yl)benzonitrile (655 mg, 3.03 mmol, 93% yield). (m/z): [M+H]$^+$ calcd for $C_{12}H_{17}N_4$ 217.15 found 217.27.

Preparation 43: N-(3-cyano-4-(4-methylpiperazin-1-yl)phenyl)formamide

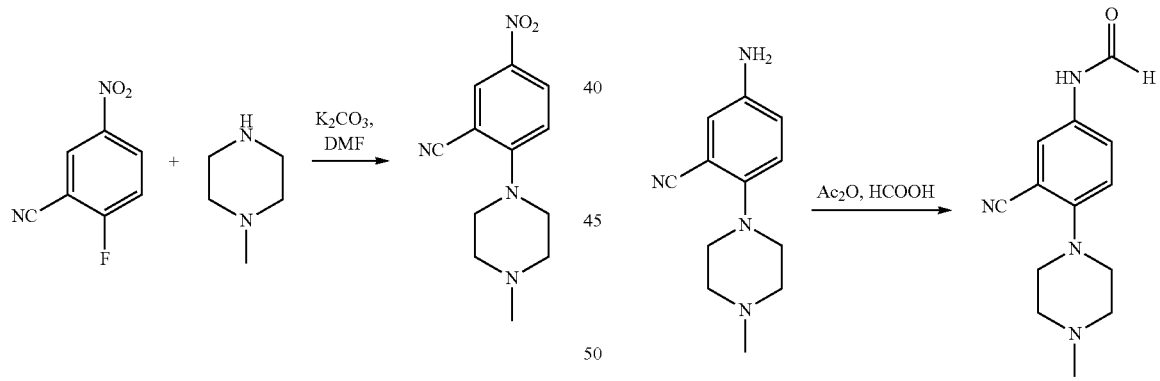

A formylating mixture (previously prepared from acetic anhydride (2.86 mL, 30.0 mmol) and formic acid (1.35 mL, 36.0 mmol), stirred at 70° C. for 1 h) was added dropwise to a solution of 5-amino-2-(4-methylpiperazin-1-yl)benzonitrile (650 mg, 3.00 mmol) in methylene chloride (10 mL) at 0° C. and the reaction mixture was stirred at rt for 1 h. Ethyl acetate was added and the mixture was washed with a saturated aqueous solution of sodium bicarbonate and a saturated aqueous solution of sodium chloride, dried over anhydrous sodium sulfate and concentrated in vacuo to yield a crude mixture. The crude mixture was triturated with n-pentane to yield N-(3-cyano-4-(4-methylpiperazin-1-yl) phenyl)formamide (405 mg, 1.66 mmol, 55% yield). (m/z): [M+H]$^+$ calcd for $C_{13}H_7N_4$ 245.14 found 245.09.

Preparation 44: tert-butyl 3-(2-(2-((3-cyano-4-(4-methylpiperazin-1-yl)phenyl)amino)-7-oxopyrido[2,3-d]pyrimidin-8(7H)-yl)ethyl)azetidine-1-carboxylate

Preparation 45: 5-((8-(2-(azetidin-3-yl)ethyl)-7-oxo-7,8-dihydropyrido[2,3-d]pyrimidin-2-yl)amino)-2-(4-methylpiperazin-1-yl)benzonitrile

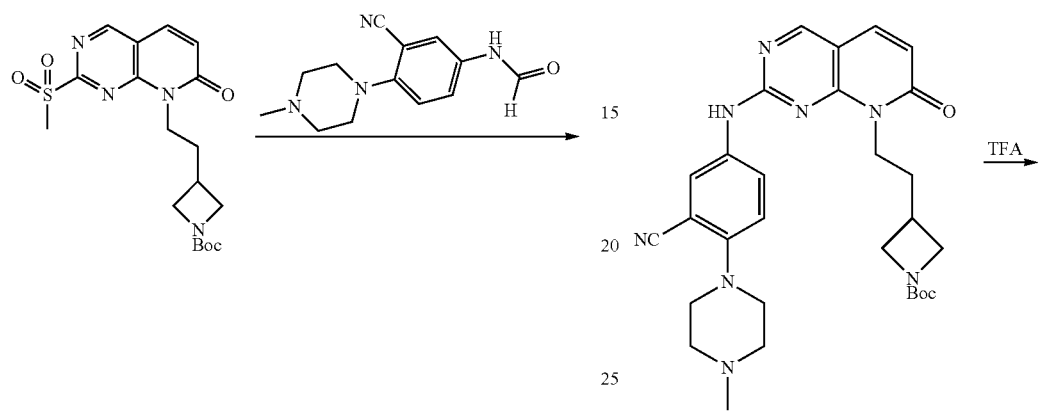

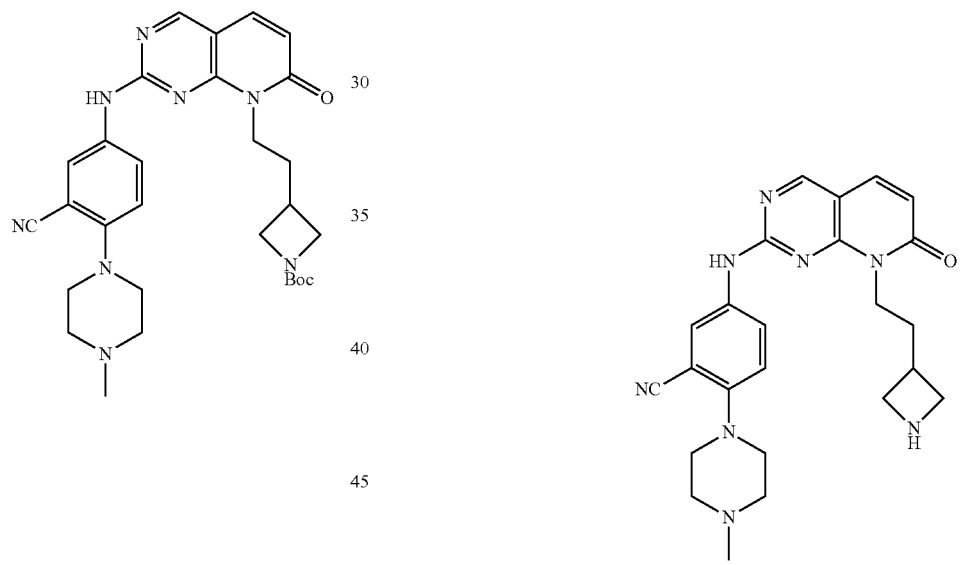

A 1 M solution of potassium bis(trimethylsilyl)amide in THF (0.318 mL, 0.318 mmol) was added to a solution of N-(3-cyano-4-(4-methylpiperazin-1-yl)phenyl)formamide (71.8 mg, 0.294 mmol) in DMF (2.4 mL) and the reaction mixture was stirred at rt for 20 min, upon which tert-butyl 3-(2-(2-(methylthio)-7-oxopyrido[2,3-d]pyrimidin-8(7H)-yl)ethyl)azetidine-1-carboxylate (100 mg, 0.245 mmol) was added and the reaction mixture was stirred at rt for 1 h. Water (10 mL) was added and the reaction mixture was extracted with ethyl acetate (3×5 mL). The ethyl acetate extracts were combined, dried over anhydrous sodium sulfate and concentrated in vacuo to yield a crude residue. The crude residue was purified via flash column chromatography using a gradient of 0-40% methanol in methylene chloride to yield tert-butyl 3-(2-(2-((3-cyano-4-(4-methylpiperazin-1-yl)phenyl)amino)-7-oxopyrido[2,3-d]pyrimidin-8(7H)-yl)ethyl)azetidine-1-carboxylate (117 mg, 0.215 mmol, 88% yield). (m/z): [M+H]$^+$ calcd for $C_{29}H_{37}N_8O_3$ 545.30 found 545.2.

Trifluoroacetic acid (0.5 mL) was added to a solution of tert-butyl 3-(2-(2-((3-cyano-4-(4-methylpiperazin-1-yl)phenyl)amino)-7-oxopyrido[2,3-d]pyrimidin-8(7H)-yl)ethyl)azetidine-1-carboxylate (117 mg, 0.215 mmol) in methylene chloride (0.5 ml) and the reaction mixture was stirred at rt for 20 min. The reaction mixture was concentrated in vacuo to yield 5-((8-(2-(azetidin-3-yl)ethyl)-7-oxo-7,8-dihydropyrido[2,3-d]pyrimidin-2-yl)amino)-2-(4-methylpiperazin-1-yl)benzonitrile, TFA salt (120 mg, 0.215 mmol, 100% yield). (m/z): [M+H]$^+$ calcd for $C_{24}H_{29}N_8O$ 445.25 found 445.2.

Example 9: 5-((8-(2-(1-acryloylazetidin-3-yl)ethyl)-7-oxo-7,8-dihydropyrido[2,3-d]pyrimidin-2-yl)amino)-2-(4-methylpiperazin-1-yl)benzonitrile

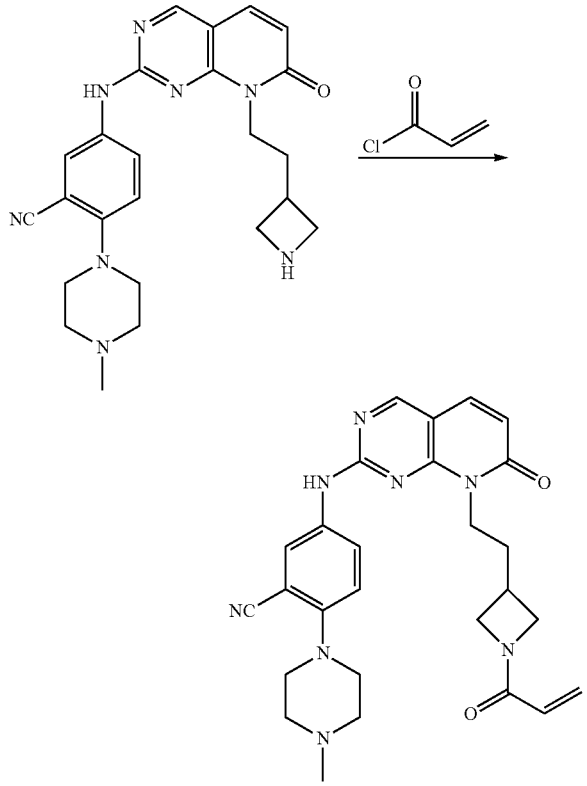

N,N-Diisopropylethylamine (0.209 mL, 1.20 mmol) was added to a solution of 5-((8-(2-(azetidin-3-yl)ethyl)-7-oxo-7,8-dihydropyrido[2,3-d]pyrimidin-2-yl)amino)-2-(4-methylpiperazin-1-yl)benzonitrile, TFA salt (120 mg, 0.215 mmol) in DMF (0.60 mL) at rt, followed by acryloyl chloride (9.2 µl, 0.114 mmol) and the reaction mixture was stirred at rt for 10 minutes. The reaction mixture was concentrated in vacuo to yield a crude mixture. The crude mixture was purified via preparatory scale C18 column chromatography using a gradient of 5-65% acetonitrile in water with 0.05% trifluoroacetic acid to yield 5-((8-(2-(1-acryloylazetidin-3-yl)ethyl)-7-oxo-7,8-dihydropyrido[2,3-d]pyrimidin-2-yl)amino)-2-(4-methylpiperazin-1-yl)benzonitrile, TFA salt (26.3 mg, 0.0429 mmol, 20% yield) as a yellow solid. (m/z): [M+H]$^+$ calcd for $C_{27}H_{31}N_8O_2$ 499.26 found 499.1.

Preparation 46: (R)-2-methyl-1-(4-nitrophenyl)piperazine

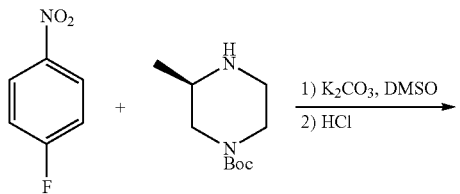

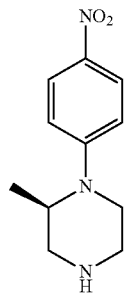

Potassium carbonate (3.9 g, 28.36 mmol) was added to a solution of 1-fluoro-4-nitrobenzene (2.0 g, 14.18 mmol) and tert-butyl (R)-3-methylpiperazine-1-carboxylate (3.4 g, 17.01 mmol) in DMSO (20 mL) and the reaction mixture was stirred at 120° C. for 16 h in a sealed tube. The reaction mixture was diluted with methylene chloride and washed with ice cold water (5×100 mL), dried over sodium sulfate and concentrated in vacuo to yield a crude solid. The crude solid was triturated with diethyl ether to yield the intermediate tert-butyl (R)-3-methyl-4-(4-nitrophenyl)piperazine-1-carboxylate.

4N Hydrochloric acid in dioxane (6 mL, 24 mmol) was added to a solution of the intermediate tert-butyl (R)-3-methyl-4-(4-nitrophenyl)piperazine-1-carboxylate in methylene chloride (15 mL) at 0° C., and the reaction mixture was stirred at rt for 2 h. The reaction mixture was concentrated in vacuo to yield a crude solid. The crude solid was triturated with diethyl ether to yield (R)-2-methyl-1-(4-nitrophenyl)piperazine, HCl salt (1.2 g, 4.66 mmol, 33% yield). (m/z): [M+H]$^+$ calcd for $C_{11}H_{16}N_3O_2$ 222.12 found 222.22.

Preparation 47: (R)-1-(3-methyl-4-(4-nitrophenyl)piperazin-1-yl)ethan-1-one

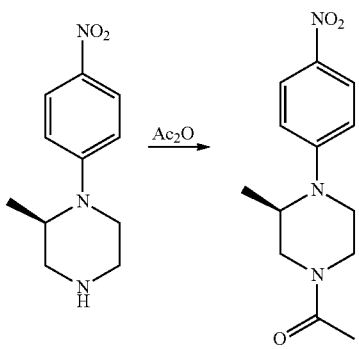 [SMILES: "Ac2O" ; C[C@@H]1CNCCN1c1ccc([N+](=O)[O-])cc1 ; CC(=O)N1CCN(c2ccc([N+](=O)[O-])cc2)[C@H](C)C1]

Triethylamine (1.63 mL, 11.64 mmol) was added to a suspension of (R)-2-methyl-1-(4-nitrophenyl)piperazine, HCl salt (1.0 g, 3.88 mmol) in methylene chloride (12 mL) at 0° C. and the reaction mixture was stirred at 0° C. for 5 min. Acetic anhydride (0.73 mL, 7.77 mmol) was added and the reaction mixture was stirred at rt for 2 h. A saturated aqueous solution of sodium bicarbonate was added and the reaction mixture was extracted with methylene chloride (3×). The methylene chloride extracts were combined, washed with water and a saturated aqueous solution of sodium chloride, dried over anhydrous sodium sulfate and concentrated in vacuo to yield (R)-1-(3-methyl-4-(4-nitrophenyl)piperazin-1-yl)ethan-1-one (1.0 g, 3.80 mmol, 98% yield). (m/z): [M+H]+ calcd for $C_{13}H_{18}N_3O_3$ 264.13 found 264.27.

Preparation 48: (R)-1-(4-(4-aminophenyl)-3-methylpiperazin-1-yl)ethan-1-one

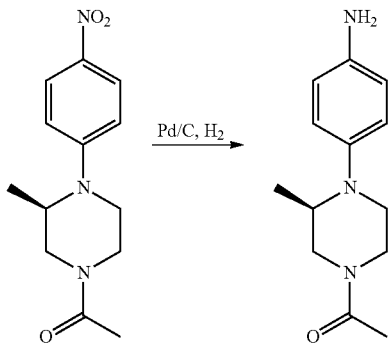

10% Palladium on charcoal (500 mg, 0.470 mmol) was added to a solution of (R)-1-(3-methyl-4-(4-nitrophenyl) piperazin-1-yl)ethan-1-one (1.0 g, 3.80 mmol) in 1:4 THF/ isopropanol (20 mL) and the reaction mixture was stirred under an atmosphere of hydrogen for 2 h. The reaction mixture was filtered through Celite, and the filtrate was concentrated in vacuo to yield (R)-1-(4-(4-aminophenyl)-3-methylpiperazin-1-yl)ethan-1-one (0.80 g, 3.43 mmol, 90% yield).

Preparation 49: (R)—N-(4-(4-acetyl-2-methylpiperazin-1-yl)phenyl)formamide

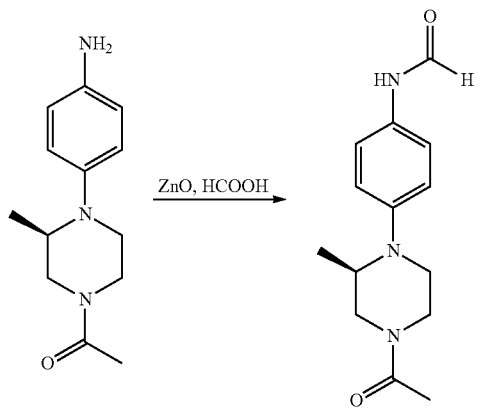

Formic acid (0.64 mL, 17.15 mmol) was added to a mixture of zinc oxide (140 mg, 1.71 mmol) and (R)-1-(4-(4-aminophenyl)-3-methylpiperazin-1-yl)ethan-1-one (800 mg, 3.43 mmol) at 0° C., and the reaction mixture was stirred at 70° C. for 1 hour. Methylene chloride was added and the reaction mixture was washed with a saturated aqueous solution of sodium bicarbonate, water and a saturated aqueous solution of sodium chloride, dried over anhydrous sodium sulfate and concentrated in vacuo to yield (R)—N-(4-(4-acetyl-2-methylpiperazin-1-yl)phenyl)formamide (800 mg, 3.06 mmol, 89% yield) as a viscous dark brown liquid.

Preparation 50: tert-butyl (R)-3-(2-(2-((4-(4-acetyl-2-methylpiperazin-1-yl)phenyl)amino)-7-oxopyrido [2,3-d]pyrimidin-8(7H)-yl)ethyl)azetidine-1-carboxylate

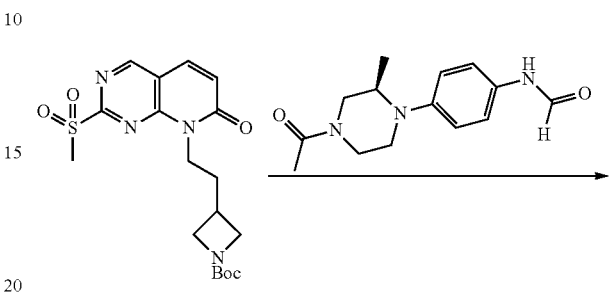

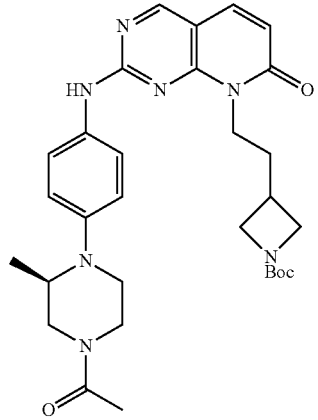

A 1 M solution of lithium bis(trimethylsilyl)amide in THF (3.20 mL, 3.20 mmol) was added to a solution of (R)—N-(4-(4-acetyl-2-methylpiperazin-1-yl)phenyl)formamide (700 mg, 2.69 mmol) in toluene (10 mL) and the reaction mixture was stirred at rt for 15 min, upon which a solution of tert-butyl 3-(2-(2-(methylthio)-7-oxopyrido[2,3-d]pyrimidin-8(7H)-yl)ethyl)azetidine-1-carboxylate (1.10 g, 2.69 mmol) in THF (6 mL) was added and the reaction mixture was stirred at rt for 1 h. Methanol (15 mL) was added and the reaction mixture was stirred at rt for 30 min. The reaction mixture was concentrated in vacuo to yield a crude residue. The crude residue was dissolved in ethyl acetate and the resulting solution was washed with water and a saturate aqueous solution of sodium chloride, dried over anhydrous sodium sulfate and concentrated in vacuo to yield a crude residue. The crude residue was triturated with ether and hexane to yield tert-butyl (R)-3-(2-(2-((4-(4-acetyl-2-methylpiperazin-1-yl)phenyl)amino)-7-oxopyrido[2,3-d] pyrimidin-8(7H)-yl)ethyl)azetidine-1-carboxylate (1.0 g, 1.78 mmol, 66% yield). (m/z): [M+H]+ calcd for $C_{30}H_{40}N_7O_4$ 562.31 found 562.44.

91

Preparation 51: (R)-2-((4-(4-acetyl-2-methylpiper-azin-1-yl)phenyl)amino)-8-(2-(azetidin-3-yl)ethyl)pyrido[2,3-d]pyrimidin-7(8H)-one

92

Example 10: (R)-2-((4-(4-acetyl-2-methylpiperazin-1-yl)phenyl)amino)-8-(2-(1-acryloylazetidin-3-yl)ethyl)pyrido[2,3-d]pyrimidin-7(8H)-one

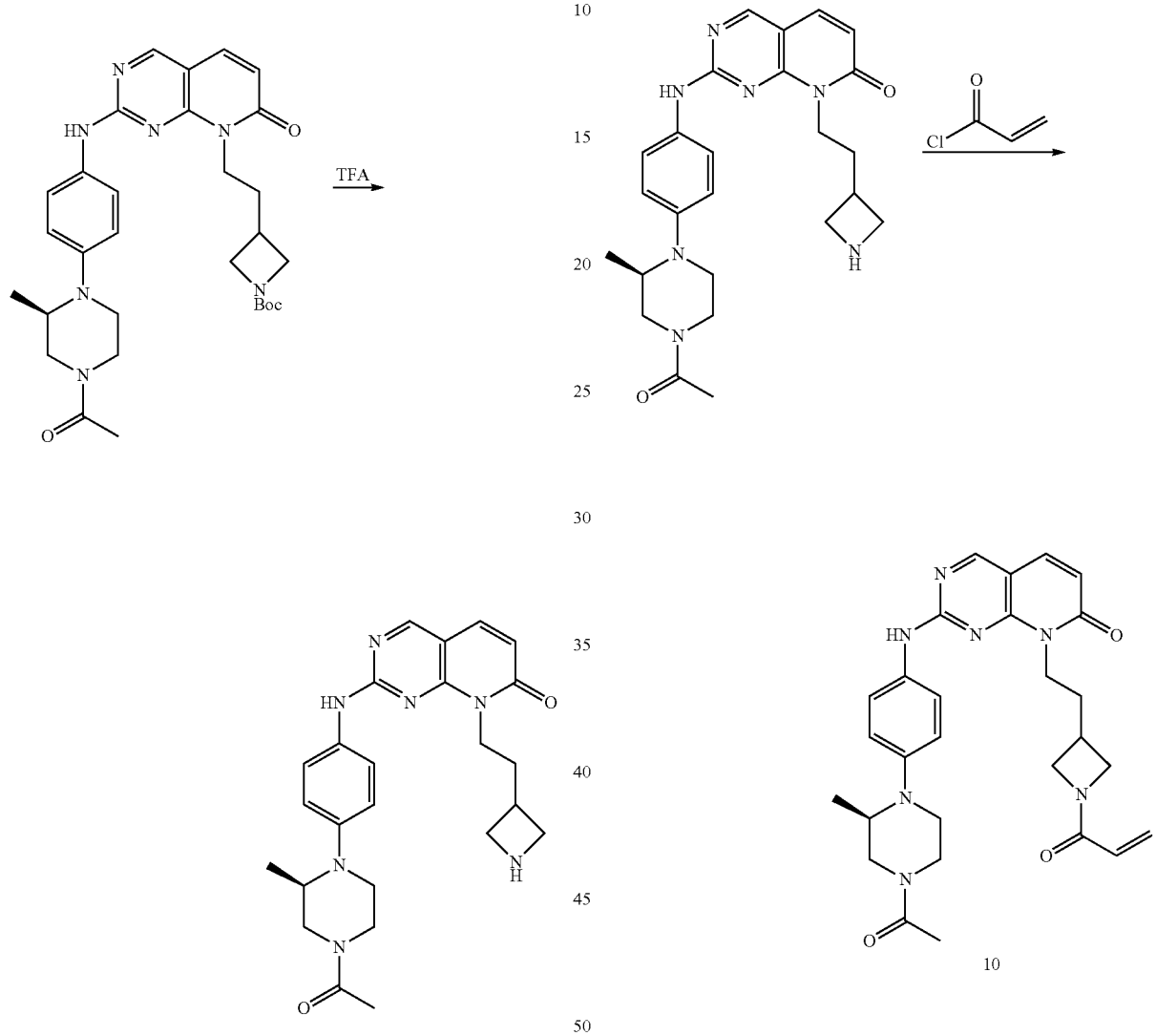

Trifluoroacetic acid (0.5 mL) was added to a solution of tert-butyl (R)-3-(2-(2-((4-(4-acetyl-2-methylpiperazin-1-yl)phenyl)amino)-7-oxopyrido[2,3-d]pyrimidin-8(7H)-yl)ethyl)azetidine-1-carboxylate (33.0 mg, 0.059 mmol) in methylene chloride (0.5 ml) and the reaction mixture was stirred at rt for 20 min. The reaction mixture was concentrated in vacuo to yield (R)-2-((4-(4-acetyl-2-methylpiperazin-1-yl)phenyl)amino)-8-(2-(azetidin-3-yl)ethyl)pyrido[2,3-d]pyrimidin-7(8H)-one, TFA salt (34.0 mg, 0.059 mmol, 100% yield). (m/z): [M+H]$^+$ calcd for $C_{25}H_{32}N_7O_2$ 462.26 found 462.2.

N,N-Diisopropylethylamine (0.090 mL, 0.516 mmol) was added to a solution of (R)-2-((4-(4-acetyl-2-methylpiperazin-1-yl)phenyl)amino)-8-(2-(azetidin-3-yl)ethyl)pyrido[2,3-d]pyrimidin-7(8H)-one, TFA salt (34.0 mg, 0.059 mmol) in DMF (0.43 mL) at rt, followed by acryloyl chloride (6.3 μl, 0.077 mmol) and the reaction mixture was stirred at rt for 5 minutes. The reaction mixture was concentrated in vacuo to yield a crude mixture. The crude mixture was purified via preparatory scale C18 column chromatography using a gradient of 5-75% acetonitrile in water with 0.05% trifluoroacetic acid to yield (R)-2-((4-(4-acetyl-2-methylpiperazin-1-yl)phenyl)amino)-8-(2-(1-acryloylazetidin-3-yl)ethyl)pyrido[2,3-d]pyrimidin-7(8H)-one, TFA salt (16.0 mg, 0.0254 mmol, 43% yield) as a yellow solid. (m/z): [M+H]$^+$ calcd for $C_{28}H_{34}N_7O_3$ 516.27 found 516.0.

Preparation 52: Ethyl (E)-3-(4,6-dichloropyridin-3-yl)acrylate

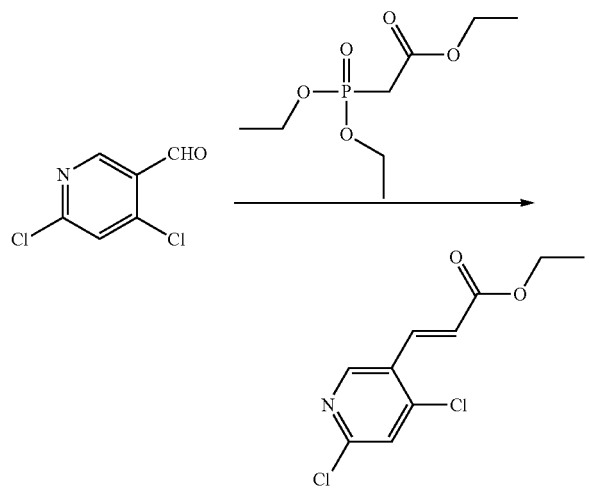

A 60% dispersion of sodium hydride in mineral oil (750 mg, 18.8 mmol) was added to a solution of ethyl 2-(diethoxyphosphoryl)acetate (2.81 g, 12.56 mmol) in THF (20 mL) at 0° C. and the reaction mixture was stirred at 0° C. for 2 h. 4,6-dichloronicotinaldehyde (2.0 g, 11.42 mmol) was added and the reaction mixture was stirred at 0° C. for 2 h. Water was added and the mixture was extracted with ethyl acetate. The ethyl acetate extract was dried over anhydrous sodium sulfate and concentrated in vacuo to yield a crude residue. The crude residue was purified via flash column chromatography using a gradient of 5-15% ethyl acetate in hexane to yield ethyl (E)-3-(4,6-dichloropyridin-3-yl)acrylate (2.2 g, 8.94 mmol, 78% yield). (m/z): [M+H]$^+$ calcd for $C_{10}H_{10}C_2NO_2$ 246.01 found 246.16.

Preparation 53: tert-butyl (E)-3-(2-((2-chloro-5-(3-ethoxy-3-oxoprop-1-en-1-yl)pyridin-4-yl)amino)ethyl)azetidine-1-carboxylate

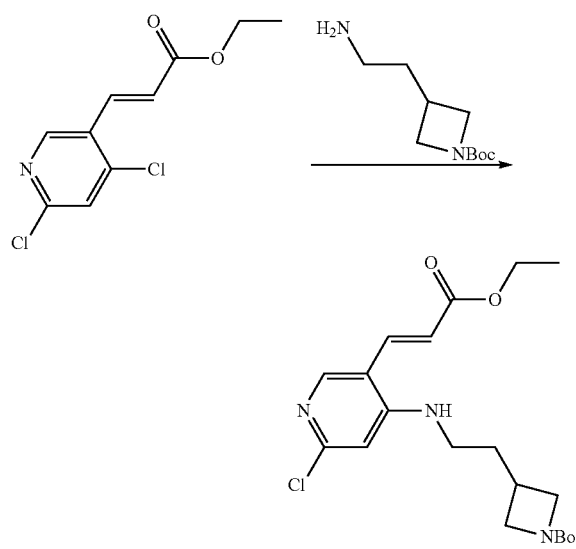

tert-Butyl 3-(2-aminoethyl)azetidine-1-carboxylate (1.7 g, 8.45 mmol) was added to a solution of ethyl (E)-3-(4,6-dichloropyridin-3-yl)acrylate (1.6 g, 6.5 mmol) in DMSO (20 mL), followed by N,N-Diisopropylethylamine (3.40 mL, 19.5 mmol) and the reaction mixture was stirred at 130° C. for 16 h. Water was added and the reaction mixture was extracted with ethyl acetate. The ethyl acetate extracts were combined, washed with water and a saturate aqueous solution of sodium chloride, dried over anhydrous sodium sulfate and concentrated in vacuo to yield a crude residue. The crude residue was purified via flash column chromatography using a gradient of 30-40% ethyl acetate in hexane to yield tert-butyl(E)-3-(2-((2-chloro-5-(3-ethoxy-3-oxoprop-1-en-1-yl)pyridin-4-yl)amino)ethyl)azetidine-1-carboxylate (1.15 g, 2.81 mmol, 43% yield). (m/z): [M+H]$^+$ calcd for $C_{20}H_{29}ClN_3O_4$ 410.18 found 410.26.

Preparation 54: tert-butyl 3-(2-(7-chloro-2-oxo-1,6-naphthyridin-1(2H)-yl)ethyl)azetidine-1-carboxylate

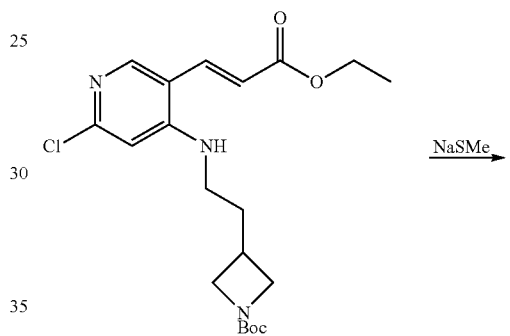

Sodium thiomethoxide (340 mg, 4.87 mmol) was added to a solution of tert-butyl (E)-3-(2-((2-chloro-5-(3-ethoxy-3-oxoprop-1-en-1-yl)pyridin-4-yl)amino)ethyl)azetidine-1-carboxylate (2.0 g, 4.87 mmol) in ethanol (20 mL) and the reaction mixture was stirred at rt for 15 min. Water was added and the mixture was extracted with ethyl acetate (3×). The ethyl acetate extracts were combined and washed with water and a saturated aqueous solution of sodium chloride, dried over anhydrous sodium sulfate and concentrated in vacuo to yield a crude residue. The crude residue was purified via flash column chromatography using 2% methanol in methylene chloride to yield tert-butyl 3-(2-(7-chloro-2-oxo-1,6-naphthyridin-1(2H)-yl)ethyl)azetidine-1-carboxylate (800 mg, 2.20 mmol, 45% yield). (m/z): [M+H]$^+$ calcd for $C_{18}H_{23}ClN_3O_3$ 364.14 found 364.25.

Preparation 55: 1-methyl-4-(6-nitropyridin-3-yl)piperazine

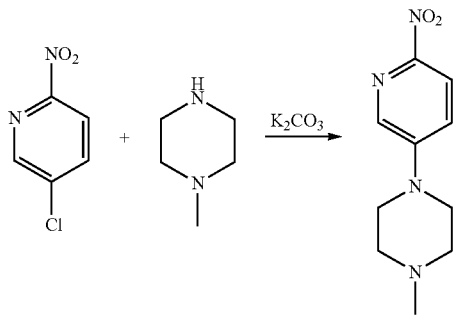

Potassium carbonate (650 mg, 4.71 mmol) was added to a solution of 5-chloro-2-nitropyridine (500 mg, 3.14 mmol) in DMF (5.0 mL) followed by 1-methylpiperazine (314 mg, 314 mmol) and the reaction mixture was stirred at 70° C. for 3 h. Water was added and the mixture was extracted with ethyl acetate (3×). The ethyl acetate extracts were combined and washed with water and a saturated aqueous solution of sodium chloride, dried over anhydrous sodium sulfate and concentrated in vacuo to yield a crude residue. The crude residue was triturated with diethyl ether and hexane to yield 1-methyl-4-(6-nitropyridin-3-yl)piperazine (0.520 mg, 2.34 mmol, 75% yield). (m/z): [M+H]$^+$ calcd for $C_{10}H_{15}N_4O_2$ 223.12 found 223.25.

Preparation 56: 5-(4-methylpiperazin-1-yl)pyridin-2-amine

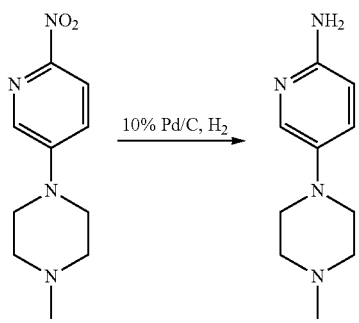

10% palladium on carbon (500 mg, 0.47 mmol) was added to a solution of 1-methyl-4-(6-nitropyridin-3-yl)piperazine (0.500 mg, 2.24 mmol) in ethyl acetate (20.0 mL) and the reaction mixture was stirred under an atmosphere of hydrogen for 16 h. The reaction mixture was filtered through Celite and the filtrate was concentrated in vacuo to yield 5-(4-methylpiperazin-1-yl)pyridin-2-amine (300 mg, 1.56 mmol, 69% yield).

Preparation 57: tert-butyl 3-(2-(7-((5-(4-methylpiperazin-1-yl)pyridin-2-yl)amino)-2-oxo-1,6-naphthyridin-1(2H)-yl)ethyl)azetidine-1-carboxylate

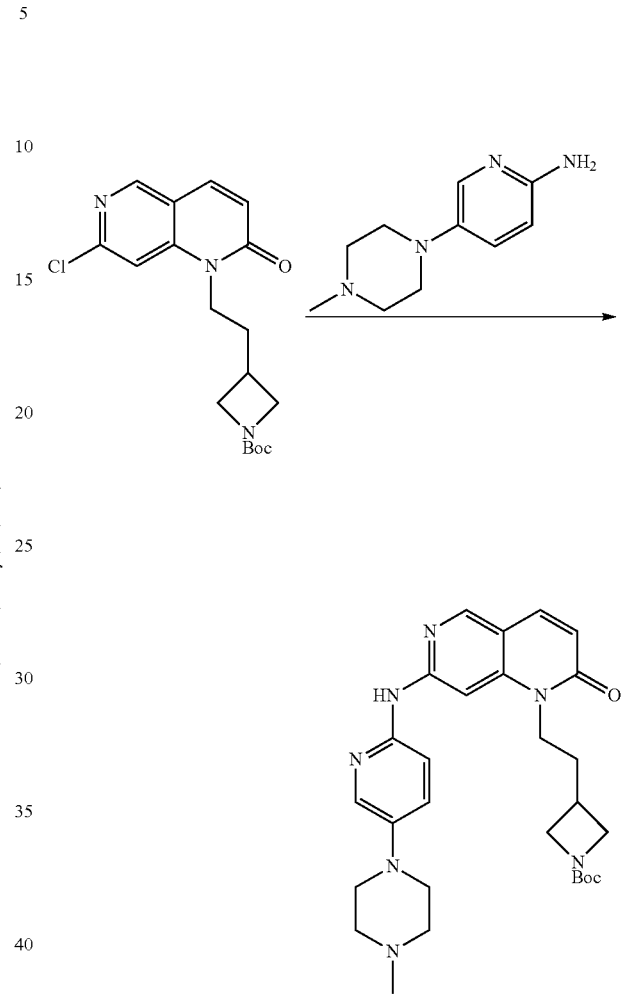

5-(4-Methylpiperazin-1-yl)pyridin-2-amine (158 mg, 0.826 mmol) was added to a solution of tert-butyl 3-(2-(7-chloro-2-oxo-1,6-naphthyridin-1(2H)-yl)ethyl)azetidine-1-carboxylate (300 mg, 0.826 mmol) in toluene (10.0 mL) followed by cesium carbonate (807 mg, 2.47 mmol) and Brettphos Pd Gi (65 mg, 0.086 mmol) and the reaction mixture was stirred at 100° C. for 4 h in a sealed tube. Water was added and the mixture was extracted with ethyl acetate (3×). The ethyl acetate extracts were combined and washed with a saturated aqueous solution of sodium chloride, dried over anhydrous sodium sulfate and concentrated in vacuo to yield a crude residue. The crude residue was purified via flash column chromatography using 80% ethyl acetate in hexane to yield tert-butyl 3-(2-(7-((5-(4-methylpiperazin-1-yl)pyridin-2-yl)amino)-2-oxo-1,6-naphthyridin-1(2H)-yl)ethyl)azetidine-1-carboxylate (0.250 mg, 0.481 mmol, 58% yield). (m/z): [M+H]$^+$ calcd for $C_{28}H_{38}N_7O_3$ 520.30 found 520.35.

Preparation 58: 1-(2-(azetidin-3-yl)ethyl)-7-((5-(4-methylpiperazin-1-yl)pyridin-2-yl)amino)-1,6-naphthyridin-2(1H)-one

Example 11: (E)-1-(2-(1-(4-(dimethylamino)but-2-enoyl)azetidin-3-yl)ethyl)-7-((5-(4-methylpiperazin-1-yl)pyridin-2-yl)amino)-1,6-naphthyridin-2(1H)-one

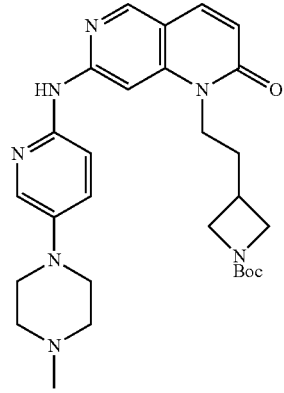

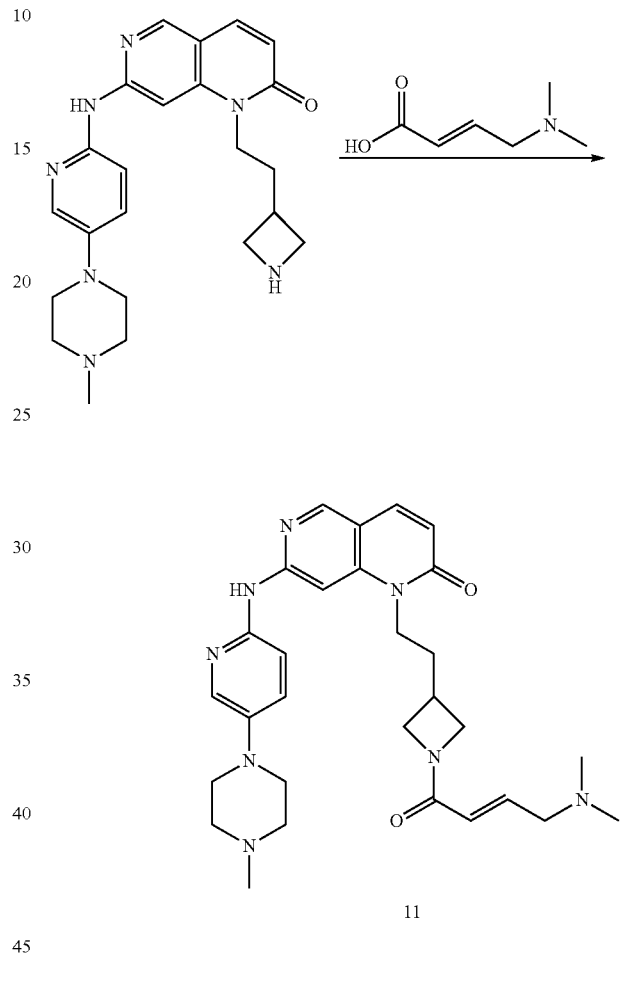

Trifluoroacetic acid (2.0 mL) was added to a solution of tert-butyl 3-(2-(7-((5-(4-methylpiperazin-1-yl)pyridin-2-yl)amino)-2-oxo-1,6-naphthyridin-1(2H)-yl)ethyl)azetidine-1-carboxylate (0.250 mg, 0.481 mmol) in methylene chloride (10.0 ml) and the reaction mixture was stirred at rt for 3 h. The reaction mixture was concentrated in vacuo to yield a crude solid. The crude solid was triturated with diethyl ether, methylene chloride and acetonitrile to yield 1-(2-(azetidin-3-yl)ethyl)-7-((5-(4-methylpiperazin-1-yl)pyridin-2-yl)amino)-1,6-naphthyridin-2(1H)-one, TFA salt (170 mg, 0.405 mmol, 84% yield). (m/z): [M+H]$^+$ calcd for $C_{23}H_{30}N_7O$ 420.25 found 420.31.

1-[Bis(dimethylamino)methylene]-1H-1,2,3-triazolo[4,5-b]pyridinium 3-oxide hexafluorophosphate (38.1 mg, 0.100 mmol) was added to a solution of (2E)-4-(dimethylamino)but-2-enoic acid hydrochloride (17.27 mg, 0.104 mmol) in DMF (1 mL) and the reaction mixture was stirred at rt for 5 minutes. 1-(2-(azetidin-3-yl)ethyl)-7-((5-(4-methylpiperazin-1-yl)pyridin-2-yl)amino)-1,6-naphthyridin-2(1H)-one, TFA salt (35.0 mg, 0.083 mmol) was added followed by N,N-diisopropylethylamine (0.073 mL, 0.417 mmol) and the reaction mixture was stirred at rt overnight. The reaction mixture was concentrated in vacuo to yield a crude mixture. The crude mixture was purified via preparatory scale C18 column chromatography using a gradient of 2-50% acetonitrile in water with 0.05% trifluoroacetic acid to yield ((E)-1-(2-(1-(4-(dimethylamino)but-2-enoyl)azetidin-3-yl)ethyl)-7-((5-(4-methylpiperazin-1-yl)pyridin-2-yl)amino)-1,6-naphthyridin-2(1H)-one, TFA salt (9.2 mg, 0.0143 mmol, 17% yield) as a yellow solid. (m/z): [M+H]$^+$ calcd for $C_{28}H_{34}N_7O_3$ 531.31 found 531.3.

Preparation 59: 8-(2-hydroxyethyl)-2-(methylthio)pyrido[2,3-d]pyrimidin-7(8H)-one

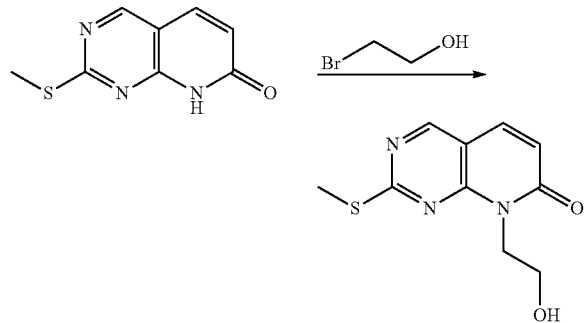

A 60% dispersion of sodium hydride in mineral oil (5.9 g, 147.66 mmol) was added to a solution of 2-(methylthio)pyrido[2,3-d]pyrimidin-7(8H)-one (19.0 g, 98.44 mmol) in DMF (160 mL) at 0° C. and the reaction mixture was stirred at rt for 20 min. 2-bromoethanol (13.86 mL, 196.9 mmol) was added dropwise at 0° C., and the reaction mixture was stirred at rt for 16 h. Water was added and the resulting white precipitate was filtered and washed with diethyl ether to yield 8-(2-hydroxyethyl)-2-(methylthio)pyrido[2,3-d]pyrimidin-7(8H)-one (19.0 g, 80.1 mmol, 81% yield) as a white solid. (m/z): [M+H]$^+$ calcd for $C_{10}H_2N_3O_2S$ 238.07 found 238.16.

Preparation 60: 8-(2-chloroethyl)-2-(methylthio)pyrido[2,3-d]pyrimidin-7(8H)-one

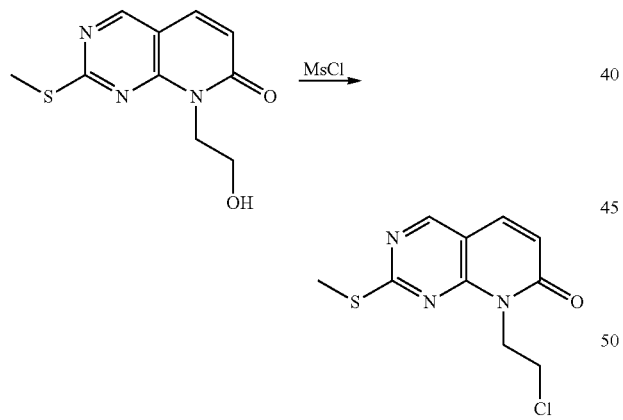

Triethylamine (25.8 mL, 183.3 mmol) was added to a solution of 8-(2-hydroxyethyl)-2-(methylthio)pyrido[2,3-d]pyrimidin-7(8H)-one (14.5 g, 61.1 mmol) in methylene chloride (150 mL) at 0° C. followed by the slow addition of methanesulfonyl chloride (5.7 mL, 73.4 mmol), and the reaction mixture was stirred at rt for 24 h. Water was added and the mixture was extracted with 5% methanol in methylene chloride (3×). The organic extracts were combined and washed with water and a saturated aqueous solution of sodium chloride, dried over anhydrous sodium sulfate and concentrated in vacuo to yield a crude residue. The crude residue was purified via flash column chromatography using a gradient of 25-30% ethyl acetate in hexane to yield 8-(2-chloroethyl)-2-(methylthio)pyrido[2,3-d]pyrimidin-7(8H)-one (10.05 mg, 39.3 mmol, 64% yield). (m/z): [M+H]$^+$ calcd for $C_{10}H_{11}ClN_3OS$ 256.03 found 256.17.

Preparation 61: 8-(2-chloroethyl)-2-(methylsulfonyl)pyrido[2,3-d]pyrimidin-7(8H)-one

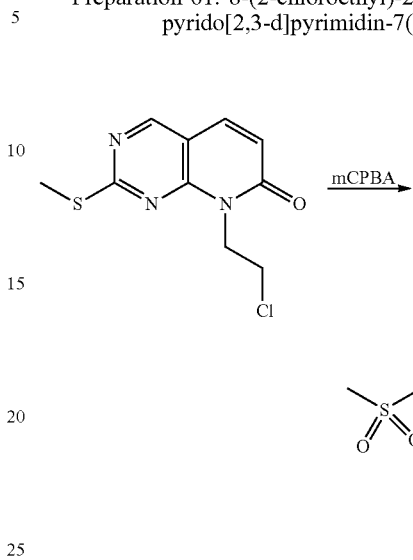

m-CPBA (33.8 g, 195.5 mmol) was added to a solution of 8-(2-chloroethyl)-2-(methylthio)pyrido[2,3-d]pyrimidin-7(8H)-one (10.0 mg, 39.1 mmol) in methylene chloride (120 mL) at 0° C. and the reaction mixture was stirred at rt for 2 h. A saturated aqueous solution of sodium bicarbonate was added and the mixture was extracted with methylene chloride. The methylene chloride extracts were combined and washed with a saturated aqueous solution of sodium bicarbonate (2×) and a saturated aqueous solution of sodium chloride, dried over anhydrous sodium sulfate and concentrated in vacuo to yield a crude mixture. The mixture was triturated with acetonitrile and diethyl ether to yield 8-(2-chloroethyl)-2-(methylsulfonyl)pyrido[2,3-d]pyrimidin-7(8H)-one (6.75 g, 23.5 mmol, 60% yield). (m/z): [M+H]$^+$ calcd for $C_{10}H_{11}ClN_3O_3S$ 288.02 found 287.99.

Preparation 62: 8-(2-chloroethyl)-2-((1-methyl-1H-pyrazol-4-yl)amino)pyrido[2,3-d]pyrimidin-7(8H)-one

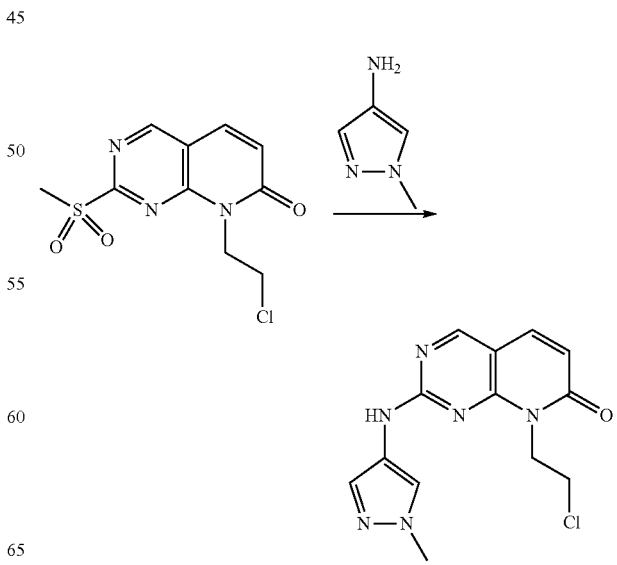

Trifluoroacetic acid (1.21 mL, 15.6 mmol) was added to a solution of (8-(2-chloroethyl)-2-(methylsulfonyl)pyrido[2,3-d]pyrimidin-7(8H)-one (1.00 g, 3.48 mmol) and 1-methyl-1H-pyrazol-4-amine (0.450 mL, 4.17 mmol) in dioxane (15 mL) and the reaction mixture was stirred at 100° C. for 1 h. The reaction mixture was concentrated in vacuo to yield a crude residue. Water was added to the crude residue and the mixture was extracted with methylene chloride (3×). The methylene chloride extracts were combined, washed with water and a saturated aqueous solution of sodium chloride, dried over anhydrous sodium sulfate and concentrated in vacuo to yield a crude mixture. The crude mixture was purified via flash column chromatography using a gradient of 20-100% ethyl acetate in hexane to yield 8-(2-chloroethyl)-2-((1-methyl-1H-pyrazol-4-yl)amino)pyrido[2,3-d]pyrimidin-7(8H)-one (340 mg, 1.12 mmol, 32% yield) as an orange solid. (m/z): [M+H]$^+$ calcd for $C_{13}H_{14}ClN_6O$ 305.09 found 304.9.

Example 12: (S)-8-(2-(4-acryloyl-2-ethylpiperazin-1-yl)ethyl)-2-((1-methyl-1H-pyrazol-4-yl)amino)pyrido[2,3-d]pyrimidin-7(8H)-one

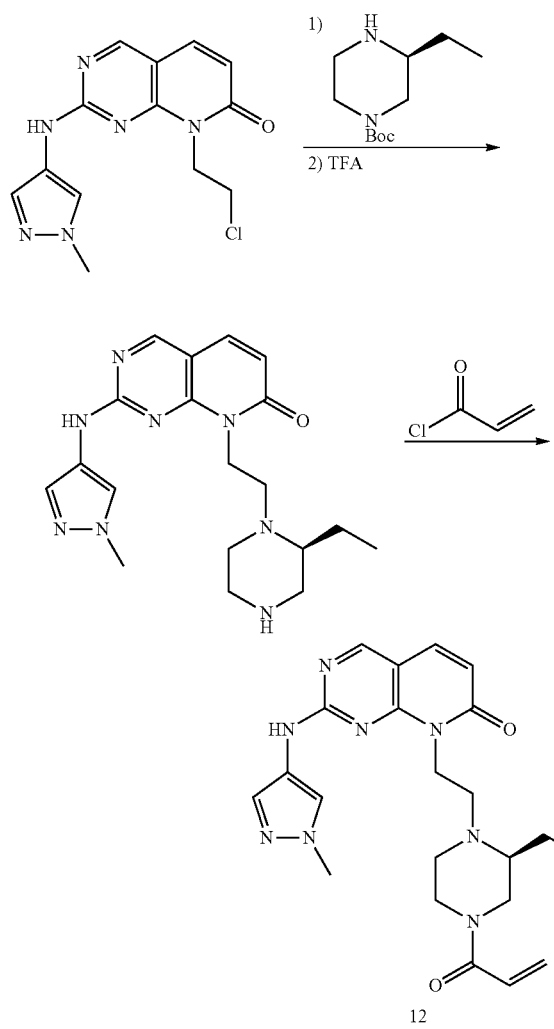

12 tert-Butyl (S)-3-ethylpiperazine-1-carboxylate (0.372 ml, 1.562 mmol) was added to a solution of 8-(2-chloroethyl)-2-((1-methyl-H-pyrazol-4-yl)amino)pyrido[2,3-d]pyrimidin-7(8H)-one (340 mg, 1.12 mmol) in acetonitrile (12 mL), followed by potassium carbonate (463 mg, 3.35 mmol) and the reaction mixture was stirred at 80° C. for 3 h. The reaction mixture was concentrated in vacuo to yield a crude mixture. The crude mixture was purified via flash column chromatography using a gradient of 0-15% methanol in methylene chloride to yield the intermediate tert-butyl (S)-3-ethyl-4-(2-(2-((1-methyl-1H-pyrazol-4-yl)amino)-7-oxopyrido[2,3-d]pyrimidin-8(7H)-yl)ethyl)piperazine-1-carboxylate.

Trifluoroacetic acid (3.0 mL, 38.9 mmol) was added to a solution of the intermediate tert-butyl (S)-3-ethyl-4-(2-(2-((1-methyl-H-pyrazol-4-yl)amino)-7-oxopyrido[2,3-d]pyrimidin-8(7H)-yl)ethyl)piperazine-1-carboxylate in methylene chloride (3.0 mL) and the reaction mixture was stirred at rt for 70 min. The reaction mixture was concentrated in vacuo to yield the intermediate (S)-8-(2-(2-ethylpiperazin-1-yl)ethyl)-2-((1-methyl-1H-pyrazol-4-yl)amino)pyrido[2,3-d]pyrimidin-7(8H)-one.

N,N-Diisopropylethylamine (0.904 mL, 0.518 mmol) was added to a solution of the intermediate (S)-8-(2-(2-ethylpiperazin-1-yl)ethyl)-2-((1-methyl-H-pyrazol-4-yl)amino)pyrido[2,3-d]pyrimidin-7(8H)-one in DMF (0.43 mL) at 0° C., followed by acryloyl chloride (85.0 µl, 1.05 mmol) and the reaction mixture was stirred at rt for 5 minutes. The reaction mixture was concentrated in vacuo to yield a crude mixture. The crude mixture was purified via preparatory scale C18 column chromatography using a gradient of 10-50% acetonitrile in water with 0.05% trifluoroacetic acid to yield (S)-8-(2-(4-acryloyl-2-ethylpiperazin-1-yl)ethyl)-2-((1-methyl-H-pyrazol-4-yl)amino)pyrido[2,3-d]pyrimidin-7(8H)-one, TFA salt (22.5 mg, 0.0409 mmol, 4% yield) as a yellow solid. (m/z): [M+H]$^+$ calcd for $C_{22}H_{29}N_8O_2$ 437.24 found 437.2.

Example 13: 8-(2-(1-acryloylazetidin-3-yl)ethyl)-2-((4-(4-(2-(methylthio)acetyl)piperazin-1-yl)phenyl)amino)pyrido[2,3-d]pyrimidin-7(8H)-one

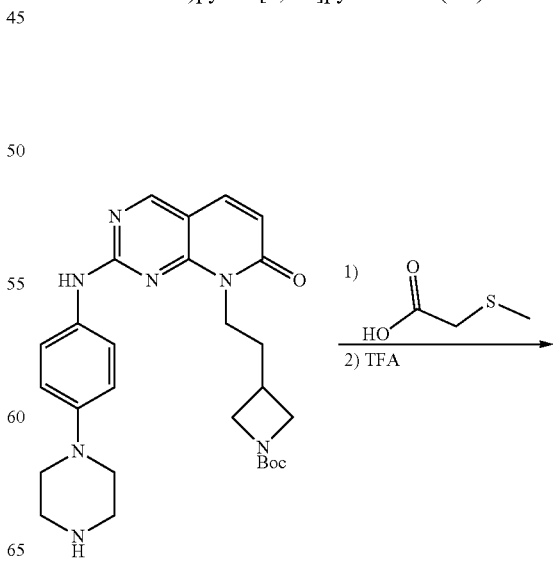

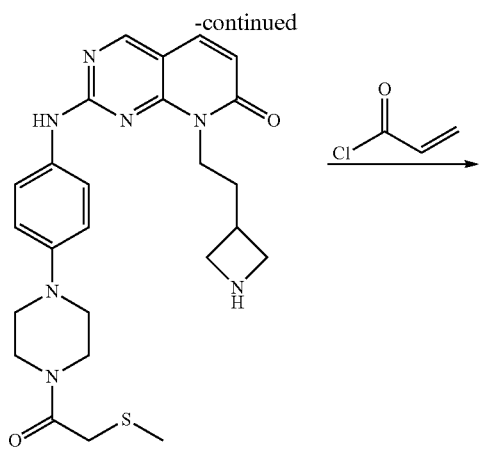

1-[Bis(dimethylamino)methylene]-1H-1,2,3-triazolo[4,5-b]pyridinium 3-oxide hexafluorophosphate (38.1 mg, 0.100 mmol) was added to a solution of (methylthio)acetic acid (46.5 μl, 0.534 mmol) in DMF (0.89 mL) followed by tert-butyl 3-(2-(7-oxo-2-((4-(piperazin-1-yl)phenyl)amino)pyrido[2,3-d]pyrimidin-8(7H)-yl)ethyl)azetidine-1-carboxylate (90 mg, 0.178 mmol) and diisopropylethyl amine (155 μL, 0.890 mmol) and the reaction mixture was stirred at rt for 2 h. The reaction mixture was concentrated in vacuo to yield the intermediate tert-butyl 3-(2-(2-((4-(4-(2-(methylthio)acetyl)piperazin-1-yl)phenyl)amino)-7-oxopyrido[2,3-d]pyrimidin-8(7H)-yl)ethyl)azetidine-1-carboxylate.

Trifluoroacetic acid (0.593 mL) was added to a solution of the intermediate tert-butyl 3-(2-(2-((4-(4-(2-(methylthio)acetyl)piperazin-1-yl)phenyl)amino)-7-oxopyrido[2,3-d]pyrimidin-8(7H)-yl)ethyl)azetidine-1-carboxylate in methylene chloride (1.19 ml) and the reaction mixture was stirred at rt for 2 h. The reaction mixture was concentrated in vacuo to yield the intermediate 8-(2-(azetidin-3-yl)ethyl)-2-((4-(4-(2-(methylthio)acetyl)piperazin-1-yl)phenyl)amino)pyrido[2,3-d]pyrimidin-7(8H)-one.

N,N-Diisopropylethylamine (0.311 mL, 1.78 mmol) was added to a solution of the intermediate 8-(2-(azetidin-3-yl)ethyl)-2-((4-(4-(2-(methylthio)acetyl)piperazin-1-yl)phenyl)amino)pyrido[2,3-d]pyrimidin-7(8H)-one in methylene chloride (0.45 mL), followed by acryloyl chloride (17.0 μl, 0.214 mmol) and the reaction mixture was stirred at rt for 15 minutes. The reaction mixture was concentrated in vacuo to yield a crude mixture. The crude mixture was purified via preparatory scale C18 column chromatography using a gradient of 10-50% acetonitrile in water with 0.05% trifluoroacetic acid to yield 8-(2-(1-acryloylazetidin-3-yl)ethyl)-2-((4-(4-(2-(methylthio)acetyl)piperazin-1-yl)phenyl)amino)pyrido[2,3-d]pyrimidin-7(8H)-one, TFA salt (26.4 mg, 0.0399 mmol, 22% yield) as a yellow solid. (m/z): [M+H]$^+$ calcd for $C_{28}H_{34}N_7O_3S$ 548.24 found 548.1.

The following compounds were made through similar synthetic schemes using the appropriate starting materials and reagents.

TABLE 1

| Ex No. | Structure | Calculated [M + H]$^+$ | Found [M + H]$^+$ |
|---|---|---|---|
| 14 | 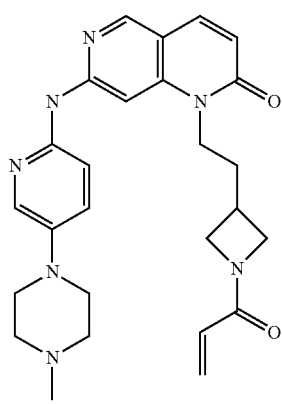 [SMILES: C=CC(=O)N1CC(CCn2c(=O)ccc3cnc(Nc4ccc(N5CCN(C)CC5)cn4)cc32)C1] | 474.25 | 474.2 |

TABLE 1-continued

| Ex No. | Structure | Calculated [M + H]⁺ | Found [M + H]⁺ |
|---|---|---|---|
| 15 | 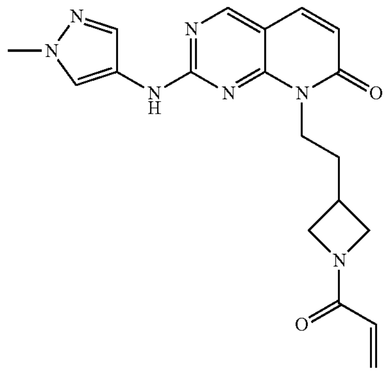 [SMILES: C=CC(=O)N1CC(CCn2c(=O)ccc3cnc(Nc4cnn(C)c4)nc32)C1] | 380.18 | 380.0 |
| 16 | 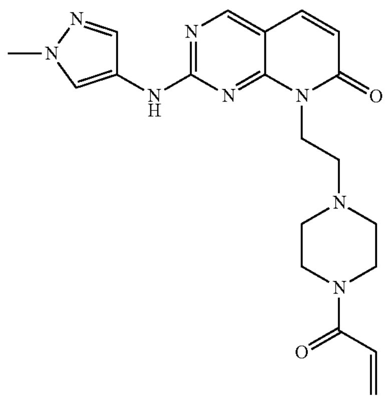 [SMILES: C=CC(=O)N1CCN(CCn2c(=O)ccc3cnc(Nc4cnn(C)c4)nc32)CC1] | 409.20 | 409.2 |
| 17 | 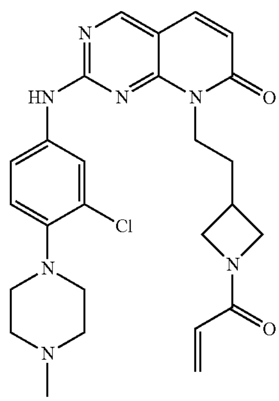 [SMILES: C=CC(=O)N1CC(CCn2c(=O)ccc3cnc(Nc4ccc(N5CCN(C)CC5)c(Cl)c4)nc32)C1] | 508.21 | 508.1 |
| 18 | 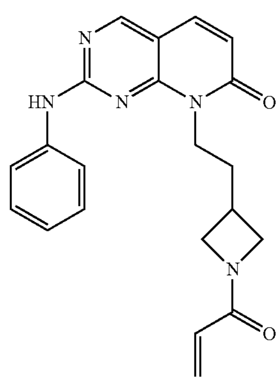 [SMILES: C=CC(=O)N1CC(CCn2c(=O)ccc3cnc(Nc4ccccc4)nc32)C1] | 376.17 | 376.1 |

TABLE 1-continued

| Ex No. | Structure | Calculated [M + H]⁺ | Found [M + H]⁺ |
|---|---|---|---|
| 19 | 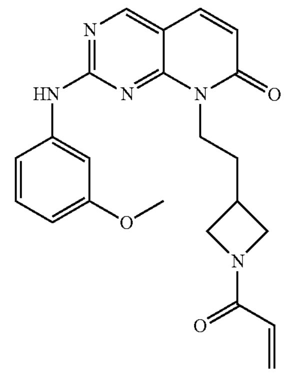 [SMILES: C=CC(=O)N1CC(CCn2c(=O)ccc3cnc(Nc4cccc(OC)c4)nc32)C1] | 406.18 | 406.4 |
| 20 | 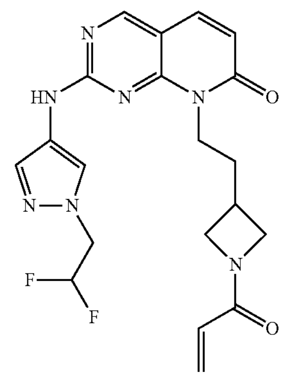 [SMILES: C=CC(=O)N1CC(CCn2c(=O)ccc3cnc(Nc4cnn(CC(F)F)c4)nc32)C1] | 430.17 | 430.1 |
| 21 | 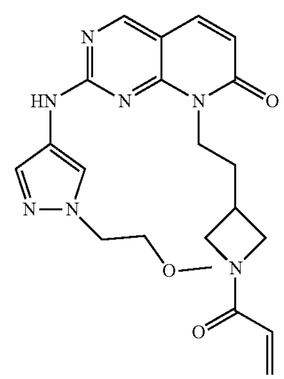 [SMILES: C=CC(=O)N1CC(CCn2c(=O)ccc3cnc(Nc4cnn(CCOC)c4)nc32)C1] | 424.20 | 424.2 |
| 22 | 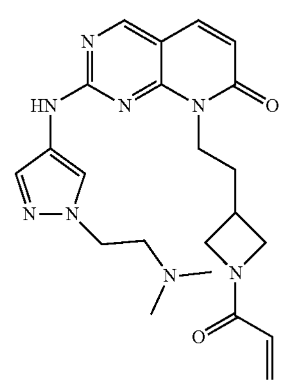 [SMILES: C=CC(=O)N1CC(CCn2c(=O)ccc3cnc(Nc4cnn(CCN(C)C)c4)nc32)C1] | 437.23 | 437.2 |

TABLE 1-continued

| Ex No. | Structure | Calculated [M + H]+ | Found [M + H]+ |
|---|---|---|---|
| 23 | 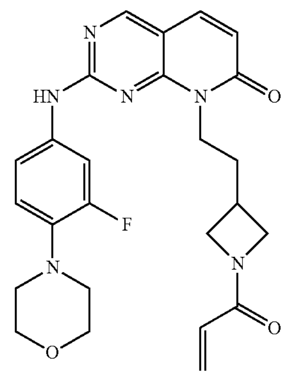 [SMILES: C=CC(=O)N1CC(CCn2c(=O)ccc3cnc(Nc4ccc(N5CCOCC5)c(F)c4)nc32)C1] | 479.21 | 479.1 |
| 24 | 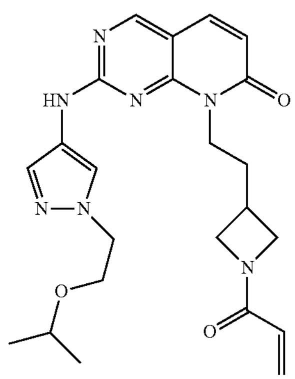 [SMILES: C=CC(=O)N1CC(CCn2c(=O)ccc3cnc(Nc4cnn(CCOC(C)C)c4)nc32)C1] | 452.23 | 452.2 |
| 25 | 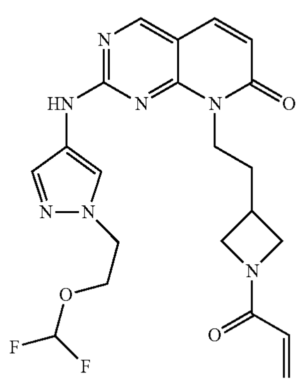 [SMILES: C=CC(=O)N1CC(CCn2c(=O)ccc3cnc(Nc4cnn(CCOC(F)F)c4)nc32)C1] | 460.18 | 460.2 |
| 26 | 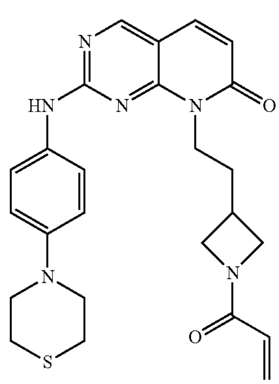 [SMILES: C=CC(=O)N1CC(CCn2c(=O)ccc3cnc(Nc4ccc(N5CCSCC5)cc4)nc32)C1] | 477.20 | 477.1 |

TABLE 1-continued
| Ex No. | Structure | Calculated [M + H]+ | Found [M + H]+ |
|---|---|---|---|
| 27 | 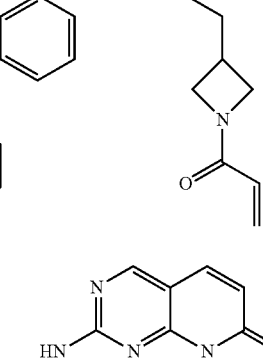 | 475.23 | 475.2 |
| 28 | 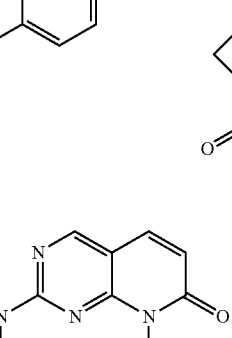 | 461.22 | 461.2 |
| 29 | 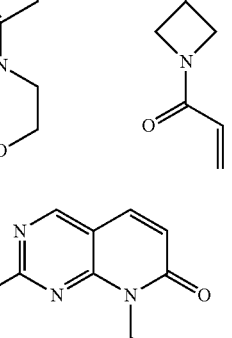 | 462.22 | 462.1 |
| 30 | 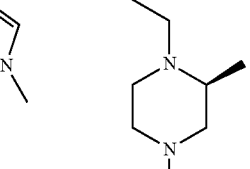 | 423.22 | 423.2 |

TABLE 1-continued

| Ex No. | Structure | Calculated [M + H]+ | Found [M + H]+ |
|---|---|---|---|
| 31 | 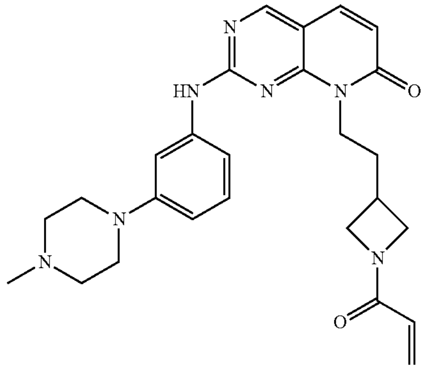 [SMILES: C=CC(=O)N1CC(CCn2c(=O)ccc3cnc(Nc4cccc(N5CCN(C)CC5)c4)nc32)C1] | 474.25 | 474.1 |
| 32 | 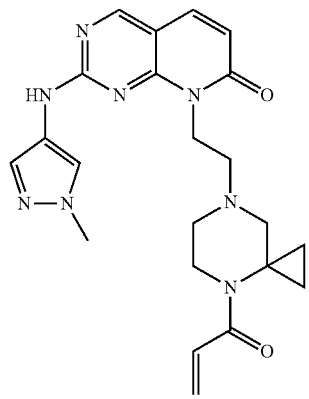 [SMILES: C=CC(=O)N1CCN(CCn2c(=O)ccc3cnc(Nc4cnn(C)c4)nc32)CC12CC2] | 435.22 | 435.1 |
| 33 | 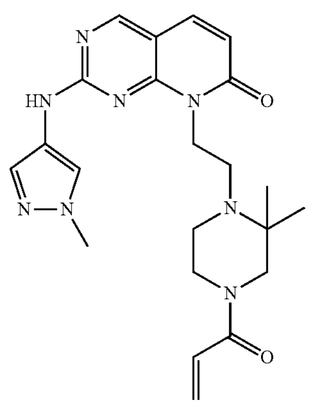 [SMILES: C=CC(=O)N1CCN(CCn2c(=O)ccc3cnc(Nc4cnn(C)c4)nc32)C(C)(C)C1] | 437.23 | 437.2 |
| 34 | 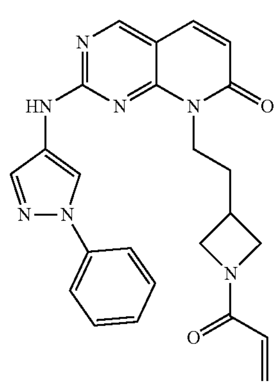 [SMILES: C=CC(=O)N1CC(CCn2c(=O)ccc3cnc(Nc4cnn(-c5ccccc5)c4)nc32)C1] | 442.19 | 442.1 |

TABLE 1-continued

| Ex No. | Structure | Calculated [M + H]+ | Found [M + H]+ |
|---|---|---|---|
| 35 | 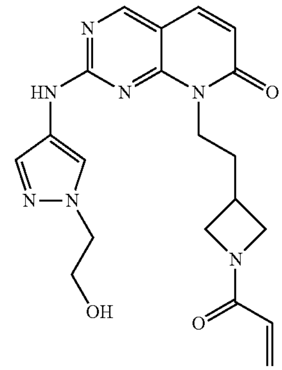 [SMILES: C=CC(=O)N1CC(CCn2c(=O)ccc3cnc(Nc4cnn(CCO)c4)nc32)C1] | 410.19 | 410.1 |
| 36 | 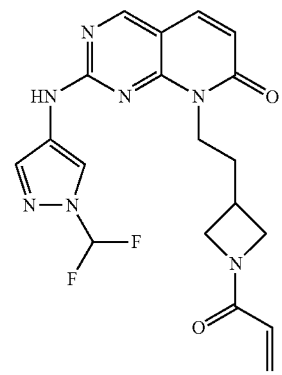 [SMILES: C=CC(=O)N1CC(CCn2c(=O)ccc3cnc(Nc4cnn(C(F)F)c4)nc32)C1] | 416.16 | 416.1 |
| 37 | 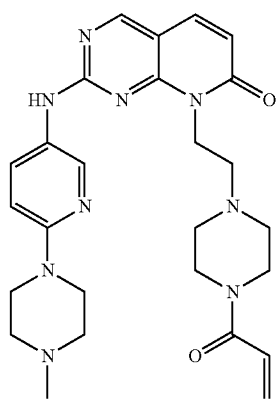 [SMILES: C=CC(=O)N1CCN(CCn2c(=O)ccc3cnc(Nc4ccc(N5CCN(C)CC5)nc4)nc32)CC1] | 504.28 | 504.1 |
| 38 | 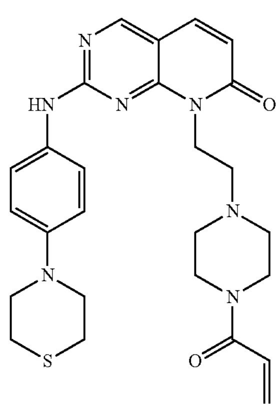 [SMILES: C=CC(=O)N1CCN(CCn2c(=O)ccc3cnc(Nc4ccc(N5CCSCC5)cc4)nc32)CC1] | 506.23 | 506.1 |

TABLE 1-continued

| Ex No. | Structure | Calculated [M + H]+ | Found [M + H]+ |
|---|---|---|---|
| 39 | 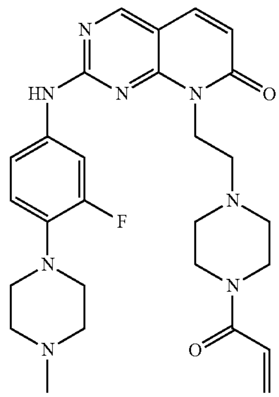 [SMILES: C=CC(=O)N1CCN(CCn2c(=O)ccc3cnc(Nc4ccc(N5CCN(C)CC5)c(F)c4)nc32)CC1] | 521.27 | 521.1 |
| 40 | 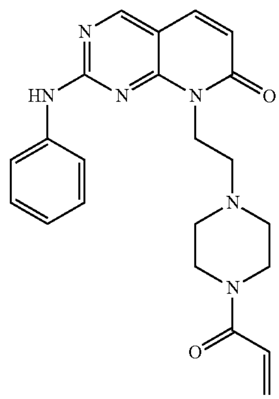 [SMILES: C=CC(=O)N1CCN(CCn2c(=O)ccc3cnc(Nc4ccccc4)nc32)CC1] | 405.20 | 405.1 |
| 41 | 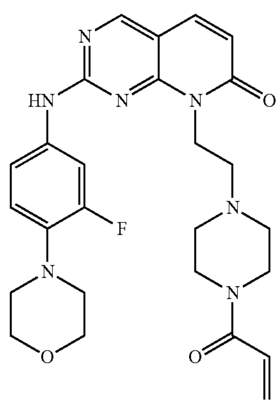 | 508.24 | 508.1 |
| 42 | 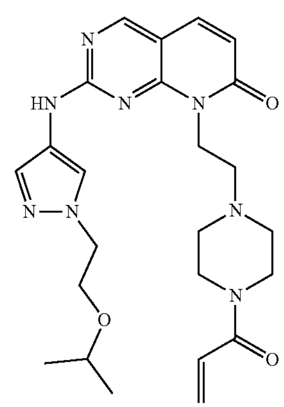 [SMILES: C=CC(=O)N1CCN(CCn2c(=O)ccc3cnc(Nc4cnn(CCOC(C)C)c4)nc32)CC1] | 481.26 | 481.1 |

TABLE 1-continued

| Ex No. | Structure | Calculated [M + H]+ | Found [M + H]+ |
|---|---|---|---|
| 43 | 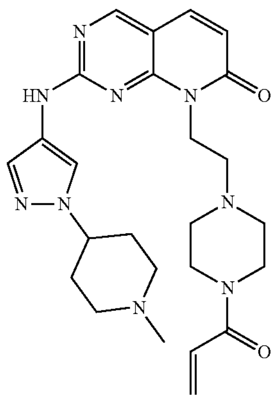 [SMILES: C=CC(=O)N1CCN(CCn2c(=O)ccc3cnc(Nc4cnn(C5CCN(C)CC5)c4)nc32)CC1] | 492.28 | 492.1 |
| 44 | 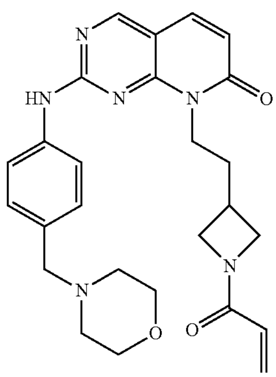 [SMILES: C=CC(=O)N1CC(CCn2c(=O)ccc3cnc(Nc4ccc(CN5CCOCC5)cc4)nc32)C1] | 475.24 | 475.1 |
| 45 | 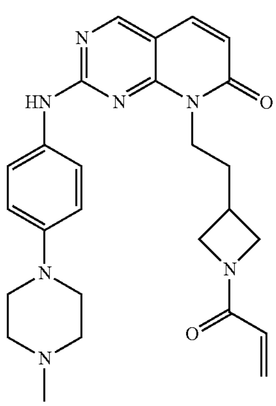 [SMILES: C=CC(=O)N1CC(CCn2c(=O)ccc3cnc(Nc4ccc(N5CCN(C)CC5)cc4)nc32)C1] | 474.25 | 474.1 |
| 46 | 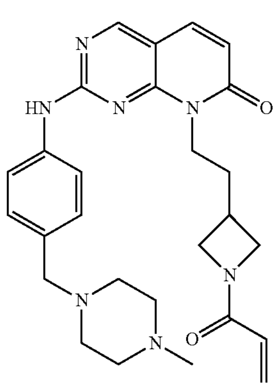 [SMILES: C=CC(=O)N1CC(CCn2c(=O)ccc3cnc(Nc4ccc(CN5CCN(C)CC5)cc4)nc32)C1] | 488.27 | 488.2 |

TABLE 1-continued
| Ex No. | Structure | Calculated [M + H]+ | Found [M + H]+ |
|---|---|---|---|
| 47 | 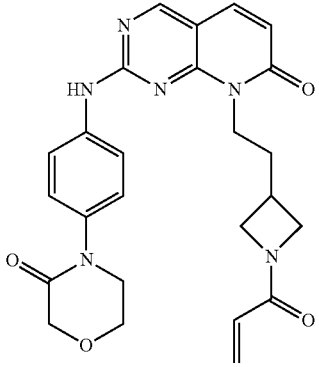 [SMILES: C=CC(=O)N1CC(CCn2c(=O)ccc3cnc(Nc4ccc(N5CCOCC5=O)cc4)nc32)C1] | 475.20 | 475.1 |
| 48 | 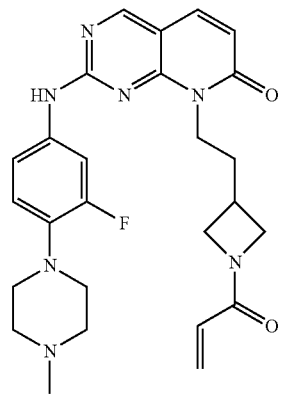 | 492.24 | 492.2 |
| 49 | 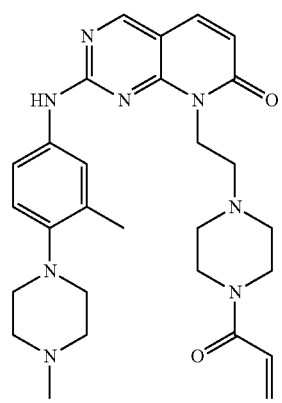 | 517.30 | 517.2 |

TABLE 1-continued

| Ex No. | Structure | Calculated [M + H]+ | Found [M + H]+ |
| --- | --- | --- | --- |
| 50 | 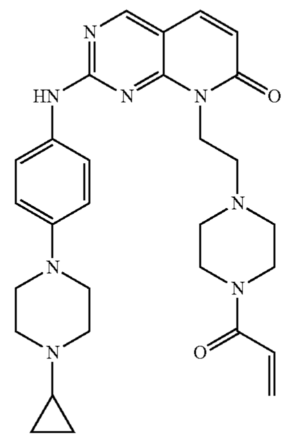 [SMILES: C=CC(=O)N1CCN(CCn2c(=O)ccc3cnc(Nc4ccc(N5CCN(C6CC6)CC5)cc4)nc32)CC1] | 529.30 | 529.2 |
| 51 | 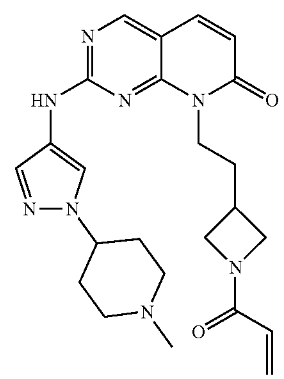 [SMILES: C=CC(=O)N1CC(CCn2c(=O)ccc3cnc(Nc4cnn(C5CCN(C)CC5)c4)nc32)C1] | 463.25 | 463.2 |
| 52 | 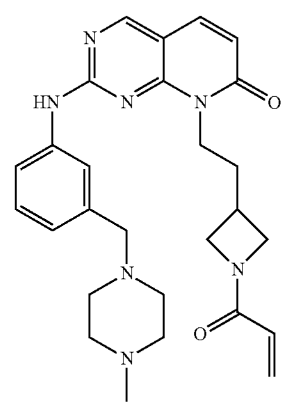 [SMILES: C=CC(=O)N1CC(CCn2c(=O)ccc3cnc(Nc4cccc(CN5CCN(C)CC5)c4)nc32)C1] | 488.27 | 488.2 |
| 53 | 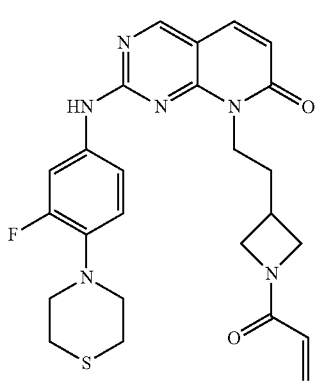 [SMILES: C=CC(=O)N1CC(CCn2c(=O)ccc3cnc(Nc4ccc(N5CCSCC5)c(F)c4)nc32)C1] | 495.19 | 495.1 |

TABLE 1-continued

| Ex No. | Structure | Calculated [M + H]+ | Found [M + H]+ |
|---|---|---|---|
| 54 | 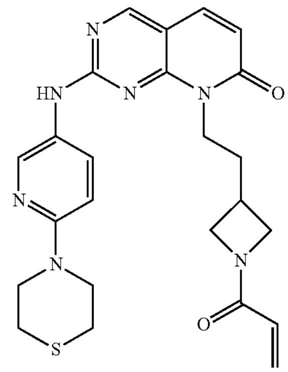 [SMILES: C=CC(=O)N1CC(CCn2c(=O)ccc3cnc(Nc4ccc(N5CCSCC5)nc4)nc32)C1] | 478.19 | 478.1 |
| 55 | 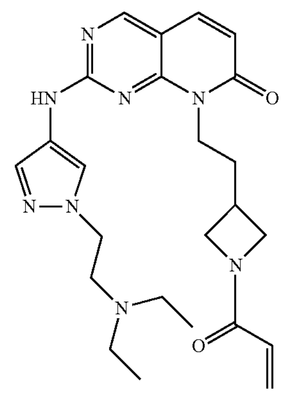 [SMILES: C=CC(=O)N1CC(CCn2c(=O)ccc3cnc(Nc4cnn(CCN(CC)CC)c4)nc32)C1] | 465.26 | 465.2 |
| 56 | 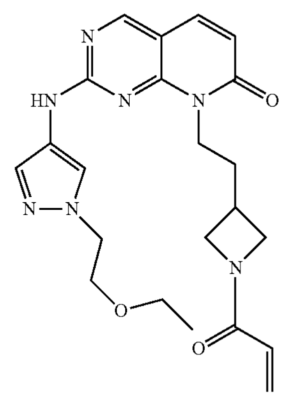 [SMILES: C=CC(=O)N1CC(CCn2c(=O)ccc3cnc(Nc4cnn(CCOCC)c4)nc32)C1] | 438.22 | 438.1 |
| 57 | 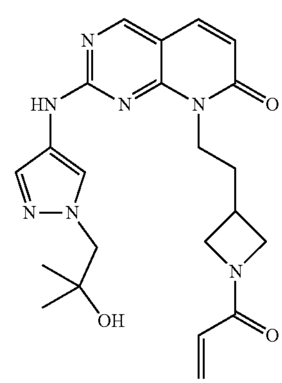 [SMILES: C=CC(=O)N1CC(CCn2c(=O)ccc3cnc(Nc4cnn(CC(C)(C)O)c4)nc32)C1] | 438.22 | 438.1 |

TABLE 1-continued

| Ex No. | Structure | Calculated [M + H]+ | Found [M + H]+ |
|---|---|---|---|
| 58 | 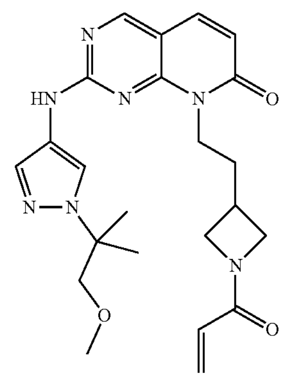 [SMILES: C=CC(=O)N1CC(CCn2c(=O)ccc3cnc(Nc4cnn(C(C)(C)COC)c4)nc32)C1] | 452.23 | 452.1 |
| 59 | 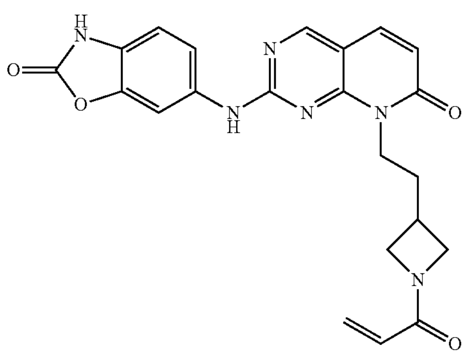 [SMILES: C=CC(=O)N1CC(CCn2c(=O)ccc3cnc(Nc4ccc5[nH]c(=O)oc5c4)nc32)C1] | 433.15 | 433.0 |
| 60 | 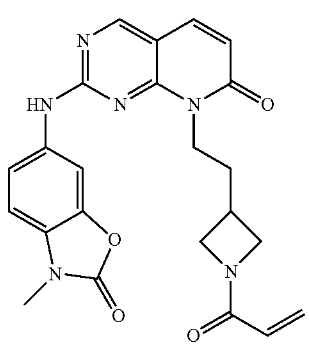 [SMILES: C=CC(=O)N1CC(CCn2c(=O)ccc3cnc(Nc4ccc5c(c4)oc(=O)n5C)nc32)C1] | 447.17 | 447.0 |
| 61 | 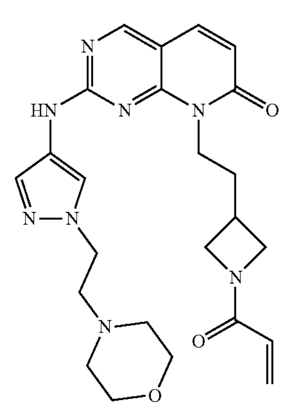 [SMILES: C=CC(=O)N1CC(CCn2c(=O)ccc3cnc(Nc4cnn(CCN5CCOCC5)c4)nc32)C1] | 479.24 | 479.0 |

TABLE 1-continued

| Ex No. | Structure | Calculated [M + H]+ | Found [M + H]+ |
|---|---|---|---|
| 62 | 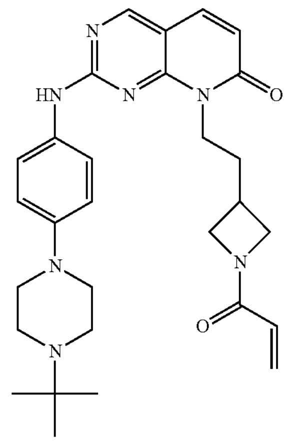 [SMILES: C=CC(=O)N1CC(CCn2c(=O)ccc3cnc(Nc4ccc(N5CCN(C(C)(C)C)CC5)cc4)nc32)C1] | 516.30 | 516.0 |
| 63 | 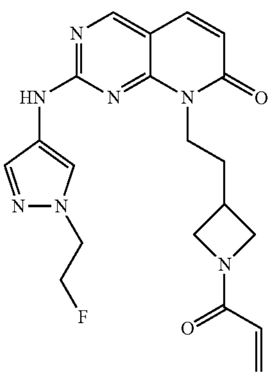 [SMILES: C=CC(=O)N1CC(CCn2c(=O)ccc3cnc(Nc4cnn(CCF)c4)nc32)C1] | 412.18 | 412.0 |
| 64 | 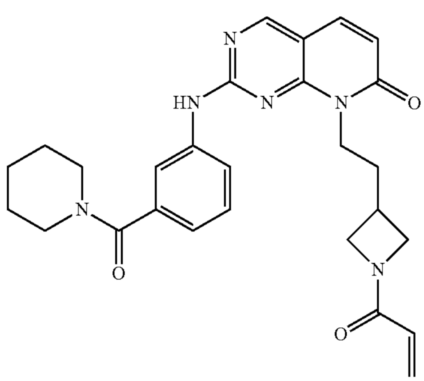 [SMILES: C=CC(=O)N1CC(CCn2c(=O)ccc3cnc(Nc4cccc(C(=O)N5CCCCC5)c4)nc32)C1] | 487.24 | 487.0 |
| 65 | 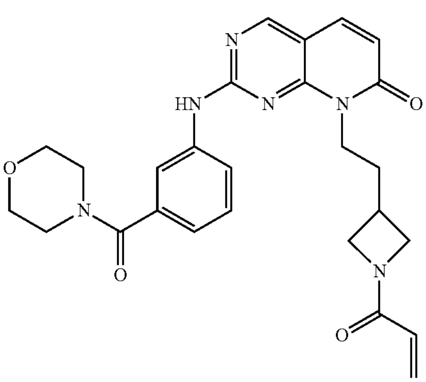 [SMILES: C=CC(=O)N1CC(CCn2c(=O)ccc3cnc(Nc4cccc(C(=O)N5CCOCC5)c4)nc32)C1] | 489.22 | 489.0 |

TABLE 1-continued

| Ex No. | Structure | Calculated [M + H]+ | Found [M + H]+ |
|---|---|---|---|
| 66 | 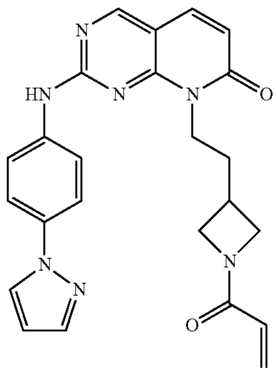 [SMILES: C=CC(=O)N1CC(CCn2c(=O)ccc3cnc(Nc4ccc(-n5cccn5)cc4)nc32)C1] | 442.19 | 442.0 |
| 67 | 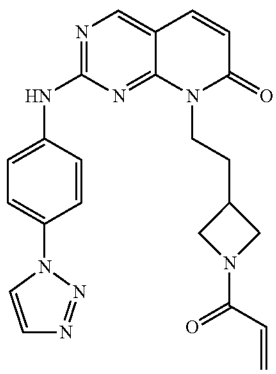 [SMILES: C=CC(=O)N1CC(CCn2c(=O)ccc3cnc(Nc4ccc(-n5ccnn5)cc4)nc32)C1] | 443.19 | 443.0 |
| 68 | 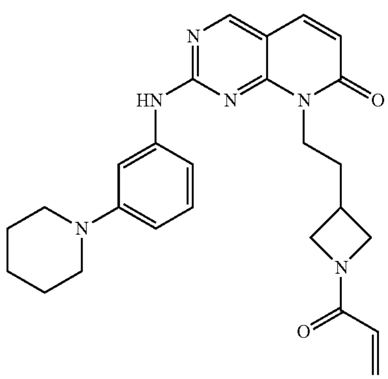 [SMILES: C=CC(=O)N1CC(CCn2c(=O)ccc3cnc(Nc4cccc(N5CCCCC5)c4)nc32)C1] | 459.24 | 459.2 |
| 69 | 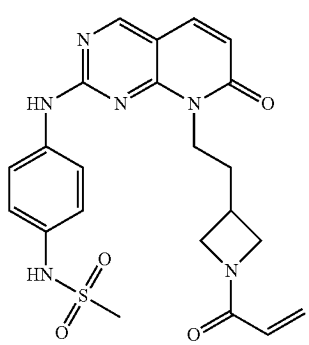 [SMILES: C=CC(=O)N1CC(CCn2c(=O)ccc3cnc(Nc4ccc(NS(C)(=O)=O)cc4)nc32)C1] | 469.16 | 469.0 |

TABLE 1-continued
| Ex No. | Structure | Calculated [M + H]+ | Found [M + H]+ |
|---|---|---|---|
| 70 | 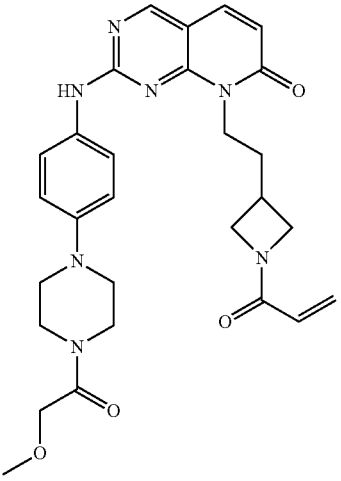 [SMILES: C=CC(=O)N1CC(CCn2c(=O)ccc3cnc(Nc4ccc(N5CCN(C(=O)COC)CC5)cc4)nc32)C1] | 432.26 | 532.0 |
| 71 | 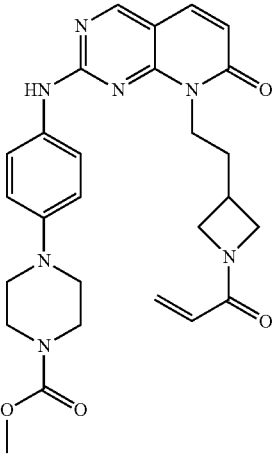 [SMILES: C=CC(=O)N1CC(CCn2c(=O)ccc3cnc(Nc4ccc(N5CCN(C(=O)OC)CC5)cc4)nc32)C1] | 518.24 | 518.0 |
| 72 | 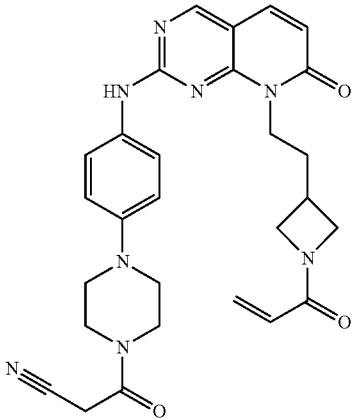 [SMILES: C=CC(=O)N1CC(CCn2c(=O)ccc3cnc(Nc4ccc(N5CCN(C(=O)CC#N)CC5)cc4)nc32)C1] | 527.24 | 527.0 |

TABLE 1-continued
| Ex No. | Structure | Calculated [M + H]+ | Found [M + H]+ |
|---|---|---|---|
| 73 | 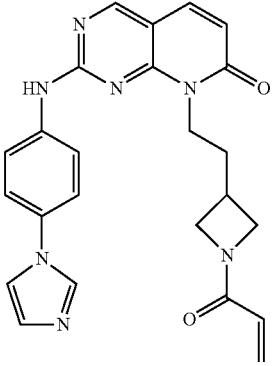 [SMILES: C=CC(=O)N1CC(CCn2c(=O)ccc3cnc(Nc4ccc(-n5ccnc5)cc4)nc32)C1] | 442.19 | 442.7 |
| 74 | 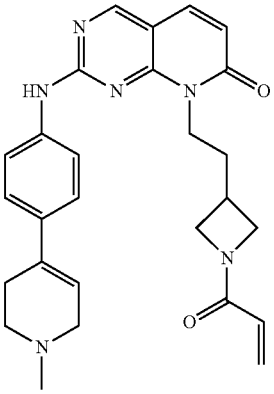 [SMILES: C=CC(=O)N1CC(CCn2c(=O)ccc3cnc(Nc4ccc(C5=CCN(C)CC5)cc4)nc32)C1] | 471.24 | 471.1 |
| 75 | 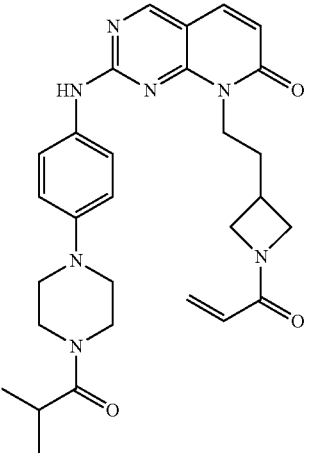 [SMILES: C=CC(=O)N1CC(CCn2c(=O)ccc3cnc(Nc4ccc(N5CCN(C(=O)C(C)C)CC5)cc4)nc32)C1] | 530.28 | 530.3 |

TABLE 1-continued
| Ex No. | Structure | Calculated [M + H]+ | Found [M + H]+ |
|---|---|---|---|
| 76 | 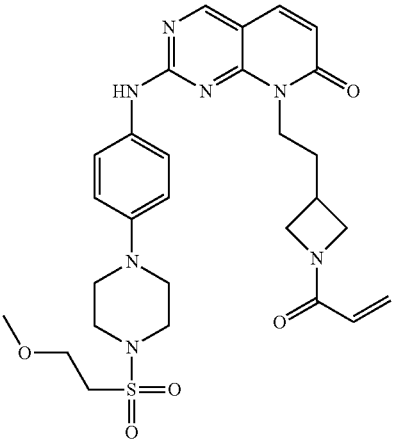 [SMILES: C=CC(=O)N1CC(CCn2c(=O)ccc3cnc(Nc4ccc(N5CCN(S(=O)(=O)CCOC)CC5)cc4)nc32)C1] | 582.24 | 582.0 |
| 77 | 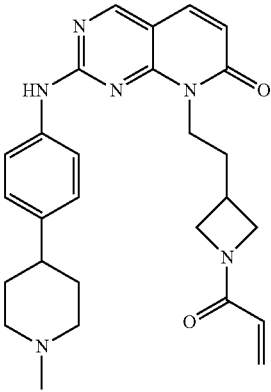 [SMILES: C=CC(=O)N1CC(CCn2c(=O)ccc3cnc(Nc4ccc(C5CCN(C)CC5)cc4)nc32)C1] | 473.26 | 473.2 |
| 78 | 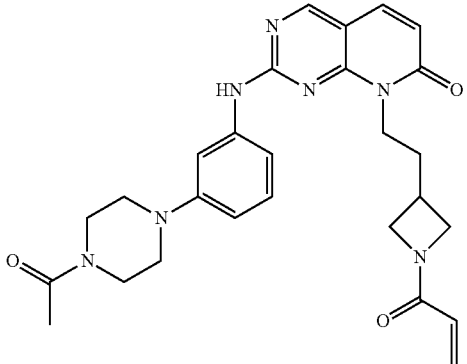 [SMILES: C=CC(=O)N1CC(CCn2c(=O)ccc3cnc(Nc4cccc(N5CCN(C(C)=O)CC5)c4)nc32)C1] | 502.25 | 502.2 |

TABLE 1-continued
| Ex No. | Structure | Calculated [M + H]+ | Found [M + H]+ |
|---|---|---|---|
| 79 | 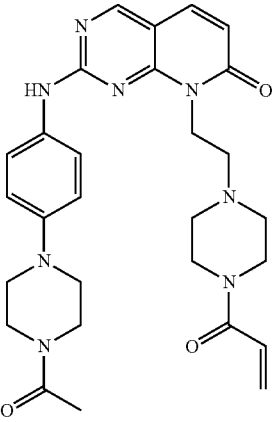 [SMILES: C=CC(=O)N1CCN(CCn2c(=O)ccc3cnc(Nc4ccc(N5CCN(C(C)=O)CC5)cc4)nc32)CC1] | 531.28 | 531.1 |
| 80 | 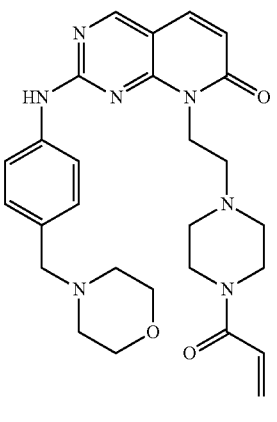 [SMILES: C=CC(=O)N1CCN(CCn2c(=O)ccc3cnc(Nc4ccc(CN5CCOCC5)cc4)nc32)CC1] | 504.26 | 504.1 |
| 81 | 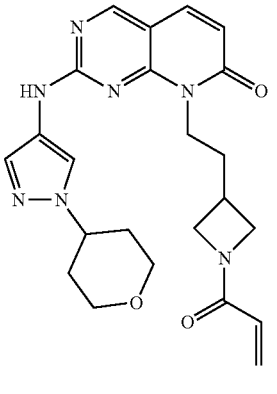 [SMILES: C=CC(=O)N1CC(CCn2c(=O)ccc3cnc(Nc4cnn(C5CCOCC5)c4)nc32)C1] | 450.22 | 450.2 |
| 82 | 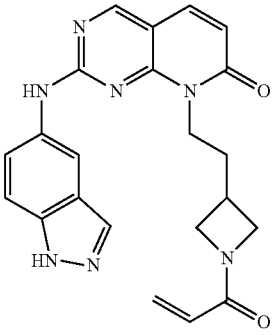 [SMILES: C=CC(=O)N1CC(CCn2c(=O)ccc3cnc(Nc4ccc5[nH]ncc5c4)nc32)C1] | 416.18 | 416.0 |

TABLE 1-continued

| Ex No. | Structure | Calculated [M + H]+ | Found [M + H]+ |
|---|---|---|---|
| 83 | 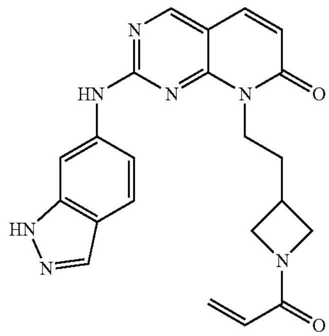 [SMILES: C=CC(=O)N1CC(CCn2c(=O)ccc3cnc(Nc4ccc5cn[nH]c5c4)nc32)C1] | 416.18 | 416.0 |
| 84 | 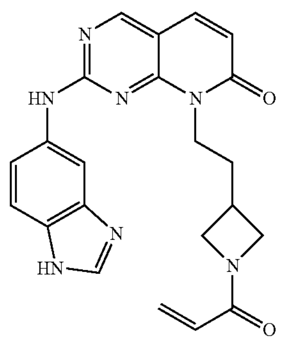 [SMILES: C=CC(=O)N1CC(CCn2c(=O)ccc3cnc(Nc4ccc5[nH]cnc5c4)nc32)C1] | 416.18 | 416.0 |
| 85 | 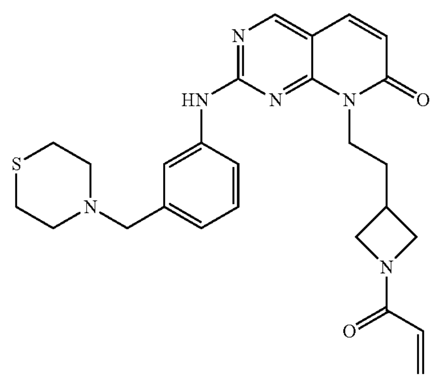 [SMILES: C=CC(=O)N1CC(CCn2c(=O)ccc3cnc(Nc4cccc(CN5CCSCC5)c4)nc32)C1] | 491.22 | 491.1 |
| 86 | 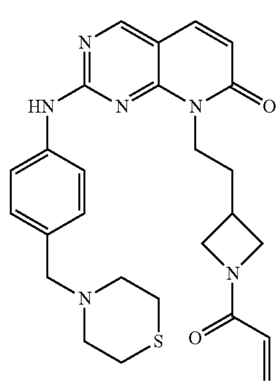 [SMILES: C=CC(=O)N1CC(CCn2c(=O)ccc3cnc(Nc4ccc(CN5CCSCC5)cc4)nc32)C1] | 491.22 | 491.0 |

TABLE 1-continued

| Ex No. | Structure | Calculated [M + H]+ | Found [M + H]+ |
|---|---|---|---|
| 87 | 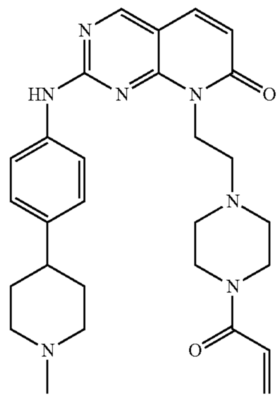 | 502.29 | 502.1 |
| 88 | 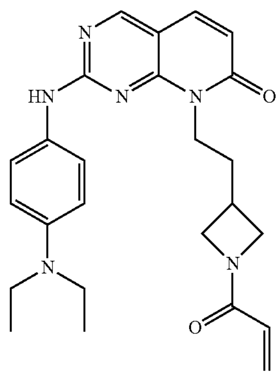 [SMILES: C=CC(=O)N1CC(CCn2c(=O)ccc3cnc(Nc4ccc(N(CC)CC)cc4)nc32)C1] | 447.24 | 447.1 |
| 89 | 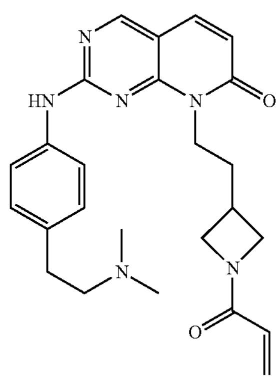 [SMILES: C=CC(=O)N1CC(CCn2c(=O)ccc3cnc(Nc4ccc(CCN(C)C)cc4)nc32)C1] | 447.24 | 447.1 |
| 90 | 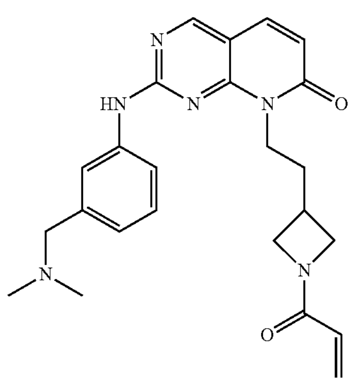 [SMILES: C=CC(=O)N1CC(CCn2c(=O)ccc3cnc(Nc4cccc(CN(C)C)c4)nc32)C1] | 433.23 | 433.1 |

TABLE 1-continued

| Ex No. | Structure | Calculated [M + H]+ | Found [M + H]+ |
|---|---|---|---|
| 91 | 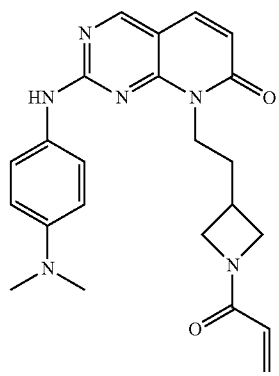 [SMILES: C=CC(=O)N1CC(CCn2c(=O)ccc3cnc(Nc4ccc(N(C)C)cc4)nc32)C1] | 419.21 | 419.1 |
| 92 | 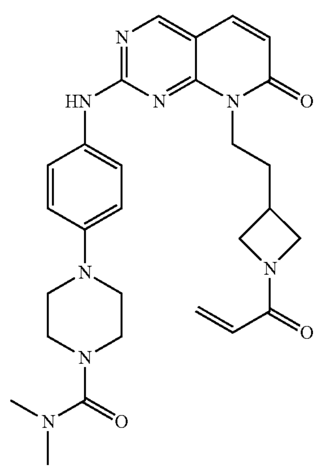 [SMILES: C=CC(=O)N1CC(CCn2c(=O)ccc3cnc(Nc4ccc(N5CCN(C(=O)N(C)C)CC5)cc4)nc32)C1] | 531.28 | 531.2 |
| 93 | 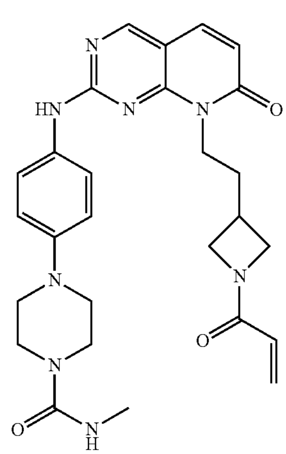 [SMILES: C=CC(=O)N1CC(CCn2c(=O)ccc3cnc(Nc4ccc(N5CCN(C(=O)NC)CC5)cc4)nc32)C1] | 517.26 | 517.0 |

TABLE 1-continued
| Ex No. | Structure | Calculated [M + H]+ | Found [M + H]+ |
|---|---|---|---|
| 94 | 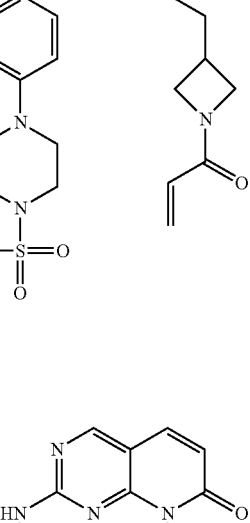 | 538.22 | 538.0 |
| 95 | 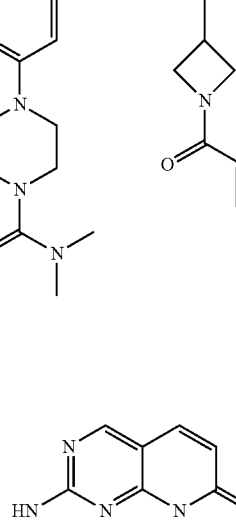 | 547.25 | 547.0 |
| 96 | 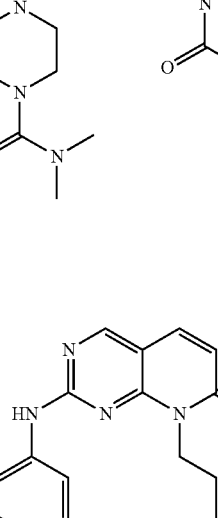 | 553.23 | 553.0 |

TABLE 1-continued
| Ex No. | Structure | Calculated [M + H]⁺ | Found [M + H]⁺ |
|---|---|---|---|
| 97 | 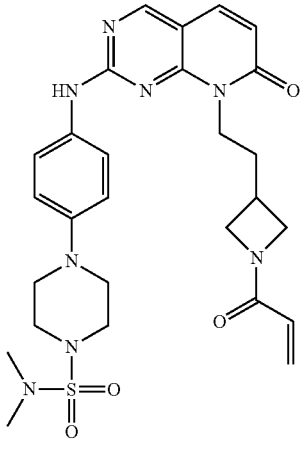 [SMILES: C=CC(=O)N1CC(CCn2c(=O)ccc3cnc(Nc4ccc(N5CCN(S(=O)(=O)N(C)C)CC5)cc4)nc32)C1] | 567.24 | 567.0 |
| 98 | 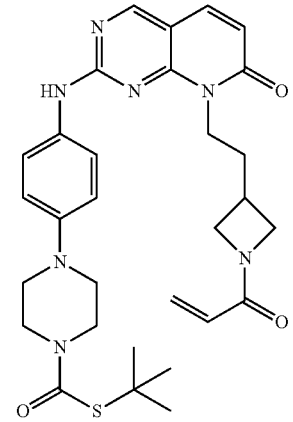 [SMILES: C=CC(=O)N1CC(CCn2c(=O)ccc3cnc(Nc4ccc(N5CCN(C(=O)SC(C)(C)C)CC5)cc4)nc32)C1] | 576.27 | 576.2 |
| 99 | 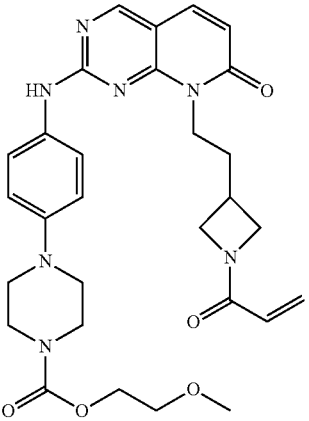 [SMILES: C=CC(=O)N1CC(CCn2c(=O)ccc3cnc(Nc4ccc(N5CCN(C(=O)OCCOC)CC5)cc4)nc32)C1] | 562.27 | 562.0 |

TABLE 1-continued
| Ex No. | Structure | Calculated [M + H]+ | Found [M + H]+ |
|---|---|---|---|
| 100 | 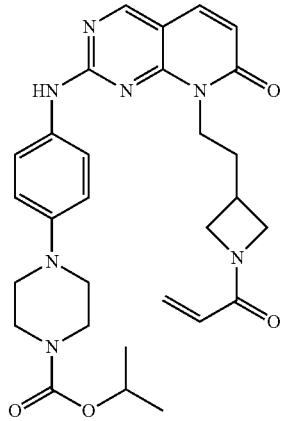 [SMILES: C=CC(=O)N1CC(CCn2c(=O)ccc3cnc(Nc4ccc(N5CCN(C(=O)OC(C)C)CC5)cc4)nc32)C1] | 546.28 | 546.2 |
| 101 | 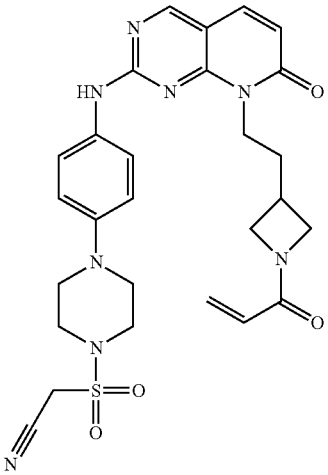 [SMILES: C=CC(=O)N1CC(CCn2c(=O)ccc3cnc(Nc4ccc(N5CCN(S(=O)(=O)CC#N)CC5)cc4)nc32)C1] | 563.21 | 563.0 |
| 102 | 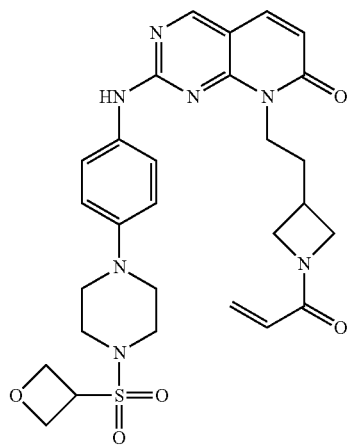 [SMILES: C=CC(=O)N1CC(CCn2c(=O)ccc3cnc(Nc4ccc(N5CCN(S(=O)(=O)C6COC6)CC5)cc4)nc32)C1] | 580.23 | 580.0 |

TABLE 1-continued

| Ex No. | Structure | Calculated [M + H]+ | Found [M + H]+ |
|---|---|---|---|
| 103 | 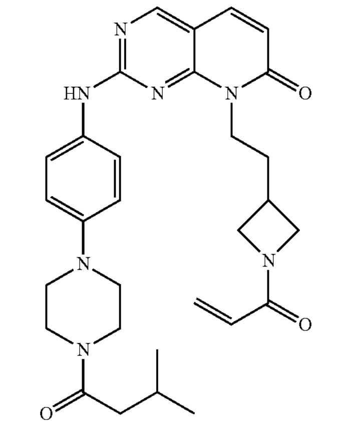 [SMILES: C=CC(=O)N1CC(CCn2c(=O)ccc3cnc(Nc4ccc(N5CCN(C(=O)CC(C)C)CC5)cc4)nc32)C1] | 544.30 | 544.0 |
| 104 | 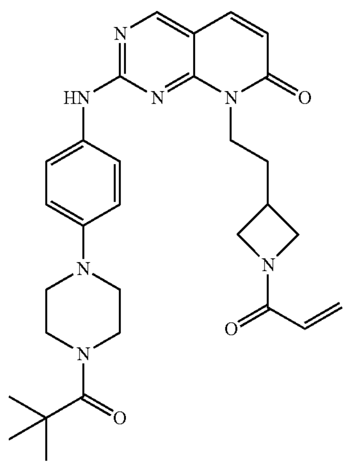 [SMILES: C=CC(=O)N1CC(CCn2c(=O)ccc3cnc(Nc4ccc(N5CCN(C(=O)C(C)(C)C)CC5)cc4)nc32)C1] | 544.30 | 544.0 |
| 105 | 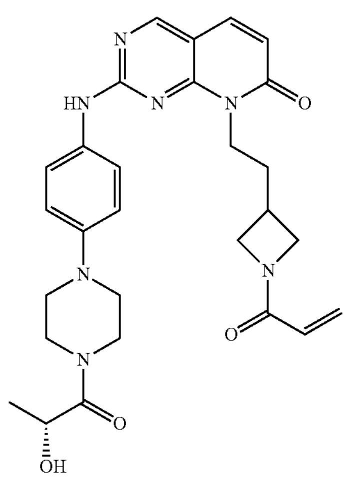 [SMILES: C=CC(=O)N1CC(CCn2c(=O)ccc3cnc(Nc4ccc(N5CCN(C(=O)[C@@H](C)O)CC5)cc4)nc32)C1] | 532.26 | 532.0 |

TABLE 1-continued
| Ex No. | Structure | Calculated [M + H]+ | Found [M + H]+ |
|---|---|---|---|
| 106 | 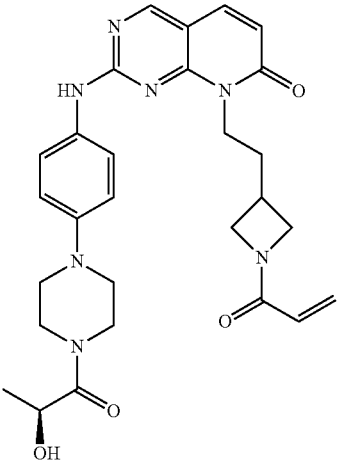 [SMILES: C=CC(=O)N1CC(CCn2c(=O)ccc3cnc(Nc4ccc(N5CCN(C(=O)[C@H](C)O)CC5)cc4)nc32)C1] | 532.26 | 532.0 |
| 107 | 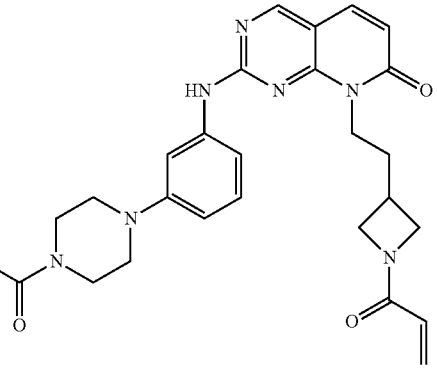 | 548.24 | 548.0 |
| 108 | 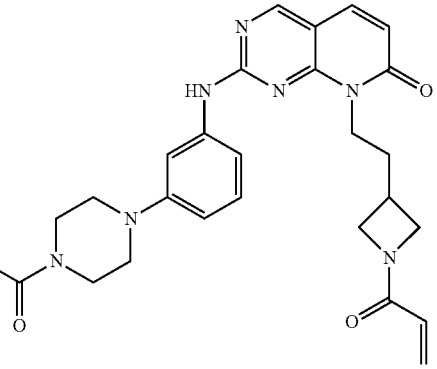 | 532.26 | 532.0 |

TABLE 1-continued

| Ex No. | Structure | Calculated [M + H]+ | Found [M + H]+ |
|---|---|---|---|
| 109 | 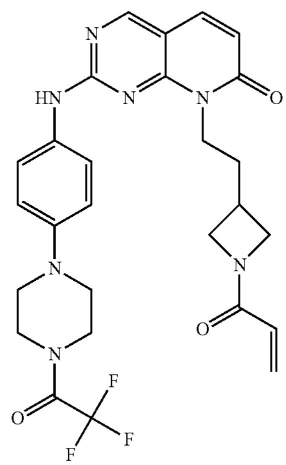 [SMILES: C=CC(=O)N1CC(CCn2c(=O)ccc3cnc(Nc4ccc(N5CCN(C(=O)C(F)(F)F)CC5)cc4)nc32)C1] | 556.22 | 556.1 |
| 110 | 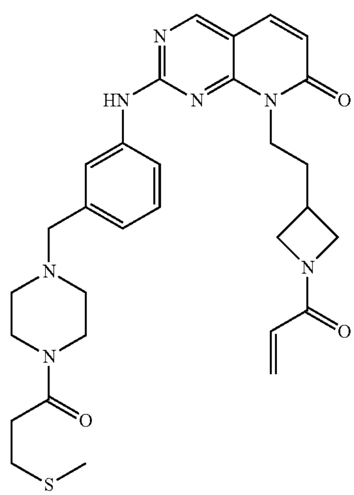 [SMILES: C=CC(=O)N1CC(CCn2c(=O)ccc3cnc(Nc4cccc(CN5CCN(C(=O)CCSC)CC5)c4)nc32)C1] | 576.27 | 576.1 |
| 111 | 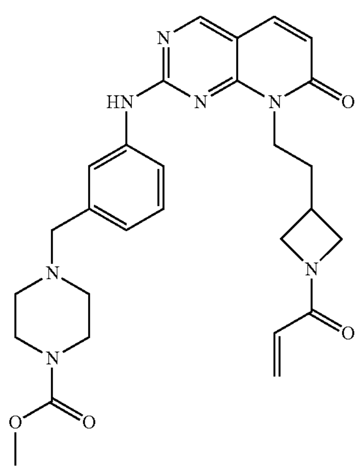 [SMILES: C=CC(=O)N1CC(CCn2c(=O)ccc3cnc(Nc4cccc(CN5CCN(C(=O)OC)CC5)c4)nc32)C1] | 532.26 | 532.1 |

TABLE 1-continued

| Ex No. | Structure | Calculated [M + H]+ | Found [M + H]+ |
|---|---|---|---|
| 112 | 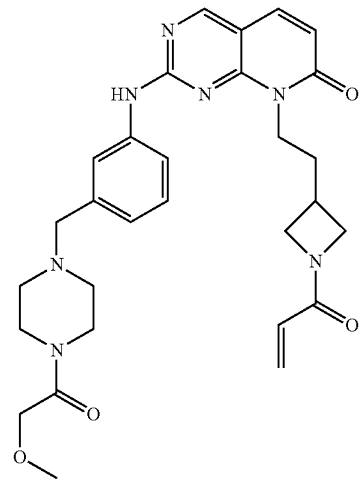 [SMILES: C=CC(=O)N1CC(CCn2c(=O)ccc3cnc(Nc4cccc(CN5CCN(C(=O)COC)CC5)c4)nc32)C1] | 546.28 | 546.1 |
| 113 | 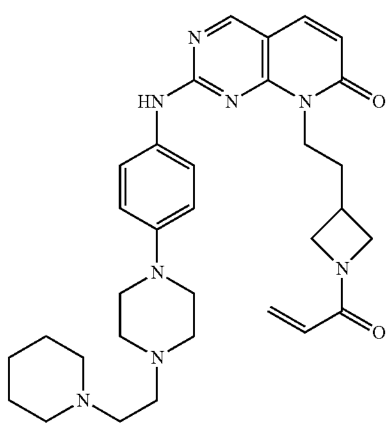 [SMILES: C=CC(=O)N1CC(CCn2c(=O)ccc3cnc(Nc4ccc(N5CCN(CCN6CCCCC6)CC5)cc4)nc32)C1] | 571.34 | 571.2 |
| 114 | 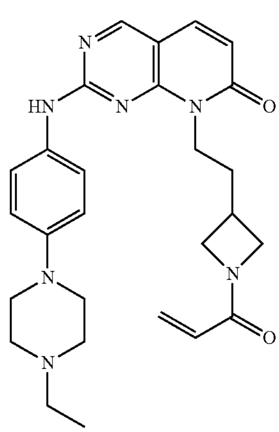 [SMILES: C=CC(=O)N1CC(CCn2c(=O)ccc3cnc(Nc4ccc(N5CCN(CC)CC5)cc4)nc32)C1] | 488.27 | 488.1 |

TABLE 1-continued

| Ex No. | Structure | Calculated [M + H]+ | Found [M + H]+ |
|---|---|---|---|
| 115 | 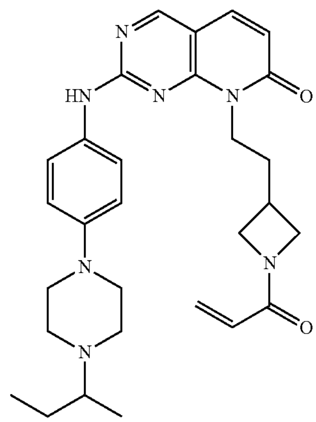 [SMILES: C=CC(=O)N1CC(CCn2c(=O)ccc3cnc(Nc4ccc(N5CCN(C(C)CC)CC5)cc4)nc32)C1] | 516.30 | 516.2 |
| 116 | 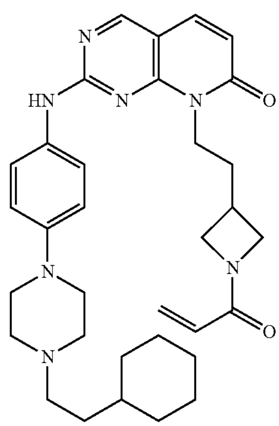 [SMILES: C=CC(=O)N1CC(CCn2c(=O)ccc3cnc(Nc4ccc(N5CCN(CCC6CCCCC6)CC5)cc4)nc32)C1] | 570.35 | 570.1 |
| 117 | 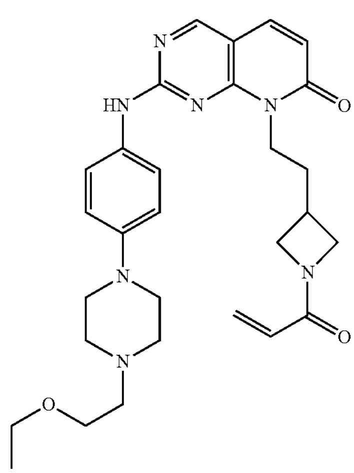 [SMILES: C=CC(=O)N1CC(CCn2c(=O)ccc3cnc(Nc4ccc(N5CCN(CCOCC)CC5)cc4)nc32)C1] | 532.30 | 532.1 |

TABLE 1-continued
| Ex No. | Structure | Calculated [M + H]+ | Found [M + H]+ |
|---|---|---|---|
| 118 | 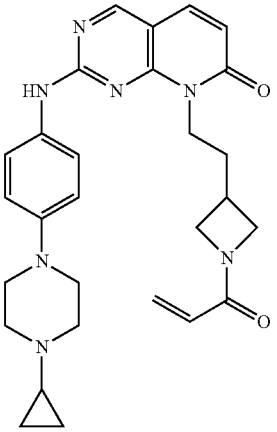 [SMILES: C=CC(=O)N1CC(CCn2c(=O)ccc3cnc(Nc4ccc(N5CCN(C6CC6)CC5)cc4)nc32)C1] | 500.27 | 500.1 |
| 119 | 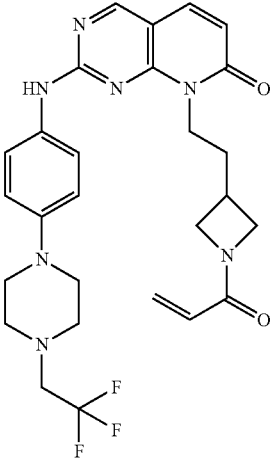 [SMILES: C=CC(=O)N1CC(CCn2c(=O)ccc3cnc(Nc4ccc(N5CCN(CC(F)(F)F)CC5)cc4)nc32)C1] | 542.24 | 542.0 |
| 120 | 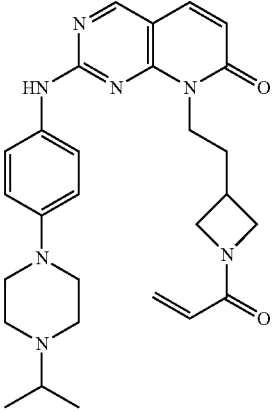 [SMILES: C=CC(=O)N1CC(CCn2c(=O)ccc3cnc(Nc4ccc(N5CCN(C(C)C)CC5)cc4)nc32)C1] | 502.29 | 502.1 |

TABLE 1-continued

| Ex No. | Structure | Calculated [M + H]+ | Found [M + H]+ |
|---|---|---|---|
| 121 | 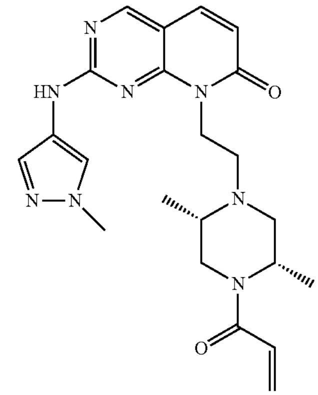 [SMILES: C=CC(=O)N1C[C@H](C)N(CCn2c(=O)ccc3cnc(Nc4cnn(C)c4)nc32)C[C@@H]1C] | 437.23 | 437.2 |
| 122 | 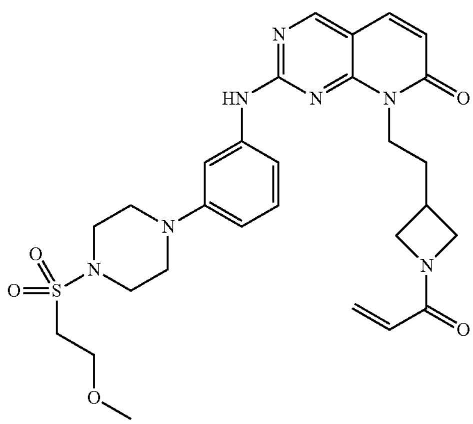 [SMILES: C=CC(=O)N1CC(CCn2c(=O)ccc3cnc(Nc4cccc(N5CCN(S(=O)(=O)CCOC)CC5)c4)nc32)C1] | 582.24 | 582.0 |
| 123 | 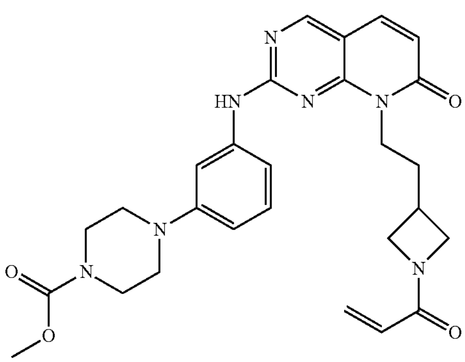 [SMILES: C=CC(=O)N1CC(CCn2c(=O)ccc3cnc(Nc4cccc(N5CCN(C(=O)OC)CC5)c4)nc32)C1] | 518.24 | 518.1 |
| 124 | 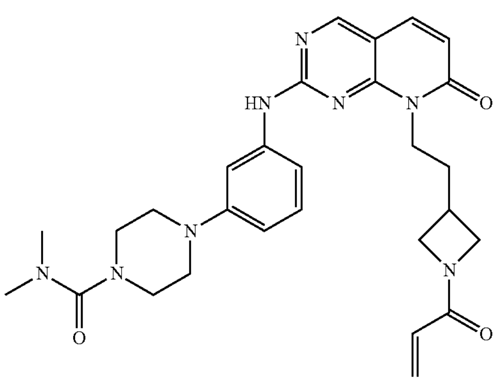 [SMILES: C=CC(=O)N1CC(CCn2c(=O)ccc3cnc(Nc4cccc(N5CCN(C(=O)N(C)C)CC5)c4)nc32)C1] | 531.28 | 531.2 |

TABLE 1-continued
| Ex No. | Structure | Calculated [M + H]+ | Found [M + H]+ |
|---|---|---|---|
| 125 | 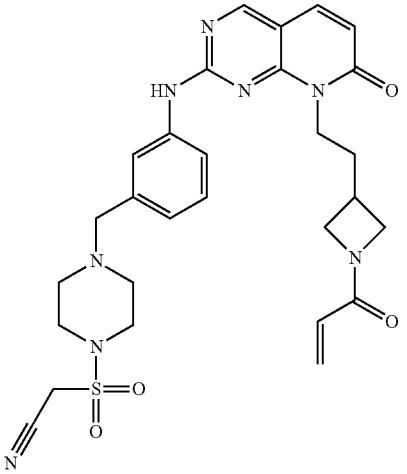 [SMILES: C=CC(=O)N1CC(CCn2c(=O)ccc3cnc(Nc4cccc(CN5CCN(S(=O)(=O)CC#N)CC5)c4)nc32)C1] | 577.23 | 577.0 |
| 126 | 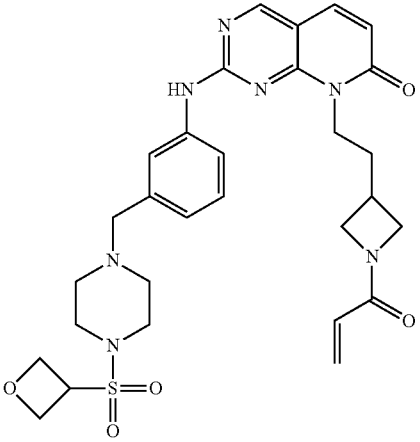 [SMILES: C=CC(=O)N1CC(CCn2c(=O)ccc3cnc(Nc4cccc(CN5CCN(S(=O)(=O)C6COC6)CC5)c4)nc32)C1] | 594.24 | 594.1 |
| 127 | 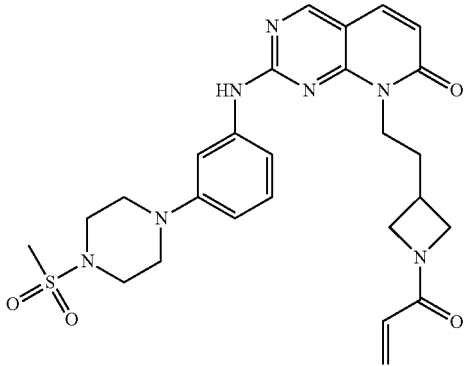 [SMILES: C=CC(=O)N1CC(CCn2c(=O)ccc3cnc(Nc4cccc(N5CCN(S(C)(=O)=O)CC5)c4)nc32)C1] | 538.22 | 538.2 |

TABLE 1-continued

| Ex No. | Structure | Calculated [M + H]+ | Found [M + H]+ |
|---|---|---|---|
| 128 | 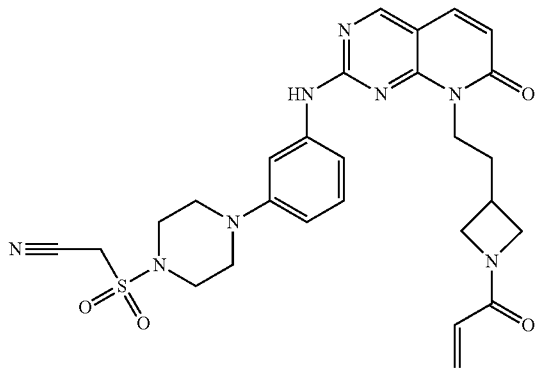 [SMILES: C=CC(=O)N1CC(CCn2c(=O)ccc3cnc(Nc4cccc(N5CCN(S(=O)(=O)CC#N)CC5)c4)nc32)C1] | 563.21 | 563.0 |
| 129 | 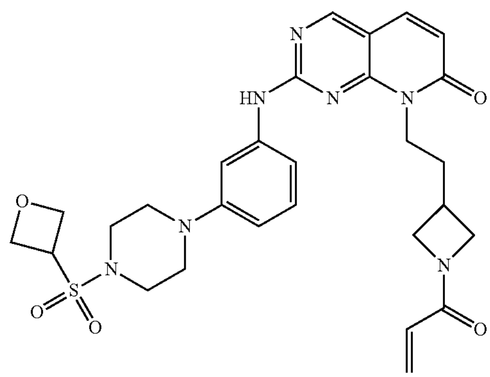 [SMILES: C=CC(=O)N1CC(CCn2c(=O)ccc3cnc(Nc4cccc(N5CCN(S(=O)(=O)C6COC6)CC5)c4)nc32)C1] | 580.23 | 580.0 |
| 130 | 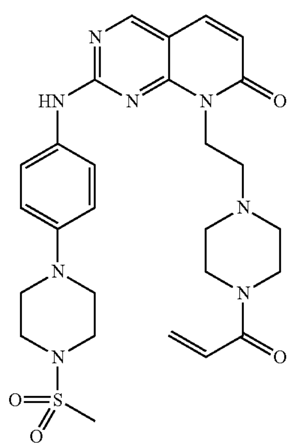 [SMILES: C=CC(=O)N1CCN(CCn2c(=O)ccc3cnc(Nc4ccc(N5CCN(S(C)(=O)=O)CC5)cc4)nc32)CC1] | 567.24 | 567.0 |
| 131 | 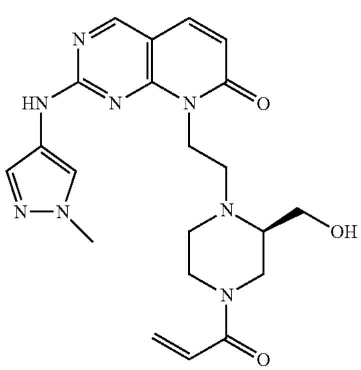 [SMILES: C=CC(=O)N1CCN(CCn2c(=O)ccc3cnc(Nc4cnn(C)c4)nc32)[C@@H](CO)C1] | 539.21 | 439.0 |

TABLE 1-continued
| Ex No. | Structure | Calculated [M + H]+ | Found [M + H]+ |
|---|---|---|---|
| 132 | 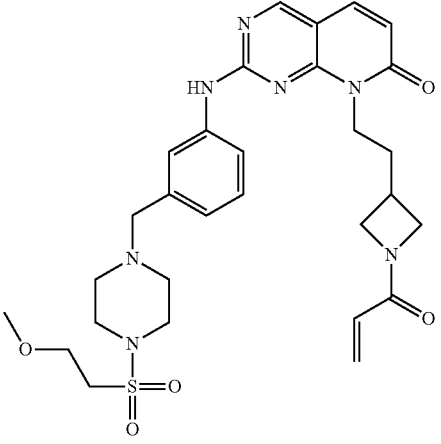 [SMILES: C=CC(=O)N1CC(CCn2c(=O)ccc3cnc(Nc4cccc(CN5CCN(S(=O)(=O)CCOC)CC5)c4)nc32)C1] | 596.26 | 596.1 |
| 133 | 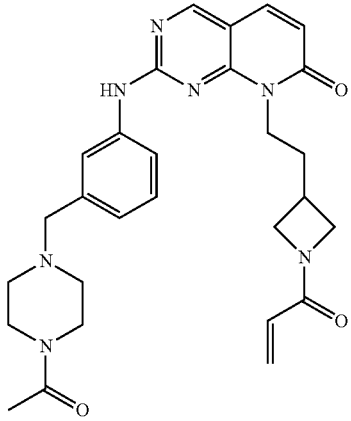 [SMILES: C=CC(=O)N1CC(CCn2c(=O)ccc3cnc(Nc4cccc(CN5CCN(C(C)=O)CC5)c4)nc32)C1] | 516.26 | 516.3 |
| 134 | 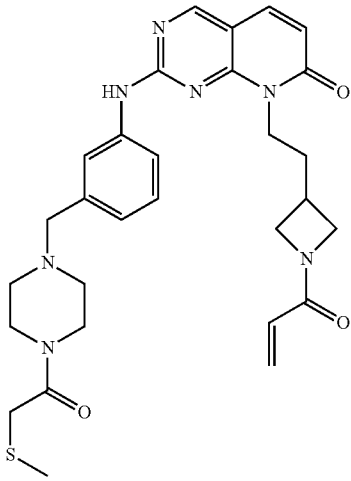 [SMILES: C=CC(=O)N1CC(CCn2c(=O)ccc3cnc(Nc4cccc(CN5CCN(C(=O)CSC)CC5)c4)nc32)C1] | 562.25 | 562.2 |

TABLE 1-continued

| Ex No. | Structure | Calculated [M + H]+ | Found [M + H]+ |
|---|---|---|---|
| 135 | 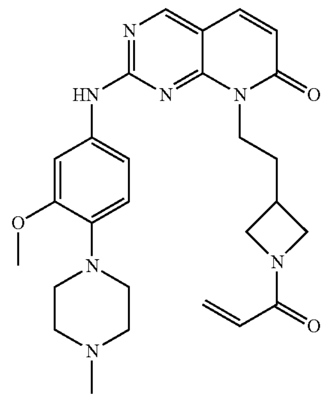 [SMILES: C=CC(=O)N1CC(CCn2c(=O)ccc3cnc(Nc4ccc(N5CCN(C)CC5)c(OC)c4)nc32)C1] | 504.26 | 504.2 |
| 136 | 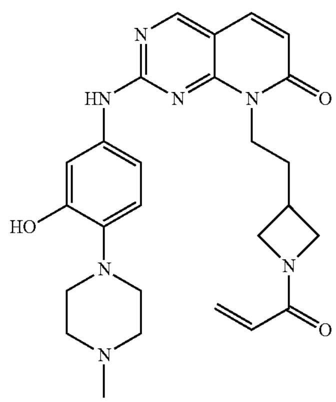 [SMILES: C=CC(=O)N1CC(CCn2c(=O)ccc3cnc(Nc4ccc(N5CCN(C)CC5)c(O)c4)nc32)C1] | 490.25 | 490.1 |
| 137 | 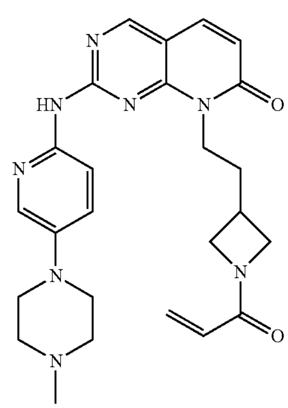 [SMILES: C=CC(=O)N1CC(CCn2c(=O)ccc3cnc(Nc4ccc(N5CCN(C)CC5)cn4)nc32)C1] | 475.25 | 475.2 |

TABLE 1-continued

| Ex No. | Structure | Calculated [M + H]+ | Found [M + H]+ |
|---|---|---|---|
| 138 | 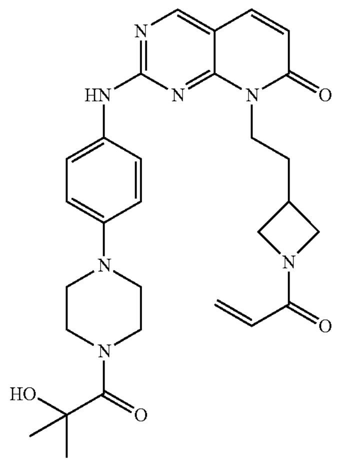 [SMILES: C=CC(=O)N1CC(CCn2c(=O)ccc3cnc(Nc4ccc(N5CCN(C(=O)C(C)(C)O)CC5)cc4)nc32)C1] | 546.28 | 546.0 |
| 139 | 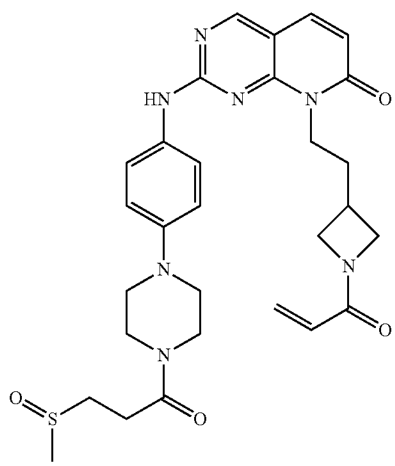 [SMILES: C=CC(=O)N1CC(CCn2c(=O)ccc3cnc(Nc4ccc(N5CCN(C(=O)CCS(C)=O)CC5)cc4)nc32)C1] | 578.25 | 578.0 |
| 140 | 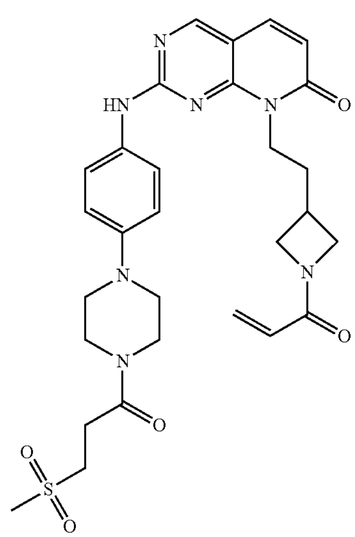 [SMILES: C=CC(=O)N1CC(CCn2c(=O)ccc3cnc(Nc4ccc(N5CCN(C(=O)CCS(C)(=O)=O)CC5)cc4)nc32)C1] | 594.24 | 594.0 |

TABLE 1-continued

| Ex No. | Structure | Calculated [M + H]+ | Found [M + H]+ |
|---|---|---|---|
| 141 | 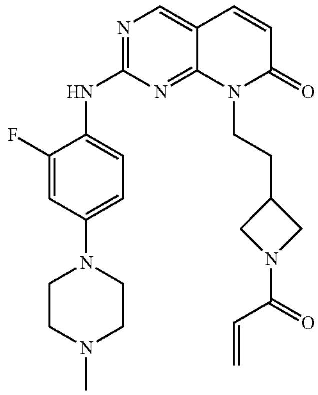 [SMILES: C=CC(=O)N1CC(CCn2c(=O)ccc3cnc(Nc4ccc(N5CCN(C)CC5)cc4F)nc32)C1] | 492.24 | 492.2 |
| 142 | 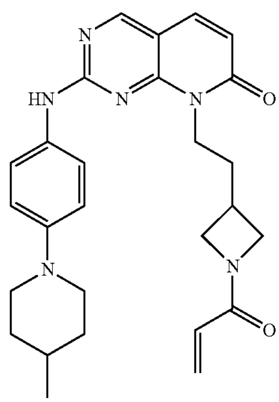 [SMILES: C=CC(=O)N1CC(CCn2c(=O)ccc3cnc(Nc4ccc(N5CCC(C)CC5)cc4)nc32)C1] | 473.26 | 473.2 |
| 143 | 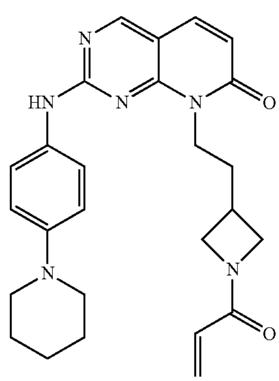 [SMILES: C=CC(=O)N1CC(CCn2c(=O)ccc3cnc(Nc4ccc(N5CCCCC5)cc4)nc32)C1] | 459.24 | 459.2 |

TABLE 1-continued
| Ex No. | Structure | Calculated [M + H]+ | Found [M + H]+ |
|---|---|---|---|
| 144 | 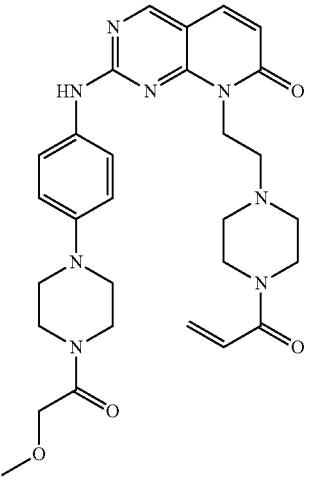 [SMILES: C=CC(=O)N1CCN(CCn2c(=O)ccc3cnc(Nc4ccc(N5CCN(C(=O)COC)CC5)cc4)nc32)CC1] | 561.29 | 561.0 |
| 145 | 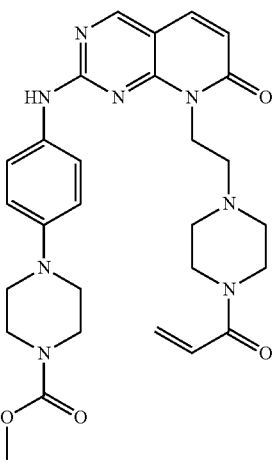 [SMILES: C=CC(=O)N1CCN(CCn2c(=O)ccc3cnc(Nc4ccc(N5CCN(C(=O)OC)CC5)cc4)nc32)CC1] | 547.27 | 547.0 |
| 146 | 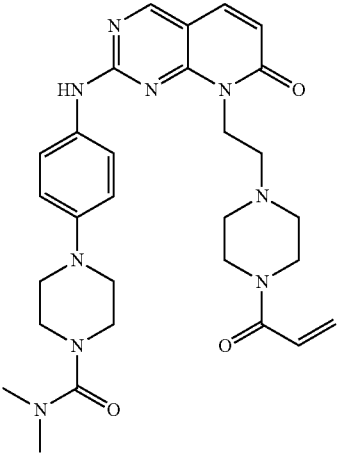 [SMILES: C=CC(=O)N1CCN(CCn2c(=O)ccc3cnc(Nc4ccc(N5CCN(C(=O)N(C)C)CC5)cc4)nc32)CC1] | 560.3 | 560.0 |

TABLE 1-continued

| Ex No. | Structure | Calculated [M + H]+ | Found [M + H]+ |
|---|---|---|---|
| 147 | 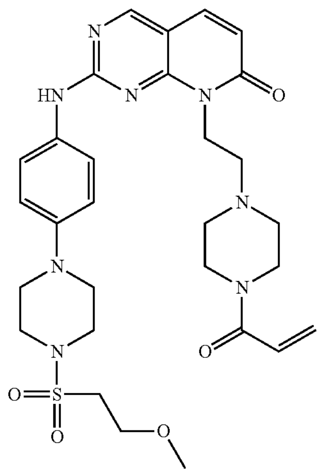 [SMILES: C=CC(=O)N1CCN(CCn2c(=O)ccc3cnc(Nc4ccc(N5CCN(S(=O)(=O)CCOC)CC5)cc4)nc32)CC1] | 611.27 | 611.0 |
| 148 | 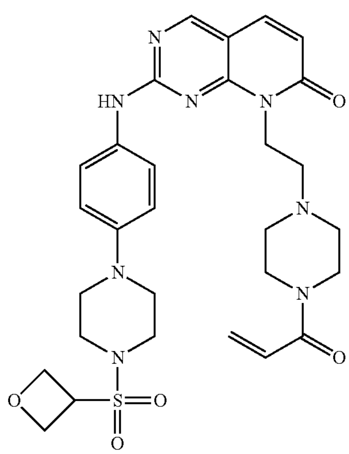 [SMILES: C=CC(=O)N1CCN(CCn2c(=O)ccc3cnc(Nc4ccc(N5CCN(S(=O)(=O)C6COC6)CC5)cc4)nc32)CC1] | 609.25 | 609.0 |
| 149 | 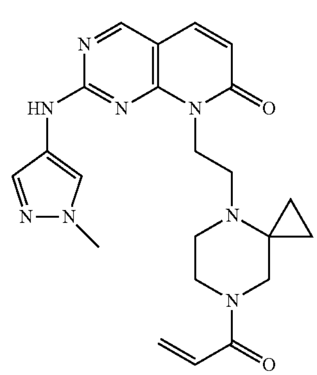 [SMILES: C=CC(=O)N1CCN(CCn2c(=O)ccc3cnc(Nc4cnn(C)c4)nc32)C2(CC2)C1] | 435.22 | 435.2 |

TABLE 1-continued
| Ex No. | Structure | Calculated [M + H]+ | Found [M + H]+ |
|---|---|---|---|
| 150 | 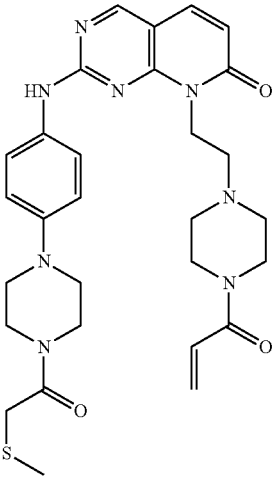 [SMILES: C=CC(=O)N1CCN(CCn2c(=O)ccc3cnc(Nc4ccc(N5CCN(C(=O)CSC)CC5)cc4)nc32)CC1] | 577.26 | 577.0 |
| 151 | 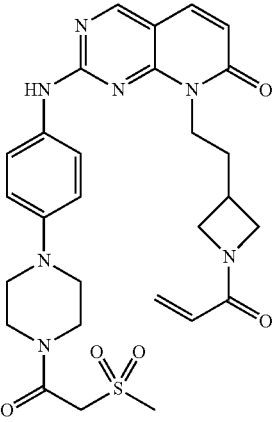 [SMILES: C=CC(=O)N1CC(CCn2c(=O)ccc3cnc(Nc4ccc(N5CCN(C(=O)CS(C)(=O)=O)CC5)cc4)nc32)C1] | 580.23 | 580.0 |
| 152 | 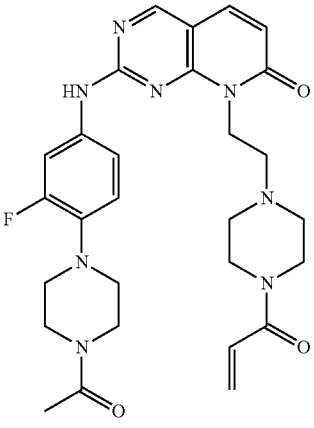 [SMILES: C=CC(=O)N1CCN(CCn2c(=O)ccc3cnc(Nc4ccc(N5CCN(C(C)=O)CC5)c(F)c4)nc32)CC1] | 549.27 | 549.2 |

TABLE 1-continued

| Ex No. | Structure | Calculated [M + H]+ | Found [M + H]+ |
|---|---|---|---|
| 153 | 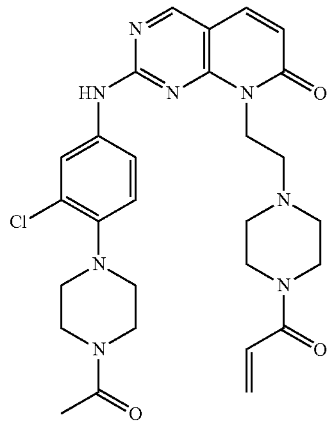 [SMILES: C=CC(=O)N1CCN(CCn2c(=O)ccc3cnc(Nc4ccc(N5CCN(C(C)=O)CC5)c(Cl)c4)nc32)CC1] | 565.24 | 565.1 |
| 154 | 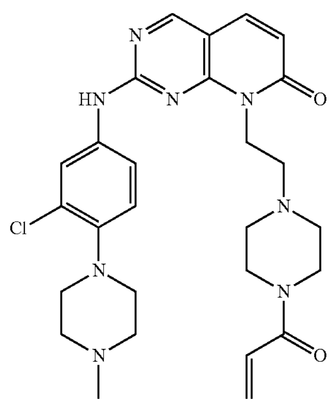 [SMILES: C=CC(=O)N1CCN(CCn2c(=O)ccc3cnc(Nc4ccc(N5CCN(C)CC5)c(Cl)c4)nc32)CC1] | 537.24 | 537.1 |
| 155 | 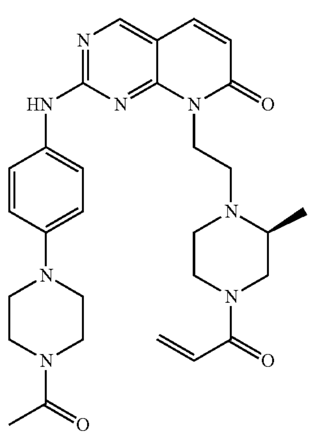 [SMILES: C=CC(=O)N1CCN(CCn2c(=O)ccc3cnc(Nc4ccc(N5CCN(C(C)=O)CC5)cc4)nc32)[C@@H](C)C1] | 545.29 | 545.6 |

TABLE 1-continued

| Ex No. | Structure | Calculated [M + H]+ | Found [M + H]+ |
|---|---|---|---|
| 156 | 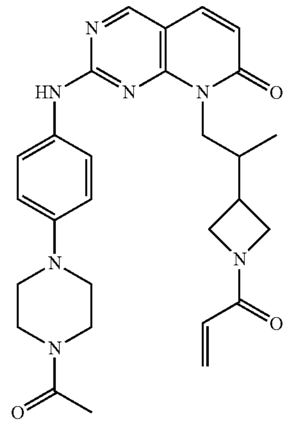 [SMILES: C=CC(=O)N1CC(C(C)Cn2c(=O)ccc3cnc(Nc4ccc(N5CCN(C(C)=O)CC5)cc4)nc32)C1] | 516.26 | 516.2 |
| 157 | 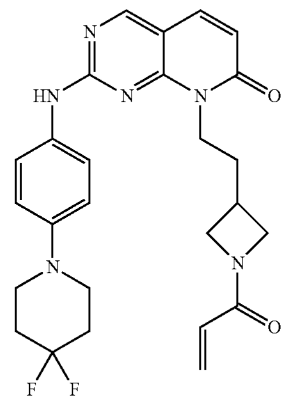 [SMILES: C=CC(=O)N1CC(CCn2c(=O)ccc3cnc(Nc4ccc(N5CCC(F)(F)CC5)cc4)nc32)C1] | 495.22 | 495.1 |
| 158 | 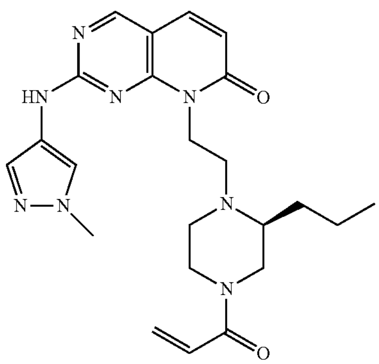 [SMILES: C=CC(=O)N1CCN(CCn2c(=O)ccc3cnc(Nc4cnn(C)c4)nc32)[C@@H](CCC)C1] | 451.25 | 451.1 |
| 159 | 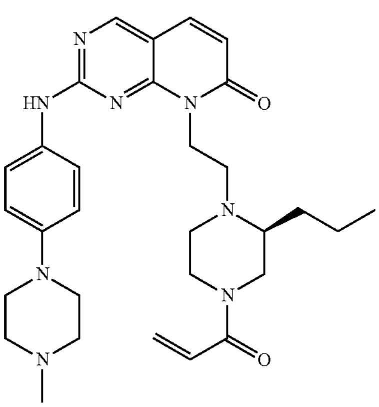 [SMILES: C=CC(=O)N1CCN(CCn2c(=O)ccc3cnc(Nc4ccc(N5CCN(C)CC5)cc4)nc32)[C@@H](CCC)C1] | 531.31 | 531.1 |

TABLE 1-continued

| Ex No. | Structure | Calculated [M + H]+ | Found [M + H]+ |
|---|---|---|---|
| 160 | 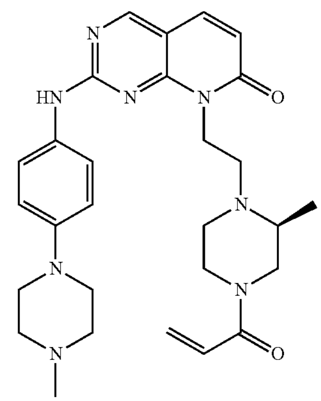 [SMILES: C=CC(=O)N1CCN(CCn2c(=O)ccc3cnc(Nc4ccc(N5CCN(C)CC5)cc4)nc32)[C@@H](C)C1] | 517.30 | 517.3 |
| 161 | 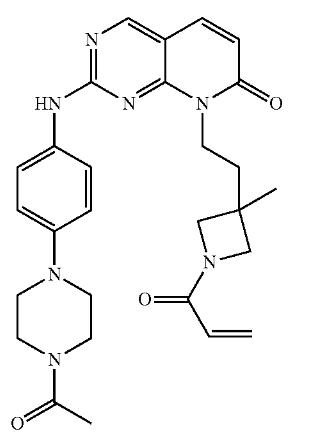 [SMILES: C=CC(=O)N1CC(C)(CCn2c(=O)ccc3cnc(Nc4ccc(N5CCN(C(C)=O)CC5)cc4)nc32)C1] | 516.26 | 516.1 |
| 162 | 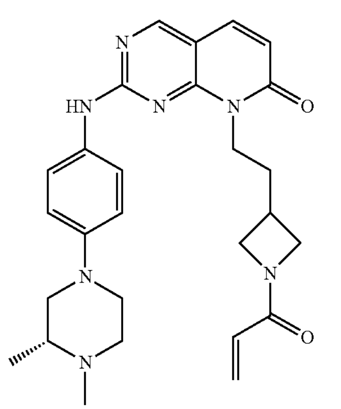 [SMILES: C=CC(=O)N1CC(CCn2c(=O)ccc3cnc(Nc4ccc(N5CCN(C)[C@H](C)C5)cc4)nc32)C1] | 488.27 | 488.2 |

TABLE 1-continued

| Ex No. | Structure | Calculated [M + H]+ | Found [M + H]+ |
|---|---|---|---|
| 163 | 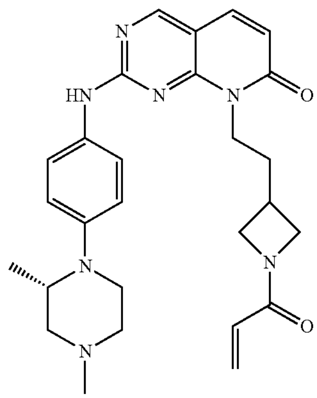 [SMILES: C=CC(=O)N1CC(CCn2c(=O)ccc3cnc(Nc4ccc(N5CCN(C)C[C@@H]5C)cc4)nc32)C1] | 488.27 | 488.2 |
| 164 | 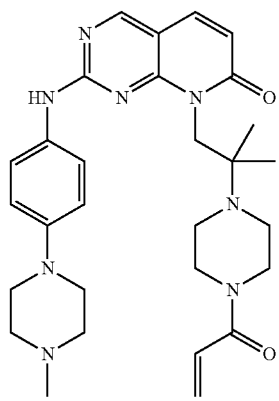 [SMILES: C=CC(=O)N1CCN(C(C)(C)Cn2c(=O)ccc3cnc(Nc4ccc(N5CCN(C)CC5)cc4)nc32)CC1] | 531.31 | 531.2 |
| 165 | 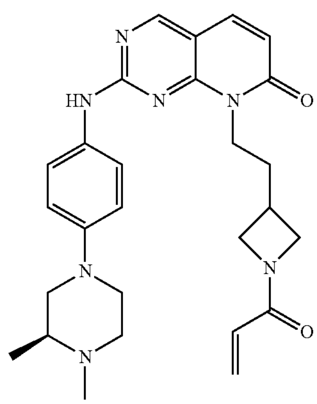 [SMILES: C=CC(=O)N1CC(CCn2c(=O)ccc3cnc(Nc4ccc(N5CCN(C)[C@@H](C)C5)cc4)nc32)C1] | 488.27 | 488.2 |
| 166 | 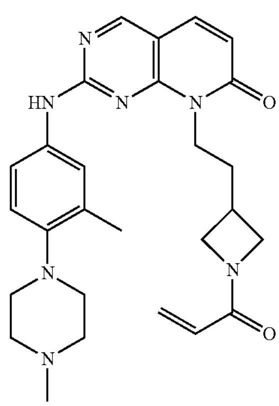 [SMILES: C=CC(=O)N1CC(CCn2c(=O)ccc3cnc(Nc4ccc(N5CCN(C)CC5)c(C)c4)nc32)C1] | 488.27 | 488.1 |

TABLE 1-continued

| Ex No. | Structure | Calculated [M + H]+ | Found [M + H]+ |
|---|---|---|---|
| 167 | 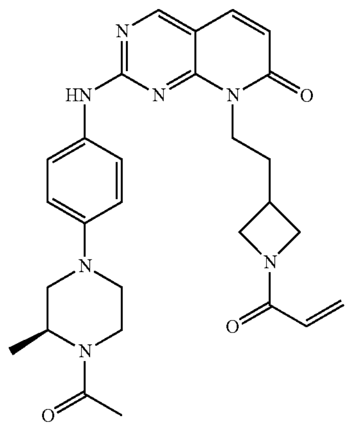 [SMILES: C=CC(=O)N1CC(CCn2c(=O)ccc3cnc(Nc4ccc(N5CCN(C(C)=O)[C@@H](C)C5)cc4)nc32)C1] | 516.26 | 516.1 |
| 168 | 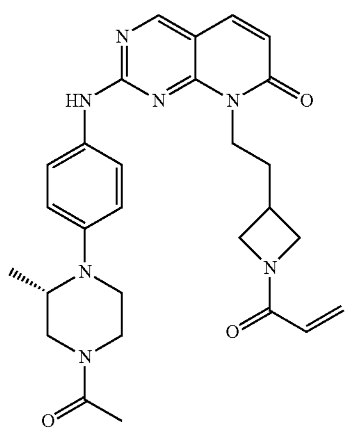 [SMILES: C=CC(=O)N1CC(CCn2c(=O)ccc3cnc(Nc4ccc(N5CCN(C(C)=O)C[C@@H]5C)cc4)nc32)C1] | 516.26 | 516.1 |
| 169 | 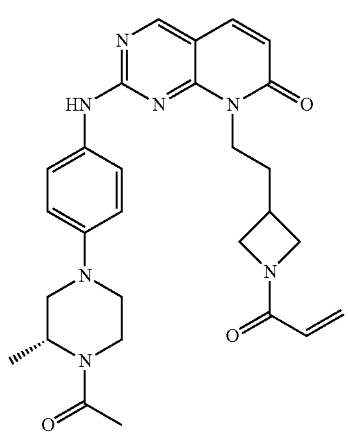 [SMILES: C=CC(=O)N1CC(CCn2c(=O)ccc3cnc(Nc4ccc(N5CCN(C(C)=O)[C@H](C)C5)cc4)nc32)C1] | 516.26 | 516.1 |

TABLE 1-continued

| Ex No. | Structure | Calculated [M + H]+ | Found [M + H]+ |
|---|---|---|---|
| 170 | 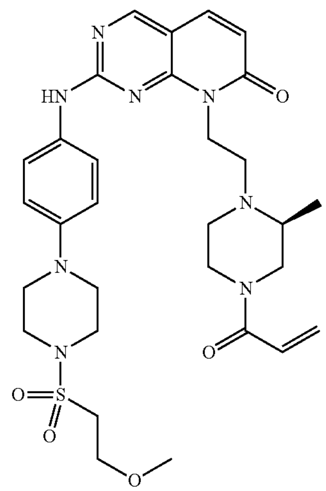 [SMILES: C=CC(=O)N1CCN(CCn2c(=O)ccc3cnc(Nc4ccc(N5CCN(S(=O)(=O)CCOC)CC5)cc4)nc32)[C@@H](C)C1] | 625.28 | 625.1 |
| 171 | 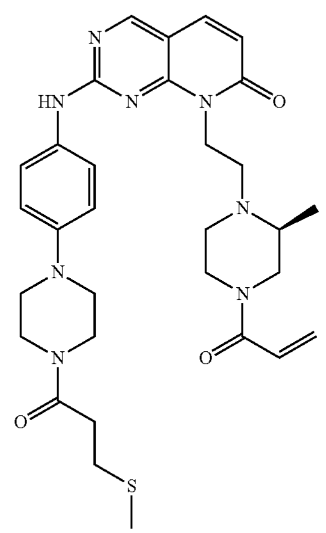 [SMILES: C=CC(=O)N1CCN(CCn2c(=O)ccc3cnc(Nc4ccc(N5CCN(C(=O)CCSC)CC5)cc4)nc32)[C@@H](C)C1] | 605.29 | 605.1 |
| 172 | 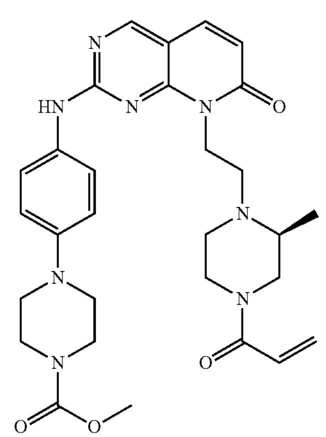 [SMILES: C=CC(=O)N1CCN(CCn2c(=O)ccc3cnc(Nc4ccc(N5CCN(C(=O)OC)CC5)cc4)nc32)[C@@H](C)C1] | 561.29 | 561.1 |

TABLE 1-continued
| Ex No. | Structure | Calculated [M + H]+ | Found [M + H]+ |
|---|---|---|---|
| 173 | 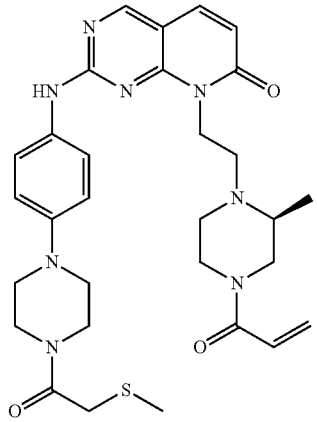 [SMILES: C=CC(=O)N1CCN(CCn2c(=O)ccc3cnc(Nc4ccc(N5CCN(C(=O)CSC)CC5)cc4)nc32)[C@@H](C)C1] | 591.28 | 591.2 |
| 174 | 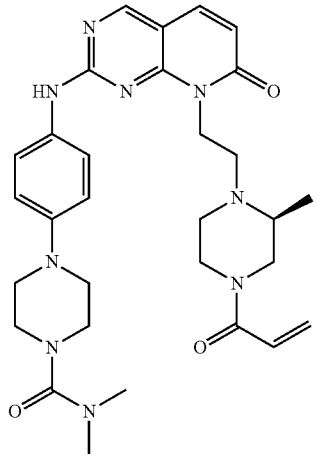 [SMILES: C=CC(=O)N1CCN(CCn2c(=O)ccc3cnc(Nc4ccc(N5CCN(C(=O)N(C)C)CC5)cc4)nc32)[C@@H](C)C1] | 574.32 | 574.2 |
| 175 | 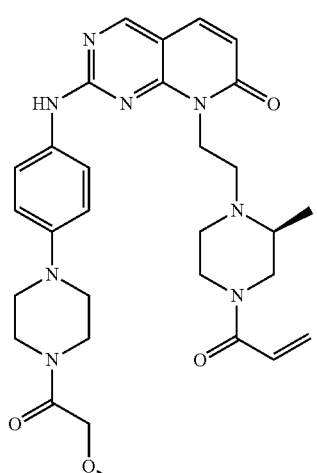 | 575.30 | 575.3 |

TABLE 1-continued

| Ex No. | Structure | Calculated [M + H]+ | Found [M + H]+ |
|---|---|---|---|
| 176 | 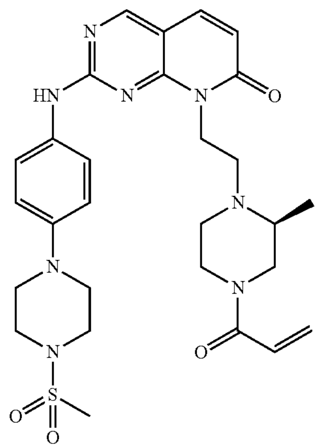 [SMILES: C=CC(=O)N1CCN(CCn2c(=O)ccc3cnc(Nc4ccc(N5CCN(S(C)(=O)=O)CC5)cc4)nc32)[C@@H](C)C1] | 581.26 | 581.2 |
| 177 | 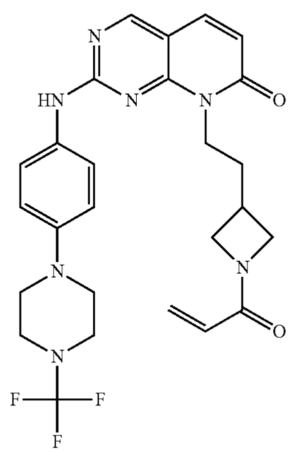 [SMILES: C=CC(=O)N1CC(CCn2c(=O)ccc3cnc(Nc4ccc(N5CCN(C(F)(F)F)CC5)cc4)nc32)C1] | 528.23 | 528.1 |
| 178 | 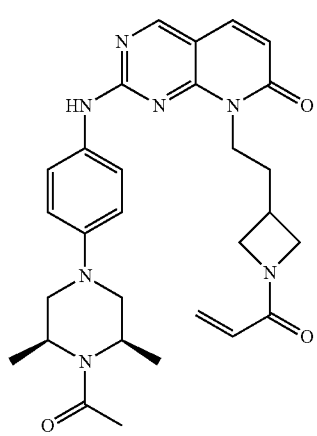 [SMILES: C=CC(=O)N1CC(CCn2c(=O)ccc3cnc(Nc4ccc(N5C[C@@H](C)N(C(C)=O)[C@@H](C)C5)cc4)nc32)C1] | 530.28 | 530.2 |

TABLE 1-continued
| Ex No. | Structure | Calculated [M + H]+ | Found [M + H]+ |
|---|---|---|---|
| 179 | 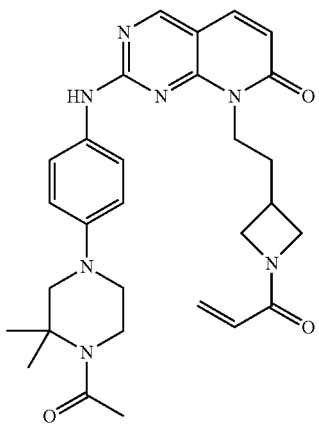 [SMILES: C=CC(=O)N1CC(CCn2c(=O)ccc3cnc(Nc4ccc(N5CCN(C(C)=O)C(C)(C)C5)cc4)nc32)C1] | 530.28 | 530.2 |
| 180 | 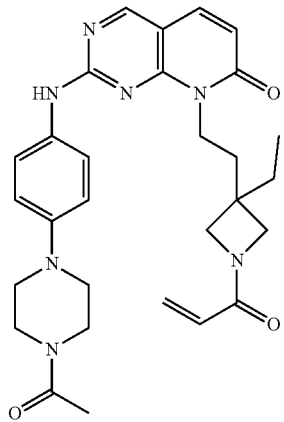 [SMILES: C=CC(=O)N1CC(CC)(CCn2c(=O)ccc3cnc(Nc4ccc(N5CCN(C(C)=O)CC5)cc4)nc32)C1] | 530.28 | 530.2 |
| 181 | 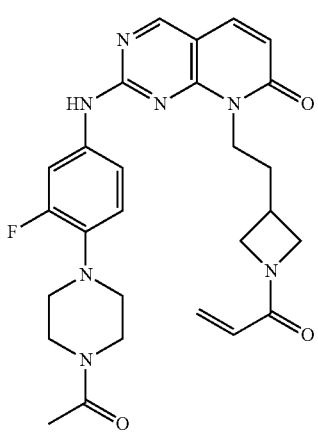 [SMILES: C=CC(=O)N1CC(CCn2c(=O)ccc3cnc(Nc4ccc(N5CCN(C(C)=O)CC5)c(F)c4)nc32)C1] | 520.24 | 520.1 |

TABLE 1-continued
| Ex No. | Structure | Calculated [M + H]+ | Found [M + H]+ |
|---|---|---|---|
| 182 | 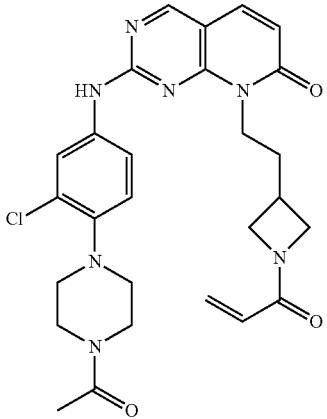 [SMILES: C=CC(=O)N1CC(CCn2c(=O)ccc3cnc(Nc4ccc(N5CCN(C(C)=O)CC5)c(Cl)c4)nc32)C1] | 536.21 | 536.0 |
| 183 | 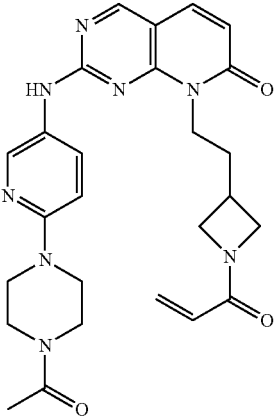 | 503.24 | 503.0 |
| 184 | 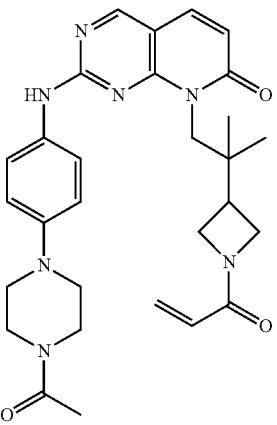 [SMILES: C=CC(=O)N1CC(C(C)(C)Cn2c(=O)ccc3cnc(Nc4ccc(N5CCN(C(C)=O)CC5)cc4)nc32)C1] | 530.28 | 530.2 |

TABLE 1-continued

| Ex No. | Structure | Calculated [M + H]+ | Found [M + H]+ |
|---|---|---|---|
| 185 | 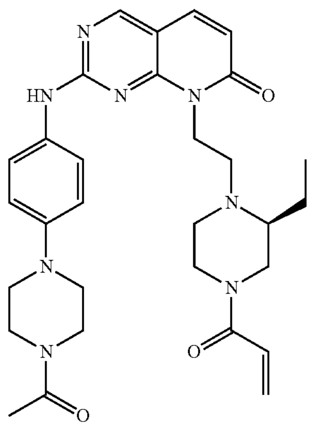 [SMILES: C=CC(=O)N1CCN(CCn2c(=O)ccc3cnc(Nc4ccc(N5CCN(C(C)=O)CC5)cc4)nc32)[C@@H](CC)C1] | 559.31 | 559.0 |
| 186 | 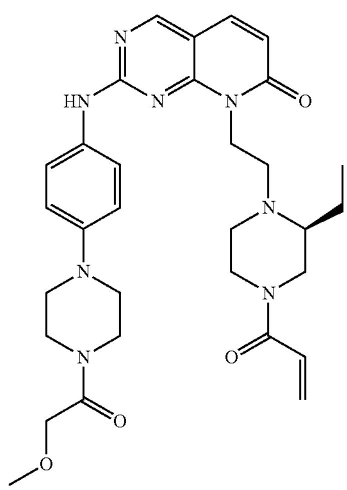 [SMILES: C=CC(=O)N1CCN(CCn2c(=O)ccc3cnc(Nc4ccc(N5CCN(C(=O)COC)CC5)cc4)nc32)[C@@H](CC)C1] | 589.32 | 589.0 |
| 187 | 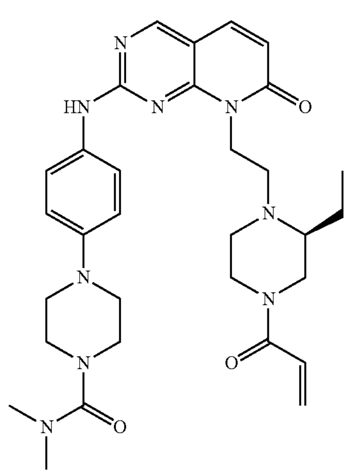 [SMILES: C=CC(=O)N1CCN(CCn2c(=O)ccc3cnc(Nc4ccc(N5CCN(C(=O)N(C)C)CC5)cc4)nc32)[C@@H](CC)C1] | 588.33 | 588.0 |

| Ex No. | Structure | Calculated [M + H]+ | Found [M + H]+ |
|---|---|---|---|
| 188 | 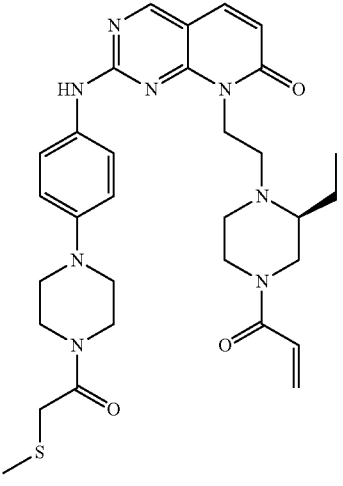 [SMILES: C=CC(=O)N1CCN(CCn2c(=O)ccc3cnc(Nc4ccc(N5CCN(C(=O)CSC)CC5)cc4)nc32)[C@@H](CC)C1] | 605.29 | 605.0 |
| 189 | 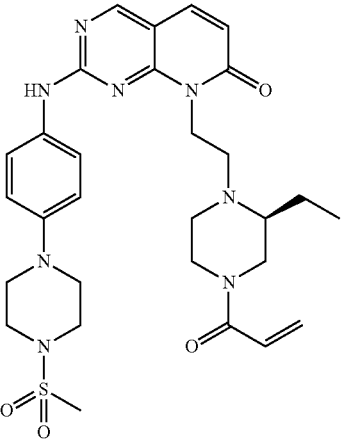 [SMILES: C=CC(=O)N1CCN(CCn2c(=O)ccc3cnc(Nc4ccc(N5CCN(S(C)(=O)=O)CC5)cc4)nc32)[C@@H](CC)C1] | 595.27 | 595.2 |
| 190 | 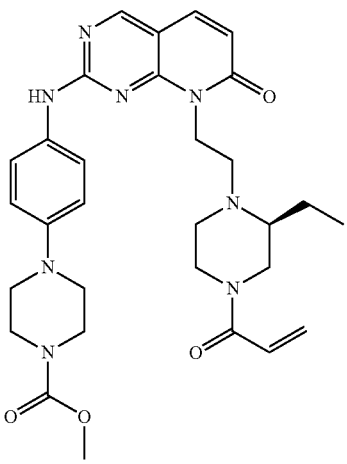 [SMILES: C=CC(=O)N1CCN(CCn2c(=O)ccc3cnc(Nc4ccc(N5CCN(C(=O)OC)CC5)cc4)nc32)[C@@H](CC)C1] | 575.30 | 575.2 |

TABLE 1-continued

| Ex No. | Structure | Calculated [M + H]+ | Found [M + H]+ |
|---|---|---|---|
| 191 | 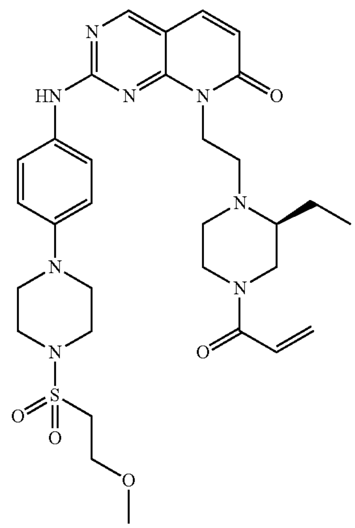 [SMILES: C=CC(=O)N1CCN(CCn2c(=O)ccc3cnc(Nc4ccc(N5CCN(S(=O)(=O)CCOC)CC5)cc4)nc32)[C@@H](CC)C1] | 639.30 | 639.2 |
| 192 | 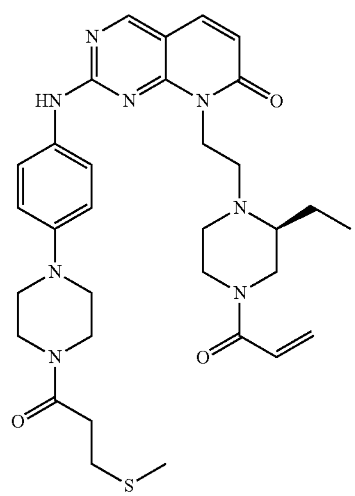 [SMILES: C=CC(=O)N1CCN(CCn2c(=O)ccc3cnc(Nc4ccc(N5CCN(C(=O)CCSC)CC5)cc4)nc32)[C@@H](CC)C1] | 619.31 | 619.3 |
| 193 | 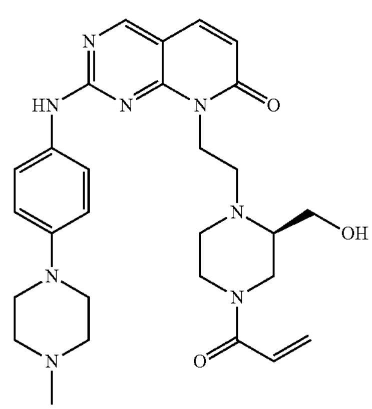 [SMILES: C=CC(=O)N1CCN(CCn2c(=O)ccc3cnc(Nc4ccc(N5CCN(C)CC5)cc4)nc32)[C@@H](CO)C1] | 533.29 | 533.2 |

TABLE 1-continued

| Ex No. | Structure | Calculated [M + H]+ | Found [M + H]+ |
|---|---|---|---|
| 194 | 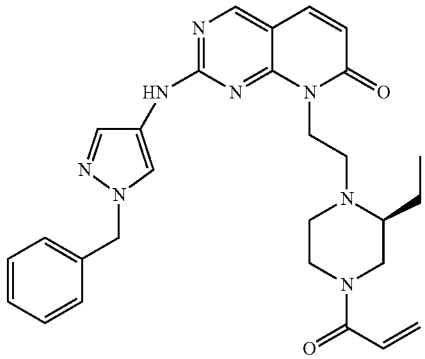 [SMILES: C=CC(=O)N1CCN(CCn2c(=O)ccc3cnc(Nc4cnn(Cc5ccccc5)c4)nc32)[C@@H](CC)C1] | 513.26 | 513.0 |
| 195 | 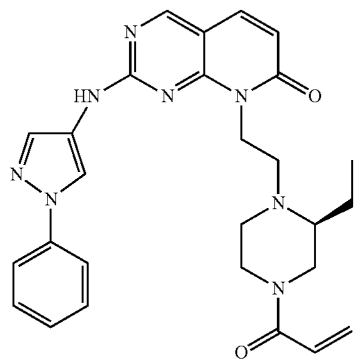 [SMILES: C=CC(=O)N1CCN(CCn2c(=O)ccc3cnc(Nc4cnn(-c5ccccc5)c4)nc32)[C@@H](CC)C1] | 499.25 | 499.0 |
| 196 | 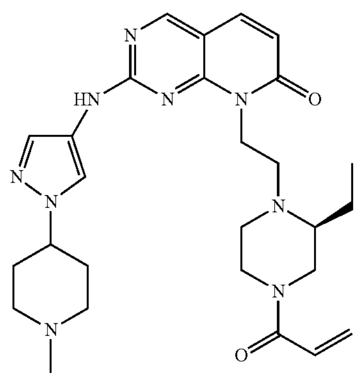 [SMILES: C=CC(=O)N1CCN(CCn2c(=O)ccc3cnc(Nc4cnn(C5CCN(C)CC5)c4)nc32)[C@@H](CC)C1] | 520.31 | 520.0 |
| 197 | 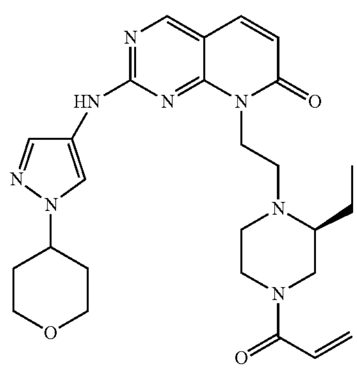 [SMILES: C=CC(=O)N1CCN(CCn2c(=O)ccc3cnc(Nc4cnn(C5CCOCC5)c4)nc32)[C@@H](CC)C1] | 507.28 | 507.0 |

TABLE 1-continued

| Ex No. | Structure | Calculated [M + H]+ | Found [M + H]+ |
|---|---|---|---|
| 198 | 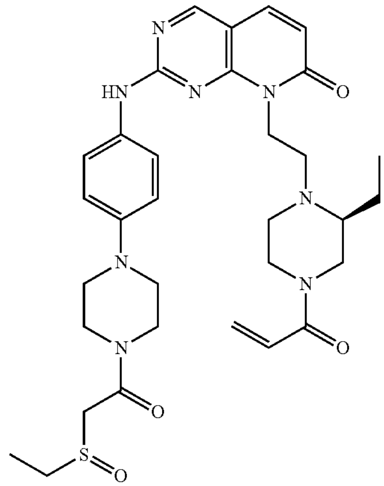 [SMILES: C=CC(=O)N1CCN(CCn2c(=O)ccc3cnc(Nc4ccc(N5CCN(C(=O)CS(=O)CC)CC5)cc4)nc32)[C@@H](CC)C1] | 635.30 | 635.0 |
| 199 | 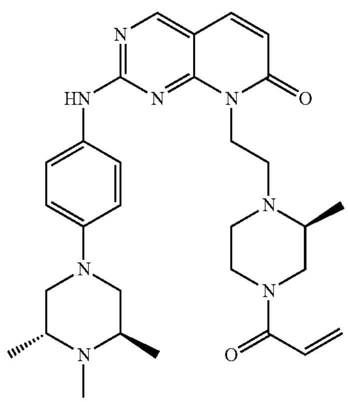 | 545.33 | 545.2 |
| 200 | 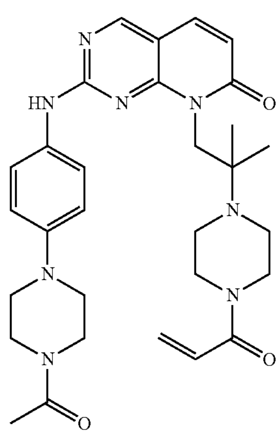 [SMILES: C=CC(=O)N1CCN(C(C)(C)Cn2c(=O)ccc3cnc(Nc4ccc(N5CCN(C(C)=O)CC5)cc4)nc32)CC1] | 559.31 | 559.1 |

TABLE 1-continued

| Ex No. | Structure | Calculated [M + H]+ | Found [M + H]+ |
|---|---|---|---|
| 201 | 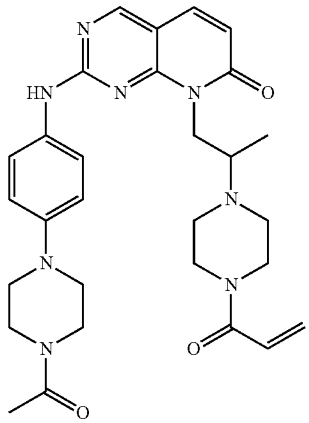 [SMILES: C=CC(=O)N1CCN(C(C)Cn2c(=O)ccc3cnc(Nc4ccc(N5CCN(C(C)=O)CC5)cc4)nc32)CC1] | 545.29 | 545.1 |
| 202 | 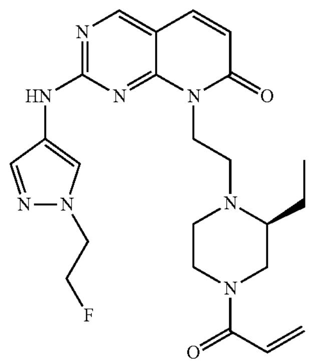 [SMILES: C=CC(=O)N1CCN(CCn2c(=O)ccc3cnc(Nc4cnn(CCF)c4)nc32)[C@@H](CC)C1] | 469.24 | 469.2 |
| 203 | 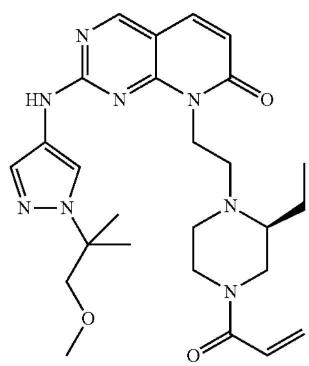 [SMILES: C=CC(=O)N1CCN(CCn2c(=O)ccc3cnc(Nc4cnn(C(C)(C)COC)c4)nc32)[C@@H](CC)C1] | 509.29 | 509.2 |
| 204 | 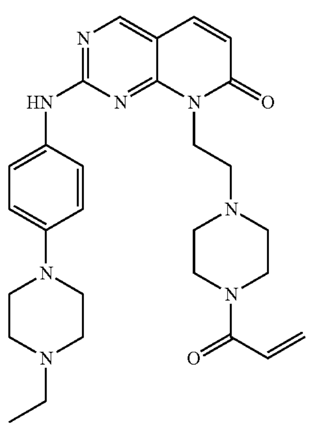 [SMILES: C=CC(=O)N1CCN(CCn2c(=O)ccc3cnc(Nc4ccc(N5CCN(CC)CC5)cc4)nc32)CC1] | 517.30 | 517.2 |

TABLE 1-continued

| Ex No. | Structure | Calculated [M + H]+ | Found [M + H]+ |
|---|---|---|---|
| 205 | 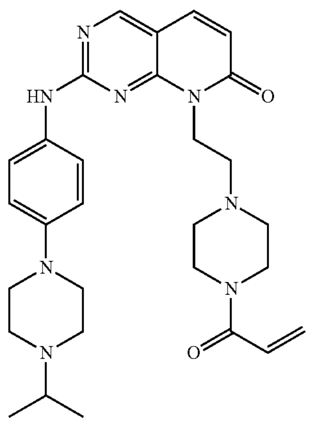 [SMILES: C=CC(=O)N1CCN(CCn2c(=O)ccc3cnc(Nc4ccc(N5CCN(C(C)C)CC5)cc4)nc32)CC1] | 531.31 | 531.2 |
| 206 | 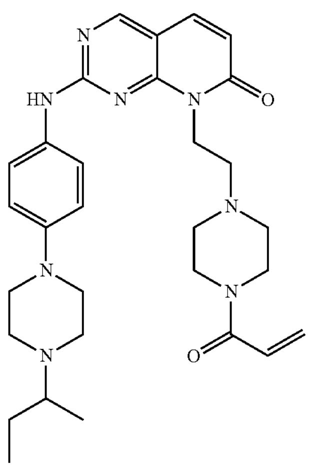 [SMILES: C=CC(=O)N1CCN(CCn2c(=O)ccc3cnc(Nc4ccc(N5CCN(C(C)CC)CC5)cc4)nc32)CC1] | 545.33 | 545.2 |
| 207 | 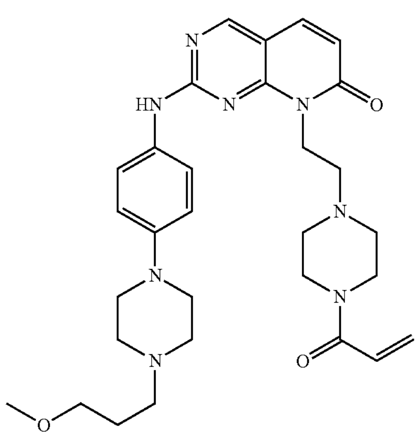 [SMILES: C=CC(=O)N1CCN(CCn2c(=O)ccc3cnc(Nc4ccc(N5CCN(CCCOC)CC5)cc4)nc32)CC1] | 561.32 | 561.2 |

TABLE 1-continued

| Ex No. | Structure | Calculated [M + H]⁺ | Found [M + H]⁺ |
|---|---|---|---|
| 208 | 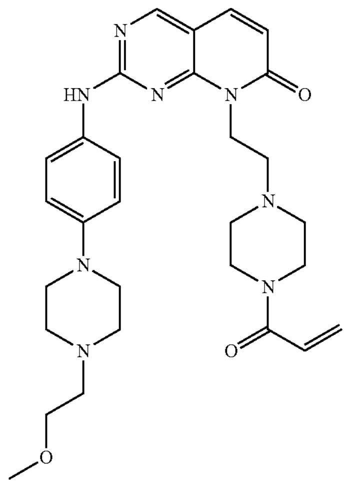 [SMILES: C=CC(=O)N1CCN(CCn2c(=O)ccc3cnc(Nc4ccc(N5CCN(CCOC)CC5)cc4)nc32)CC1] | 547.31 | 547.3 |
| 209 | 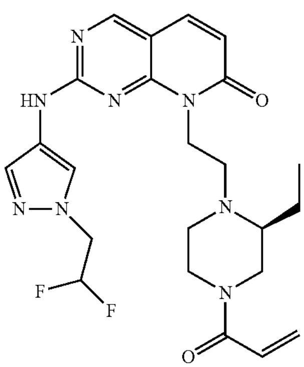 [SMILES: C=CC(=O)N1CCN(CCn2c(=O)ccc3cnc(Nc4cnn(CC(F)F)c4)nc32)[C@@H](CC)C1] | 487.23 | 487.1 |
| 210 | 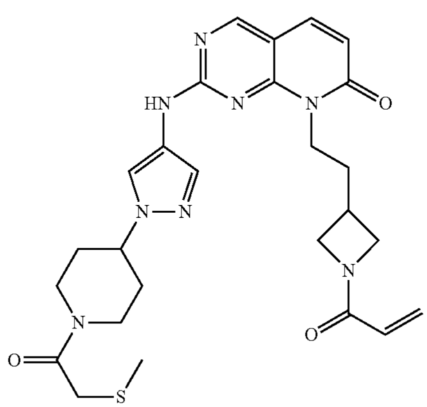 [SMILES: C=CC(=O)N1CC(CCn2c(=O)ccc3cnc(Nc4cnn(C5CCN(C(=O)CSC)CC5)c4)nc32)C1] | 537.23 | 537.1 |

TABLE 1-continued

| Ex No. | Structure | Calculated [M + H]+ | Found [M + H]+ |
|---|---|---|---|
| 211 | 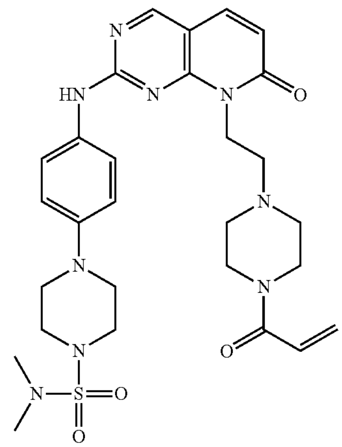 [SMILES: C=CC(=O)N1CCN(CCn2c(=O)ccc3cnc(Nc4ccc(N5CCN(S(=O)(=O)N(C)C)CC5)cc4)nc32)CC1] | 596.27 | 596.0 |
| 212 | 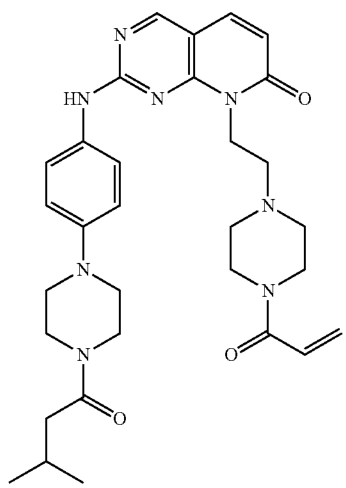 [SMILES: C=CC(=O)N1CCN(CCn2c(=O)ccc3cnc(Nc4ccc(N5CCN(C(=O)CC(C)C)CC5)cc4)nc32)CC1] | 573.32 | 573 |
| 213 | 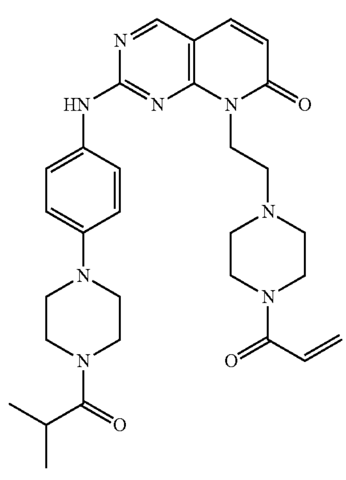 [SMILES: C=CC(=O)N1CCN(CCn2c(=O)ccc3cnc(Nc4ccc(N5CCN(C(=S)N(C)C)CC5)cc4)nc32)CC1] | 559.31 | 559 |

TABLE 1-continued
| Ex No. | Structure | Calculated [M + H]+ | Found [M + H]+ |
|---|---|---|---|
| 214 | 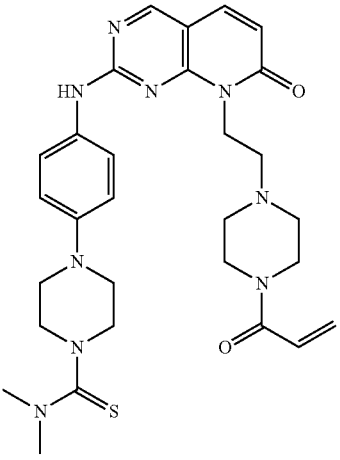 | 576.28 | 576 |
| 215 | 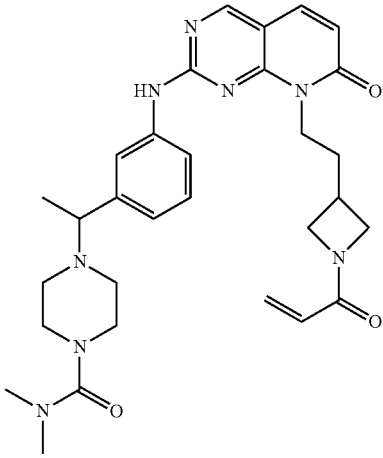 [SMILES: C=CC(=O)N1CC(CCn2c(=O)ccc3cnc(Nc4cccc(C(C)N5CCN(C(=O)N(C)C)CC5)c4)nc32)C1] | 559.31 | 559.1 |
| 216 | 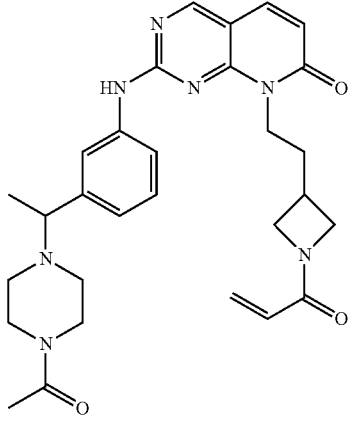 [SMILES: C=CC(=O)N1CC(CCn2c(=O)ccc3cnc(Nc4cccc(C(C)N5CCN(C(C)=O)CC5)c4)nc32)C1] | 530.28 | 530.1 |

TABLE 1-continued

| Ex No. | Structure | Calculated [M + H]+ | Found [M + H]+ |
|---|---|---|---|
| 217 | 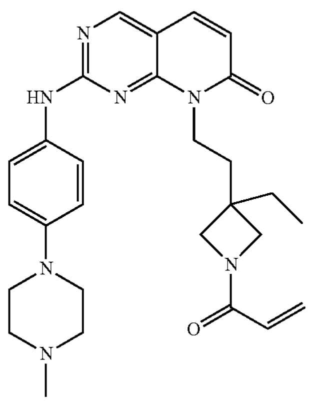 [SMILES: C=CC(=O)N1CC(CC)(CCn2c(=O)ccc3cnc(Nc4ccc(N5CCN(C)CC5)cc4)nc32)C1] | 502.29 | 502.1 |
| 218 | 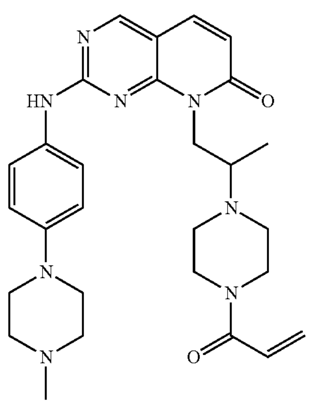 [SMILES: C=CC(=O)N1CCN(C(C)Cn2c(=O)ccc3cnc(Nc4ccc(N5CCN(C)CC5)cc4)nc32)CC1] | 517.30 | 517.2 |
| 219 | 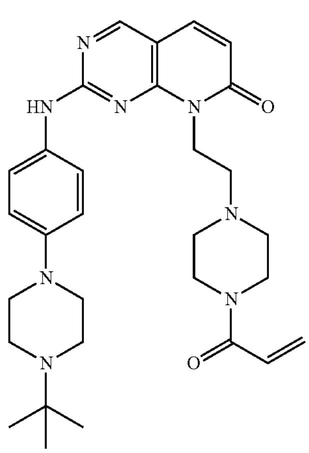 [SMILES: C=CC(=O)N1CCN(CCn2c(=O)ccc3cnc(Nc4ccc(N5CCN(C(C)(C)C)CC5)cc4)nc32)CC1] | 545.33 | 545.2 |

TABLE 1-continued

| Ex No. | Structure | Calculated [M + H]+ | Found [M + H]+ |
|---|---|---|---|
| 220 | 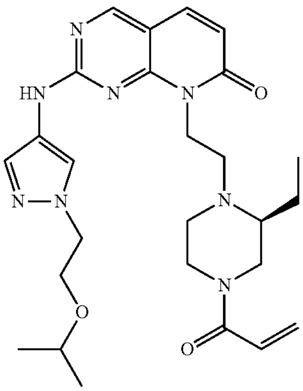 [SMILES: C=CC(=O)N1CCN(CCn2c(=O)ccc3cnc(Nc4cnn(CCOC(C)C)c4)nc32)[C@@H](CC)C1] | 509.29 | 509.1 |
| 221 | 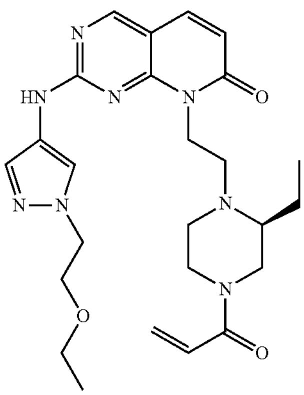 [SMILES: C=CC(=O)N1CCN(CCn2c(=O)ccc3cnc(Nc4cnn(CCOCC)c4)nc32)[C@@H](CC)C1] | 495.28 | 495.1 |
| 222 | 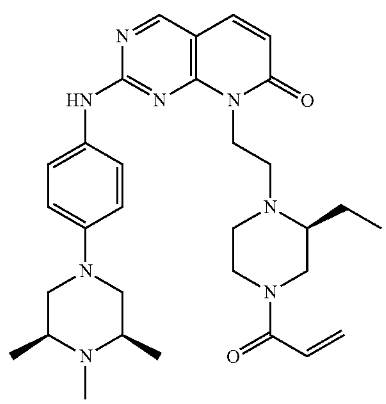 [SMILES: C=CC(=O)N1CCN(CCn2c(=O)ccc3cnc(Nc4ccc(N5C[C@@H](C)N(C)[C@@H](C)C5)cc4)nc32)[C@@H](CC)C1] | 559.34 | 559.3 |
| 223 | 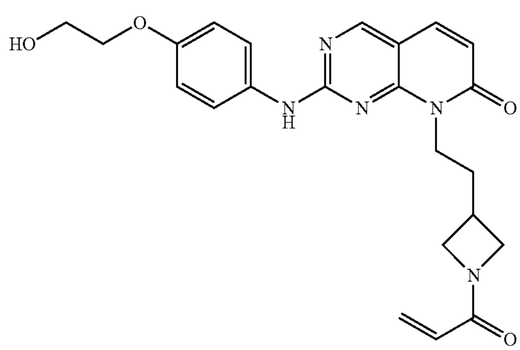 [SMILES: C=CC(=O)N1CC(CCn2c(=O)ccc3cnc(Nc4ccc(OCCO)cc4)nc32)C1] | 436.19 | 436.1 |

TABLE 1-continued

| Ex No. | Structure | Calculated [M + H]+ | Found [M + H]+ |
|---|---|---|---|
| 224 | 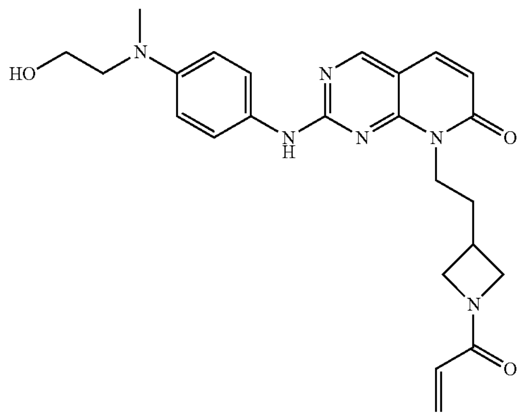 [SMILES: C=CC(=O)N1CC(CCn2c(=O)ccc3cnc(Nc4ccc(N(C)CCO)cc4)nc32)C1] | 449.22 | 449.1 |
| 225 | 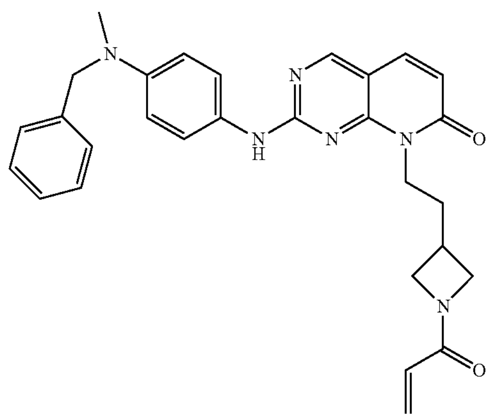 [SMILES: C=CC(=O)N1CC(CCn2c(=O)ccc3cnc(Nc4ccc(N(C)Cc5ccccc5)cc4)nc32)C1] | 495.24 | 495.1 |
| 226 | 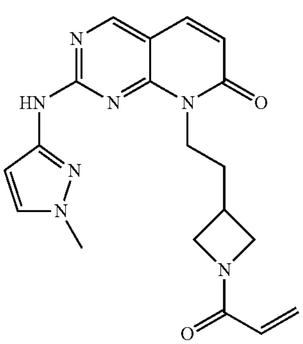 [SMILES: C=CC(=O)N1CC(CCn2c(=O)ccc3cnc(Nc4ccn(C)n4)nc32)C1] | 380.18 | 380.1 |
| 227 | 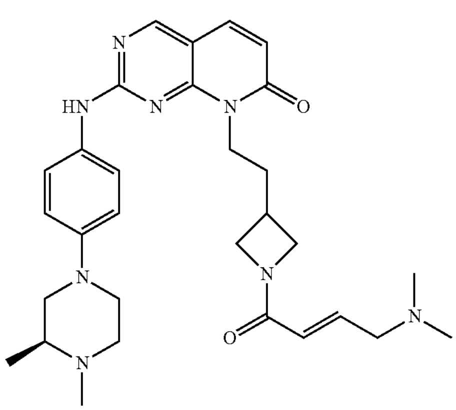 | 545.33 | 545.2 |

TABLE 1-continued
| Ex No. | Structure | Calculated [M + H]+ | Found [M + H]+ |
|---|---|---|---|
| 228 | 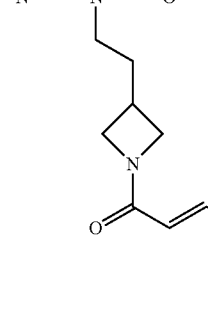 | 545.33 | 545.2 |
| 229 | 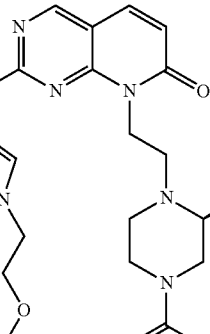 | 481.26 | 481.0 |
| 230 | 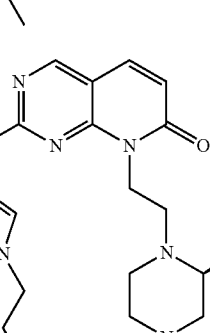 | 495.28 | 495.2 |
| 231 | 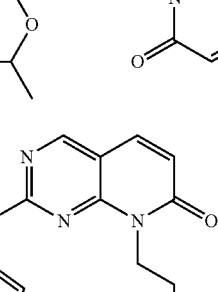 | 506.29 | 506.1 |

TABLE 1-continued

| Ex No. | Structure | Calculated [M + H]+ | Found [M + H]+ |
|---|---|---|---|
| 232 | 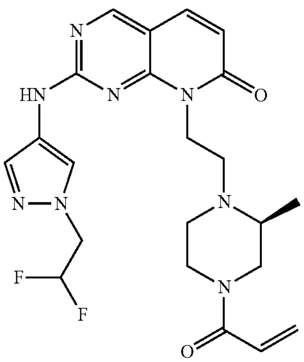 [SMILES: C=CC(=O)N1CCN(CCn2c(=O)ccc3cnc(Nc4cnn(CC(F)F)c4)nc32)[C@@H](C)C1] | 473.21 | 473.1 |
| 233 | 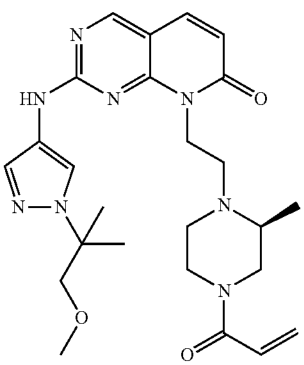 [SMILES: C=CC(=O)N1CCN(CCn2c(=O)ccc3cnc(Nc4cnn(C(C)(C)COC)c4)nc32)[C@@H](C)C1] | 495.28 | 495.1 |
| 234 | 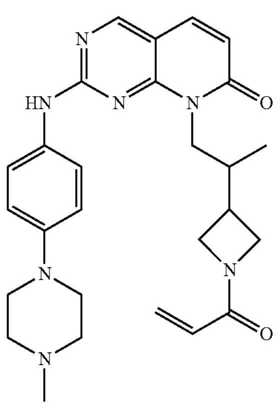 [SMILES: C=CC(=O)N1CC(C(C)Cn2c(=O)ccc3cnc(Nc4ccc(N5CCN(C)CC5)cc4)nc32)C1] | 488.27 | 488.1 |
| 235 | 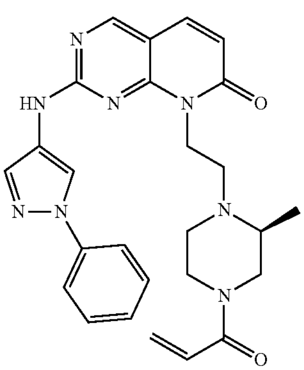 [SMILES: C=CC(=O)N1CCN(CCn2c(=O)ccc3cnc(Nc4cnn(-c5ccccc5)c4)nc32)[C@@H](C)C1] | 485.23 | 485.1 |

TABLE 1-continued

| Ex No. | Structure | Calculated [M + H]+ | Found [M + H]+ |
|---|---|---|---|
| 236 | 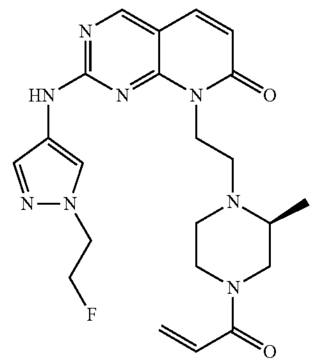 [SMILES: C=CC(=O)N1CCN(CCn2c(=O)ccc3cnc(Nc4cnn(CCF)c4)nc32)[C@@H](C)C1] | 455.22 | 455.1 |
| 237 | 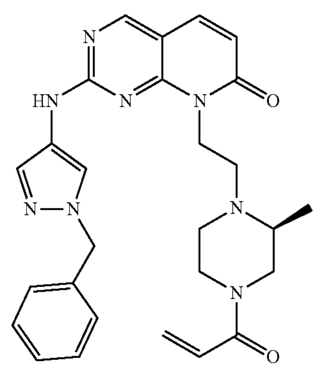 [SMILES: C=CC(=O)N1CCN(CCn2c(=O)ccc3cnc(Nc4cnn(Cc5ccccc5)c4)nc32)[C@@H](C)C1] | 499.25 | 499.1 |
| 238 | 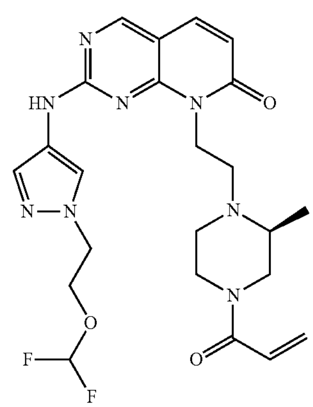 [SMILES: C=CC(=O)N1CCN(CCn2c(=O)ccc3cnc(Nc4cnn(CCOC(F)F)c4)nc32)[C@@H](C)C1] | 503.23 | 503.2 |
| 239 | 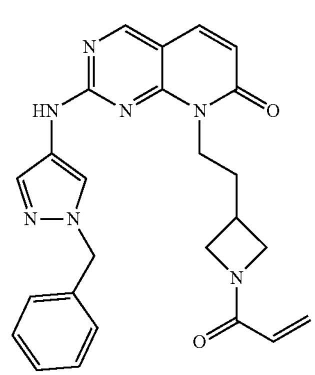 [SMILES: C=CC(=O)N1CC(CCn2c(=O)ccc3cnc(Nc4cnn(Cc5ccccc5)c4)nc32)C1] | 456.21 | 456.2 |

TABLE 1-continued

| Ex No. | Structure | Calculated [M + H]+ | Found [M + H]+ |
|---|---|---|---|
| 240 | 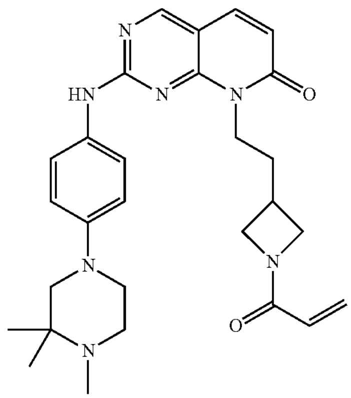 [SMILES: C=CC(=O)N1CC(CCn2c(=O)ccc3cnc(Nc4ccc(N5CCN(C)C(C)(C)C5)cc4)nc32)C1] | 502.29 | 502.2 |
| 241 | 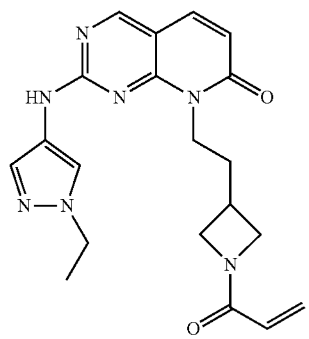 [SMILES: C=CC(=O)N1CC(CCn2c(=O)ccc3cnc(Nc4cnn(CC)c4)nc32)C1] | 394.19 | 394.2 |
| 242 | 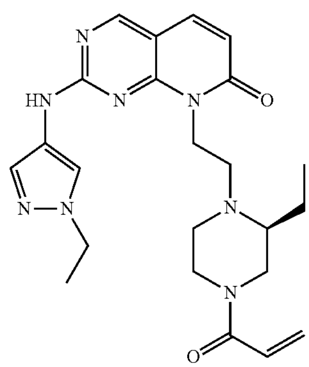 [SMILES: C=CC(=O)N1CCN(CCn2c(=O)ccc3cnc(Nc4cnn(CC)c4)nc32)[C@@H](CC)C1] | 451.25 | 451.1 |
| 243 | 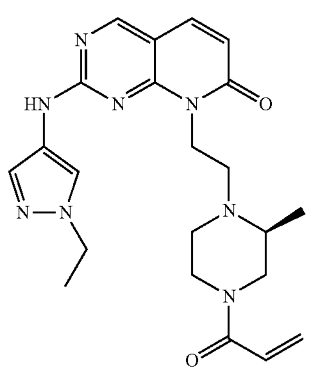 [SMILES: C=CC(=O)N1CCN(CCn2c(=O)ccc3cnc(Nc4cnn(CC)c4)nc32)[C@@H](C)C1] | 437.23 | 437.1 |

TABLE 1-continued

| Ex No. | Structure | Calculated [M + H]+ | Found [M + H]+ |
| --- | --- | --- | --- |
| 244 | 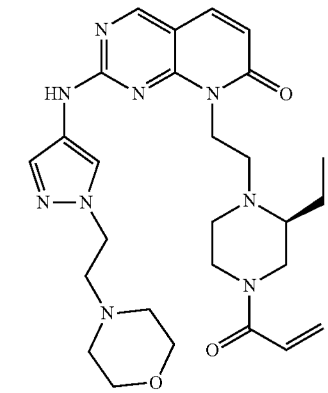 [SMILES: C=CC(=O)N1CCN(CCn2c(=O)ccc3cnc(Nc4cnn(CCN5CCOCC5)c4)nc32)[C@@H](CC)C1] | 536.30 | 536.3 |
| 245 | 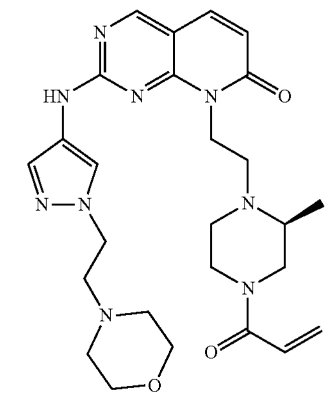 [SMILES: C=CC(=O)N1CCN(CCn2c(=O)ccc3cnc(Nc4cnn(CCN5CCOCC5)c4)nc32)[C@@H](C)C1] | 522.29 | 522.2 |
| 246 | 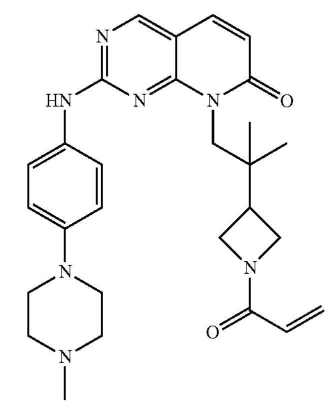 [SMILES: C=CC(=O)N1CC(C(C)(C)Cn2c(=O)ccc3cnc(Nc4ccc(N5CCN(C)CC5)cc4)nc32)C1] | 502.29 | 502.2 |
| 247 | 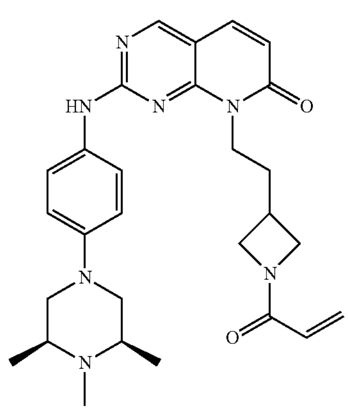 [SMILES: C=CC(=O)N1CC(CCn2c(=O)ccc3cnc(Nc4ccc(N5C[C@@H](C)N(C)[C@@H](C)C5)cc4)nc32)C1] | 502.29 | 502.2 |

TABLE 1-continued

| Ex No. | Structure | Calculated [M + H]+ | Found [M + H]+ |
|---|---|---|---|
| 248 | 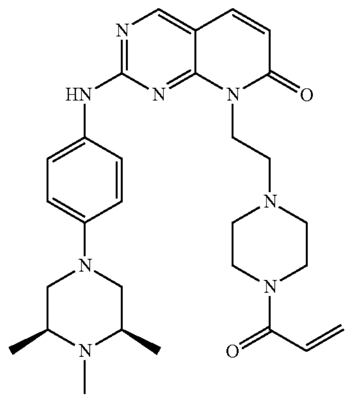 [SMILES: C=CC(=O)N1CCN(CCn2c(=O)ccc3cnc(Nc4ccc(N5C[C@@H](C)N(C)[C@@H](C)C5)cc4)nc32)CC1] | 531.31 | 531.2 |
| 249 | 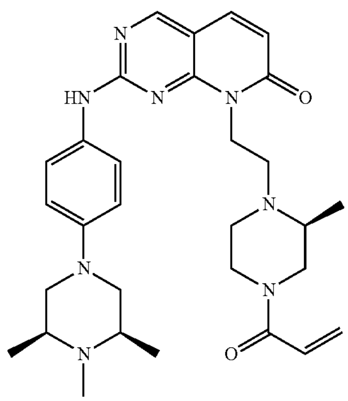 | 545.33 | 545.2 |
| 250 | 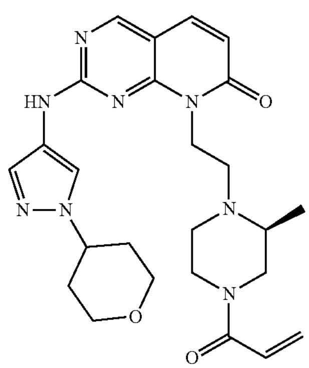 [SMILES: C=CC(=O)N1CCN(CCn2c(=O)ccc3cnc(Nc4cnn(C5CCOCC5)c4)nc32)[C@@H](C)C1] | 493.26 | 493.1 |
| 251 | 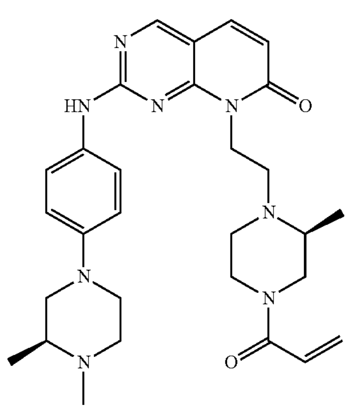 | 531.31 | 531.1 |

TABLE 1-continued

| Ex No. | Structure | Calculated [M + H]+ | Found [M + H]+ |
|---|---|---|---|
| 252 | 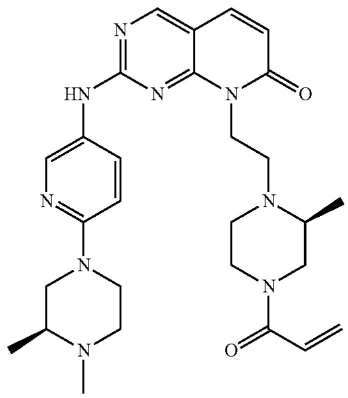 | 532.31 | 532.2 |
| 253 | 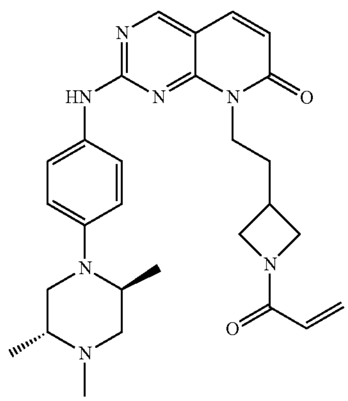 [SMILES: C=CC(=O)N1CC(CCn2c(=O)ccc3cnc(Nc4ccc(N5C[C@@H](C)N(C)C[C@@H]5C)cc4)nc32)C1] | 502.29 | 502.2 |
| 254 | 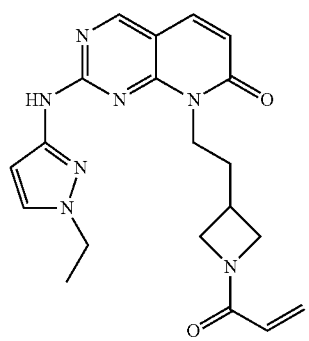 [SMILES: C=CC(=O)N1CC(CCn2c(=O)ccc3cnc(Nc4ccn(CC)n4)nc32)C1] | 394.19 | 394.2 |
| 255 | 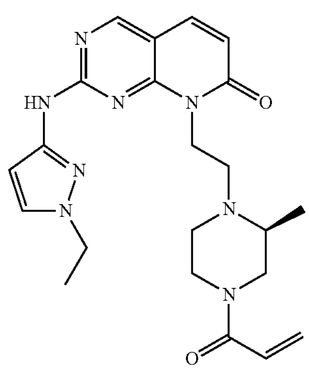 [SMILES: C=CC(=O)N1CCN(CCn2c(=O)ccc3cnc(Nc4ccn(CC)n4)nc32)[C@@H](C)C1] | 437.23 | 437.3 |

TABLE 1-continued

| Ex No. | Structure | Calculated [M + H]+ | Found [M + H]+ |
|---|---|---|---|
| 256 | 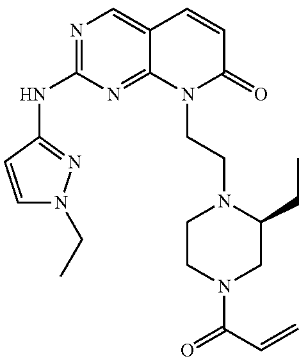 [SMILES: C=CC(=O)N1CCN(CCn2c(=O)ccc3cnc(Nc4ccn(CC)n4)nc32)[C@@H](CC)C1] | 451.25 | 451.2 |
| 257 | 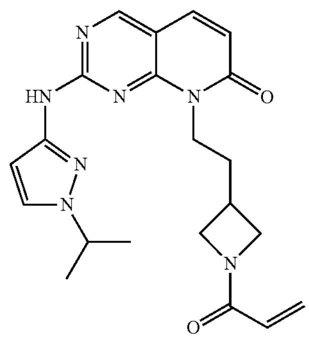 [SMILES: C=CC(=O)N1CC(CCn2c(=O)ccc3cnc(Nc4ccn(C(C)C)n4)nc32)C1] | 408.21 | 408.2 |
| 258 | 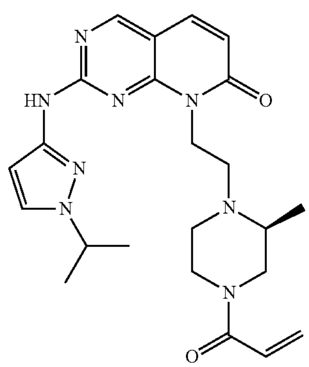 [SMILES: C=CC(=O)N1CCN(CCn2c(=O)ccc3cnc(Nc4ccn(C(C)C)n4)nc32)[C@@H](C)C1] | 451.25 | 451.2 |
| 259 | 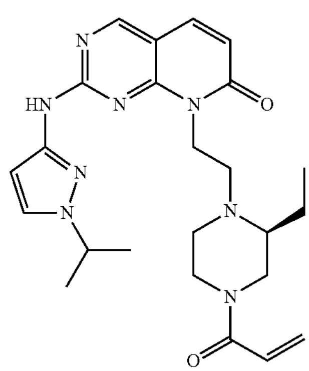 [SMILES: C=CC(=O)N1CCN(CCn2c(=O)ccc3cnc(Nc4ccn(C(C)C)n4)nc32)[C@@H](CC)C1] | 465.26 | 465.2 |

TABLE 1-continued

| Ex No. | Structure | Calculated [M + H]+ | Found [M + H]+ |
|---|---|---|---|
| 260 | 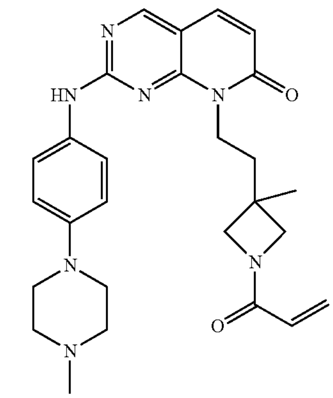 [SMILES: C=CC(=O)N1CC(C)(CCn2c(=O)ccc3cnc(Nc4ccc(N5CCN(C)CC5)cc4)nc32)C1] | 488.27 | 488.2 |
| 261 | 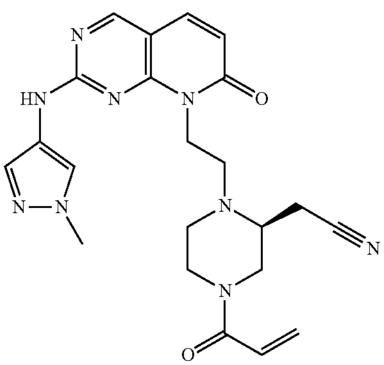 [SMILES: C=CC(=O)N1CCN(CCn2c(=O)ccc3cnc(Nc4cnn(C)c4)nc32)[C@@H](CC#N)C1] | 448.21 | 448.1 |
| 262 | 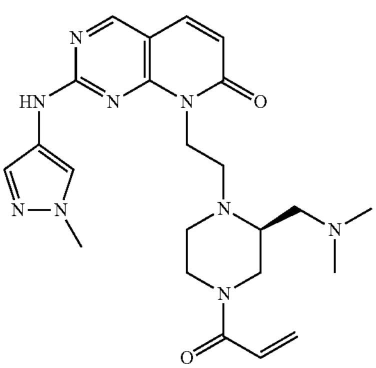 [SMILES: C=CC(=O)N1CCN(CCn2c(=O)ccc3cnc(Nc4cnn(C)c4)nc32)[C@@H](CN(C)C)C1] | 466.26 | 466.1 |
| 263 | 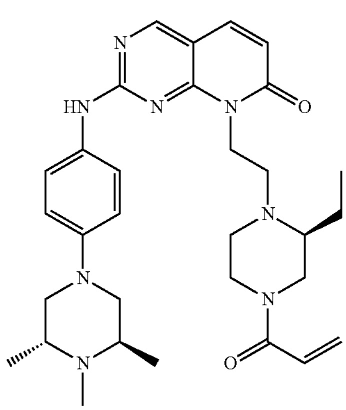 [SMILES: C=CC(=O)N1CCN(CCn2c(=O)ccc3cnc(Nc4ccc(N5C[C@@H](C)N(C)[C@H](C)C5)cc4)nc32)[C@@H](CC)C1] | 559.34 | 559.2 |

TABLE 1-continued

| Ex No. | Structure | Calculated [M + H]+ | Found [M + H]+ |
|---|---|---|---|
| 264 | 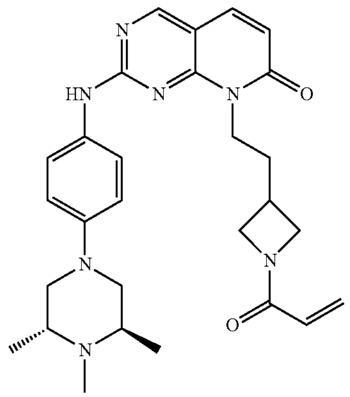 [SMILES: C=CC(=O)N1CC(CCn2c(=O)ccc3cnc(Nc4ccc(N5C[C@@H](C)N(C)[C@H](C)C5)cc4)nc32)C1] | 502.29 | 502.3 |

Biological Assays

The compounds of the disclosure have been characterized in one or more of the following biological assays.

Assay 1: Biochemical JAK and Tyk2 Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially or discretely diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to pKi (negative logarithm of dissociation constant, Ki) using the Cheng-Prusoff equation.

Assay 2: Cellular JAK3 Potency Assay: Inhibition of IL-2 Stimulated pSTAT5 in Tall-1 T Cells The potency of test compounds for inhibition of interleukin-2 (IL-2) stimulated STAT5 phosphorylation was measured in the Tall-1 human T cell line (DSMZ) using AlphaLisa. Because IL-2 signals through JAK3, this assay provides a measure of JAK3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1x Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 μL/well) and plates shaken at 900 rpm for 10 ins. Cells were seeded at 45,000 cells/well in assay media (4 μL/well), and incubated at 37° C., 5% $CO_2$ for 1 hour, followed by the addition of IL-2 (R&D Systems; final concentration 300 ng/ml) in pre-warmed assay media (4 μL) for 30 minutes. After cytokine stimulation, cells were lysed with 6 ul of 3x AlphaLisa Lysis Buffer (PerkinElmer) containing 1x PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 μL) under green filtered <100 lux light. Plates were shaken at 900 rpm for 2 mins, briefly spun down, and incubated for 2 hrs at RT in the dark. Donor beads were dispensed (5 μL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean standard deviation).

Assay 3: JAK Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the disclosure were tested in this assay and exhibited $pCC_{15}$ values between 5 and about 6.

Assay 4: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

CacoReady 24-well transwell plates were obtained from ADMEcell (Alameda, Calif.). The compounds were evaluated at a concentration of 5 µM from 10 mM DMSO stock solutions in duplicate (n=2). The passive permeability of the compounds tested was evaluated using Caco-2 cell monolayers along with Verapamil (25 µM) to inhibit P-gp transport proteins in the apical to basolateral (A-B) direction. The experiment was conducted in a 37° C., 5% $CO_2$ incubator. Caco-2 culture media consisted of standard filtered DMEM, FCS 10%, L-Glutamine 1% and PenStrep 1%. Basal assay plate was prepared by adding 750 µL of transport buffer to A-B wells. A CacoReady™ plate was prepared by removing the Caco-2 media from the apical wells and replacing with fresh transport media (200 µL repeated for a total of 3 washes). Blank media (200 µL) was then replaced with diluted compound for A-B wells. To begin the incubation, the basal plate was removed from the incubator and the apical section was added on top of it. Samples (40 µL) were collected from the apical and basal compartments for time zero (t0). Samples were collected again after 120 minutes (t120) from the apical and basal compartments. All samples were diluted and prepared for bioanalysis by LC-MS/MS. The permeation coefficient ($K_p$, mean A to B+ Verapamil Papparent) in cm/sec was calculated as dQ (flux)/(dt×Area× concentration).

In this assay, a $K_p$ value less than about $5\times10^{-6}$ cm/sec is considered favorable to minimize systemic exposure and target the colon. A $K_p$ value less than about $10\times10^{-6}$ cm/sec may also be sufficient to minimize systemic exposure and target the colon. By comparison, PF-06651600, a JAK3 inhibitor available systemically (2-propen-1-one, 1-[(2S, 5R)-2-methyl-5-(7H-pyrrolo[2,3-d]-pyridin-4-ylamino)-1-piperidinyl]) exhibited a $K_p$ value of 25.

In Vitro Assay Results

The examples of the disclosure were tested in one or more of the assays described above.

In Table below, for the JAK1, JAK 2, JAK3, and TYK2 enzyme assays, A represents a $pK_i$ value≥10 ($K_i$≤0.1 nM), B represents $pK_i$ value between 9 and 10 ($K_i$ between 1 nM and 0.1 nM), C represents a $pK_i$ value between 8 and 9 ($K_i$ between 10 nM and 1 nM), D represents a $pK_i$ value between 7 and 8 ($K_i$ between 100 nM and 10 nM), and E represents a $pK_i$ value of 7 or below ($K_i$ of 100 nM or above). For the Tall-1 Potency assay, A represents a $pIC_{50}$ value≥7.5 ($IC_{50}$≤32 nM), B represents a $pC_{50}$ value between 6.7 (included) and 7.5 ($IC_{50}$ between 200 nM and 32 nM), and C represents a $pIC_{50}$ value between 6 and 6.7 ($IC_{50}$ between 1 µM and 200 nM). For the JAK3 (pKi)-JAK1 ($pK_i$) values, A represents a value of 3 or above, and B represents a value of 2.5 to 3. For the Caco assay, A represents a value below $5\times10^{-6}$ cm/sec, B represents a value between $5\times10^{-6}$ and $10\times10^{-6}$ cm/sec, C represents a value between $10\times10^{-6}$ and $30\times10^{-6}$ cm/sec, and D represents a value over $30\times10^{-6}$ cm/sec.

TABLE 2

| Ex No. | JAK 1 (pKi) | JAK 2 (pKi) | JAK 3 (pKi) | Tyk 2 (pKi) | Tall-1 (pIC$_{50}$) | JAK3 (pKi)- JAK1 (pKi) | Caco K$_p$ $10^{-6}$ cm/sec |
|---|---|---|---|---|---|---|---|
| 1 | E | E | B | E | B | A | B |
| 2 | E | E | A | E | B | A | A |
| 3 | E | E | A | E | B | A | A |
| 4 | E | E | B | E | B | A | A |
| 5 | E | E | A | E | B | A | A |
| 6 | E | E | B | E | B | A | A |
| 7 | E | E | B | E | B | A | B |
| 8 | E | E | B | E | B | A | A |
| 9 | E | E | B | E | B | A | |
| 10 | E | E | A | E | A | A | A |
| 11 | E | E | B | E | B | A | |
| 12 | E | E | B | E | B | A | B |
| 13 | E | E | B | E | B | A | A |
| 14 | E | E | B | E | A | A | A |
| 15 | E | E | B | E | B | A | B |
| 16 | E | E | B | E | C | A | A |
| 17 | E | E | B | E | B | A | |
| 18 | E | E | A | E | B | A | C |
| 19 | E | E | B | E | C | A | C |
| 20 | E | | B | | C | A | B |
| 21 | E | | B | | C | A | |
| 22 | E | | B | | C | A | |
| 23 | E | E | B | E | B | A | |
| 24 | E | E | B | E | B | A | B |
| 25 | E | E | B | E | C | A | B |
| 26 | E | E | B | E | B | A | C |
| 27 | E | E | B | E | B | A | C |
| 28 | E | | B | | C | A | C |
| 29 | E | | B | | C | A | |
| 30 | E | E | A | E | B | A | A |
| 31 | E | E | B | E | B | A | A |
| 32 | E | E | B | E | B | A | B |
| 33 | E | E | A | E | B | A | |
| 34 | E | E | B | E | B | A | |
| 35 | E | | B | | C | A | A |
| 36 | E | | B | | C | A | C |
| 37 | E | E | B | E | B | A | |
| 38 | E | E | B | E | B | A | C |
| 39 | E | E | B | E | B | A | |
| 40 | E | | B | | C | A | |
| 41 | E | | B | | C | A | |
| 42 | E | | B | | C | A | |
| 43 | E | | B | | C | A | |
| 44 | E | E | B | E | B | A | |
| 45 | E | E | B | E | B | A | |
| 46 | E | E | B | E | B | A | |
| 47 | E | | B | | C | A | A |
| 48 | E | E | B | E | B | A | |
| 49 | E | E | B | E | B | A | |
| 50 | E | | B | | C | A | |
| 51 | E | E | B | E | B | A | A |
| 52 | E | E | B | E | B | A | A |
| 53 | E | E | B | E | B | A | |
| 54 | E | | B | | C | A | C |

TABLE 2-continued

| Ex No. | JAK 1 (pKi) | JAK 2 (pKi) | JAK 3 (pKi) | Tyk 2 (pKi) | Tall-1 (pIC$_{50}$) | JAK3 (pKi)-JAK1 (pKi) | Caco K$_p$ 10$^{-6}$ cm/sec |
|---|---|---|---|---|---|---|---|
| 55 | E | E | B | E | B | A | A |
| 56 | E | E | B | E | C | A | |
| 57 | E | E | B | E | C | A | |
| 58 | E | E | B | E | B | A | |
| 59 | E | E | B | E | C | A | |
| 60 | E | E | B | E | B | A | B |
| 61 | E | E | B | E | B | A | A |
| 62 | E | E | B | E | A | A | B |
| 63 | E | E | B | E | B | A | A |
| 64 | E | E | B | E | C | A | |
| 65 | E | E | B | E | C | A | |
| 66 | E | E | B | E | B | A | C |
| 67 | E | E | B | E | B | A | B |
| 68 | E | E | B | E | C | A | |
| 69 | E | E | A | E | B | A | A |
| 70 | E | E | B | E | B | A | A |
| 71 | E | E | B | E | B | A | B |
| 72 | E | E | B | E | B | A | A |
| 73 | E | E | C | E | C | B | |
| 74 | E | E | B | E | B | A | A |
| 75 | E | E | C | E | C | B | |
| 76 | E | E | B | E | B | A | B |
| 77 | E | | B | | B | A | A |
| 78 | E | E | B | E | B | A | A |
| 79 | E | E | B | E | B | A | A |
| 80 | E | E | B | E | B | A | C |
| 81 | E | | B | | B | A | A |
| 82 | E | E | B | E | C | A | A |
| 83 | E | E | B | E | C | A | A |
| 84 | E | E | B | E | C | A | |
| 85 | E | E | A | E | B | A | C |
| 86 | E | E | B | E | B | A | C |
| 87 | E | E | B | E | A | A | |
| 88 | E | E | A | E | B | A | D |
| 89 | E | E | B | E | A | A | A |
| 90 | E | E | B | E | B | A | A |
| 91 | E | E | A | E | B | A | D |
| 92 | E | E | B | E | B | A | A |
| 93 | E | E | A | E | B | A | |
| 94 | E | E | A | E | A | A | A |
| 95 | E | E | A | E | A | A | A |
| 96 | E | E | A | E | B | A | A |
| 97 | E | E | B | E | A | A | |
| 98 | E | E | A | E | B | A | A |
| 99 | E | E | A | E | B | A | A |
| 100 | E | E | A | E | A | A | A |
| 101 | E | E | A | E | B | A | A |
| 102 | E | E | A | E | B | A | A |
| 103 | E | E | A | E | A | A | |
| 104 | E | E | A | E | A | A | |
| 105 | E | E | A | E | B | A | A |
| 106 | E | E | A | E | B | A | A |
| 107 | E | E | B | E | B | A | A |
| 108 | E | E | B | E | A | A | A |
| 109 | D | E | B | E | B | B | C |
| 110 | E | E | A | E | A | A | B |
| 111 | E | E | B | E | B | A | |
| 112 | E | E | A | E | B | A | A |
| 113 | E | E | B | E | A | A | |
| 114 | E | E | A | E | A | A | |
| 115 | E | E | B | E | A | A | |
| 116 | E | E | B | E | B | B | |
| 117 | E | E | A | E | A | A | C |
| 118 | E | E | B | E | B | A | |
| 119 | E | E | A | E | B | A | |
| 120 | E | E | B | E | A | A | |
| 121 | E | E | B | E | C | B | |
| 122 | E | E | B | E | B | A | |
| 123 | E | E | B | E | B | A | C |
| 124 | E | E | B | E | B | A | B |
| 125 | E | E | A | E | B | A | B |
| 126 | E | E | A | E | B | A | |
| 127 | E | E | A | E | B | A | A |
| 128 | E | E | A | E | B | A | |
| 129 | E | E | A | E | B | A | |
| 130 | E | E | B | E | B | A | A |
| 131 | E | E | B | E | C | A | A |
| 132 | E | E | A | E | B | A | |
| 133 | E | E | A | E | B | A | A |
| 134 | E | E | A | E | B | A | A |
| 135 | E | E | B | E | B | A | A |
| 136 | E | E | B | E | A | A | A |
| 137 | E | E | B | E | B | A | A |
| 138 | E | D | A | E | B | A | A |
| 139 | E | E | A | E | C | A | A |
| 140 | E | E | A | E | C | A | A |
| 141 | E | E | B | E | B | A | C |
| 142 | E | E | A | E | B | A | C |
| 143 | E | E | A | E | B | A | C |
| 144 | E | E | A | E | B | A | |
| 145 | E | E | B | E | B | A | B |
| 146 | E | E | B | E | B | A | |
| 147 | E | E | B | E | C | A | |
| 148 | E | E | B | E | C | A | |
| 149 | E | E | B | E | C | A | |
| 150 | E | E | A | E | B | A | A |
| 151 | E | E | B | E | C | A | A |
| 152 | E | E | B | E | C | A | |
| 153 | E | E | B | E | C | A | |
| 154 | E | E | B | E | B | A | |
| 155 | E | E | B | E | B | A | A |
| 156 | E | E | B | E | B | A | |
| 157 | E | E | A | E | B | A | C |
| 158 | E | E | B | E | C | A | |
| 159 | E | E | B | E | A | A | B |
| 160 | E | E | B | E | A | A | |
| 161 | E | E | B | E | A | A | |
| 162 | E | E | A | E | A | A | C |
| 163 | E | E | B | E | A | A | |
| 164 | E | E | B | E | C | A | |
| 165 | E | E | A | E | A | A | |
| 166 | E | E | A | E | A | A | |
| 167 | E | E | A | E | B | A | A |
| 168 | E | E | A | E | A | A | |
| 169 | E | E | A | E | A | A | |
| 170 | E | E | A | E | A | A | B |
| 171 | E | E | A | E | A | A | B |
| 172 | E | E | B | E | A | A | C |
| 173 | E | E | B | E | B | A | A |
| 174 | E | E | B | E | B | A | B |
| 175 | E | E | B | E | B | A | A |
| 176 | E | E | A | E | B | A | |
| 177 | E | E | B | E | B | A | |
| 178 | E | E | A | E | B | A | C |
| 179 | E | E | A | E | B | A | C |
| 180 | E | E | B | E | B | A | A |
| 181 | E | E | B | E | B | A | |
| 182 | E | E | A | E | B | A | |
| 183 | E | E | A | E | C | A | |
| 184 | E | E | A | E | B | A | |
| 185 | E | E | A | E | B | A | B |
| 186 | E | E | B | E | B | A | A |
| 187 | E | E | B | E | B | A | C |
| 188 | E | E | B | E | B | A | C |
| 189 | E | E | A | E | B | A | B |
| 190 | E | E | B | E | B | A | C |
| 191 | E | E | A | E | B | A | B |
| 192 | E | E | B | E | B | A | C |
| 193 | E | E | B | E | B | A | A |
| 194 | E | E | B | E | B | A | C |
| 195 | E | E | B | E | B | A | |
| 196 | E | E | B | E | B | A | A |
| 197 | E | E | B | E | B | A | A |
| 198 | E | E | B | E | C | A | A |
| 199 | E | | B | | A | A | |
| 200 | E | E | C | E | C | B | |
| 201 | E | E | B | E | B | A | A |
| 202 | E | E | B | E | B | A | A |
| 203 | E | E | B | E | B | A | C |
| 204 | E | E | A | E | A | A | |

TABLE 2-continued

| Ex No. | JAK 1 (pKi) | JAK 2 (pKi) | JAK 3 (pKi) | Tyk 2 (pKi) | Tall-1 (pIC$_{50}$) | JAK3 (pKi)- JAK1 (pKi) | Caco K$_p$ 10$^{-6}$ cm/sec |
|---|---|---|---|---|---|---|---|
| 205 | E | E | B | E | A | A | B |
| 206 | E | E | A | E | A | A | C |
| 207 | E | E | B | E | B | A | B |
| 208 | E | E | B | E | B | A | B |
| 209 | E | E | B | E | B | A | A |
| 210 | E | E | A | E | B | A | A |
| 211 | E | E | A | E | B | A |   |
| 212 | E | E | A | E | B | A |   |
| 213 | E | E | A | E | B | A |   |
| 214 | E | E | B | E | B | A |   |
| 215 | E | E | B | E | B | A |   |
| 216 | E | E | B | E | C | A |   |
| 217 | E | D | B | E | A | A |   |
| 218 | E |   | C |   | C | B |   |
| 219 | E | E | B | E | A | A |   |
| 220 | E | E | B | E | B | A |   |
| 221 | E | E | B | E | B | A |   |
| 222 | E |   | B |   | A | A |   |
| 223 | E | E | A | E | B | A |   |
| 224 | E | E | B | E | B | A |   |
| 225 | E | E | B | E | C | A |   |
| 226 | E | E | B | E | C | A |   |
| 227 | E | E | B | E | C | A |   |
| 228 | E | E | B | E | C | A |   |
| 229 | E | E | B | E | B | A |   |
| 230 | E | E | B | E | B | A |   |
| 231 | E | E | B | E | B | A |   |
| 232 | E | E | A | E | B | A |   |
| 233 | E | E | B | E | B | A |   |
| 234 | E | E | B | E | B | A |   |
| 235 | E | E | B | E | B | A |   |
| 236 | E | E | B | E | B | A |   |
| 237 | E | E | B | E | B | A |   |
| 238 | E | E | B | E | C | A |   |
| 239 | E | E | B | E | B | A |   |
| 240 | E | E | A | E | A | A |   |
| 241 | E | E | B | E | B | A |   |
| 242 | E | E | B | E | B | A |   |
| 243 | E | E | B | E | B | A |   |
| 244 | E | E | B | E | B | A |   |
| 245 | E | E | B | E | B | A |   |
| 246 | E | E | B | E | B | A |   |
| 247 | E | E | B | E | A | A |   |
| 248 | E | E | B | E | A | A |   |
| 249 | E | E | B | E | A | A |   |
| 250 | E | E | B | E | B | A |   |
| 251 | E | E | B | E | B | A |   |
| 252 | E | E | B | E | B | A |   |
| 253 | E |   | A |   | B | A |   |
| 254 | E |   | B |   | B | A |   |
| 255 | E |   | B |   | C | A |   |
| 256 | E |   | B |   | C | A |   |
| 257 | E |   | B |   | B | A |   |
| 258 | E |   | B |   | C | A |   |
| 259 | E |   | B |   | C | A |   |
| 260 | E |   | B |   | A | A |   |
| 261 | E |   | B |   | B | A |   |
| 262 | E |   | C |   | C | B |   |
| 263 | E |   | B |   | A | A |   |
| 264 | E |   | B |   | A | A |   |

Assay 5: Colon and Plasma Mouse Pharmacokinetics

To 6 male Balb/c mice was administered 10 mg/kg of compound in 1% HPMC+0.1% Tween-80 by PO administration. At 0.5, 2 and 6 hours after dose administration, animals were anesthetized, and terminal blood samples were collected by cardiac puncture, followed by collection of colon contents and colon tissue.

Blood samples were collected into K$_2$EDTA and stored on wet ice until processed to plasma by centrifugation (12000 rpm at 4° C.). Plasma samples were transferred to cluster tubes and placed on dry ice prior to freezer storage. The colon contents from each animal were collected at each terminal blood collection time point. The colon tissues were flushed with saline and patted dry. The colon and colon content tissues were homogenized using sterile water containing 0.1% formic acid 9:1 (water:tissue, v/w). The homogenized tissues and colon contents were transferred to cluster tubes and placed on dry ice prior to freezer storage. All samples were analyzed using LC/MS/MS against analytical standards.

The composite pharmacokinetic parameters of the compounds were determined by non-compartmental analysis using Phoenix WinNonlin Version 6 (Certara, St. Louis, Mo.) and using mean values from 2 animals/time point. For plasma concentrations below the quantification limit (BQL), the lowest concentration measurable or the BLOQ (below limit of quantification) was used.

A colon to plasma ratio was determined as the ratio of the colon AUC to the plasma AUC. Compounds 1, 3, 4, 13, 26, 38, 79, 102, 110, 155, and 171 exhibited a colon to plasma ratio in excess of 1000. Compounds 2, 5, 6, 7, 8, 15, 24, 27, 52, 74, 89, 92, 112, 133, 134, 150, 173, and 175 exhibited a colon to plasma ratio in excess of 100. Compounds 12, 31, 44, 107, and 159 exhibited a colon to plasma ratio in excess of 50. Compounds 76, 88, 156, and 174 exhibited a colon to plasma ratio in excess of 14.

In contrast, the reference compound 2-propen-1-one, 1-[(2S,5R)-2-methyl-5-(7-pyrrolo[2,3-d]pyrimidin-4-ylamino)-1-piperidinyl] (PF-06651600, a JAK3 inhibitor available systemically) exhibited a colon to plasma ratio of 2.8.

Assay 6: Mouse Model of Oxazolone-Induced Colitis

Oxazolone-induced colitis is an experimental model that has a histological resemblance to human ulcerative colitis (Heller et al. *Immunology*, 2002, 17, 629-638). Adult BALB/C mice from Harlan were used in the assay. On day 1, animals were lightly anesthetized with isoflurane and the hairs between the shoulder were carefully removed before oxazolone (4%, 150 µL, 4:1 acetone: olive oil formulation) or vehicle solution was slowly applied for skin sensitization. Seven days after skin sensitization, the mice were fasted around 6 hours prior, anesthetized with ketamine/xylazine injection, and a 1 mL syringe equipped with a 3.5-F catheter, filled with oxazolone solution, was inserted carefully about 4 cm into the colon of the mouse. Following insertion, 50 µL of the oxazolone solution (0.8% in 1:1 ethanol:water formulation) was injected very slowly (over 30 sec using an injection pump) into the colon. Drug treatment (PO, QD or BID or TID) or vehicle was initiated a day prior to the oxazolone intrarectal (IR) challenge. Two-day post oxazolone intrarectal challenge, the disease was assessed by treatment-blinded experimenters for each mouse according to the criteria score: stool consistency score (0, normal; 2, loose; 4, diarrhea), gross bleeding score (0, absence; 2, blood tinged; 4, presence); Combined stool score endpoint=stool consistency score+stool blood score.

Select compounds were tested in the assay. Efficacy in the model is evidenced by a statistically significant decrease in combined stool score endpoint as compared with the score from vehicle treated animals.

The compounds 2, 4, 7 and 12 exhibited a statistically significant decrease in combined stool score endpoint as compared with vehicle treated animals in the oxazolone model at a dose of 1 mg/kg (PO, BID). The compounds 1, 5, and 13 exhibited a statistically significant decrease in combined stool score endpoint as compared with vehicle treated animals in the oxazolone model at a dose of 1 and 3 mg/kg (PO, BID).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula (I):

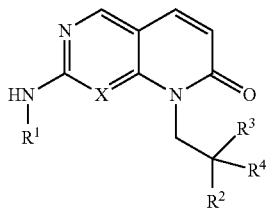

or a pharmaceutically acceptable salt thereof, wherein
X is CH or N;
$R^1$ is selected from the group consisting of:

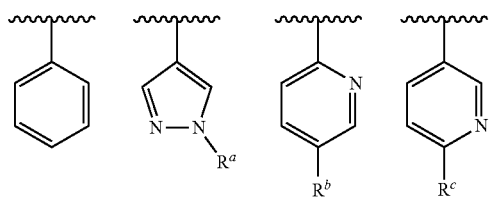

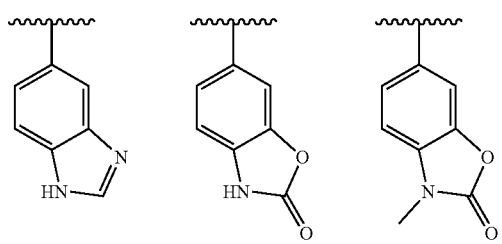

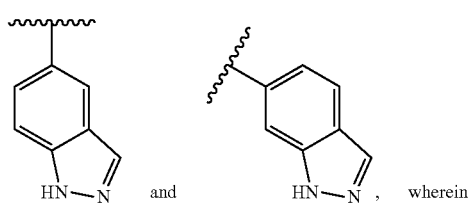

and

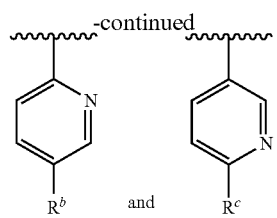

are optionally substituted with 1 or 2 F, wherein

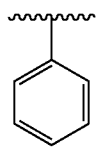 [SMILES: *c1ccccc1]

is optionally substituted with 1 to 3 substituents independently selected from:
(i) $C_{1-6}$ alkoxy optionally substituted with OH,
(ii) $C_{1-6}$ alkyl, halogen, CN, OH, $NR^pR^q$, —$NHCO_2C_{1-6}$ alkyl, —$NHSO_2C_{1-6}$ alkyl, 5 membered ring heteroaryl, partially unsaturated heterocyclic,
wherein the $C_{1-6}$ alkyl is optionally substituted with $NR^pR^q$,
wherein $R^p$ and $R^q$ are each independently selected from the group consisting of H, $C_{1-6}$ alkyl, $C_{2-6}$ alkyl-OH, $C_{1-6}$ alkyl-$C_{1-6}$ alkoxy, and —$C_{1-6}$ alkyl-aryl,
(iii) a 6 membered ring heterocyclic group optionally substituted with 1 to 3 substituents independently selected from:
(a) F, $C_{1-6}$ alkyl, $C_{1-6}$ alkyl-$CF_3$, $CF_3$, $CHF_2$, $CH_2F$, 3 to 8 membered ring cycloalkyl, —$C_{1-6}$ alkyl-$C_{1-6}$ alkoxy, —$C_{1-6}$ alkyl-$C_{3-8}$ cycloalkyl, $SO_2$ linked to a 4 to 8 membered ring heterocyclic group, $C_{1-6}$ alkyl substituted with a 4 to 8 membered ring heterocyclic group, —$COCF_3$, —C(O)S—$C_{1-6}$ alkyl, $SO_2$—NHMe, $SO_2NMe_2$, $SO_2NR^xR^y$, $CONR^xR^y$, $CSNR^xR^y$,
(b) $SO_2C_{1-6}$ alkyl optionally substituted with $C_{1-6}$ alkoxy or CN,
(c) $CO_2C_{1-6}$ alkyl optionally substituted with $C_{1-6}$ alkoxy,
(d) $COC_{1-6}$ alkyl optionally substituted with OH, $C_{1-6}$ alkoxy, —$SO_2C_{1-6}$ alkyl, —$SOC_{1-6}$ alkyl, —S—$C_{1-6}$ alkyl, CN or —S—$C_{1-6}$ alkyl,
and wherein a carbon of the 6 membered ring heterocyclic group may optionally form a carbonyl,
(iv) —$CH_2$—$R^5$, —CHMe-$R^5$
wherein $R^5$ is a 6 membered ring heterocyclic group optionally substituted with 1 to 3 substituents independently selected from:
(a) F, $C_{1-6}$ alkyl, —$C_{1-6}$ alkyl-$CF_3$, $CF_3$, $CHF_2$, $CH_2F$, 3 to 8 membered ring cycloalkyl, —$C_{1-6}$ alkyl-$C_{1-6}$ alkoxy, —$C_{1-6}$ alkyl-$C_{3-8}$ cycloalkyl, $SO_2$ linked to a 4 to 8 membered ring heterocyclic group, $C_{1-6}$ alkyl substituted with a 4 to 8 membered ring heterocyclic, —$COCF_3$, —C(O)S—$C_{1-6}$ alkyl, $SO_2NR^xR^y$, $CONR^xR^y$, $CO_2C_{1-6}$ alkyl,
(b) —$SO_2C_{1-6}$ alkyl optionally substituted with $C_{1-6}$ alkoxy or CN, (c) COC$_{1-6}$ alkyl optionally substituted with C$_{1-6}$ alkoxy or —S—C$_{1-6}$ alkyl, and (v) —CO—R$^6$ wherein R$^6$ is a 6 membered ring heterocyclic group optionally substituted with 1 to 3 substituents independently selected from:

(a) F, C$_{1-6}$ alkyl, —C$_{1-6}$ alkyl-CF$_3$, CF$_3$, CHF$_2$, CH$_2$F, 3 to 8 membered ring cycloalkyl, —C$_{1-6}$ alkyl-C$_{1-6}$ alkoxy, —C$_{1-6}$ alkyl-C$_{3-8}$ cycloalkyl, SO$_2$ linked to a 4 to 8 membered ring heterocyclic group, C$_{1-6}$ alkyl substituted with a 4 to 8 membered ring heterocyclic, —COCF$_3$, —C(O)S—C$_{1-6}$ alkyl, SO$_2$NR$^x$R$^y$, CONR$^x$R$^y$, (b) —SO$_2$C$_{1-6}$ alkyl optionally substituted with C$_{1-6}$ alkoxy or CN, R$^a$ is selected from the group consisting of C$_{1-6}$ alkyl, a 4 to 8 membered ring heterocyclic group, a 3 to 8 membered ring cycloalkyl group, and an aryl group, wherein the 4 to 8 membered ring heterocyclic group and the 3 to 8 membered ring cycloalkyl group are optionally substituted with 1 to 3 substituents independently selected from C$_{1-6}$ alkyl, —CO—C$_{1-6}$ alkyl, —CO—C$_{1-6}$ alkyl-S—C$_{1-6}$ alkyl, and —CO—C$_{1-6}$ alkyl-O—C$_{1-6}$ alkyl, wherein the C$_{1-6}$ alkyl is optionally substituted with OH, NR$^x$R$^y$, 1 to 3 F, an aryl group, a 4 to 8 membered ring heterocyclic group, a 3 to 8 membered ring cycloalkyl group, or C$_{1-6}$ alkoxy optionally substituted with 1 to 3 F, R$^x$ and R$^y$ are each independently selected from H, and C$_{1-6}$ alkyl, or R$^x$ and R$^y$ are joined to form a 4 to 7 membered ring heterocyclic ring;

R$^b$ is a 4 to 8 membered ring heterocyclic group optionally substituted with 1 to 3 substituents independently selected from C$_{1-6}$ alkyl, and CO—C$_{1-6}$ alkyl;

R$^c$ is a 4 to 8 membered ring heterocyclic group optionally substituted with 1 to 3 substituents independently selected from C$_{1-6}$ alkyl, and CO—C$_{1-6}$ alkyl;

R$^2$ is selected from the group consisting of:

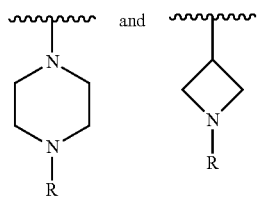

which are optionally substituted with 1 to 3 R$^k$, each R$^k$ is independently C$_{1-4}$ alkyl, wherein the C$_{1-4}$ alkyl is optionally substituted with NR$^u$R$^v$, OH, O—C$_{1-4}$ alkyl, CN, or 1 to 3 F, wherein two R$^k$ substituents on the same carbon may optionally form a spiro C$_{3-5}$ cycloalkyl;

R$^u$ and R$^v$ are each independently selected from H and C$_{1-4}$ alkyl;

R is selected from the group consisting of:

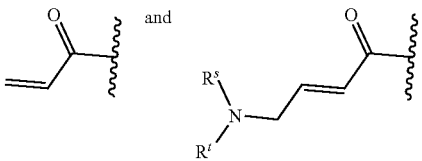

wherein R$^s$ and R$^t$ are each independently selected from the group consisting of H, C$_{3-5}$ cycloalkyl and C$_{1-6}$ alkyl, wherein the C$_{1-6}$ alkyl group may be optionally substituted with 1 to 3 substituents independently selected from the group consisting of C$_{1-3}$ alkoxy and —S—C$_{1-3}$ alkyl, or R$^s$ and R$^t$ form a 4 to 6 membered monocyclic heterocyclic group optionally substituted with 1 to 3 substituents independently selected from the group consisting of C$_{1-6}$ alkyl, C$_{1-3}$ alkoxy, —S—C$_{1-3}$ alkyl and —C$_{1-3}$ alkyl-C$_{1-3}$ alkoxy; and R$^3$ and R$^4$ are each independently selected from C$_{1-4}$ alkyl and H.

2. The compound of claim 1, or a pharmaceutically acceptable salt thereof, wherein X is N.

3. The compound of claim 2, or a pharmaceutically acceptable salt thereof, wherein R$^3$ and R$^4$ are each independently selected from C$_{1-2}$ alkyl and H.

4. The compound of claim 2, or a pharmaceutically acceptable salt thereof, wherein R$^3$ and R$^4$ are each independently selected from methyl and H.

5. The compound of claim 2, or a pharmaceutically acceptable salt thereof, wherein R$^3$ and R$^4$ are both H.

6. The compound of claim 2, or a pharmaceutically acceptable salt thereof, wherein R$^1$ is selected from the group consisting of:

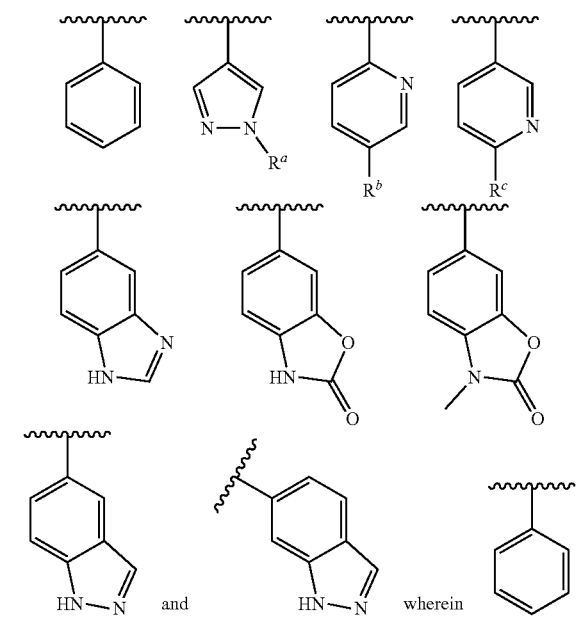

is optionally substituted with 1 to 2 substituents independently selected from:

(i) C$_{1-2}$ alkoxy optionally substituted with OH, (ii) C$_{1-2}$ alkyl, F, Cl, CN, OH, NR$^p$R$^q$, —NHSO$_2$Me, triazolyl, pyrazolyl, imidazolyl, tetrahydropyridinyl, wherein the $C_{1-2}$ alkyl is optionally substituted with $NR^pR^q$, wherein $R^p$ and $R^q$ are each independently selected from $C_{1-2}$ alkyl, $(CH_2)_2$—OH, and —$CH_2$-phenyl, (iii) piperazinyl, morpholinyl, thiomorpholinyl, morpholinonyl, piperidinyl optionally substituted with one methyl or 2 F, wherein the piperazinyl is optionally substituted with 1 to 3 substituents independently selected from F, Me, Et, iPr, t-Bu, sec-Bu, $CF_3$, $CH_2$—$CF_3$, cyclopropyl, —$C_{2-3}$ alkyl-$C_{1-2}$ alkoxy, —$C_2$alkyl-cyclohexyl, —$C_2$alkyl-piperidinyl, $COCF_3$, $COC_{1-4}$alkyl, $COCH_2OMe$, $COCH_2SMe$, $CO(CH_2)_2SMe$, $COCH_2SO_2Me$, $CO(CH_2)_2SOMe$, $CO(CH_2)_2SO_2Me$, $COCH_2SOEt$, $COCH_2CN$, —$CO_2C_{1-3}$ alkyl, $CO_2$—$(CH_2)_2$—OMe, C(O)StBu, $SO_2Me$, —$SO_2$-oxetanyl, $SO_2$—$(CH_2)_2$—OMe, $SO_2$—$CH_2$—CN, $SO_2$—NHMe, $SO_2NMe_2$, $CO_2Me$, CO—NHMe, $CONMe_2$, $C(S)NMe_2$, $COCH_2OMe$, $COCH_2SMe$, $CO(CH_2)_2SMe$, $COC_{2-3}$alkyl substituted with OH;

(iv) —$CH_2$-piperazinyl, —$CH_2$-morpholinyl, —$CH_2$-thiomorpholinyl, and —CHMe-piperazinyl, wherein the piperazinyl is optionally substituted with 1 substituent selected from the group consisting of Me, $SO_2Me$, $SO_2$—$CH_2CN$, $SO_2$—$(CH_2)_2$—OMe, —$SO_2$-oxetanyl, $CO_2Me$, COMe, CO—$CH_2$—OMe, CO—$CH_2$—SMe, and $CONMe_2$, and (v) —CO-morpholinyl, —CO-piperidinyl;

$R^a$ is selected from the group consisting of $C_{1-4}$ alkyl, piperidinyl, tetrahydropyranyl, and phenyl, wherein the piperidinyl and tetrahydropyranyl are optionally substituted with Me or CO—$CH_2$—SMe, wherein the $C_{1-4}$ alkyl is optionally substituted with OH, OMe, OEt, OiPr, —$OCHF_2$, $NR^xR^y$, 1 to 2 F, phenyl, or morpholinyl, $R^x$ and $R^y$ are each independently selected from $C_{1-2}$ alkyl, or $R^x$ and $R^y$ are joined to form a morpholinyl ring;

$R^b$ is selected from the group consisting of morpholinyl and piperazinyl wherein the piperazinyl is substituted by a methyl group; and $R^c$ is selected from the group consisting of thiomorpholinyl and piperazinyl wherein the piperazinyl is substituted with 1 or 2 methyl groups or a COMe group.

7. The compound of claim 2, or a pharmaceutically acceptable salt thereof, wherein $R^1$ is selected from the group consisting of:

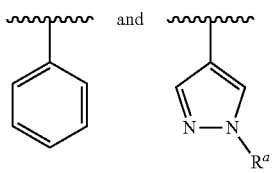

and wherein $R^a$ is $C_{1-4}$ alkyl,
wherein

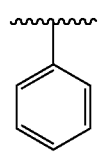

is substituted with piperazinyl, wherein the piperazinyl is substituted with a substituent selected from the group consisting of $C_{1-4}$ alkyl, —CO—$C_{1-4}$ alkyl, —$COCH_2SMe$, —$CO(CH_2)_2SMe$, and —$CONMe_2$.

8. The compound of claim 2, or a pharmaceutically acceptable salt thereof, wherein $R^1$ is selected from the group consisting of:

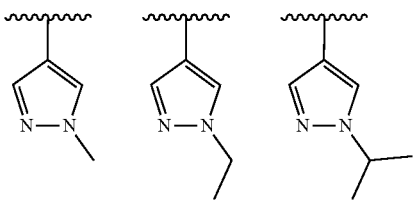

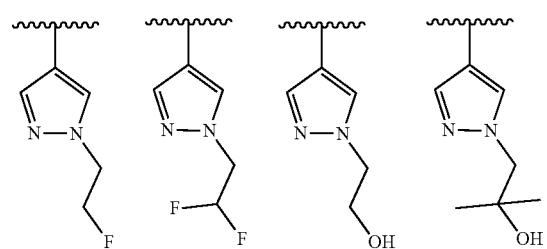

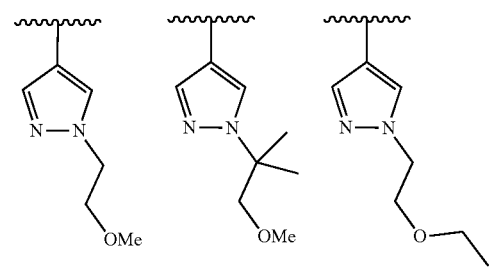

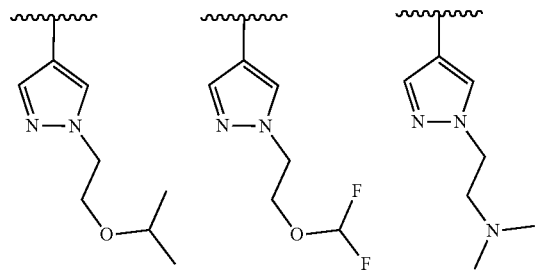

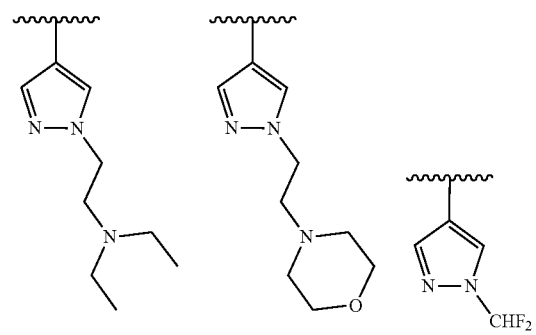

-continued
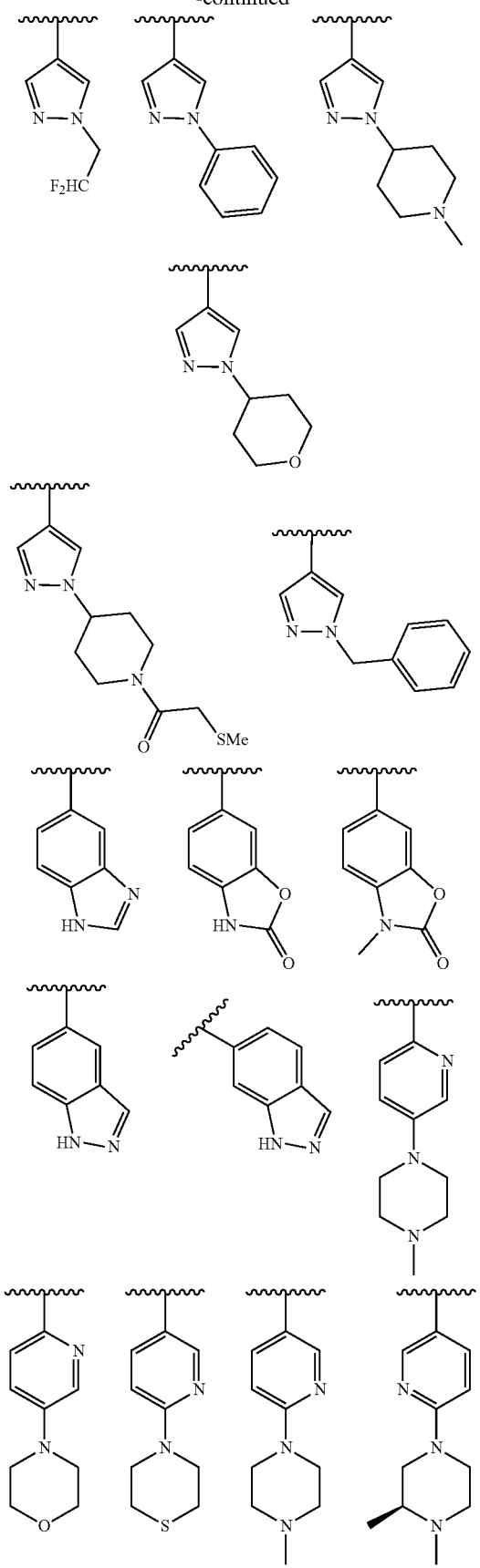
-continued
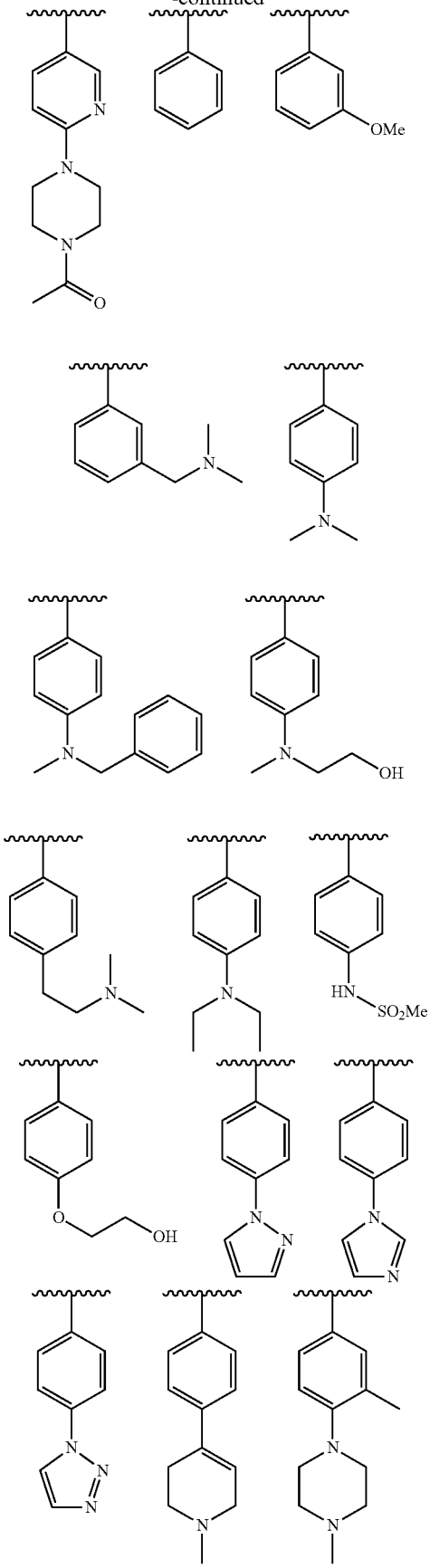

265
-continued
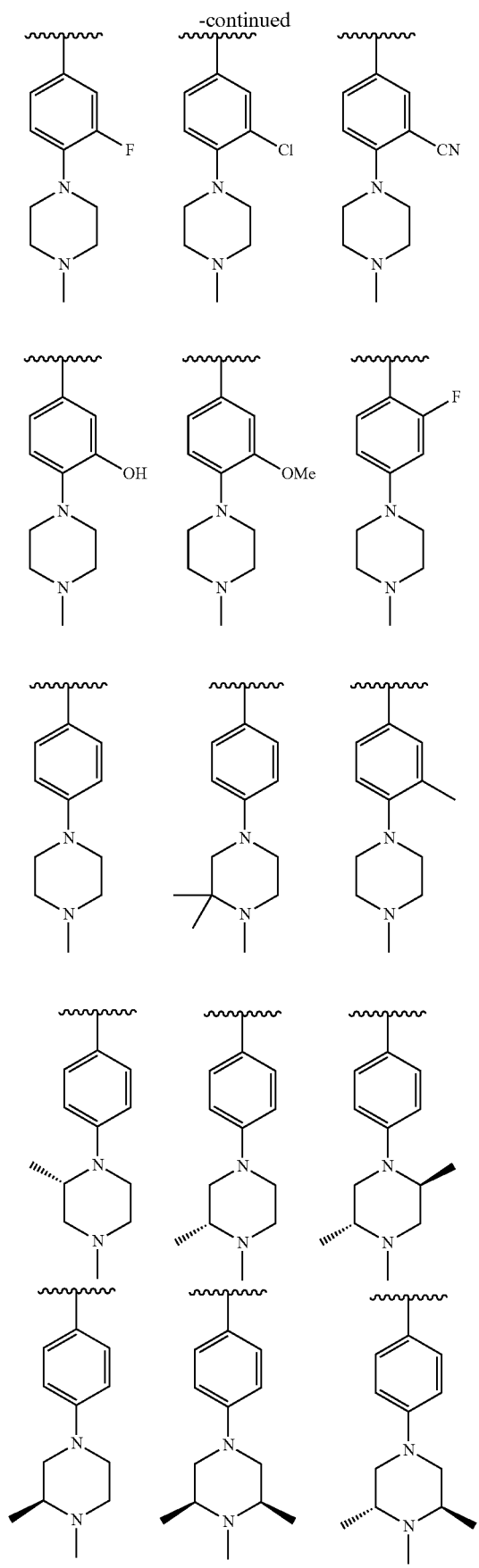
266
-continued
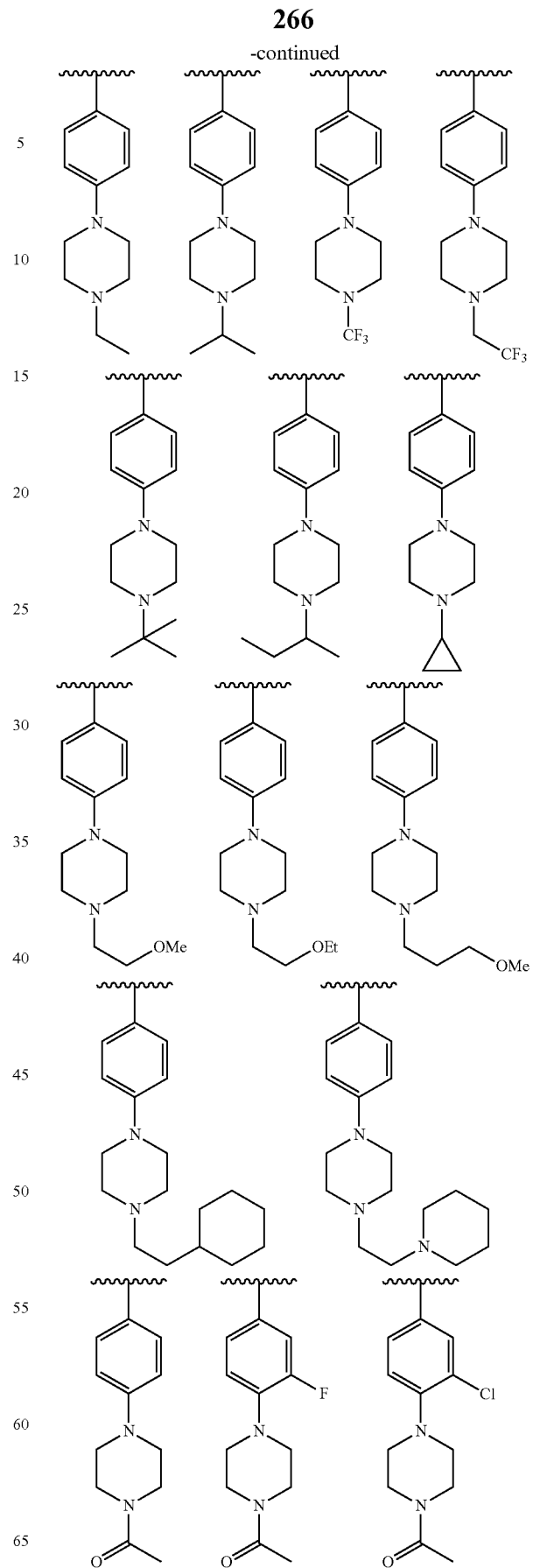

267
-continued
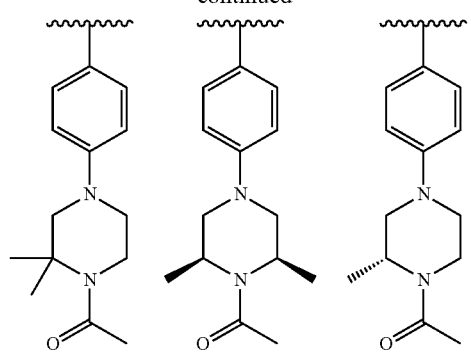
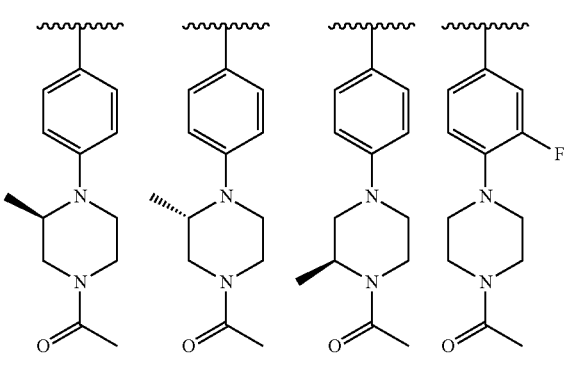
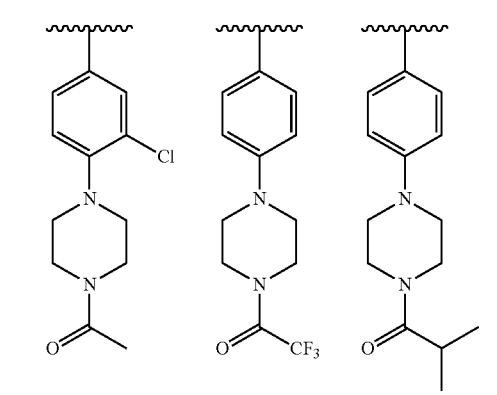
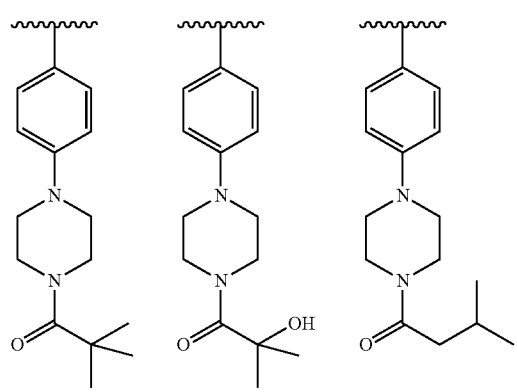
268
-continued
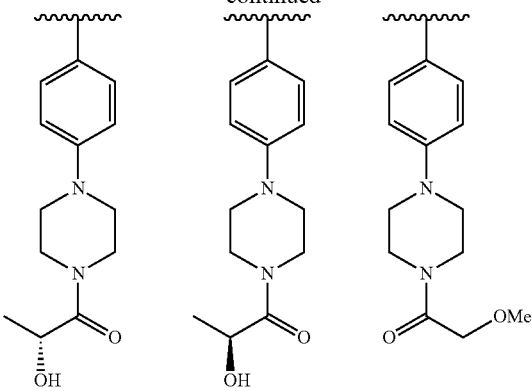

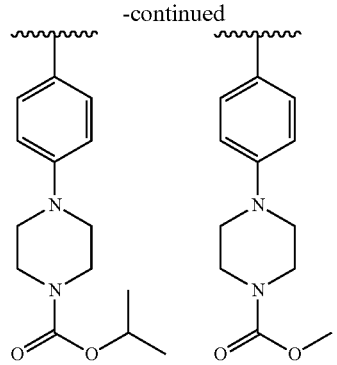
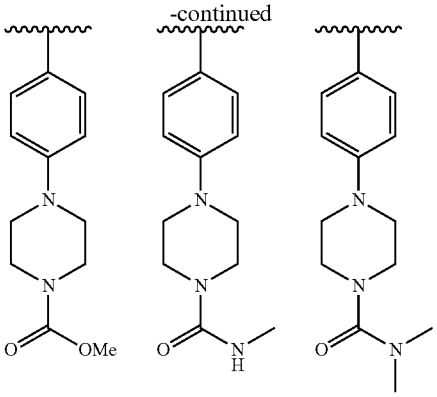
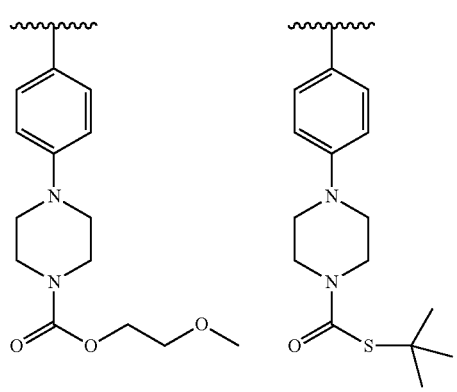
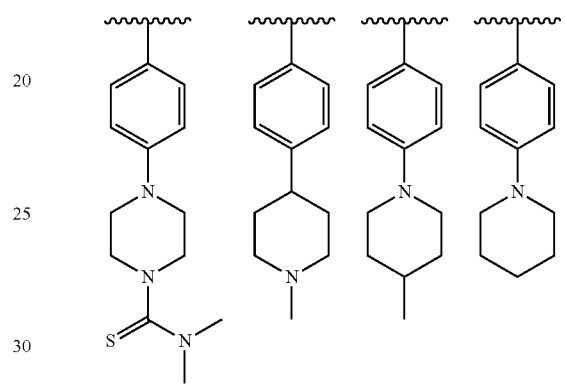
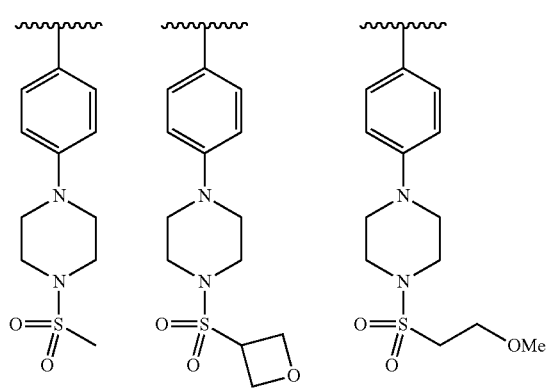
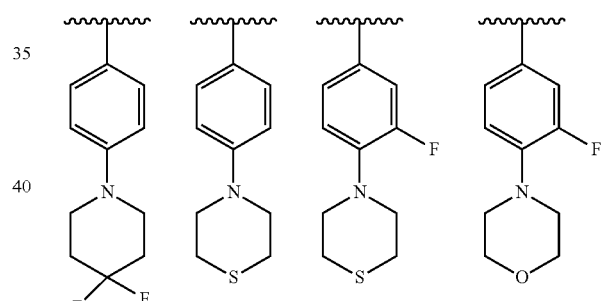
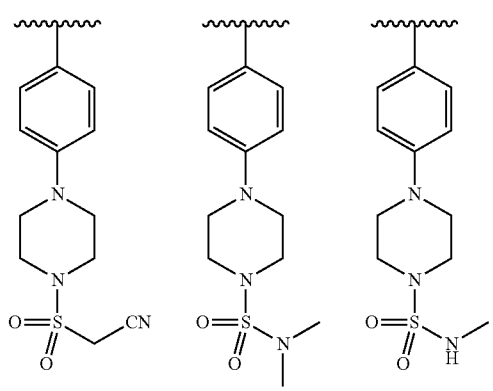
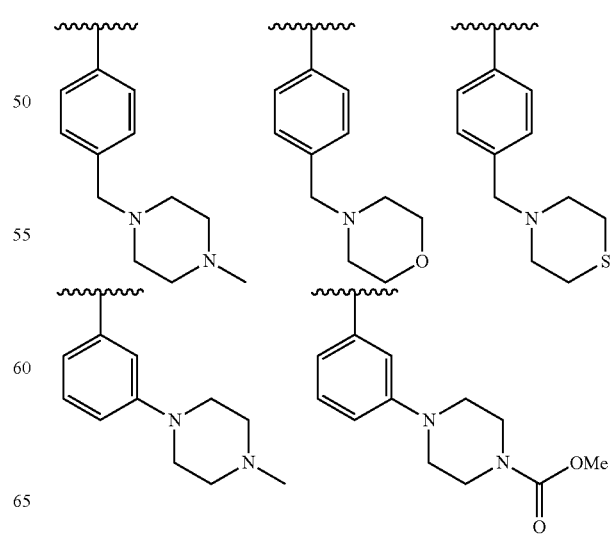

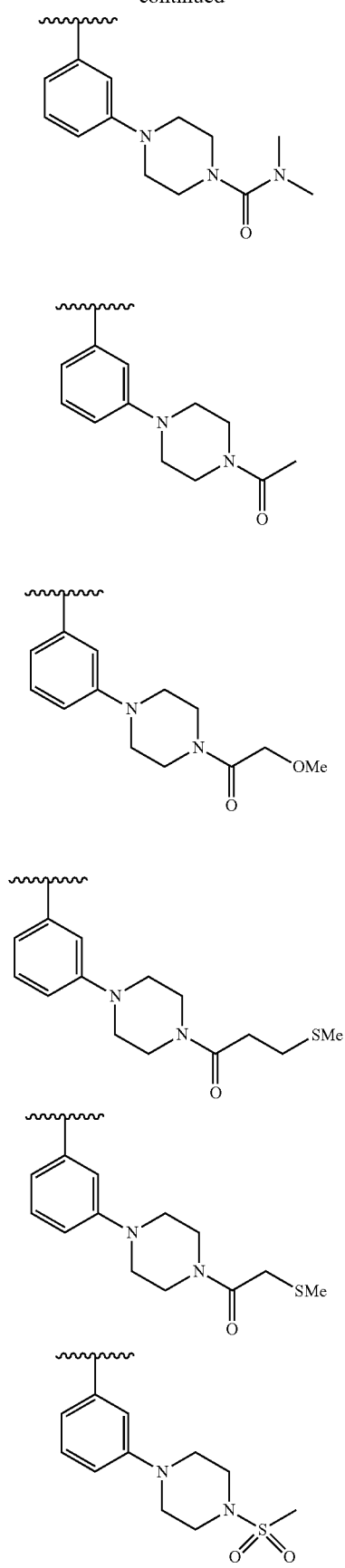
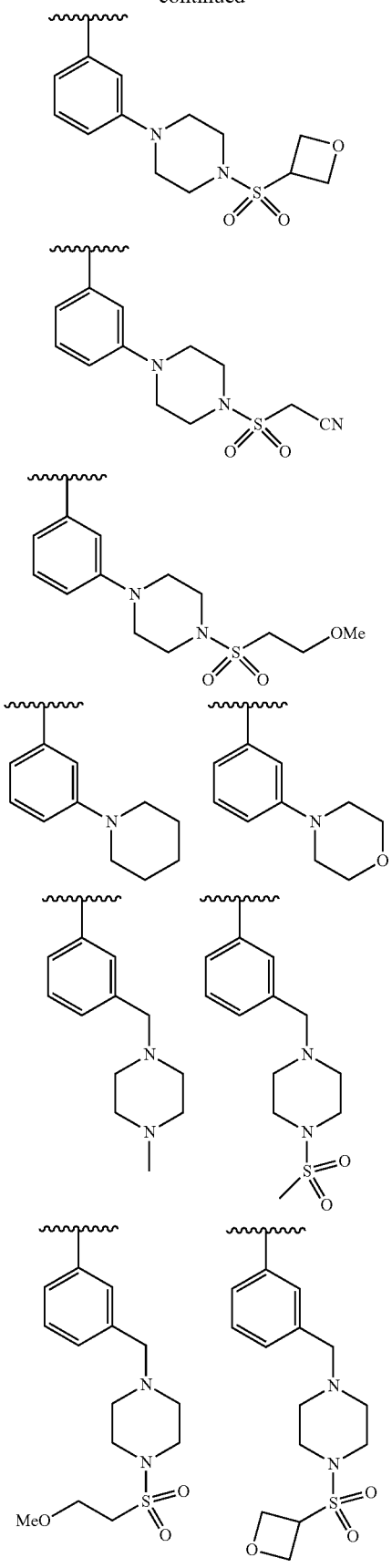

10. The compound of claim 2, or a pharmaceutically acceptable salt thereof, wherein R is

11. The compound of claim 2, or a pharmaceutically acceptable salt thereof, wherein $R^2$ is selected from the group consisting of:

which are optionally substituted with 1 to 2 $R^k$, each $R^k$ is independently selected from the group consisting of $C_{1-3}$ alkyl, $CH_2OH$, $CH_2CN$, and $CH_2NMe_2$, wherein two $R^k$ substituents on the same carbon may optionally form a cyclopropyl.

12. The compound of claim 2, or a pharmaceutically acceptable salt thereof, wherein $R^2$ is selected from the group consisting of:

9. The compound of claim 2, or a pharmaceutically acceptable salt thereof, wherein R is selected from the group consisting of:

-continued

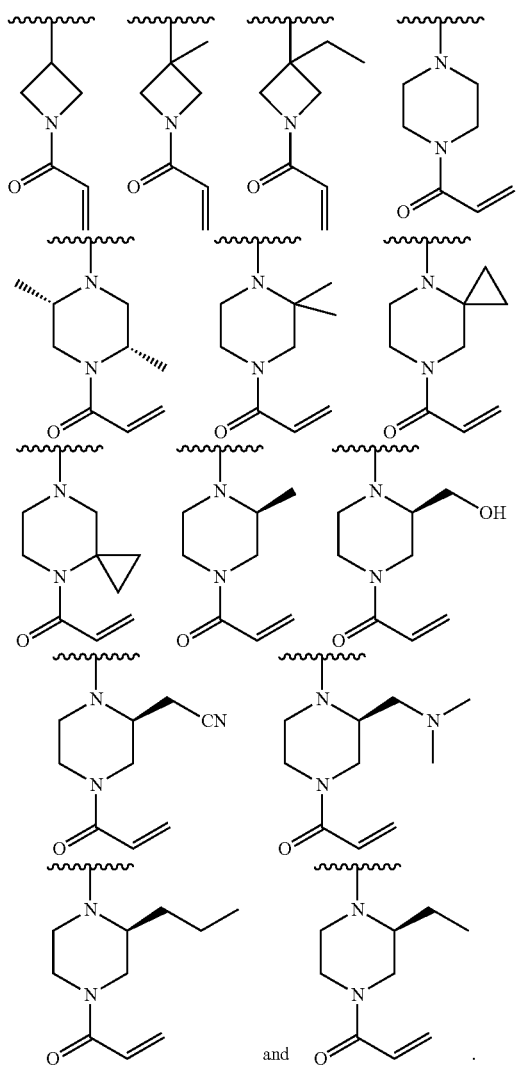

13. The compound of claim 2, or a pharmaceutically acceptable salt thereof, wherein R² is selected from the group consisting of:

14. The compound of claim 2, or a pharmaceutically acceptable salt thereof, wherein R² is selected from the group consisting of:

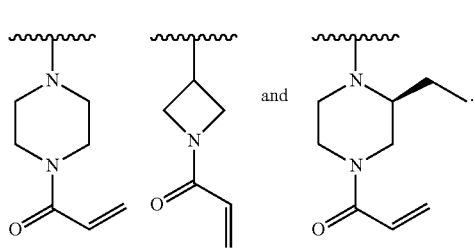

15. The compound of claim 1, or a pharmaceutically acceptable salt thereof, wherein
X is N;
R¹ is selected from the group consisting of:

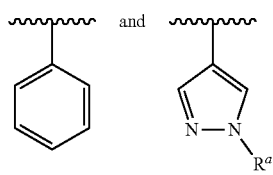

wherein $R^a$ is $C_{1-4}$ alkyl,
wherein

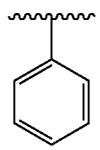 [SMILES: *c1ccccc1]

is substituted with piperazinyl, wherein the piperazinyl is substituted with a substituent selected from the group consisting of $C_{1-4}$ alkyl, —CO—$C_{1-4}$ alkyl, —COCH₂SMe, —CO(CH₂)₂SMe, and —CONMe₂;
R² is selected from the group consisting of:

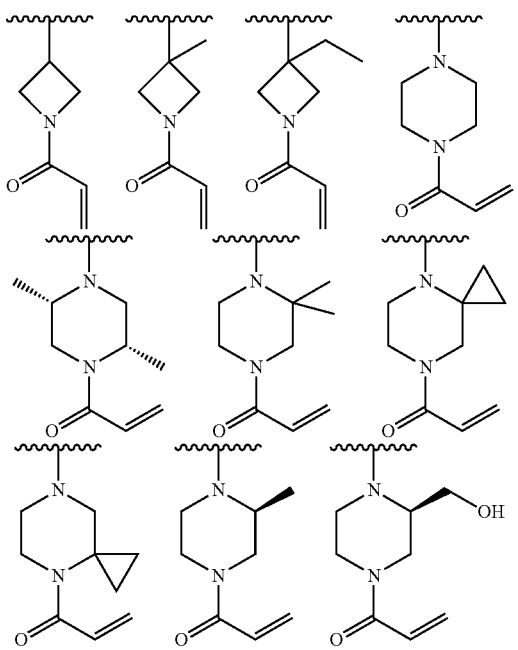

277
-continued
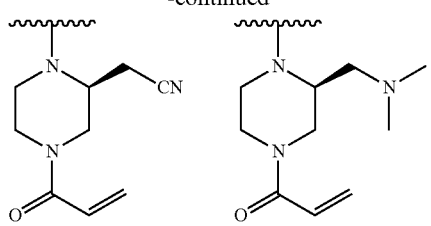
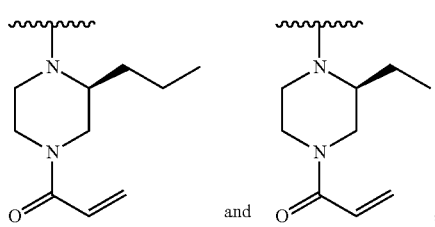
and R³ and R⁴ are both H.
16. The compound of claim 1, or a pharmaceutically acceptable salt thereof, wherein the compound is selected from the group consisting of:
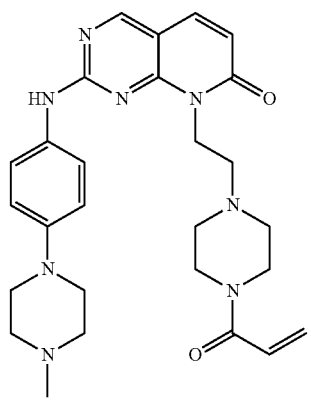
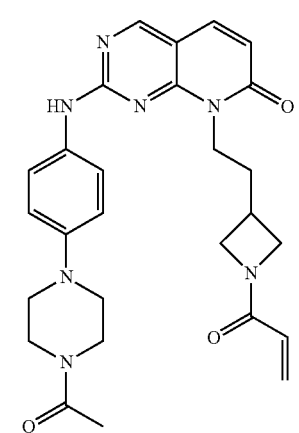
278
-continued
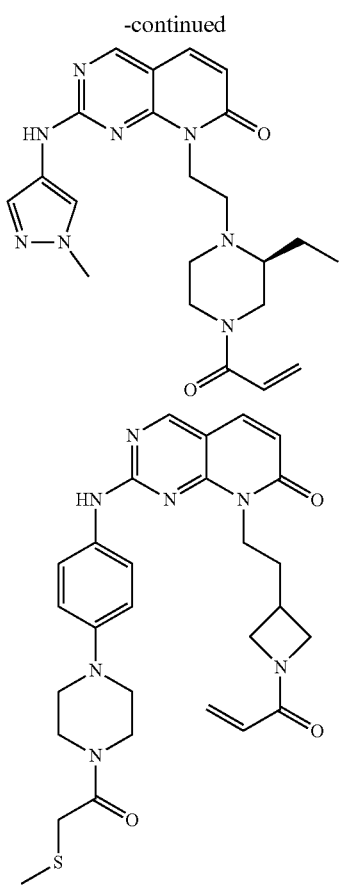
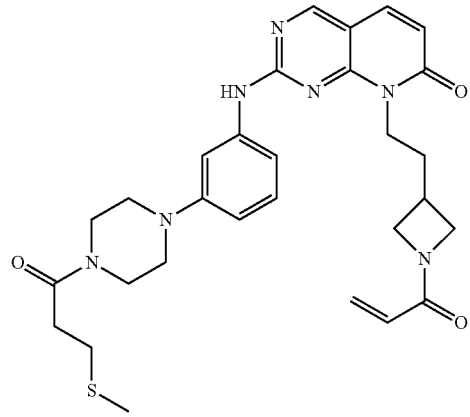
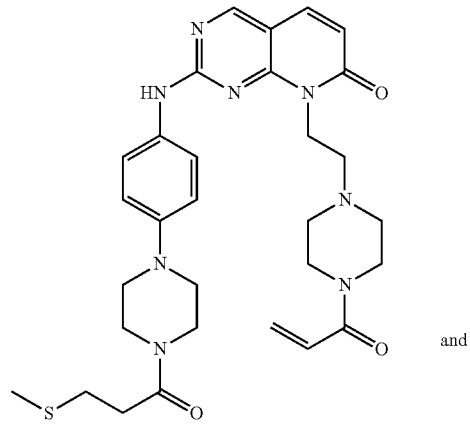
and

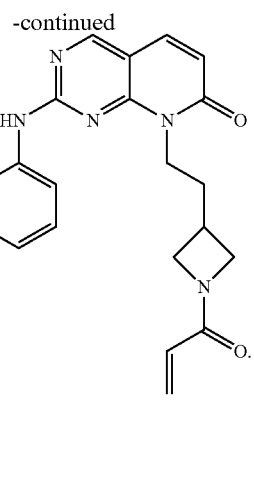

17. A pharmaceutical composition comprising the compound of claim 1, or a pharmaceutically acceptable salt thereof, and a pharmaceutically-acceptable carrier.

18. The pharmaceutical composition of claim 17, further comprising one or more other therapeutic agents useful for treating a gastrointestinal inflammatory disease.

19. A method of treating a gastrointestinal inflammatory disease in a mammal, the method comprising administering to the mammal the compound of claim 1, or a pharmaceutically acceptable salt thereof, and a pharmaceutically-acceptable carrier, wherein the gastrointestinal inflammatory disease is selected from the group consisting of ulcerative colitis, Crohn's disease, celiac disease, immune checkpoint inhibitor induced colitis, CTLA-4 inhibitor-induced colitis, graft versus host disease-related colitis, celiac disease, collagenous colitis, lymphocytic colitis, Behcet's disease, ileitis, eosinophilic esophagitis, and infectious colitis.

20. The method of claim 19, wherein the gastrointestinal inflammatory disease is ulcerative colitis.

21. The method of claim 19, wherein the gastrointestinal inflammatory disease is Crohn's disease.

22. The method of claim 19, wherein the gastrointestinal inflammatory disease is celiac disease.

* * * * *